US012569548B2

(12) United States Patent
Shattock et al.

(10) Patent No.: US 12,569,548 B2
(45) Date of Patent: Mar. 10, 2026

(54) RNA CONSTRUCT

(71) Applicant: IMPERIAL COLLEGE INNOVATIONS LIMITED, London (GB)

(72) Inventors: Robin Shattock, London (GB); Anna Blakney, London (GB); Paul McKay, London (GB)

(73) Assignee: IMPERIAL COLLEGE INNOVATIONS LIMITED, London (GB)

( * ) Notice: Subject to any disclaimer, the term of this patent is extended or adjusted under 35 U.S.C. 154(b) by 1097 days.

(21) Appl. No.: 17/617,831

(22) PCT Filed: Jun. 18, 2020

(86) PCT No.: PCT/GB2020/051465
§ 371 (c)(1),
(2) Date: Dec. 9, 2021

(87) PCT Pub. No.: WO2020/254804
PCT Pub. Date: Dec. 24, 2020

(65) Prior Publication Data
US 2022/0265807 A1 Aug. 25, 2022

(30) Foreign Application Priority Data

Jun. 18, 2019 (GB) ...................................... 1908729

(51) Int. Cl.
| | |
|---|---|
| C07K 14/005 | (2006.01) |
| A61K 39/00 | (2006.01) |
| A61K 39/12 | (2006.01) |
| A61P 31/14 | (2006.01) |
| C07K 14/08 | (2006.01) |
| C07K 14/52 | (2006.01) |
| C12N 15/86 | (2006.01) |

(52) U.S. Cl.
CPC .............. *A61K 39/12* (2013.01); *A61P 31/14* (2018.01); *C07K 14/005* (2013.01); *C12N 15/86* (2013.01); *A61K 2039/53* (2013.01); *A61K 2039/70* (2013.01); *C12N 2760/18022* (2013.01); *C12N 2760/20134* (2013.01); *C12N 2770/20022* (2013.01); *C12N 2770/20034* (2013.01); *C12N 2770/36143* (2013.01)

(58) Field of Classification Search
CPC .... A61K 2039/53; A61K 39/12; A61K 38/00; C07K 14/005; C07K 14/4703
See application file for complete search history.

(56) References Cited

U.S. PATENT DOCUMENTS

2009/0068222 A1 3/2009 Sadoff et al.

FOREIGN PATENT DOCUMENTS

| | | |
|---|---|---|
| JP | 2010-537645 | 12/2010 |
| WO | 2009/029770 | 3/2009 |
| WO | 2018/106615 | 6/2018 |

OTHER PUBLICATIONS

Bjoern Meyer et al: Inhibition of Innate Immune Responses Is Key to Pathogenesis by Arenaviruses11 , Journal of VI RO LOGY, vol. 90, No. 8, Apr. 15, 2016 (Apr. 15, 2016) pp. 3810-3818.
GB Search and Examination Report dated Dec. 2, 2019 for GB Application No. GB1908729.5 .
Jesse H. Erasmus et al: An Alphavirus-derived replicon RNA vaccine induces SARS-CoV-2 neutralizing antibody and T cell responses in mice and nonhuman primates 11, Science Translational Medicine, vol. 12, No. 555, Jul. 20, 2020 (Jul. 20, 2020), p. eabc9396.
Liu Y et al., Nucleic Acid Therapeutics, 2018, vol. 28 No. 3, "Modulation of mRNA Translation and Cell Viability by Influenza A Virus Derived Nonstructural Protein 1", pp. 200-208.
PCT International Search Report dated Nov. 6, 2020 for PCT Application No. PCT/GB2020/051465.
Phua Kyle KL Etal: 11 Non-linear enhancement of mRNA delivery efficiencies by influenza A derived NSI protein engendering host gene inhibition property, Biomaterials, Elsevier, Amsterdam, NL, vol. 133, Apr. 12, 2017 (Apr. 12, 2017), pp. 29-36.
Tim Beissert et al: "Improvement of In Vivo Expression of Genes Delivered by Self-Amplifying RNA Using Vaccinia Virus Immune Evasion Proteins", Human Gene Therapy, vol. 28, No. 12, Dec. 1, 2017 (Dec. 1, 2017), pp. 1138-1146.
Japanese Notice of Reasons for Rejection (with English translation) dated Jul. 1, 2024 for Japanese Patent Application No. 2021-575438.
Reconsideration Report by Examiner before Appeal dated Jul. 24, 2025 for Japanese Patent Application No. 2021-575438.
Menachery, V.D., et al., "Middle East Respiratory Syndrome Coronavirus Nonstructural Protein 16 Is Necessary for Interferon Resistance and Viral Pathogenesis", American Society for Microbiology, mSphere, Nov./Dec. 2017, pp. 1-12, vol. 2, Issue 6.

(Continued)

*Primary Examiner* — Barry A Chestnut

(74) *Attorney, Agent, or Firm* — GATES & COOPER LLP

(57) ABSTRACT

The invention relates to RNA constructs encoding (i) at least one therapeutic biomolecule; and (ii) at least one innate inhibitor protein (IIP). The constructs are RNA replicons and saRNA molecules, and the invention includes genetic constructs or vectors encoding such RNA replicons. The invention extends to the use of such RNA constructs and replicons in therapy, for example in treating diseases and/or in vaccine delivery. The invention extends to pharmaceutical compositions comprising such RNA constructs, and methods and uses thereof.

24 Claims, 35 Drawing Sheets
Specification includes a Sequence Listing.

(56)　　　　　References Cited

OTHER PUBLICATIONS

Almazan, F., et al., "Engineering a Replication-Competent, Propagation-Defective Middle East Respiratory Syndrome Coronavirus as a Vaccine Candidate", ASM Journals, mBio, 2013, pp. 1-11, vol. 4, Issue 5.

Reimann, I., et al., "Trans-complementation of autonomously replicating Bovine viral diarrhea virus replicons with deletions in the E2 coding region", Virology, 2003, pp. 213-227, vol. 137.

Wei, H., et al., "Developing a platform system for gene delivery: amplifying virus-like particles (AVLP) as an influenza vaccine", Vaccines, 2017, pp. 1-10.

Figure 1

Stealthicon GOI-PIV5 Map
10,854 bp b)

a)

b)

a)

SEQUENCE LISTING

```
<160> NUMBER OF SEQ ID NOS: 57

<210> SEQ ID NO 1
<211> LENGTH: 196
<212> TYPE: PRT
<213> ORGANISM: human herpesvirus 2

<400> SEQUENCE: 1

Val Arg Asp Cys Tyr Leu Met Gly Tyr Cys Arg Thr Arg Leu Gly Pro
1               5                   10                  15

Arg Thr Trp Gly Arg Leu Leu Gln Ile Ser Gly Gly Thr Trp Asp Val
            20                  25                  30

Arg Leu Arg Asn Ala Ile Arg Glu Val Glu Ala His Phe Glu Pro Ala
        35                  40                  45

Ala Glu Pro Val Cys Glu Leu Pro Cys Leu Asn Ala Arg Arg Tyr Gly
    50                  55                  60

Pro Glu Cys Asp Val Gly Asn Leu Glu Thr Asn Gly Gly Ser Thr Ser
65                  70                  75                  80

Asp Asp Glu Ile Ser Asp Ala Thr Asp Ser Asp Asp Thr Leu Ala Ser
                85                  90                  95

His Ser Asp Thr Glu Gly Gly Pro Ser Pro Ala Gly Arg Glu Asn Pro
            100                 105                 110

Glu Ser Ala Ser Gly Gly Ala Ile Ala Ala Arg Leu Glu Cys Glu Phe
            115                 120                 125

Gly Thr Phe Asp Trp Thr Ser Glu Glu Gly Ser Gln Pro Trp Leu Ser
        130                 135                 140

Ala Val Val Ala Asp Thr Ser Ser Ala Glu Arg Ser Gly Leu Pro Ala
145                 150                 155                 160

Pro Gly Ala Cys Arg Ala Thr Glu Ala Pro Glu Arg Glu Asp Gly Cys
                165                 170                 175

Arg Lys Met Arg Phe Pro Ala Ala Cys Pro Tyr Pro Cys Gly His Thr
            180                 185                 190

Phe Leu Arg Pro
            195

<210> SEQ ID NO 2
<211> LENGTH: 588
<212> TYPE: DNA
<213> ORGANISM: human herpesvirus 2

<400> SEQUENCE: 2
gtgagagact gctacctgat gggctactgc cggacaagac tgggacctag aacatggggc      60
agactgctgc agatcagcgg cggaacatgg gatgtgcggc tgagaaacgc catcagagag     120
gtggaagccc acttcgagcc tgccgctgaa cctgtgtgtg aactgccctg tctgaacgct     180
agaagatacg gccctgagtg cgacgtgggc aacctggaaa caaatggcgg cagcaccagc     240
gacgacgaga tttccgatgc caccgacagc gacgatacac tggccagcca cagcgataca     300
gaaggcggac atctcctgc cggaagagag aatcctgagt ctgcctctgg cggagccatt     360
```

```
gccgctagac tggaatgcga gttcggcacc ttcgactgga caagcgagga aggctctcag      420
ccttggctgt ctgctgtggt ggccgataca agctctgccg agagaagtgg acttcctgct      480
cctggcgcct gtagagctac agaggctcct gaaagagagg acggctgcag aaagatgcgg      540
ttccctgccg cctgtcctta tccttgcggc cacacatttc tgcggccc                   588
```

<210> SEQ ID NO 3
<211> LENGTH: 395
<212> TYPE: PRT
<213> ORGANISM: human herpesvirus 1

<400> SEQUENCE: 3

```
Val Arg Asp Cys Tyr Leu Met Gly Tyr Cys Arg Thr Arg Leu Gly Pro
1               5                   10                  15

Arg Thr Trp Gly Arg Leu Leu Gln Ile Ser Gly Gly Thr Trp Asp Val
            20                  25                  30

Arg Leu Arg Asn Ala Ile Arg Glu Val Glu Ala His Phe Glu Pro Ala
        35                  40                  45

Ala Glu Pro Val Cys Glu Leu Pro Cys Leu Asn Ala Arg Arg Tyr Gly
    50                  55                  60

Pro Glu Cys Asp Val Gly Asn Leu Glu Thr Asn Gly Gly Ser Thr Ser
65                  70                  75                  80

Asp Asp Glu Ile Ser Asp Ala Thr Asp Ser Asp Asp Thr Leu Ala Ser
                85                  90                  95

His Ser Asp Thr Glu Gly Gly Pro Ser Pro Ala Gly Arg Glu Asn Pro
            100                 105                 110

Glu Ser Ala Ser Gly Gly Ala Ile Ala Ala Arg Leu Glu Cys Glu Phe
        115                 120                 125

Gly Thr Phe Asp Trp Thr Ser Glu Glu Gly Ser Gln Pro Trp Leu Ser
        130                 135                 140

Ala Val Val Ala Asp Ile Arg Asp Cys Tyr Leu Met Gly Tyr Cys Arg
145                 150                 155                 160

Ala Arg Leu Ala Pro Arg Thr Trp Cys Arg Leu Leu Gln Val Ser Gly
                165                 170                 175

Gly Thr Trp Gly Met His Leu Arg Asn Thr Ile Arg Glu Val Glu Ala
            180                 185                 190

Arg Phe Asp Ala Thr Ala Glu Pro Val Cys Lys Leu Pro Cys Leu Glu
        195                 200                 205

Thr Arg Arg Tyr Gly Pro Glu Cys Asp Leu Ser Asn Leu Glu Ile His
    210                 215                 220

Leu Ser Ala Thr Ser Asp Asp Glu Ile Ser Asp Ala Thr Asp Leu Glu
225                 230                 235                 240

Ala Ala Gly Ser Asp His Thr Leu Ala Ser Gln Ser Asp Thr Glu Asp
                245                 250                 255

Ala Pro Ser Pro Val Thr Leu Glu Thr Pro Glu Pro Arg Gly Ser Leu
            260                 265                 270

Ala Val Arg Leu Glu Asp Glu Phe Gly Glu Phe Asp Trp Thr Pro Gln
        275                 280                 285

Glu Gly Ser Gln Pro Trp Leu Ser Ala Val Val Ala Asp Thr Ser Ser
    290                 295                 300

Val Glu Arg Pro Gly Pro Ser Asp Ser Gly Ala Gly Arg Ala Ala Glu
305                 310                 315                 320

Asp Arg Lys Cys Leu Asp Gly Cys Arg Lys Met Arg Phe Ser Thr Ala
                325                 330                 335
```

```
Cys Pro Tyr Pro Cys Ser Asp Thr Phe Leu Arg Pro Thr Ser Ser Ala
            340                 345                 350

Glu Arg Ser Gly Leu Pro Ala Pro Gly Ala Cys Arg Ala Thr Glu Ala
            355                 360                 365

Pro Glu Arg Glu Asp Gly Cys Arg Lys Met Arg Phe Pro Ala Ala Cys
            370                 375                 380

Pro Tyr Pro Cys Gly His Thr Phe Leu Arg Pro
385                 390                 395
```

<210> SEQ ID NO 4
<211> LENGTH: 597
<212> TYPE: DNA
<213> ORGANISM: human herpesvirus 1

<400> SEQUENCE: 4

```
atcagagact gctacctgat gggctactgc cgggctagac tggcccctag aacatggtgc        60
agactgctgc aagtgtctgg cggcacatgg ggcatgcacc tgagaaacac catcagagag       120
gtggaagcca gattcgacgc cacagccgag cctgtgtgca agctgccttg tctggaaact       180
cggagatacg gccccgagtg cgacctgagc aatctggaaa ttcacctgag cgccaccagc       240
gacgacgaga tttctgatgc caccgacctg gaagccgccg gatctgatca tacactggcc       300
agccagagcg acaccgagga tgctccatct ccagtgactc tggaaacccc tgagcctaga       360
ggatctctgg ccgtgcgact ggaagatgag ttcggcgagt cgactggac ccctcaagag        420 ggatctcagc cttggctgtc tgccgtggtg gccgatacaa gcagcgtgga aagacccgga       480
cctagcgatt ctggtgctgg cagagccgcc gaggatagaa agtgcctgga tggctgccgg       540
aagatgcggt tctctaccgc ctgtccatat ccttgcagcg acaccttcct gcggcct        597
```

<210> SEQ ID NO 5
<211> LENGTH: 161
<212> TYPE: PRT
<213> ORGANISM: human herpesvirus 1

<400> SEQUENCE: 5

```
Met Ser Gln Thr Gln Pro Pro Ala Pro Val Gly Pro Gly Asp Pro Asp
1               5                   10                  15

Val Tyr Leu Lys Gly Val Pro Ser Ala Gly Met His Pro Arg Gly Val
            20                  25                  30

His Ala Pro Arg Gly His Pro Arg Met Ile Ser Gly Pro Pro Gln Arg
            35                  40                  45

Gly Asp Asn Asp Gln Ala Ala Gly Gln Cys Gly Asp Ser Gly Leu Leu
            50                  55                  60

Arg Val Gly Ala Asp Thr Thr Ile Ser Lys Pro Ser Glu Ala Val Arg
65                  70                  75                  80

Pro Pro Thr Ile Pro Arg Thr Pro Arg Val Pro Arg Glu Pro Arg Val
                85                  90                  95

Pro Arg Pro Pro Arg Glu Pro Arg Glu Pro Arg Val Pro Arg Ala Pro
            100                 105                 110

Arg Asp Pro Arg Val Pro Arg Asp Pro Arg Asp Pro Arg Gln Pro Arg
            115                 120                 125

Ser Pro Arg Glu Pro Arg Ser Pro Arg Glu Pro Arg Ser Pro Arg Glu
            130                 135                 140

Pro Arg Thr Pro Arg Thr Pro Arg Glu Pro Arg Thr Ala Arg Gly Ser
145                 150                 155                 160
```

Val

<210> SEQ ID NO 6
<211> LENGTH: 483
<212> TYPE: DNA
<213> ORGANISM: human herpesvirus 1

<400> SEQUENCE: 6
atgagccaga cacagcctcc agctccagtt ggacctggcg accctgatgt gtatctgaag      60
ggcgtgccaa gcgccggcat gcatcctaga ggtgttcatg cccctagagg acaccccaga     120
atgatctctg ccctcctca gagaggcgac aacgatcagg ctgctggaca gtgtggcgat      180
agcggactgc tgagagtggg cgccgatacc acaatcagca agccatctga ggctgtgcgg      240
cctcctacaa tccccagaac acctagagtg ccccgcgagc caagagtgcc tagacctcct      300
agagagccca gagaacccag agtgccaagg gctcccagag atcctagagt ccctcgggac      360
cctagggacc caagacaacc tagatcaccc agagagcctc ggagcccaag agagccaaga     420
agccctaggg aaccccggac accaagaaca cccagggaac ctagaaccgc cagaggcagc      480
gtg                                                                   483

<210> SEQ ID NO 7
<211> LENGTH: 183
<212> TYPE: PRT
<213> ORGANISM: Orf virus

<400> SEQUENCE: 7

Met Ala Cys Glu Cys Ala Ser Leu Ile Leu Glu Leu Leu Arg Lys Ser
1               5                   10                  15

Asp Asp Lys Leu Pro Ala Lys Gln Ile Ala Lys Glu Leu Gly Ile Ser
            20                  25                  30

Lys His Glu Ala Asn Arg Gln Leu Tyr Arg Leu Leu Asp Ser Asp Glu
        35                  40                  45

Val Cys Cys Glu Asp Gly Asn Pro Pro Arg Trp Phe Val Glu Cys Ala
    50                  55                  60

Pro Ser Ala Pro Thr Glu Glu Asp Glu Asn Ser Asp Thr Glu Pro Met
65                  70                  75                  80

Glu Thr Glu Ala Gly Cys Asp Thr Leu Phe Gly Gly Asp Ile Asp Ile
                85                  90                  95

Met Thr Gln Ser Ala Val Ile Arg Leu Lys Ser Leu Asn Pro Val Ser
            100                 105                 110

Ala Val Asn Glu Phe Cys Met Met Thr His Arg Pro Leu Glu Phe Cys
        115                 120                 125

Glu Thr Arg Ala Gly Gly Glu Asp His Cys Pro Arg Phe Thr Cys Thr
    130                 135                 140

Ile Thr Ile Ser Gly Lys Val Val Ala Val Ala Asp Gly Ala Ser Lys
145                 150                 155                 160

Lys Leu Ala Arg His Thr Ala Cys Ser Ser Ala Leu Thr Ile Leu Ile
                165                 170                 175

Asn Asn Cys Gly Ile Ser Phe
            180

<210> SEQ ID NO 8
<211> LENGTH: 549
<212> TYPE: DNA
<213> ORGANISM: Orf virus

<400> SEQUENCE: 8

```
atggcctgtg aatgcgccag cctgatcctg gaactgctga gaaagagcga cgacaagctg      60
cccgccaagc agatcgccaa agagctgggc atctctaagc acgaggccaa ccggcagctg     120
taccggctgc tggattctga cgaagtgtgc tgcgaggacg gcaatcctcc tcgttggttc     180
gtggaatgtg cccctagcgc tcccaccgaa gaggacgaga atagcgacac cgagcctatg     240
gaaaccgagg ccggctgcga tacactgttt ggcggagaca tcgacatcat gacccagagc     300
gccgtgatcc ggctgaagtc cctgaatcct gtgtccgccg tgaacgagtt ctgcatgatg     360
acccaccggc tctggaatt ttgcgagaca agagccggcg gagaggatca ctgccccaga     420
ttcacctgta ccatcaccat cagcggcaag gtggtggctg ttgccgatgg cgcctctaag     480
aaactggcca gacacaccgc ctgtagcagc gccctgacaa tcctgatcaa caactgcggc     540
atcagcttc                                                            549
```

```
<210> SEQ ID NO 9
<211> LENGTH: 168
<212> TYPE: PRT
<213> ORGANISM: pestivirus type 1

<400> SEQUENCE: 9

Met Glu Leu Ile Thr Asn Glu Leu Leu Tyr Lys Thr Tyr Lys Gln Lys
1               5                   10                  15

Pro Val Gly Val Glu Glu Pro Val Tyr Asp Gln Ala Gly Asp Pro Leu
                20                  25                  30

Phe Gly Glu Arg Gly Ala Val His Pro Gln Ser Thr Leu Lys Leu Pro
            35                  40                  45

His Lys Arg Gly Glu Arg Asp Val Pro Thr Asn Leu Ala Ser Leu Pro
        50                  55                  60

Lys Arg Gly Asp Cys Arg Thr Gly Asn Ser Arg Gly Pro Val Ser Gly
65                  70                  75                  80

Ile Tyr Leu Lys Pro Gly Pro Leu Phe Tyr Gln Asp Tyr Lys Gly Pro
                85                  90                  95

Val Tyr His Arg Ala Pro Leu Glu Leu Phe Glu Glu Gly Ser Met Cys
            100                 105                 110

Glu Thr Thr Lys Arg Ile Gly Arg Val Thr Gly Ser Asp Gly Lys Leu
        115                 120                 125

Tyr His Ile Tyr Val Cys Ile Asp Gly Cys Ile Ile Ile Lys Ser Ala
    130                 135                 140

Thr Arg Ser Tyr Gln Arg Val Phe Arg Trp Val His Asn Arg Leu Asp
145                 150                 155                 160

Cys Pro Leu Trp Val Thr Ser Cys
                165
```

```
<210> SEQ ID NO 10
<211> LENGTH: 504
<212> TYPE: DNA
<213> ORGANISM: pestivirus type 1

<400> SEQUENCE: 10
atggaactga tcaccaacga gctgctgtac aagacctaca gcagaaacc cgtgggcgtc      60 gaggaacccg tgtatgatca agctggcgac cctctgtttg gcgagagagg cgctgttcac     120
cctcagagca cactgaagct gccccacaag cggggcgaaa gagatgtgcc taccaacctg     180
gccagcctgc ctaagagagg cgattgcaga accggcaata gcagaggccc tgtgtccggc     240
atctacctga aacctggacc actgttctac caggactaca agggacccgt gtaccacaga     300
```

-continued

```
gcccctctgg aactgtttga agagggcagc atgtgcgaaa ccaccaagcg gatcggaaga     360
gtgaccggct ctgacggcaa gctgtaccac atctacgtgt gcatcgacgg ctgcatcatc     420
atcaagagcg ccaccagatc ctaccagcgg gtgttcagat gggtgcacaa cagactggac     480
tgccctctgt gggtcaccag ctgc                                            504
```

```
<210> SEQ ID NO 11
<211> LENGTH: 222
<212> TYPE: PRT
<213> ORGANISM: Simian parainfluenza virus 5

<400> SEQUENCE: 11

Met Asp Pro Thr Asp Leu Ser Phe Ser Pro Asp Glu Ile Asn Lys Leu
1               5                   10                  15

Ile Glu Thr Gly Leu Asn Thr Val Glu Tyr Phe Thr Ser Gln Gln Val
            20                  25                  30

Thr Gly Thr Ser Ser Leu Gly Lys Asn Thr Ile Pro Pro Gly Val Thr
        35                  40                  45

Gly Leu Leu Thr Asn Ala Ala Glu Ala Lys Ile Gln Glu Ser Thr Asn
    50                  55                  60

His Gln Lys Gly Ser Val Gly Gly Gly Ala Lys Pro Lys Lys Pro Arg
65                  70                  75                  80

Pro Lys Ile Ala Ile Val Pro Ala Asp Asp Lys Thr Val Pro Gly Lys
                85                  90                  95

Pro Ile Pro Asn Pro Leu Leu Gly Leu Asp Ser Thr Pro Ser Thr Gln
            100                 105                 110

Thr Val Leu Asp Leu Ser Gly Lys Thr Leu Pro Ser Gly Ser Tyr Lys
        115                 120                 125

Gly Val Lys Leu Ala Lys Phe Gly Lys Glu Asn Leu Met Thr Arg Phe
    130                 135                 140

Ile Glu Glu Pro Arg Glu Asn Pro Ile Ala Thr Ser Ser Pro Ile Asp
145                 150                 155                 160

Phe Lys Arg Gly Arg Asp Thr Gly Gly Phe His Arg Arg Glu Tyr Ser
                165                 170                 175

Ile Gly Trp Val Gly Asp Glu Val Lys Val Thr Glu Trp Cys Asn Pro
            180                 185                 190

Ser Cys Ser Pro Ile Thr Ala Ala Ala Arg Arg Phe Glu Cys Thr Cys
        195                 200                 205

His Gln Cys Pro Val Thr Cys Ser Glu Cys Glu Arg Asp Thr
    210                 215                 220
```

```
<210> SEQ ID NO 12
<211> LENGTH: 666
<212> TYPE: DNA
<213> ORGANISM: Simian parainfluenza virus 5

<400> SEQUENCE: 12 atggaccccta ccgacctgag cttcagcccc gacgagatca caagctgat cgagacaggc      60 ctgaacaccg tggaatactt caccagccag caagtgaccg gcacaagcag cctgggcaag     120
aacacaattc ctccaggcgt gaccggcctg ctgacaaatg ctgccgaggc caagatccaa     180
gagagcacca accaccagaa gggctctgtt ggaggcggag ccaagcctaa gaagcccaga     240
cctaagatcg ccatcgtgcc cgccgacgat aagacagtgc ctggcaagcc cattcctaat     300
cctctgctgg gcctcgacag caccccctagc acacagacag tgctggatct gagcggcaag     360
```

-continued

```
acactgccta gcggcagcta taagggcgtg aagctggcca agttcggcaa agaaaacctg        420
atgacccggt tcatcgagga acccagagag aaccctatcg ccaccagctc tcccatcgac        480
ttcaagagag gcagagacac cggcggcttc cacagaagag agtacagcat tggctgggtc        540
ggagatgaag tgaaagtgac cgagtggtgc aaccccagct gcagccctat tacagccgcc        600
gctagaagat tcgagtgcac ctgtcaccag tgtcctgtga cctgtagcga gtgcgagcgg        660
gacaca                                                                   666
```

```
<210> SEQ ID NO 13
<211> LENGTH: 230
<212> TYPE: PRT
<213> ORGANISM: Influenza virus

<400> SEQUENCE: 13

Met Asp Ser Asn Thr Val Ser Ser Phe Gln Val Asp Cys Phe Leu Trp
1               5                   10                  15

His Val Arg Lys Gln Val Ala Asp Gln Glu Leu Gly Asp Ala Pro Phe
            20                  25                  30

Leu Asp Arg Leu Arg Arg Asp Gln Lys Ser Leu Lys Gly Arg Gly Ser
        35                  40                  45

Thr Leu Gly Leu Asn Ile Glu Thr Ala Thr Cys Val Gly Lys Gln Ile
    50                  55                  60

Val Glu Arg Ile Leu Lys Glu Glu Ser Asp Glu Ala Phe Arg Met Thr
65                  70                  75                  80

Met Ala Ser Ala Leu Ala Ser Arg Tyr Leu Thr Asp Met Thr Ile Glu
                85                  90                  95

Glu Met Ser Arg Asp Trp Phe Met Leu Met Pro Lys Gln Lys Val Ala
            100                 105                 110

Gly Pro Leu Cys Val Arg Met Asp Gln Ala Ile Met Asp Lys Asn Ile
        115                 120                 125

Ile Leu Lys Ala Asn Phe Ser Val Ile Phe Asp Arg Leu Glu Thr Leu
    130                 135                 140

Thr Leu Leu Arg Ala Phe Thr Glu Glu Gly Ala Ile Val Gly Glu Ile
145                 150                 155                 160

Ser Pro Leu Pro Ser Leu Pro Gly His Thr Asn Glu Asp Val Lys Asn
                165                 170                 175

Ala Ile Gly Val Leu Ile Gly Gly Leu Glu Trp Asn Asp Asn Thr Val
            180                 185                 190

Arg Val Ser Glu Thr Leu Gln Arg Phe Ala Trp Arg Ser Ser Asn Glu
        195                 200                 205

Asn Gly Gly Pro Pro Leu Thr Pro Thr Gln Lys Arg Lys Met Ala Gly
    210                 215                 220

Lys Ile Arg Ser Glu Val
225                 230
```

```
<210> SEQ ID NO 14
<211> LENGTH: 693
<212> TYPE: DNA
<213> ORGANISM: Influenza virus

<400> SEQUENCE: 14
atggattcca acactgtgtc aagctttcag gtagattgct tcctttggca tgtccgcaaa         60
caagttgcag accaagagct aggtgatgcc ccattccttg atcggcttcg ccgagatcag        120
aagtccctaa agggaagagg cagcactctc ggtctgaaca tcgaaacagc cacctgtgtt        180
```

```
ggaaagcaaa tagtagagag gattctgaag gaagaatccg atgaggcatt tagaatgacc       240
atggcctccg cacttgcttc gcgataccta actgacatga ctattgaaga gatgtcaagg       300
gactggttca tgctcatgcc caagcagaaa gtggcaggcc ctctttgtgt cagaatggac       360
caggcgataa tggataagaa catcatactg aaagcgaatt tcagtgtgat ttttgaccgg       420
ttggagactc tgacattact aagggctttc accgaagagg gagcaattgt tggcgaaatt       480
tcaccattgc cttctcttcc aggacatact aatgaggatg tcaaaaatgc aattggggtc       540
ctcatcgggg gacttgaatg gaatgataac acagttcgag tctctgaaac tctacagaga       600
ttcgcttgga gaagcagtaa tgagaatggg ggacctccac tcactccaac acagaaacgg       660
aaaatggcgg gaaaaattag gtcagaagtt tga                                    693
```

```
<210> SEQ ID NO 15
<211> LENGTH: 109
<212> TYPE: PRT
<213> ORGANISM: Middle East respiratory syndrome related coronavirus

<400> SEQUENCE: 15

Met Asp Tyr Val Ser Leu Leu Asn Gln Ile Trp Gln Lys Tyr Leu Asn
1               5                   10                  15

Ser Pro Tyr Thr Thr Cys Leu Tyr Ile Pro Lys Pro Thr Ala Lys Tyr
            20                  25                  30

Thr Pro Leu Val Gly Thr Ser Leu His Pro Val Leu Trp Asn Cys Gln
        35                  40                  45

Leu Ser Phe Ala Gly Tyr Thr Glu Ser Ala Val Asn Ser Thr Lys Ala
    50                  55                  60

Leu Ala Lys Gln Asp Ala Ala Gln Arg Ile Ala Trp Leu Leu His Lys
65                  70                  75                  80

Asp Gly Gly Ile Pro Asp Gly Cys Ser Leu Tyr Leu Arg His Ser Ser
                85                  90                  95

Leu Phe Ala Gln Ser Glu Glu Glu Glu Ser Phe Ser Asn
            100                 105
```

```
<210> SEQ ID NO 16
<211> LENGTH: 327
<212> TYPE: DNA
<213> ORGANISM: Middle East respiratory syndrome related coronavirus

<400> SEQUENCE: 16
atggactacg tgtccctgct gaaccagatt tggcagaagt acctgaacag cccctacacc        60
acctgtctgt acatccccaa gcctaccgcc aagtacacac tctcgtgggg cacatctctg       120
caccccgtgc tgtggaattg ccagctgagc tttgccggct acaccgagtc tgccgtgaac       180
agcacaaagg ccctggccaa acaggacgcc gctcagagaa ttgcctggct gctgcacaag       240
gatggcggca tccctgatgg ctgtagcctg tacctgagac acagcagcct gttcgcccag       300
agcgaggaag aggaatcctt cagcaac                                           327
```

```
<210> SEQ ID NO 17
<211> LENGTH: 381
<212> TYPE: PRT
<213> ORGANISM: Langat virus

<400> SEQUENCE: 17

Val Phe Lys Asp Lys Val Asp Thr Lys Ala Gln Glu Pro Gln Pro Gly
1               5                   10                  15

Thr Lys Ile Ile Met Arg Ala Val Asn Asp Trp Leu Leu Glu Arg Leu
```

```
                20                 25                 30

Val Lys Lys Ser Arg Pro Arg Met Cys Ser Arg Glu Glu Phe Ile Ala
         35                 40                 45

Lys Val Arg Ser Asn Ala Ala Leu Gly Ala Trp Ser Asp Glu Gln Asn
     50                 55                 60

Lys Trp Lys Ser Ala Arg Glu Ala Val Glu Asp Pro Glu Phe Trp Ser
 65                 70                 75                 80

Leu Val Glu Ala Glu Arg Glu Arg His Leu Gln Gly Arg Cys Ala His
                 85                 90                 95

Cys Val Tyr Asn Met Met Gly Lys Arg Glu Lys Lys Leu Gly Glu Phe
                100                105                110

Gly Val Ala Lys Gly Ser Arg Ala Ile Trp Tyr Met Trp Leu Gly Ser
            115                120                125

Arg Phe Leu Glu Phe Glu Ala Leu Gly Phe Leu Asn Glu Asp His Trp
        130                135                140

Ala Ser Arg Ala Ser Ser Gly Ala Gly Val Glu Gly Ile Ser Leu Asn
145                150                155                160

Tyr Leu Gly Trp His Leu Lys Lys Leu Ala Ser Leu Ser Gly Gly Leu
                165                170                175

Phe Tyr Ala Asp Asp Thr Ala Gly Trp Asp Thr Lys Ile Thr Asn Ala
                180                185                190

Asp Leu Asp Asp Glu Glu Gln Ile Leu Arg Tyr Met Asp Gly Asp His
                195                200                205

Lys Lys Leu Ala Ala Thr Val Leu Arg Lys Ala Tyr His Ala Lys Val
        210                215                220

Val Arg Val Ala Arg Pro Ser Arg Glu Gly Gly Cys Val Met Asp Ile
225                230                235                240

Ile Thr Arg Arg Asp Gln Arg Gly Ser Gly Gln Val Val Thr Tyr Ala
                245                250                255

Leu Asn Thr Ile Thr Asn Ile Lys Val Gln Leu Val Arg Met Met Glu
                260                265                270

Gly Glu Gly Val Ile Glu Val Ala Asp Ser His Asn Pro Arg Leu Leu
            275                280                285

Arg Val Glu Lys Trp Leu Glu Glu His Gly Glu Glu Arg Leu Ser Arg
        290                295                300

Met Leu Val Ser Gly Asp Asp Cys Val Val Arg Pro Val Asp Asp Arg
305                310                315                320

Phe Ser Lys Ala Leu Tyr Phe Leu Asn Asp Met Ala Lys Thr Arg Lys
                325                330                335

Asp Thr Gly Glu Trp Glu Pro Ser Thr Gly Phe Ala Ser Trp Glu Glu
            340                345                350

Val Pro Phe Cys Ser His His Phe His Glu Leu Val Met Lys Asp Gly
            355                360                365

Arg Ala Leu Val Val Pro Cys Arg Asp Gln Asp Glu Leu
    370                375                380
```

<210> SEQ ID NO 18
<211> LENGTH: 1143
<212> TYPE: DNA
<213> ORGANISM: Langat virus
<400> SEQUENCE: 18
gtgttcaagg acaaggtgga caccaaggct caagagcctc agcctggcac caagatcatc      60
atgagagccg tgaacgactg gctgctggaa cggctggtca agaaaagcag accccggatg     120

```
tgcagccggg aagagtttat cgccaaagtg cggagcaatg ccgctctcgg agcttggagt      180
gacgagcaga acaagtggaa gtccgccaga gaagccgtgg aagatcccga gttttggagc      240
ctggtggaag ccgagagaga gaggcatctg cagggaagat gtgcccactg cgtgtacaac      300
atgatgggca agagagagaa gaagctgggc gagttcggag tggccaaagg cagcagagcc      360
atctggtata tgtggctggg cagccgcttc ctggaatttg aggccctggg cttcctgaac      420
gaggatcact gggctagcag agcctcttct ggtgctggcg tggaaggcat cagcctgaat      480
tatctcggct ggcacctgaa gaaactggcc tctctgtctg gcggcctgtt ctacgccgat      540
gatacagccg gatgggacac aaagatcacc aacgccgacc tggacgacga ggaacagatc      600
ctgagatata tggacggcga ccacaaaaag ctggccgcca ccgtgctgag aaaggcctat      660
cacgccaagg tcgtcagagt ggccagacct agtagagaag cggctgcgt gatggacatc      720 atcaccagaa gggaccagcg cggctctggc caggttgtga catacgccct gaacaccatc      780
accaacatca aggtgcagct cgtgcggatg atggaaggcg agggcgtgat cgaagtggcc      840
gacagccata tcctcggct gctgagagtg gaaaagtggc tggaagaaca cggcgaagaa      900
cggctgagca gaatgctggt gtccggcgac gattgtgttg tgcggcccgt ggacgacaga      960
ttcagcaagg ccctgtactt tctgaatgac atggccaaga ccagaaagga caccggcgag     1020
tgggagcctt ctacaggctt tgccagctgg aagaagtgc ctttctgcag ccaccacttc      1080
cacgagctgg tcatgaagga tggcagagcc ctggtggtgc cctgcagaga tcaggacgaa     1140
ctg                                                                    1143

<210> SEQ ID NO 19
<211> LENGTH: 693
<212> TYPE: RNA
<213> ORGANISM: Influenza virus

<400> SEQUENCE: 19
auggauucca acacuguguc aagcuuucag guagauugcu uccuuuggca uguccgcaaa       60
caaguugcag accaagagcu agguguagcc ccauuccuug aucggcuucg ccgagaucag      120 aaguccuaa agggaagagg cagcacucuc ggucugaaca ucgaaacagc caccugugu       180 ggaaagcaaa uaguagagag gauucugaag gaagaauccg augaggcauu uagaaugacc      240
auggccuccg cacuugcuuc gcgauaccua acugacauga cuauugaaga gaugucaagg      300
gacugguuca ugcucaugcc caagcagaaa guggcaggcc cucuuugugu cagaauggac      360
caggcgauaa uggauaagaa caucauacug aaagcgaauu ucagugugau uuuugaccgg      420
uuggagacuc ugacauuacu aagggcuuuc accgaagagg agcaauugu ggcgaaauu       480 ucaccauugc cuucucucc aggacauacu aaugaggaug ucaaaaaugc aauuggggguc      540 cucaucgggg gacuugaaug gaaugauaac acaguucgag ucucugaaac ucuacagaga      600
uucgcuugga aagcaguaa ugagaauggg ggaccuccac ucacuccaac acagaaacgg      660
aaaauggcgg gaaaaauuag gucagaaguu uga                                   693

<210> SEQ ID NO 20
<211> LENGTH: 78
<212> TYPE: PRT
<213> ORGANISM: Severe acute respiratory syndrome coronavirus 2

<400> SEQUENCE: 20

Met Met Pro Thr Ile Phe Phe Ala Gly Ile Leu Ile Val Thr Thr Ile
1               5                   10                  15
```

-continued

```
Val Tyr Leu Thr Ile Val Gln Leu Leu Gln Leu Ser Leu Leu Gln Val
            20                  25                  30

Met Ala Gln Gln Val Leu Phe Leu Asn Met Thr Thr Arg Leu Val Val
            35                  40                  45

Ile Leu Lys Asn Gly Asn Leu Glu Gln Lys Thr Val Leu Tyr Tyr Thr
            50                  55                  60

Val Thr Ser Leu Gln Thr Ile Thr Ser Cys Thr Gln Leu Asn
65                  70                  75

<210> SEQ ID NO 21
<211> LENGTH: 19
<212> TYPE: PRT
<213> ORGANISM: porcine teschovirus

<400> SEQUENCE: 21

Ala Thr Asn Phe Ser Leu Leu Lys Gln Ala Gly Asp Val Glu Glu Asn
1               5                   10                  15

Pro Gly Pro

<210> SEQ ID NO 22
<211> LENGTH: 20
<212> TYPE: PRT
<213> ORGANISM: Thosea asigna virus

<400> SEQUENCE: 22

Gln Cys Thr Asn Tyr Ala Leu Leu Lys Leu Ala Gly Asp Val Glu Ser
1               5                   10                  15

Asn Pro Gly Pro
            20

<210> SEQ ID NO 23
<211> LENGTH: 22
<212> TYPE: PRT
<213> ORGANISM: Equine Rhinovirus type 1

<400> SEQUENCE: 23

Val Lys Gln Thr Leu Asn Phe Asp Leu Leu Lys Leu Ala Gly Asp Val
1               5                   10                  15

Glu Ser Asn Pro Gly Pro
            20

<210> SEQ ID NO 24
<211> LENGTH: 4
<212> TYPE: PRT
<213> ORGANISM: Artificial Sequence
<220> FEATURE:
<223> OTHER INFORMATION: furin cleavage site

<400> SEQUENCE: 24

Arg Asn Asn Arg
1

<210> SEQ ID NO 25
<211> LENGTH: 6
<212> TYPE: PRT
<213> ORGANISM: Artificial Sequence
<220> FEATURE:
<223> OTHER INFORMATION: Optimised furin cleavage site

<400> SEQUENCE: 25

Arg Arg Arg Arg Arg Arg
1               5
```

-continued

```
<210> SEQ ID NO 26
<211> LENGTH: 27
<212> TYPE: PRT
<213> ORGANISM: Artificial Sequence
<220> FEATURE:
<223> OTHER INFORMATION: furin/T2A

<400> SEQUENCE: 26

Arg Arg Arg Arg Arg Arg Gly Ser Gly Glu Gly Arg Gly Ser Leu Leu
1               5                   10                  15

Thr Cys Gly Asp Val Glu Glu Asn Pro Gly Pro
            20                  25

<210> SEQ ID NO 27
<211> LENGTH: 535
<212> TYPE: PRT
<213> ORGANISM: Artificial Sequence
<220> FEATURE:
<223> OTHER INFORMATION: nsP1

<400> SEQUENCE: 27

Met Glu Lys Val His Val Asp Ile Glu Glu Asp Ser Pro Phe Leu Arg
1               5                   10                  15

Ala Leu Gln Arg Ser Phe Pro Gln Phe Glu Val Glu Ala Lys Gln Val
            20                  25                  30

Thr Asp Asn Asp His Ala Asn Ala Arg Ala Phe Ser His Leu Ala Ser
        35                  40                  45

Lys Leu Ile Glu Thr Glu Val Asp Pro Ser Asp Thr Ile Leu Asp Ile
    50                  55                  60

Gly Ser Ala Pro Ala Arg Arg Met Tyr Ser Lys His Lys Tyr His Cys
65                  70                  75                  80

Ile Cys Pro Met Arg Cys Ala Glu Asp Pro Asp Arg Leu Tyr Lys Tyr
                85                  90                  95

Ala Thr Lys Leu Lys Lys Asn Cys Lys Glu Ile Thr Asp Lys Glu Leu
            100                 105                 110

Asp Lys Lys Met Lys Glu Leu Ala Ala Val Met Ser Asp Pro Asp Leu
        115                 120                 125

Glu Thr Glu Thr Met Cys Leu His Asp Asp Glu Ser Cys Arg Tyr Glu
    130                 135                 140

Gly Gln Val Ala Val Tyr Gln Asp Val Tyr Ala Val Asp Gly Pro Thr
145                 150                 155                 160

Ser Leu Tyr His Gln Ala Asn Lys Gly Val Arg Val Ala Tyr Trp Ile
                165                 170                 175

Gly Phe Asp Thr Thr Pro Phe Met Phe Lys Asn Leu Ala Gly Ala Tyr
                180                 185                 190

Pro Ser Tyr Ser Thr Asn Trp Ala Asp Glu Thr Val Leu Thr Ala Arg
            195                 200                 205

Asn Ile Gly Leu Cys Ser Ser Asp Val Met Glu Arg Ser Arg Arg Gly
        210                 215                 220

Met Ser Ile Leu Arg Lys Lys Tyr Leu Lys Pro Ser Asn Asn Val Leu
225                 230                 235                 240

Phe Ser Val Gly Ser Thr Ile Tyr His Glu Lys Arg Asp Leu Leu Arg
                245                 250                 255

Ser Trp His Leu Pro Ser Val Phe His Leu Arg Gly Lys Gln Asn Tyr
            260                 265                 270

Thr Cys Arg Cys Glu Thr Ile Val Ser Cys Asp Gly Tyr Val Val Lys
```

-continued

```
              275                 280                 285
Arg Ile Ala Ile Ser Pro Gly Leu Tyr Gly Lys Pro Ser Gly Tyr Ala
    290                 295                 300
Ala Thr Met His Arg Glu Gly Phe Leu Cys Cys Lys Val Thr Asp Thr
305                 310                 315                 320
Leu Asn Gly Glu Arg Val Ser Phe Pro Val Cys Thr Tyr Val Pro Ala
                325                 330                 335
Thr Leu Cys Asp Gln Met Thr Gly Ile Leu Ala Thr Asp Val Ser Ala
            340                 345                 350
Asp Asp Ala Gln Lys Leu Leu Val Gly Leu Asn Gln Arg Ile Val Val
            355                 360                 365
Asn Gly Arg Thr Gln Arg Asn Thr Asn Thr Met Lys Asn Tyr Leu Leu
    370                 375                 380
Pro Val Val Ala Gln Ala Phe Ala Arg Trp Ala Lys Glu Tyr Lys Glu
385                 390                 395                 400
Asp Gln Glu Asp Glu Arg Pro Leu Gly Leu Arg Asp Arg Gln Leu Val
                405                 410                 415
Met Gly Cys Cys Trp Ala Phe Arg Arg His Lys Ile Thr Ser Ile Tyr
            420                 425                 430
Lys Arg Pro Asp Thr Gln Thr Ile Ile Lys Val Asn Ser Asp Phe His
            435                 440                 445
Ser Phe Val Leu Pro Arg Ile Gly Ser Asn Thr Leu Glu Ile Gly Leu
    450                 455                 460
Arg Thr Arg Ile Arg Lys Met Leu Glu Glu His Lys Glu Pro Ser Pro
465                 470                 475                 480
Leu Ile Thr Ala Glu Asp Val Gln Glu Ala Lys Cys Ala Ala Asp Glu
                485                 490                 495
Ala Lys Glu Val Arg Glu Ala Glu Glu Leu Arg Ala Ala Leu Pro Pro
            500                 505                 510
Leu Ala Ala Asp Val Glu Glu Pro Thr Leu Glu Ala Asp Val Asp Leu
            515                 520                 525
Met Leu Gln Glu Ala Gly Ala
    530                 535
```

```
<210> SEQ ID NO 28
<211> LENGTH: 1605
<212> TYPE: DNA
<213> ORGANISM: Artificial Sequence
<220> FEATURE:
<223> OTHER INFORMATION: nsP1  coding sequence

<400> SEQUENCE: 28
atggagaaag ttcacgttga catcgaggaa gacagcccat tcctcagagc tttgcagcgg      60
agcttcccgc agtttgaggt agaagccaag caggtcactg ataatgacca tgctaatgcc     120
agagcgtttt cgcatctggc ttcaaaactg atcgaaacgg aggtggaccc atccgacacg     180
atccttgaca ttggaagtgc gcccgcccgc agaatgtatt ctaagcacaa gtatcattgt     240
atctgtccga tgagatgtgc ggaagatccg gacagattgt ataagtatgc aactaagctg     300
aagaaaaact gtaaggaaat aactgataag gaattggaca agaaaatgaa ggagctggcc     360
gccgtcatga gcgaccctga cctggaaact gagactatgt gcctccacga cgacgagtcg     420
tgtcgctacg aagggcaagt cgctgtttac caggatgtat acgcggttga cggaccgaca     480
agtctctatc accaagccaa taagggagtt agagtcgcct actggatagg ctttgacacc     540
acccctttta tgtttaagaa cttggctgga gcatatccat catactctac caactgggcc     600
```

-continued

```
gacgaaaccg tgttaacggc tcgtaacata ggcctatgca gctctgacgt tatggagcgg     660
tcacgtagag ggatgtccat tcttagaaag aagtatttga aaccatccaa caatgttcta     720
ttctctgttg gctcgaccat ctaccacgag aagagggact tactgaggag ctggcacctg     780
ccgtctgtat ttcacttacg tggcaagcaa aattacacat gtcggtgtga gactatagtt     840
agttgcgacg ggtacgtcgt taaaagaata gctatcagtc caggcctgta tgggaagcct     900
tcaggctatg ctgctacgat gcaccgcgag ggattcttgt gctgcaaagt gacagacaca     960
ttgaacgggg agagggtctc tttctcccgtg tgcacgtatg tgccagctac attgtgtgac    1020
caaatgactg gcatactggc aacagatgtc agtgcggacg acgcgcaaaa actgctggtt    1080
gggctcaacc agcgtatagt cgtcaacggt cgcacccaga gaaacaccaa taccatgaaa    1140
aattaccttt tgcccgtagt ggcccaggca tttgctaggt gggcaaagga atataaggaa    1200
gatcaagaag atgaaaggcc actaggacta cgagatagac agttagtcat ggggtgttgt    1260
tgggctttta gaaggcacaa gataacatct atttataagc gcccggatac ccaaaccatc    1320
atcaaagtga acagcgattt ccactcattc gtgctgccca ggataggcag taacacattg    1380
gagatcgggc tgagaacaag aatcaggaaa atgttagagg agcacaagga gccgtcacct    1440
ctcattaccg ccgaggacgt acaagaagct aagtgcgcag ccgatgaggc taaggaggtg    1500
cgtgaagccg aggagttgcg cgcagctcta ccacctttgg cagctgatgt tgaggagccc    1560
actctggaag ccgatgtcga cttgatgtta caagaggctg gggcc                    1605
```

<210> SEQ ID NO 29
<211> LENGTH: 794
<212> TYPE: PRT
<213> ORGANISM: Artificial Sequence
<220> FEATURE:
<223> OTHER INFORMATION: nsP2

<400> SEQUENCE: 29

```
Gly Ser Val Glu Thr Pro Arg Gly Leu Ile Lys Val Thr Ser Tyr Asp
1               5                   10                  15

Gly Glu Asp Lys Ile Gly Ser Tyr Ala Val Leu Ser Pro Gln Ala Val
            20                  25                  30

Leu Lys Ser Glu Lys Leu Ser Cys Ile His Pro Leu Ala Glu Gln Val
        35                  40                  45

Ile Val Ile Thr His Ser Gly Arg Lys Gly Arg Tyr Ala Val Glu Pro
    50                  55                  60

Tyr His Gly Lys Val Val Val Pro Glu Gly His Ala Ile Pro Val Gln
65                  70                  75                  80

Asp Phe Gln Ala Leu Ser Glu Ser Ala Thr Ile Val Tyr Asn Glu Arg
                85                  90                  95

Glu Phe Val Asn Arg Tyr Leu His His Ile Ala Thr His Gly Gly Ala
            100                 105                 110

Leu Asn Thr Asp Glu Glu Tyr Tyr Lys Thr Val Lys Pro Ser Glu His
        115                 120                 125

Asp Gly Glu Tyr Leu Tyr Asp Ile Asp Arg Lys Gln Cys Val Lys Lys
    130                 135                 140

Glu Leu Val Thr Gly Leu Gly Leu Thr Gly Glu Leu Val Asp Pro Pro
145                 150                 155                 160

Phe His Glu Phe Ala Tyr Glu Ser Leu Arg Thr Arg Pro Ala Ala Pro
                165                 170                 175

Tyr Gln Val Pro Thr Ile Gly Val Tyr Gly Val Pro Gly Ser Gly Lys
```

-continued

```
                   180               185               190
Ser Gly Ile Ile Lys Ser Ala Val Thr Lys Lys Asp Leu Val Val Ser
            195               200               205

Ala Lys Lys Glu Asn Cys Ala Glu Ile Ile Arg Asp Val Lys Lys Met
        210               215               220

Lys Gly Leu Asp Val Asn Ala Arg Thr Val Asp Ser Val Leu Leu Asn
225               230               235               240

Gly Cys Lys His Pro Val Glu Thr Leu Tyr Ile Asp Glu Ala Phe Ala
            245               250               255

Cys His Ala Gly Thr Leu Arg Ala Leu Ile Ala Ile Ile Arg Pro Lys
            260               265               270

Lys Ala Val Leu Cys Gly Asp Pro Lys Gln Cys Gly Phe Phe Asn Met
        275               280               285

Met Cys Leu Lys Val His Phe Asn His Glu Ile Cys Thr Gln Val Phe
290               295               300

His Lys Ser Ile Ser Arg Arg Cys Thr Lys Ser Val Thr Ser Val Val
305               310               315               320

Ser Thr Leu Phe Tyr Asp Lys Lys Met Arg Thr Thr Asn Pro Lys Glu
            325               330               335

Thr Lys Ile Val Ile Asp Thr Thr Gly Ser Thr Lys Pro Lys Gln Asp
            340               345               350

Asp Leu Ile Leu Thr Cys Phe Arg Gly Trp Val Lys Gln Leu Gln Ile
        355               360               365

Asp Tyr Lys Gly Asn Glu Ile Met Thr Ala Ala Ala Ser Gln Gly Leu
        370               375               380

Thr Arg Lys Gly Val Tyr Ala Val Arg Tyr Lys Val Asn Glu Asn Pro
385               390               395               400

Leu Tyr Ala Pro Thr Ser Glu His Val Asn Val Leu Leu Thr Arg Thr
            405               410               415

Glu Asp Arg Ile Val Trp Lys Thr Leu Ala Gly Asp Pro Trp Ile Lys
            420               425               430

Thr Leu Thr Ala Lys Tyr Pro Gly Asn Phe Thr Ala Thr Ile Glu Glu
        435               440               445

Trp Gln Ala Glu His Asp Ala Ile Met Arg His Ile Leu Glu Arg Pro
        450               455               460

Asp Pro Thr Asp Val Phe Gln Asn Lys Ala Asn Val Cys Trp Ala Lys
465               470               475               480

Ala Leu Val Pro Val Leu Lys Thr Ala Gly Ile Asp Met Thr Thr Glu
            485               490               495

Gln Trp Asn Thr Val Asp Tyr Phe Glu Thr Asp Lys Ala His Ser Ala
            500               505               510

Glu Ile Val Leu Asn Gln Leu Cys Val Arg Phe Phe Gly Leu Asp Leu
        515               520               525

Asp Ser Gly Leu Phe Ser Ala Pro Thr Val Pro Leu Ser Ile Arg Asn
        530               535               540

Asn His Trp Asp Asn Ser Pro Ser Pro Asn Met Tyr Gly Leu Asn Lys
545               550               555               560

Glu Val Val Arg Gln Leu Ser Arg Arg Tyr Pro Gln Leu Pro Arg Ala
            565               570               575

Val Ala Thr Gly Arg Val Tyr Asp Met Asn Thr Gly Thr Leu Arg Asn
            580               585               590

Tyr Asp Pro Arg Ile Asn Leu Val Pro Val Asn Arg Arg Leu Pro His
            595               600               605
```

-continued

```
Ala Leu Val Leu His His Asn Glu His Pro Gln Ser Asp Phe Ser Ser
    610             615             620
```

```
Phe Val Ser Lys Leu Lys Gly Arg Thr Val Leu Val Val Gly Glu Lys
625             630             635             640
```

```
Leu Ser Val Pro Gly Lys Met Val Asp Trp Leu Ser Asp Arg Pro Glu
            645             650             655
```

```
Ala Thr Phe Arg Ala Arg Leu Asp Leu Gly Ile Pro Gly Asp Val Pro
            660             665             670
```

```
Lys Tyr Asp Ile Ile Phe Val Asn Val Arg Thr Pro Tyr Lys Tyr His
            675             680             685
```

```
His Tyr Gln Gln Cys Glu Asp His Ala Ile Lys Leu Ser Met Leu Thr
    690             695             700
```

```
Lys Lys Ala Cys Leu His Leu Asn Pro Gly Gly Thr Cys Val Ser Ile
705             710             715             720
```

```
Gly Tyr Gly Tyr Ala Asp Arg Ala Ser Glu Ser Ile Ile Gly Ala Ile
            725             730             735
```

```
Ala Arg Gln Phe Lys Phe Ser Arg Val Cys Lys Pro Lys Ser Ser Leu
            740             745             750
```

```
Glu Glu Thr Glu Val Leu Phe Val Phe Ile Gly Tyr Asp Arg Lys Ala
            755             760             765
```

```
Arg Thr His Asn Ser Tyr Lys Leu Ser Ser Thr Leu Thr Asn Ile Tyr
    770             775             780
```

```
Thr Gly Ser Arg Leu His Glu Ala Gly Cys
785             790
```

```
<210> SEQ ID NO 30
<211> LENGTH: 2382
<212> TYPE: DNA
<213> ORGANISM: Artificial Sequence
<220> FEATURE:
<223> OTHER INFORMATION: nsP2 coding sequence

<400> SEQUENCE: 30
ggctcagtgg agacacctcg tggcttgata aaggttacca gctacgatgg cgaggacaag      60
atcggctctt acgctgtgct ttctccgcag gctgtactca agagtgaaaa attatcttgc     120
atccaccctc tcgctgaaca agtcatagtg ataacacact ctggccgaaa agggcgttat     180
gccgtggaac cataccatgg taaagtagtg gtgccagagg acatgcaat acccgtccag      240 gactttcaag ctctgagtga aagtgccacc attgtgtaca cgaacgtga gttcgtaaac      300 aggtacctgc accatattgc cacacatgga ggagcgctga cactgatga agaatattac      360 aaaactgtca gcccagcga gcacgacggc gaatacctgt acgacatcga caggaaacag      420
tgcgtcaaga agaactagt cactgggcta gggctcacag gcgagctggt ggatcctccc       480
ttccatgaat cgcctacga gagtctgaga cacgaccag ccgctcctta ccaagtacca       540 accataggg tgtatggcgt gccaggatca ggcaagtctg gcatcattaa aagcgcagtc       600
accaaaaaag atctagtggt gagcgccaag aaagaaaact gtgcagaaat tataagggac     660
gtcaagaaaa tgaaagggct ggacgtcaat gccagaactg tggactcagt gctcttgaat     720
ggatgcaaac accccgtaga gaccctgtat attgacgaag cttttgcttg tcatgcaggt     780
actctcagag cgctcatagc cattataaga cctaaaaagg cagtgctctg cggggatccc     840
aaacagtgcg gtttttttaa catgatgtgc ctgaaagtgc attttaacca cgagatttgc     900
acacaagtct tccacaaaag catctctcgc cgttgcacta aatctgtgac ttcggtcgtc     960
```

-continued

```
tcaaccttgt tttacgacaa aaaaatgaga acgacgaatc cgaaagagac taagattgtg    1020
attgacacta ccggcagtac caaacctaag caggacgatc tcattctcac ttgtttcaga    1080
gggtgggtga agcagttgca aatagattac aaaggcaacg aaataatgac ggcagctgcc    1140
tctcaagggc tgacccgtaa aggtgtgtat gccgttcggt acaaggtgaa tgaaaatcct    1200
ctgtacgcac ccacctcaga acatgtgaac gtcctactga cccgcacgga ggaccgcatc    1260
gtgtggaaaa cactagccgg cgacccatgg ataaaaacac tgactgccaa gtaccctggg    1320
aatttcactg ccacgataga ggagtggcaa gcagagcatg atgccatcat gaggcacatc    1380
ttggagagac cggaccctac cgacgtcttc cagaataagg caaacgtgtg ttgggccaag    1440
gctttagtgc cggtgctgaa gaccgctggc atagacatga ccactgaaca atggaacact    1500
gtggattatt ttgaaacgga caaagctcac tcagcagaga tagtattgaa ccaactatgc    1560
gtgaggttct ttgactcga tctggactcc ggtctatttt ctgcacccac tgttccgtta    1620
tccattagga ataatcactg ggataactcc ccgtcgccta acatgtacgg gctgaataaa    1680
gaagtggtcc gtcagctctc tcgcaggtac ccacaactgc ctcgggcagt tgccactgga    1740
agagtctatg acatgaacac tggtacactg cgcaattatg atccgcgcat aaacctagta    1800
cctgtaaaca gaagactgcc tcatgcttta gtcctccacc ataatgaaca cccacagagt    1860
gacttttctt cattcgtcag caaattgaag ggcagaactg tcctggtggt cggggaaaag    1920
ttgtccgtcc caggcaaaat ggttgactgg ttgtcagacc ggcctgaggc taccttcaga    1980
gctcggctgg atttaggcat cccaggtgat gtgcccaaat atgacataat atttgttaat    2040
gtgaggaccc catataaata ccatcactat cagcagtgtg aagaccatgc cattaagctt    2100
agcatgttga ccaagaaagc ttgtctgcat ctgaatcccg gcggaacctg tgtcagcata    2160
ggttatggtt acgctgacag ggccagcgaa agcatcattg gtgctatagc gcggcagttc    2220 aagtttttccc gggtatgcaa accgaaatcc tcacttgaag agacggaagt tctgtttgta    2280
ttcattgggt acgatcgcaa ggcccgtacg cacaattctt acaagctttc atcaaccttg    2340
accaacattt atacaggttc cagactccac gaagccggat gt                        2382
```

```
<210> SEQ ID NO 31
<211> LENGTH: 556
<212> TYPE: PRT
<213> ORGANISM: Artificial Sequence
<220> FEATURE:
<223> OTHER INFORMATION: nsP3

<400> SEQUENCE: 31

Ala Pro Ser Tyr His Val Val Arg Gly Asp Ile Ala Thr Ala Thr Glu
1               5                   10                  15

Gly Val Ile Ile Asn Ala Ala Asn Ser Lys Gly Gln Pro Gly Gly Gly
                20                  25                  30

Val Cys Gly Ala Leu Tyr Lys Lys Phe Pro Glu Ser Phe Asp Leu Gln
            35                  40                  45

Pro Ile Glu Val Gly Lys Ala Arg Leu Val Lys Gly Ala Ala Lys His
        50                  55                  60

Ile Ile His Ala Val Gly Pro Asn Phe Asn Lys Val Ser Glu Val Glu
65                  70                  75                  80

Gly Asp Lys Gln Leu Ala Glu Ala Tyr Glu Ser Ile Ala Lys Ile Val
                85                  90                  95

Asn Asp Asn Asn Tyr Lys Ser Val Ala Ile Pro Leu Leu Ser Thr Gly
            100                 105                 110
```

-continued

```
Ile Phe Ser Gly Asn Lys Asp Arg Leu Thr Gln Ser Leu Asn His Leu
        115             120             125

Leu Thr Ala Leu Asp Thr Thr Asp Ala Asp Val Ala Ile Tyr Cys Arg
    130             135             140

Asp Lys Lys Trp Glu Met Thr Leu Lys Glu Ala Val Ala Arg Arg Glu
145             150             155             160

Ala Val Glu Glu Ile Cys Ile Ser Asp Asp Ser Ser Val Thr Glu Pro
            165             170             175

Asp Ala Glu Leu Val Arg Val His Pro Lys Ser Ser Leu Ala Gly Arg
            180             185             190

Lys Gly Tyr Ser Thr Ser Asp Gly Lys Thr Phe Ser Tyr Leu Glu Gly
            195             200             205

Thr Lys Phe His Gln Ala Ala Lys Asp Ile Ala Glu Ile Asn Ala Met
    210             215             220

Trp Pro Val Ala Thr Glu Ala Asn Glu Gln Val Cys Met Tyr Ile Leu
225             230             235             240

Gly Glu Ser Met Ser Ser Ile Arg Ser Lys Cys Pro Val Glu Glu Ser
            245             250             255

Glu Ala Ser Thr Pro Pro Ser Thr Leu Pro Cys Leu Cys Ile His Ala
            260             265             270

Met Thr Pro Glu Arg Val Gln Arg Leu Lys Ala Ser Arg Pro Glu Gln
    275             280             285

Ile Thr Val Cys Ser Ser Phe Pro Leu Pro Lys Tyr Arg Ile Thr Gly
    290             295             300

Val Gln Lys Ile Gln Cys Ser Gln Pro Ile Leu Phe Ser Pro Lys Val
305             310             315             320

Pro Ala Tyr Ile His Pro Arg Lys Tyr Leu Val Glu Thr Pro Pro Val
            325             330             335

Asp Glu Thr Pro Glu Pro Ser Ala Glu Asn Gln Ser Thr Glu Gly Thr
            340             345             350

Pro Glu Gln Pro Pro Leu Ile Thr Glu Asp Glu Thr Arg Thr Arg Thr
            355             360             365

Pro Glu Pro Ile Ile Ile Glu Glu Glu Glu Asp Ser Ile Ser Leu
    370             375             380

Leu Ser Asp Gly Pro Thr His Gln Val Leu Gln Val Glu Ala Asp Ile
385             390             395             400

His Gly Pro Pro Ser Val Ser Ser Ser Trp Ser Ile Pro His Ala
            405             410             415

Ser Asp Phe Asp Val Asp Ser Leu Ser Ile Leu Asp Thr Leu Glu Gly
            420             425             430

Ala Ser Val Thr Ser Gly Ala Thr Ser Ala Glu Thr Asn Ser Tyr Phe
            435             440             445

Ala Lys Ser Met Glu Phe Leu Ala Arg Pro Val Pro Ala Pro Arg Thr
    450             455             460

Val Phe Arg Asn Pro Pro His Pro Ala Pro Arg Thr Arg Thr Pro Ser
465             470             475             480

Leu Ala Pro Ser Arg Ala Cys Ser Arg Thr Ser Leu Val Ser Thr Pro
            485             490             495

Pro Gly Val Asn Arg Val Ile Thr Arg Glu Glu Leu Glu Ala Leu Thr
            500             505             510

Pro Ser Arg Thr Pro Ser Arg Ser Val Ser Arg Thr Ser Leu Val Ser
            515             520             525

Asn Pro Pro Gly Val Asn Arg Val Ile Thr Arg Glu Glu Phe Glu Ala
```

-continued

```
           530              535              540
Phe Val Ala Gln Gln Gln Arg Phe Asp Ala Gly Ala
545                  550                  555

<210> SEQ ID NO 32
<211> LENGTH: 1671
<212> TYPE: DNA
<213> ORGANISM: Artificial Sequence
<220> FEATURE:
<223> OTHER INFORMATION: nsP3  coding sequence

<400> SEQUENCE: 32
gcaccctcat atcatgtggt gcgaggggat attgccacgg ccaccgaagg agtgattata      60
aatgctgcta acagcaaagg acaacctggc ggaggggtgt gcggagcgct gtataagaaa     120
ttcccggaaa gcttcgattt acagccgatc gaagtaggaa aagcgcgact ggtcaaaggt     180
gcagctaaac atatcattca tgccgtagga ccaaacttca caaagtttc ggaggttgaa     240 ggtgacaaac agttggcaga ggcttatgag tccatcgcta agattgtcaa cgataacaat     300
tacaagtcag tagcgattcc actgttgtcc accggcatct tttccgggaa caaagatcga     360
ctaacccaat cattgaacca tttgctgaca gctttagaca ccactgatgc agatgtagcc     420
atatactgca gggacaagaa atgggaaatg actctcaagg aagcagtggc taggagagaa     480
gcagtggagg agatatgcat atccgacgac tcttcagtga cagaacctga tgcagagctg     540
gtgagggtgc atccgaagag ttctttggct ggaaggaagg gctacagcac aagcgatggc     600
aaaactttct catatttgga agggaccaag tttcaccagg cggccaagga tatagcagaa     660
attaatgcca tgtggcccgt tgcaacggag gccaatgagc aggtatgcat gtatatcctc     720
ggagaaagca tgagcagtat taggtcgaaa tgccccgtcg aagagtcgga agcctccaca     780
ccacctagca cgctgccttg cttgtgcatc catgccatga ctccagaaag agtacagcgc     840
ctaaaagcct cacgtccaga acaaattact gtgtgctcat cctttccatt gccgaagtat     900
agaatcactg gtgtgcagaa gatccaatgc tcccagccta tattgttctc accgaaagtg     960
cctgcgtata ttcatccaag gaagtatctc gtgaaacac caccggtaga cgagactccg    1020
gagccatcgg cagagaacca atccacagag gggacacctg aacaaccacc acttataacc    1080
gaggatgaga ccaggactag aacgcctgag ccgatcatca tcgaagagga agaagaggat    1140
agcataagtt tgctgtcaga tggcccgacc caccaggtgc tgcaagtcga ggcagacatt    1200
cacgggccgc cctctgtatc tagctcatcc tggtccattc ctcatgcatc cgactttgat    1260
gtggacagtt atccatact tgacaccctg gagggagcta gcgtgaccag cgggggcaacg    1320 tcagccgaga ctaactctta cttcgcaaag agtatggagt ttctggcgcg accggtgcct    1380
gcgcctcgaa cagtattcag gaaccctcca catcccgctc cgcgcacaag aacaccgtca    1440
cttgcaccca gcagggcctg ctcgagaacc agcctagttt ccaccccgcc aggcgtgaat    1500
agggtgatca ctagagagga gctcgaggcg cttacccccgt cacgcactcc tagcaggtcg    1560
gtctcgagaa ccagcctggt ctccaacccg ccaggcgtaa ataggggtgat tacaagagag    1620 gagtttgagg cgttcgtagc acaacaacaa tgacggtttg atgcgggtgc a              1671

<210> SEQ ID NO 33
<211> LENGTH: 607
<212> TYPE: PRT
<213> ORGANISM: Artificial Sequence
<220> FEATURE:
<223> OTHER INFORMATION: nsP4
```

-continued

<400> SEQUENCE: 33

```
Tyr Ile Phe Ser Ser Asp Thr Gly Gln Gly His Leu Gln Gln Lys Ser
1               5                   10                  15

Val Arg Gln Thr Val Leu Ser Glu Val Val Leu Glu Arg Thr Glu Leu
                20                  25                  30

Glu Ile Ser Tyr Ala Pro Arg Leu Asp Gln Glu Lys Glu Glu Leu Leu
            35                  40                  45

Arg Lys Lys Leu Gln Leu Asn Pro Thr Pro Ala Asn Arg Ser Arg Tyr
        50                  55                  60

Gln Ser Arg Lys Val Glu Asn Met Lys Ala Ile Thr Ala Arg Arg Ile
65                  70                  75                  80

Leu Gln Gly Leu Gly His Tyr Leu Lys Ala Glu Gly Lys Val Glu Cys
                85                  90                  95

Tyr Arg Thr Leu His Pro Val Pro Leu Tyr Ser Ser Ser Val Asn Arg
            100                 105                 110

Ala Phe Ser Ser Pro Lys Val Ala Val Glu Ala Cys Asn Ala Met Leu
            115                 120                 125

Lys Glu Asn Phe Pro Thr Val Ala Ser Tyr Cys Ile Ile Pro Glu Tyr
        130                 135                 140

Asp Ala Tyr Leu Asp Met Val Asp Gly Ala Ser Cys Cys Leu Asp Thr
145                 150                 155                 160

Ala Ser Phe Cys Pro Ala Lys Leu Arg Ser Phe Pro Lys Lys His Ser
                165                 170                 175

Tyr Leu Glu Pro Thr Ile Arg Ser Ala Val Pro Ser Ala Ile Gln Asn
            180                 185                 190

Thr Leu Gln Asn Val Leu Ala Ala Ala Thr Lys Arg Asn Cys Asn Val
        195                 200                 205

Thr Gln Met Arg Glu Leu Pro Val Leu Asp Ser Ala Ala Phe Asn Val
        210                 215                 220

Glu Cys Phe Lys Lys Tyr Ala Cys Asn Asn Glu Tyr Trp Glu Thr Phe
225                 230                 235                 240

Lys Glu Asn Pro Ile Arg Leu Thr Glu Glu Asn Val Val Asn Tyr Ile
            245                 250                 255

Thr Lys Leu Lys Gly Pro Lys Ala Ala Ala Leu Phe Ala Lys Thr His
            260                 265                 270

Asn Leu Asn Met Leu Gln Asp Ile Pro Met Asp Arg Phe Val Met Asp
        275                 280                 285

Leu Lys Arg Asp Val Lys Val Thr Pro Gly Thr Lys His Thr Glu Glu
        290                 295                 300

Arg Pro Lys Val Gln Val Ile Gln Ala Ala Asp Pro Leu Ala Thr Ala
305                 310                 315                 320

Tyr Leu Cys Gly Ile His Arg Glu Leu Val Arg Arg Leu Asn Ala Val
            325                 330                 335

Leu Leu Pro Asn Ile His Thr Leu Phe Asp Met Ser Ala Glu Asp Phe
            340                 345                 350

Asp Ala Ile Ile Ala Glu His Phe Gln Pro Gly Asp Cys Val Leu Glu
            355                 360                 365

Thr Asp Ile Ala Ser Phe Asp Lys Ser Glu Asp Asp Ala Met Ala Leu
        370                 375                 380

Thr Ala Leu Met Ile Leu Glu Asp Leu Gly Val Asp Ala Glu Leu Leu
385                 390                 395                 400

Thr Leu Ile Glu Ala Ala Phe Gly Glu Ile Ser Ser Ile His Leu Pro
                405                 410                 415
```

```
Thr Lys Thr Lys Phe Lys Phe Gly Ala Met Met Lys Ser Gly Met Phe
            420             425             430
Leu Thr Leu Phe Val Asn Thr Val Ile Asn Ile Val Ile Ala Ser Arg
            435             440             445
Val Leu Arg Glu Arg Leu Thr Gly Ser Pro Cys Ala Ala Phe Ile Gly
            450             455             460
Asp Asp Asn Ile Val Lys Gly Val Lys Ser Asp Lys Leu Met Ala Asp
465             470             475             480
Arg Cys Ala Thr Trp Leu Asn Met Glu Val Lys Ile Ile Asp Ala Val
                485             490             495
Val Gly Glu Lys Ala Pro Tyr Phe Cys Gly Gly Phe Ile Leu Cys Asp
            500             505             510
Ser Val Thr Gly Thr Ala Cys Arg Val Ala Asp Pro Leu Lys Arg Leu
            515             520             525
Phe Lys Leu Gly Lys Pro Leu Ala Ala Asp Asp Glu His Asp Asp Asp
            530             535             540
Arg Arg Arg Ala Leu His Glu Glu Ser Thr Arg Trp Asn Arg Val Gly
545             550             555             560
Ile Leu Ser Glu Leu Cys Lys Ala Val Glu Ser Arg Tyr Glu Thr Val
                565             570             575
Gly Thr Ser Ile Ile Val Met Ala Met Thr Thr Leu Ala Ser Ser Val
                580             585             590
Lys Ser Phe Ser Tyr Leu Arg Gly Ala Pro Ile Thr Leu Tyr Gly
            595             600             605

<210> SEQ ID NO 34
<211> LENGTH: 1821
<212> TYPE: DNA
<213> ORGANISM: Artificial Sequence
<220> FEATURE:
<223> OTHER INFORMATION: nsP4 encoding sequence

<400> SEQUENCE: 34
tacatctttt cctccgacac cggtcaaggg catttacaac aaaaatcagt aaggcaaacg      60
gtgctatccg aagtggtgtt ggagaggacc gaattggaga tttcgtatgc cccgcgcctc     120
gaccaagaaa aagaagaatt actacgcaag aaattacagt taaatcccac acctgctaac     180
agaagcagat accagtccag gaaggtggag aacatgaaag ccataacagc tagacgtatt     240
ctgcaaggcc tagggcatta tttgaaggca gaaggaaaag tggagtgcta ccgaaccctg     300
catcctgttc ctttgtattc atctagtgtg aaccgtgcct tttcaagccc caaggtcgca     360
gtggaagcct gtaacgccat gttgaaagag aactttccga ctgtggcttc ttactgtatt     420
attccagagt acgatgccta tttggacatg gttgacggag cttcatgctg cttagacact     480
gccagttttt gccctgcaaa gctgcgcagc tttccaaaga aacactccta tttggaaccc     540
acaatacgat cggcagtgcc ttcagcgatc cagaacacgc tccagaacgt cctggcagct     600
gccacaaaaa gaaattgcaa tgtcacgcaa atgagagaat gcccgtatt ggattcggcg     660 gcctttaatg tggaatgctt caagaaatat gcgtgtaata atgaatattg ggaaacgttt     720
aaagaaaacc ccatcaggct tactgaagaa acgtggtaa attacattac caaattaaaa     780
ggaccaaaag ctgctgctct ttttgcgaag acacataatt tgaatatgtt gcaggacata     840
ccaatggaca ggtttgtaat ggacttaaag agagacgtga aagtgactcc aggaacaaaa     900
catactgaag aacggcccaa ggtacaggtg atccaggctg ccgatccgct agcaacagcg     960
```

-continued

```
tatctgtgcg gaatccaccg agagctggtt aggagattaa atgcggtcct gcttccgaac    1020
attcatacac tgtttgatat gtcggctgaa gactttgacg ctattatagc cgagcacttc    1080
cagcctgggg attgtgttct ggaaactgac atcgcgtcgt ttgataaaag tgaggacgac    1140
gccatggctc tgaccgcgtt aatgattctg gaagacttag gtgtggacgc agagctgttg    1200
acgctgattg aggcggcttt cggcgaaatt tcatcaatac atttgcccac taaaactaaa    1260
tttaaattcg gagccatgat gaaatctgga atgttcctca cactgtttgt gaacacagtc    1320
attaacattg taatcgcaag cagagtgttg agagaacggc taaccggatc accatgtgca    1380
gcattcattg gagatgacaa tatcgtgaaa ggagtcaaat cggacaaatt aatggcagac    1440
aggtgcgcca cctggttgaa tatggaagtc aagattatag atgctgtggt gggcgagaaa    1500
gcgccttatt tctgtggagg gtttattttg tgtgactccg tgaccggcac agcgtgccgt    1560
gtggcagacc ccctaaaaag gctgtttaag cttggcaaac ctctggcagc agacgatgaa    1620
catgatgatg acaggagaag ggcattgcat gaagagtcaa cacgctggaa ccgagtgggt    1680
attctttcag agctgtgcaa ggcagtagaa tcaaggtatg aaaccgtagg aacttccatc    1740
atagttatgg ccatgactac tctagctagc agtgttaaat cattcagcta cctgagaggg    1800
gcccctataa ctctctacgg c                                             1821
```

<210> SEQ ID NO 35
<211> LENGTH: 9561
<212> TYPE: DNA
<213> ORGANISM: Artificial Sequence
<220> FEATURE:
<223> OTHER INFORMATION: recombinant vector
<220> FEATURE:
<221> NAME/KEY: misc_feature
<222> LOCATION: (7614)..(7615)
<223> OTHER INFORMATION: A GOI is present between positions 7614 and
      7615

<400> SEQUENCE: 35

```
cgccagcaac gcgagctcta atacgactca ctatagatgg gcggcgcatg agagaagccc     60
agaccaatta cctacccaaa atggagaaag ttcacgttga catcgaggaa gacagcccat    120
tcctcagagc tttgcagcgg agcttcccgc agtttgaggt agaagccaag caggtcactg    180
ataatgacca tgctaatgcc agagcgtttt cgcatctggc ttcaaaactg atcgaaacgg    240
aggtggaccc atccgacacg atccttgaca ttggaagtgc gcccgcccgc agaatgtatt    300
ctaagcacaa gtatcattgt atctgtccga tgagatgtgc ggaagatccg gacagattgt    360
ataagtatgc aactaagctg aagaaaaact gtaggaaat aactgataag gaattggaca    420
agaaaatgaa ggagctggcc gccgtcatga gcgaccctga cctggaaact gagactatgt    480
gcctccacga cgacgagtcg tgtcgctacg aagggcaagt cgctgtttac caggatgtat    540
acgcggttga cggaccgaca agtctctatc accaagccaa taagggagtt agagtcgcct    600 actgatagc ctttgacacc accccttta tgtttaagaa cttggctgga gcatatccat    660
catactctac caactgggcc gacgaaaccg tgttaacggc tcgtaacata ggcctatgca    720
gctctgacgt tatggagcgg tcacgtagag ggatgtccat tcttagaaag aagtatttga    780
aaccatccaa caatgttcta ttctctgttg gctcgaccat ctaccacgag aagagggact    840
tactgaggag ctggcacctg ccgtctgtat ttcacttacg tggcaagcaa aattacacat    900
gtcggtgtga gactatagtt agttgcgacg ggtacgtcgt taaaagaata gctatcagtc    960
caggcctgta tgggaagcct tcaggctatg ctgctacgat gcaccgcgag ggattcttgt    1020
```

-continued

```
gctgcaaagt gacagacaca ttgaacgggg agagggtctc tttttcccgtg tgcacgtatg   1080 tgccagctac attgtgtgac caaatgactg gcatactggc aacagatgtc agtgcggacg   1140
acgcgcaaaa actgctggtt gggctcaacc agcgtatagt cgtcaacggt cgcacccaga   1200
gaaacaccaa taccatgaaa aattaccttt tgcccgtagt ggcccaggca tttgctaggt   1260
gggcaaagga atataaggaa gatcaagaag atgaaaggcc actaggacta cgagatagac   1320
agttagtcat ggggtgttgt tgggctttta gaaggcacaa gataacatct atttataagc   1380
gcccggatac ccaaaccatc atcaaagtga acagcgattt ccactcattc gtgctgccca   1440
ggataggcag taacacattg gagatcgggc tgagaacaag aatcaggaaa atgttagagg   1500
agcacaagga gccgtcacct ctcattaccg ccgaggacgt acaagaagct aagtgcgcag   1560
ccgatgaggc taaggaggtg cgtgaagccg aggagttgcg cgcagctcta ccacctttgg   1620
cagctgatgt tgaggagccc actctggaag ccgatgtcga cttgatgtta caagaggctg   1680
gggccggctc agtggagaca cctcgtggct tgataaaggt taccagctac gatggcgagg   1740
acaagatcgg ctcttacgct gtgctttctc cgcaggctgt actcaagagt gaaaaattat   1800
cttgcatcca ccctctcgct gaacaagtca tagtgataac acactctggc cgaaaagggc   1860
gttatgccgt ggaaccatac catggtaaag tagtggtgcc agagggacat gcaatacccg   1920
tccaggactt tcaagctctg agtgaaagtg ccaccattgt gtacaacgaa cgtgagttcg   1980
taaacaggta cctgcaccat attgccacac atggaggagc gctgaacact gatgaagaat   2040
attacaaaac tgtcaagccc agcgagcacg acggcgaata cctgtacgac atcgacagga   2100
aacagtgcgt caagaaagaa ctagtcactg ggctagggct cacaggcgag ctggtggatc   2160 ctccttcca tgaattcgcc tacgagagtc tgagaacacg accagccgct ccttaccaag   2220
taccaaccat aggggtgtat ggcgtgccag gatcaggcaa gtctggcatc attaaaagcg   2280
cagtcaccaa aaaagatcta gtggtgagcg ccaagaaaga aaactgtgca gaaattataa   2340
gggacgtcaa gaaaatgaaa gggctggacg tcaatgccag aactgtggac tcagtgctct   2400
tgaatggatg caaacacccc gtagagaccc tgtatattga cgaagctttt gcttgtcatg   2460
caggtactct cagagcgctc atagccatta taagacctaa aaaggcagtg ctctgcgggg   2520
atcccaaaca gtgcggtttt tttaacatga tgtgcctgaa agtgcatttt aaccacgaga   2580
tttgcacaca agtcttccac aaaagcatct ctcgccgttg cactaaatct gtgacttcgg   2640
tcgtctcaac cttgtttttac gacaaaaaaa tgagaacgac gaatccgaaa gagactaaga   2700
ttgtgattga cactaccggc agtaccaaac ctaagcagga cgatctcatt ctcacttgtt   2760
tcagagggtg ggtgaagcag ttgcaaatag attacaaagg caacgaaata atgacggcag   2820
ctgcctctca agggctgacc cgtaaaggtg tgtatgccgt tcggtacaag gtgaatgaaa   2880
atcctctgta cgcacccacc tcagaacatg tgaacgtcct actgacccgc acggaggacc   2940
gcatcgtgtg gaaaacacta gccggcgacc catggataaa aacactgact gccaagtacc   3000
ctgggaattt cactgccacg atagaggagt ggcaagcaga gcatgatgcc atcatgaggc   3060
acatcttgga gagaccggac cctaccgacg tcttccagaa taaggcaaac gtgtgttggg   3120
ccaaggcttt agtgccggtg ctgaagaccg ctggcataga catgaccact gaacaatgga   3180
acactgtgga ttattttgaa acggacaaag ctcactcagc agagatagta ttgaaccaac   3240
tatgcgtgag gttctttgga ctcgatctgg actccggtct attttctgca cccactgttc   3300
cgttatccat taggaataat cactgggata actccccgtc gcctaacatg tacgggctga   3360
ataaagaagt ggtccgtcag ctctctcgca ggtacccaca actgcctcgg gcagttgcca   3420
```

```
ctggaagagt ctatgacatg aacactggta cactgcgcaa ttatgatccg cgcataaacc    3480
tagtacctgt aaacagaaga ctgcctcatg ctttagtcct ccaccataat gaacacccac    3540
agagtgactt ttcttcattc gtcagcaaat tgaagggcag aactgtcctg gtggtcgggg    3600
aaaagttgtc cgtcccaggc aaaatggttg actggttgtc agaccggcct gaggctacct    3660
tcagagctcg gctggattta ggcatcccag gtgatgtgcc caaatatgac ataatatttg    3720
ttaatgtgag gaccccatat aaataccatc actatcagca gtgtgaagac catgccatta    3780
agcttagcat gttgaccaag aaagcttgtc tgcatctgaa tcccggcgga acctgtgtca    3840
gcataggtta tggttacgct gacagggcca gcgaaagcat cattggtgct atagcgcggc    3900
agttcaagtt ttcccgggta tgcaaaccga aatcctcact tgaagagacg gaagttctgt    3960
ttgtattcat tgggtacgat cgcaaggccc gtacgcacaa ttcttacaag ctttcatcaa    4020
ccttgaccaa catttataca ggttccagac tccacgaagc cggatgtgca ccctcatatc    4080
atgtggtgcg aggggatatt gccacggcca ccgaaggagt gattataaat gctgctaaca    4140
gcaaaggaca acctggcgga ggggtgtgcg gagcgctgta taagaaattc ccggaaagct    4200
tcgatttaca gccgatcgaa gtaggaaaag cgcgactggt caaaggtgca gctaaacata    4260
tcattcatgc cgtaggacca aacttcaaca aagtttcgga ggttgaaggt gacaaacagt    4320
tggcagaggc ttatgagtcc atcgctaaga ttgtcaacga taacaattac aagtcagtag    4380
cgattccact gttgtccacc ggcatctttt ccgggaacaa agatcgacta acccaatcat    4440
tgaaccattt gctgacagct ttagacacca ctgatgcaga tgtagccata tactgcaggg    4500
acaagaaatg ggaaatgact ctcaaggaag cagtggctag gagagaagca gtggaggaga    4560
tatgcatatc cgacgactct tcagtgacag aacctgatgc agagctggtg agggtgcatc    4620
cgaagagttc tttggctgga aggaagggct acagcacaag cgatggcaaa actttctcat    4680
atttggaagg gaccaagttt caccaggcgg ccaaggatat agcagaaatt aatgccatgt    4740
ggcccgttgc aacggaggcc aatgagcagg tatgcatgta tatcctcgga gaaagcatga    4800
gcagtattag gtcgaaatgc cccgtcgaag agtcggaagc ctccacacca cctagcacgc    4860
tgccttgctt gtgcatccat gccatgactc cagaaagagt acagcgccta aaagcctcac    4920
gtccagaaca aattactgtg tgctcatcct ttccattgcc gaagtataga atcactggtg    4980
tgcagaagat ccaatgctcc cagcctatat tgttctcacc gaaagtgcct gcgtatattc    5040
atccaaggaa gtatctcgtg gaaacaccac cggtagacga gactccggag ccatcggcag    5100
agaaccaatc cacagagggg acacctgaac aaccaccact tataaccgag gatgagacca    5160
ggactagaac gcctgagccg atcatcatcg aagaggaaga gaggatagc ataagtttgc    5220 tgtcagatgg cccgacccac caggtgctgc aagtcgaggc agacattcac gggccgccct    5280
ctgtatctag ctcatcctgg tccattcctc atgcatccga ctttgatgtg gacagtttat    5340
ccatacttga caccctggag ggagctagcg tgaccagcgg ggcaacgtca gccgagacta    5400
actcttactt cgcaaagagt atggagtttc tggcgcgacc ggtgcctgcg cctcgaacag    5460
tattcaggaa ccctccacat cccgctccgc gcacaagaac accgtcactt gcacccagca    5520
gggcctgctc gagaaccagc ctagtttcca ccccgccagg cgtgaatagg gtgatcacta    5580
gagaggagct cgaggcgctt accccgtcac gcactcctag caggtcggtc tcgagaacca    5640
gcctggtctc caacccgcca ggcgtaaata gggtgattac aagagaggag tttgaggcgt    5700
tcgtagcaca acaacaatga cggtttgatg cgggtgcata catcttttcc tccgacaccg    5760
```

-continued

```
gtcaagggca tttacaacaa aaatcagtaa ggcaaacggt gctatccgaa gtggtgttgg   5820
agaggaccga attggagatt tcgtatgccc cgcgcctcga ccaagaaaaa gaagaattac   5880
tacgcaagaa attacagtta aatcccacac ctgctaacag aagcagatac cagtccagga   5940
aggtggagaa catgaaagcc ataacagcta gacgtattct gcaaggccta gggcattatt   6000
tgaaggcaga aggaaaagtg gagtgctacc gaaccctgca tcctgttcct ttgtattcat   6060
ctagtgtgaa ccgtgccttt tcaagcccca aggtcgcagt ggaagcctgt aacgccatgt   6120
tgaaagagaa ctttccgact gtggcttctt actgtattat tccagagtac gatgcctatt   6180
tggacatggt tgacggagct tcatgctgct tagacactgc cagtttttgc cctgcaaagc   6240
tgcgcagctt tccaaagaaa cactcctatt tggaacccac aatacgatcg gcagtgcctt   6300
cagcgatcca gaacacgctc cagaacgtcc tggcagctgc cacaaaaaga aattgcaatg   6360
tcacgcaaat gagagaattg cccgtattgg attcggcggc ctttaatgtg gaatgcttca   6420
agaaatatgc gtgtaataat gaatattggg aaacgtttaa agaaaacccc atcaggctta   6480
ctgaagaaaa cgtggtaaat tacattacca aattaaaagg accaaaagct gctgctcttt   6540
ttgcgaagac acataatttg aatatgttgc aggacatacc aatggacagg tttgtaatgg   6600
acttaaagag agacgtgaaa gtgactccag gaacaaaaca tactgaagaa cggcccaagg   6660
tacaggtgat ccaggctgcc gatccgctag caacagcgta tctgtgcgga atccaccgag   6720
agctggttag gagattaaat gcggtcctgc ttccgaacat tcatacactg tttgatatgt   6780
cggctgaaga ctttgacgct attatagccg agcacttcca gcctggggat tgtgttctgg   6840
aaactgacat cgcgtcgttt gataaaagtg aggacgacgc catggctctg accgcgttaa   6900
tgattctgga agacttaggt gtggacgcag agctgttgac gctgattgag gcggctttcg   6960
gcgaaatttc atcaatacat ttgcccacta aaactaaatt taaattcgga gccatgatga   7020
aatctggaat gttcctcaca ctgtttgtga acacagtcat taacattgta atcgcaagca   7080
gagtgttgag agaacggcta accggatcac catgtgcagc attcattgga gatgacaata   7140
tcgtgaaagg agtcaaatcg gacaaattaa tggcagacag gtgcgccacc tggttgaata   7200
tggaagtcaa gattatagat gctgtggtgg cgagaaagc gccttatttc tgtggagggt   7260
ttattttgtg tgactccgtg accggcacag cgtgccgtgt ggcagacccc ctaaaaaggc   7320
tgtttaagct tggcaaacct ctggcagcag acgatgaaca tgatgatgac aggagaaggg   7380
cattgcatga agagtcaaca cgctggaacc gagtgggtat tctttcagag ctgtgcaagg   7440
cagtagaatc aaggtatgaa accgtaggaa cttccatcat agttatggcc atgactactc   7500
tagctagcag tgttaaatca ttcagctacc tgagaggggc ccctataact ctctacggct   7560
aacctgaatg gactacgaca tagtctagtc cgccaagtct agcatatggc cacctgatga   7620
gcggccgcga attggcaagc tgcttacata gaactcgcgg cgattggcat gccgccttaa   7680
aatttttatt ttattttct tttctttcc gaatcggatt ttgttttaa tatttcaaaa   7740 aaaaaaaaaa aaaaaaaaaa aaaaaaaaa acgcgtcgag gggaattaat tcttgaagac   7800
gaaagggcca ggtggcactt ttcggggaaa tgtgcgcgga accctattt gtttatttt   7860 ctaaatacat tcaaatatgt atccgctcat gagacaataa ccctgataaa tgcttcaata   7920
atattgaaaa aggaagagta tgagtattca acatttccgt gtcgccctta ttccctttt   7980 tgcggcattt tgccttcctg tttttgctca cccagaaacg ctggtgaaag taaaagatgc   8040
tgaagatcag ttgggtgcac gagtgggtta catcgaactg gatctcaaca gcggtaagat   8100
ccttgagagt tttcgccccg aagaacgttt tccaatgatg agcacttta aagttctgct   8160
```

-continued

```
atgtggcgcg gtattatccc gtgttgacgc cgggcaagag caactcggtc gccgcataca      8220
ctattctcag aatgacttgg ttgagtactc accagtcaca gaaaagcatc ttacggatgg      8280
catgacagta agagaattat gcagtgctgc cataaccatg agtgataaca ctgcggccaa      8340
cttacttctg acaacgatcg gaggaccgaa ggagctaacc gcttttttgc acaacatggg      8400
ggatcatgta actcgccttg atcgttggga accggagctg aatgaagcca taccaaacga      8460
cgagcgtgac accacgatgc ctgtagcaat ggcaacaacg ttgcgcaaac tattaactgg      8520
cgaactactt actctagctt cccggcaaca attaatagac tggatggagg cggataaagt      8580
tgcaggacca cttctgcgct cggcccttcc ggctggctgg tttattgctg ataaatctgg      8640
agccggtgag cgtgggtctc gcggtatcat tgcagcactg gggccagatg gtaagccctc      8700
ccgtatcgta gttatctaca cgacggggag tcaggcaact atggatgaac gaaatagaca      8760
gatcgctgag ataggtgcct cactgattaa gcattggtaa ctgtcagacc aagtttactc      8820
atatatactt tagattgatt taaaacttca ttttaattt aaaaggatct aggtgaagat       8880 ccttttttgat aatctcatga ccaaaatccc ttaacgtgag ttttcgttcc actgagcgtc      8940
agaccccgta gaaaagatca aaggatcttc ttgagatcct ttttttctgc gcgtaatctg      9000
ctgcttgcaa acaaaaaaac caccgctacc agcggtggtt tgtttgccgg atcaagagct      9060
accaactctt tttccgaagg taactggctt cagcagagcg cagataccaa atactgtcct      9120
tctagtgtag ccgtagttag gccaccactt caagaactct gtagcaccgc ctacatacct      9180
cgctctgcta atcctgttac cagtggctgc tgccagtggc gataagtcgt gtcttaccgg      9240
gttggactca agacgatagt taccggataa ggcgcagcgg tcgggctgaa cggggggttc      9300
gtgcacacag cccagcttgg agcgaacgac ctacaccgaa ctgagatacc tacagcgtga      9360
gcattgagaa agcgccacgc ttcccgaagg gagaaaggcg gacaggtatc cggtaagcgg      9420
cagggtcgga acaggagagc gcacgaggga gcttccaggg ggaaacgcct ggtatcttta      9480
tagtcctgtc gggtttcgcc acctctgact tgagcgtcga ttttttgtgat gctcgtcagg      9540 ggggcggagc ctatggaaaa a                                                9561
```

<210> SEQ ID NO 36
<211> LENGTH: 9963
<212> TYPE: DNA
<213> ORGANISM: Artificial Sequence
<220> FEATURE:
<223> OTHER INFORMATION: vector comprising a nucleic acid sequence that
      encodes an RNA construct comprising PIV5
<220> FEATURE:
<221> NAME/KEY: misc_feature
<223> OTHER INFORMATION: GOI is present between positions 7614 and 7615
<220> FEATURE:
<221> NAME/KEY: misc_feature
<222> LOCATION: (7614)..(7615)
<223> OTHER INFORMATION: GOI is present between positions 7614 and 7615

<400> SEQUENCE: 36

```
cgccagcaac gcgagctcta atacgactca ctatagatgg gcggcgcatg agagaagccc        60
agaccaatta cctacccaaa atggagaaag ttcacgttga catcgaggaa gacagcccat       120
tcctcagagc tttgcagcgg agcttcccgc agtttgaggt agaagccaag caggtcactg       180
ataatgacca tgctaatgcc agagcgtttt cgcatctggc ttcaaaactg atcgaaacgg       240
aggtggaccc atccgacacg atccttgaca ttggaagtgc gcccgccgc agaatgtatt        300 ctaagcacaa gtatcattgt atctgtccga tgagatgtgg ggaagatccg gacagattgt       360
```

-continued

```
ataagtatgc aactaagctg aagaaaaact gtaaggaaat aactgataag gaattggaca      420
agaaaatgaa ggagctggcc gccgtcatga gcgaccctga cctggaaact gagactatgt      480
gcctccacga cgacgagtcg tgtcgctacg aagggcaagt cgctgtttac caggatgtat      540
acgcggttga cggaccgaca agtctctatc accaagccaa taagggagtt agagtcgcct      600
actggatagg ctttgacacc accccttta tgtttaagaa cttggctgga gcatatccat       660
catactctac caactgggcc gacgaaaccg tgttaacggc tcgtaacata ggcctatgca      720
gctctgacgt tatggagcgg tcacgtagag ggatgtccat tcttagaaag aagtatttga      780
aaccatccaa caatgttcta ttctctgttg gctcgaccat ctaccacgag aagagggact      840
tactgaggag ctggcacctg ccgtctgtat ttcacttacg tggcaagcaa aattacacat      900
gtcggtgtga gactatagtt agttgcgacg ggtacgtcgt taaaagaata gctatcagtc      960
caggcctgta tgggaagcct tcaggctatg ctgctacgat gcaccgcgag ggattcttgt     1020
gctgcaaagt gacagacaca ttgaacgggg agagggtctc ttttcccgtg tgcacgtatg     1080
tgccagctac attgtgtgac caaatgactg gcatactggc aacagatgtc agtgcggacg     1140
acgcgcaaaa actgctggtt gggctcaacc agcgtatagt cgtcaacggt cgcacccaga     1200
gaaacaccaa taccatgaaa aattaccttt tgcccgtagt ggcccaggca tttgctaggt     1260
gggcaaagga atataaggaa gatcaagaag atgaaaggcc actaggacta cgagatagac     1320
agttagtcat ggggtgttgt tgggctttta gaaggcacaa gataacatct atttataagc     1380
gcccggatac ccaaaccatc atcaaagtga acagcgattt ccactcattc gtgctgccca     1440
ggataggcag taacacattg gagatcgggc tgagaacaag aatcaggaaa atgttagagg     1500
agcacaagga gccgtcacct ctcattaccg ccgaggacgt acaagaagct aagtgcgcag     1560
ccgatgaggc taaggaggtg cgtgaagccg aggagttgcg cgcagctcta ccacctttgg     1620
cagctgatgt tgaggagccc actctggaag ccgatgtcga cttgatgtta caagaggctg     1680
gggccggctc agtggagaca cctcgtggct tgataaaggt taccagctac gatggcgagg     1740
acaagatcgg ctcttacgct gtgctttctc cgcaggctgt actcaagagt gaaaaattat     1800
cttgcatcca ccctctcgct gaacaagtca tagtgataac acactctggc cgaaaagggc     1860
gttatgccgt ggaaccatac catggtaaag tagtggtgcc agagggacat gcaatacccg     1920
tccaggactt tcaagctctg agtgaaagtg ccaccattgt gtacaacgaa cgtgagttcg     1980
taaacaggta cctgcaccat attgccacac atggaggagc gctgaacact gatgaagaat     2040
attacaaaac tgtcaagccc agcgagcacg acggcgaata cctgtacgac atcgacagga     2100
aacagtgcgt caagaaagaa ctagtcactg ggctagggct cacaggcgag ctggtggatc     2160
ctccCttcca tgaattcgcc tacgagagtc tgagaacacg accagccgct ccttaccaag     2220
taccaaccat aggggtgtat ggcgtgccag gatcaggcaa gtctggcatc attaaaagcg     2280
cagtcaccaa aaaagatcta gtggtgagcg ccaagaaaga aaactgtgca gaaattataa     2340
gggacgtcaa gaaaatgaaa gggctggacg tcaatgccag aactgtggac tcagtgctct     2400
tgaatggatg caaacacccc gtagagaccc tgtatattga cgaagctttt gcttgtcatg     2460
caggtactct cagagcgctc atagccatta taagacctaa aaaggcagtg ctctgcgggg     2520
atcccaaaca gtgcggtttt tttaacatga tgtgcctgaa agtgcatttt aaccacgaga     2580
tttgcacaca agtcttccac aaaagcatct ctcgccgttg cactaaatct gtgacttcgg     2640
tcgtctcaac cttgttttac gacaaaaaaa tgagaacgac gaatccgaaa gagactaaga     2700
ttgtgattga cactaccggc agtaccaaac ctaagcagga cgatctcatt ctcacttgtt     2760
```

```
tcagagggtg ggtgaagcag ttgcaaatag attacaaagg caacgaaata atgacggcag    2820
ctgcctctca agggctgacc cgtaaaggtg tgtatgccgt tcggtacaag gtgaatgaaa    2880
atcctctgta cgcacccacc tcagaacatg tgaacgtcct actgacccgc acggaggacc    2940
gcatcgtgtg gaaaacacta gccggcgacc catggataaa aacactgact gccaagtacc    3000
ctgggaattt cactgccacg atagaggagt ggcaagcaga gcatgatgcc atcatgaggc    3060
acatcttgga gagaccggac cctaccgacg tcttccagaa taaggcaaac gtgtgttggg    3120
ccaaggcttt agtgccggtg ctgaagaccg ctggcataga catgaccact gaacaatgga    3180
acactgtgga ttattttgaa acggacaaag ctcactcagc agagatagta ttgaaccaac    3240
tatgcgtgag gttctttgga ctcgatctgg actccggtct attttctgca cccactgttc    3300
cgttatccat taggaataat cactgggata actccccgtc gcctaacatg tacgggctga    3360
ataaagaagt ggtccgtcag ctctctcgca ggtacccaca actgcctcgg gcagttgcca    3420
ctggaagagt ctatgacatg aacactggta cactgcgcaa ttatgatccg cgcataaacc    3480
tagtacctgt aaacagaaga ctgcctcatg ctttagtcct ccaccataat gaacacccac    3540
agagtgactt ttcttcattc gtcagcaaat tgaagggcag aactgtcctg gtggtcgggg    3600
aaaagttgtc cgtcccaggc aaaatggttg actggttgtc agaccggcct gaggctacct    3660
tcagagctcg gctggattta ggcatcccag gtgatgtgcc caaatatgac ataatatttg    3720
ttaatgtgag gaccccatat aaataccatc actatcagca gtgtgaagac catgccatta    3780
agcttagcat gttgaccaag aaagcttgtc tgcatctgaa tcccggcgga acctgtgtca    3840
gcataggtta tggttacgct gacagggcca gcgaaagcat cattggtgct atagcgcggc    3900
agttcaagtt ttcccgggta tgcaaaccga aatcctcact tgaagagacg gaagttctgt    3960
ttgtattcat tgggtacgat cgcaaggccc gtacgcacaa ttcttacaag ctttcatcaa    4020
ccttgaccaa catttataca ggttccagac tccacgaagc cggatgtgca ccctcatatc    4080
atgtggtgcg aggggatatt gccacggcca ccgaaggagt gattataaat gctgctaaca    4140
gcaaaggaca acctggcgga ggggtgtgcg gagcgctgta taagaaattc ccggaaagct    4200
tcgatttaca gccgatcgaa gtaggaaaag cgcgactggt caaaggtgca gctaaacata    4260
tcattcatgc cgtaggacca aacttcaaca aagtttcgga ggttgaaggt gacaaacagt    4320
tggcagaggc ttatgagtcc atcgctaaga ttgtcaacga taacaattac aagtcagtag    4380
cgattccact gttgtccacc ggcatctttt ccgggaacaa agatcgacta acccaatcat    4440
tgaaccattt gctgacagct ttagacacca ctgatgcaga tgtagccata tactgcaggg    4500
acaagaaatg ggaaatgact ctcaaggaag cagtggctag gagagaagca gtggaggaga    4560
tatgcatatc cgacgactct tcagtgacag aacctgatgc agagctggtg agggtgcatc    4620
cgaagagttc tttggctgga aggaagggct acagcacaag cgatggcaaa actttctcat    4680
atttggaagg gaccaagttt caccaggcgg ccaaggatat agcagaaatt aatgccatgt    4740
ggcccgttgc aacggaggcc aatgagcagg tatgcatgta tatcctcgga gaaagcatga    4800
gcagtattag gtcgaaatgc cccgtcgaag agtcggaagc ctccacacca cctagcacgc    4860
tgccttgctt gtgcatccat gccatgactc cagaaagagt acagcgccta aaagcctcac    4920
gtccagaaca aattactgtg tgctcatcct ttccattgcc gaagtataga atcactggtg    4980
tgcagaagat ccaatgctcc cagcctatat gttctcacc gaaagtgcct gcgtatattc    5040
atccaaggaa gtatctcgtg gaaacaccac cggtagacga gactccggag ccatcggcag    5100
```

-continued

```
agaaccaatc cacagagggg acacctgaac aaccaccact tataaccgag gatgagacca    5160
ggactagaac gcctgagccg atcatcatcg aagaggaaga agaggatagc ataagtttgc    5220
tgtcagatgg cccgacccac caggtgctgc aagtcgaggc agacattcac gggccgccct    5280
ctgtatctag ctcatcctgg tccattcctc atgcatccga ctttgatgtg gacagtttat    5340
ccatacttga caccctggag ggagctagcg tgaccagcgg ggcaacgtca gccgagacta    5400
actcttactt cgcaaagagt atggagtttc tggcgcgacc ggtgcctgcg cctcgaacag    5460
tattcaggaa ccctccacat cccgctccgc gcacaagaac accgtcactt gcacccagca    5520
gggcctgctc gagaaccagc ctagtttcca ccccgccagg cgtgaatagg gtgatcacta    5580
gagaggagct cgaggcgctt accccgtcac gcactcctag caggtcggtc tcgagaacca    5640
gcctggtctc caacccgcca ggcgtaaata gggtgattac aagagaggag tttgaggcgt    5700
tcgtagcaca acaacaatga cggtttgatg cgggtgcata catcttttcc tccgacaccg    5760
gtcaagggca tttacaacaa aaatcagtaa ggcaaacggt gctatccgaa gtggtgttgg    5820
agaggaccga attggagatt tcgtatgccc cgcgcctcga ccaagaaaaa gaagaattac    5880
tacgcaagaa attacagtta aatcccacac ctgctaacag aagcagatac cagtccagga    5940
aggtggagaa catgaaagcc ataacagcta gacgtattct gcaaggccta gggcattatt    6000
tgaaggcaga aggaaaagtg gagtgctacc gaaccctgca tcctgttcct ttgtattcat    6060
ctagtgtgaa ccgtgccttt tcaagcccca aggtcgcagt ggaagcctgt aacgccatgt    6120
tgaaagagaa ctttccgact gtggcttctt actgtattat tccagagtac gatgcctatt    6180
tggacatggt tgacggagct tcatgctgct tagacactgc cagtttttgc cctgcaaagc    6240
tgcgcagctt tccaaagaaa cactcctatt tggaacccac aatacgatcg gcagtgcctt    6300
cagcgatcca gaacacgctc cagaacgtcc tggcagctgc cacaaaaaga aattgcaatg    6360
tcacgcaaat gagagaattg cccgtattgg attcggcggc ctttaatgtg gaatgcttca    6420
agaaatatgc gtgtaataat gaatattggg aaacgtttaa agaaaacccc atcaggctta    6480
ctgaagaaaa cgtggtaaat tacattacca aattaaaagg accaaaagct gctgctcttt    6540
ttgcgaagac acataatttg aatatgttgc aggacatacc aatggacagg tttgtaatgg    6600
acttaaagag agacgtgaaa gtgactccag gaacaaaaca tactgaagaa cggcccaagg    6660
tacaggtgat ccaggctgcc gatccgctag caacagcgta tctgtgcgga atccaccgag    6720
agctggttag gagattaaat gcggtcctgc ttccgaacat tcatacactg tttgatatgt    6780
cggctgaaga ctttgacgct attatagccg agcacttcca gcctggggat tgtgttctgg    6840
aaactgacat cgcgtcgttt gataaaagtg aggacgacgc catggctctg accgcgttaa    6900
tgattctgga agacttaggt gtggacgcag agctgttgac gctgattgag gcggctttcg    6960
gcgaaatttc atcaatacat ttgcccacta aaactaaatt taaattcgga gccatgatga    7020
aatctggaat gttcctcaca ctgtttgtga acacagtcat taacattgta atcgcaagca    7080
gagtgttgag agaacggcta accggatcac catgtgcagc attcattgga gatgacaata    7140
tcgtgaaagg agtcaaatcg acaaaattaa tggcagacag gtgcgccacc tggttgaata    7200
tggaagtcaa gattatagat gctgtggtgg gcgagaaagc gccttatttc tgtggagggt    7260 ttatttttgtg tgactccgtg accggcacag cgtgccgtgt ggcagacccc ctaaaaaggc    7320
tgtttaagct tggcaaacct ctggcagcag acgatgaaca tgatgatgac aggagaaggg    7380
cattgcatga gagagtcaaca cgctggaacc gagtgggtat tctttcagag ctgtgcaagg    7440
cagtagaatc aaggtatgaa accgtaggaa cttccatcat agttatggcc atgactactc    7500
```

-continued

```
tagctagcag tgttaaatca ttcagctacc tgagaggggc ccctataact ctctacggct    7560
aacctgaatg gactacgaca tagtctagtc cgccaagtct agcatatggc cacccggaga    7620
aagagaggct ctggcgaagg cagaggcagc ctgcttacat gtggcgacgt ggaagagaac    7680
cccggaccta tggactacgt gtccctgctg aaccagattt ggcagaagta cctgaacagc    7740
ccctacacca cctgtctgta catccccaag cctaccgcca agtacacacc tctcgtgggc    7800
acatctctgc accccgtgct gtggaattgc cagctgagct ttgccggcta caccgagtct    7860
gccgtgaaca gcacaaaggc cctggccaaa caggacgccg ctcagagaat tgcctggctg    7920
ctgcacaagt atggcggcat ccctgatggc tgtagcctgt acctgagaca cagcagcctg    7980
ttcgcccaga gcgaggaaga ggaatccttc agcaactgat gagcggccgc gaattggcaa    8040
gctgcttaca tagaactcgc ggcgattggc atgccgcctt aaaattttta ttttattttt    8100
cttttctttt ccgaatcgga ttttgttttt aatatttcaa aaaaaaaaa aaaaaaaaaa    8160 aaaaaaaaaa aaacgcgtcg aggggaatta attcttgaag acgaaagggc caggtggcac    8220
ttttcgggga aatgtgcgcg gaacccctat ttgtttattt ttctaaatac attcaaatat    8280
gtatccgctc atgagacaat aaccctgata aatgcttcaa taatattgaa aaaggaagag    8340
tatgagtatt caacatttcc gtgtcgccct tattcccttt tttgcggcat tttgccttcc    8400
tgtttttgct cacccagaaa cgctggtgaa agtaaaagat gctgaagatc agttgggtgc    8460
acgagtgggt tacatcgaac tggatctcaa cagcggtaag atccttgaga gttttcgccc    8520
cgaagaacgt tttccaatga tgagcacttt taaagttctg ctatgtggcg cggtattatc    8580
ccgtgttgac gccgggcaag agcaactcgg tcgccgcata cactattctc agaatgactt    8640
ggttgagtac tcaccagtca cagaaaagca tcttacggat ggcatgacag taagagaatt    8700
atgcagtgct gccataacca tgagtgataa cactgcggcc aacttacttc tgacaacgat    8760
cggaggaccg aaggagctaa ccgctttttt gcacaacatg ggggatcatg taactcgcct    8820
tgatcgttgg gaaccggagc tgaatgaagc cataccaaac gacgagcgtg acaccacgat    8880
gcctgtagca atggcaacaa cgttgcgcaa actattaact ggcgaactac ttactctagc    8940
ttcccggcaa caattaatag actggatgga ggcggataaa gttgcaggac cacttctgcg    9000
ctcggccctt ccggctggct ggtttattgc tgataaatct ggagccggtg agcgtgggtc    9060
tcgcggtatc attgcagcac tggggccaga tggtaagccc tcccgtatcg tagttatcta    9120
cacgacgggg agtcaggcaa ctatggatga acgaaataga cagatcgctg agataggtgc    9180
ctcactgatt aagcattggt aactgtcaga ccaagtttac tcatatatac tttagattga    9240
tttaaaactt catttttaat ttaaaaggat ctaggtgaag atcctttttg ataatctcat    9300
gaccaaaatc ccttaacgtg agttttcgtt ccactgagcg tcagaccccg tagaaaagat    9360
caaaggatct tcttgagatc ctttttttct gcgcgtaatc tgctgcttgc aaacaaaaaa    9420
accaccgcta ccagcggtgg tttgtttgcc ggatcaagag ctaccaactc tttttccgaa    9480
ggtaactggc ttcagcagag cgcagatacc aaatactgtc cttctagtgt agccgtagtt    9540
aggccaccac ttcaagaact ctgtagcacc gcctacatac ctcgctctgc taatcctgtt    9600
accagtggct gctgccagtg gcgataagtc gtgtcttacc gggttggact caagacgata    9660
gttaccggat aaggcgcagc ggtcgggctg aacggggggt tcgtgcacac agcccagctt    9720
ggagcgaacg acctacaccg aactgagata cctacagcgt gagcattgag aaagcgccac    9780
gcttcccgaa gggagaaagg cggacaggta tccggtaagc ggcagggtcg aacaggaga     9840
```

-continued

```
gcgcacgagg gagcttccag ggggaaacgc ctggtatctt tatagtcctg tcgggtttcg    9900
ccacctctga cttgagcgtc gatttttgtg atgctcgtca gggggggcgga gcctatggaa    9960 aaa                                                                   9963

<210> SEQ ID NO 37
<211> LENGTH: 10302
<212> TYPE: DNA
<213> ORGANISM: Artificial Sequence
<220> FEATURE:
<223> OTHER INFORMATION: vector comprising a nucleic acid sequence that
      encodes an RNA construct comprising PIV5
<220> FEATURE:
<221> NAME/KEY: misc_feature
<223> OTHER INFORMATION: GOI present between positions 7614 and 7615

<400> SEQUENCE: 37
cgccagcaac gcgagctcta atacgactca ctatagatgg gcggcgcatg agagaagccc      60
agaccaatta cctacccaaa atggagaaag ttcacgttga catcgaggaa gacagcccat     120
tcctcagagc tttgcagcgg agcttcccgc agtttgaggt agaagccaag caggtcactg     180
ataatgacca tgctaatgcc agagcgtttt cgcatctggc ttcaaaactg atcgaaacgg     240
aggtggaccc atccgacacg atccttgaca ttggaagtgc gcccgcccgc agaatgtatt     300
ctaagcacaa gtatcattgt atctgtccga tgagatgtgc ggaagatccg gacagattgt     360
ataagtatgc aactaagctg aagaaaaact gtaaggaaat aactgataag gaattggaca     420
agaaaatgaa ggagctggcc gccgtcatga gcgaccctga cctggaaact gagactatgt     480
gcctccacga cgacgagtcg tgtcgctacg aagggcaagt cgctgtttac caggatgtat     540
acgcggttga cggaccgaca agtctctatc accaagccaa taagggagtt agagtcgcct     600
actggatagg ctttgacacc accccttttta tgtttaagaa cttggctgga gcatatccat     660
catactctac caactgggcc gacgaaaccg tgttaacggc tcgtaacata ggcctatgca     720
gctctgacgt tatggagcgg tcacgtagag ggatgtccat tcttagaaag aagtatttga     780
aaccatccaa caatgttcta ttctctgttg gctcgaccat ctaccacgag aagagggact     840
tactgaggag ctggcacctg ccgtctgtat ttcacttacg tggcaagcaa aattacacat     900
gtcggtgtga gactatagtt agttgcgacg ggtacgtcgt aaaagaata gctatcagtc     960 caggcctgta tgggaagcct tcaggctatg ctgctacgat gcaccgcgag ggattcttgt    1020
gctgcaaagt gacagacaca ttgaacgggg agagggtctc tttttcccgtg tgcacgtatg    1080 tgccagctac attgtgtgac caaatgactg gcatactggc aacagatgtc agtgcggacg    1140
acgcgcaaaa actgctggtt gggctcaacc agcgtatagt cgtcaacggt cgcacccaga    1200
gaaacaccaa taccatgaaa aattaccttt tgcccgtagt ggcccaggca tttgctaggt    1260
gggcaaagga atataaggaa gatcaagaag atgaaaggcc actaggacta cgagatagac    1320
agttagtcat ggggtgttgt tgggcttttta gaaggcacaa gataacatct atttataagc    1380
gcccggatac ccaaaccatc atcaaagtga acagcgattt ccactcattc gtgctgccca    1440
ggataggcag taacacattg gagatcgggc tgagaacaag aatcaggaaa atgttagagg    1500
agcacaagga gccgtcacct ctcattaccg ccgaggacgt acaagaagct aagtgcgcag    1560
ccgatgaggc taaggaggtg cgtgaagccg aggagttgcg cgcagctcta ccacctttgg    1620
cagctgatgt tgaggagccc actctggaag ccgatgtcga cttgatgtta caagaggctg    1680
gggccggctc agtggagaca cctcgtggct tgataaaggt taccagctac gatgcgcgagg    1740 acaagatcgg ctcttacgct gtgctttctc gcaggctgt actcaagagt gaaaaattat    1800
```

-continued

```
cttgcatcca ccctctcgct gaacaagtca tagtgataac acactctggc cgaaaagggc   1860
gttatgccgt ggaaccatac catggtaaag tagtggtgcc agagggacat gcaatacccg   1920
tccaggactt tcaagctctg agtgaaagtg ccaccattgt gtacaacgaa cgtgagttcg   1980
taaacaggta cctgcaccat attgccacac atggaggagc gctgaacact gatgaagaat   2040
attacaaaac tgtcaagccc agcgagcacg acggcgaata cctgtacgac atcgacagga   2100
aacagtgcgt caagaaagaa ctagtcactg ggctagggct cacaggcgag ctggtggatc   2160
ctcccttcca tgaattcgcc tacgagagtc tgagaacacg accagccgct ccttaccaag   2220
taccaaccat aggggtgtat ggcgtgccag gatcaggcaa gtctggcatc attaaaagcg   2280
cagtcaccaa aaaagatcta gtggtgagcg ccaagaaaga aaactgtgca gaaattataa   2340
gggacgtcaa gaaaatgaaa gggctggacg tcaatgccag aactgtggac tcagtgctct   2400
tgaatggatg caaacacccc gtagagaccc tgtatattga cgaagctttt gcttgtcatg   2460
caggtactct cagagcgctc atagccatta taagacctaa aaaggcagtg ctctgcgggg   2520
atcccaaaca gtgcggtttt tttaacatga tgtgcctgaa agtgcatttt aaccacgaga   2580
tttgcacaca agtcttccac aaaagcatct ctcgccgttg cactaaatct gtgacttcgg   2640
tcgtctcaac cttgttttac gacaaaaaaa tgagaacgac gaatccgaaa gagactaaga   2700
ttgtgattga cactaccggc agtaccaaac ctaagcagga cgatctcatt ctcacttgtt   2760
tcagagggtg ggtgaagcag ttgcaaatag attacaaagg caacgaaata atgacggcag   2820
ctgcctctca agggctgacc cgtaaaggtg tgtatgccgt tcggtacaag gtgaatgaaa   2880
atcctctgta cgcacccacc tcagaacatg tgaacgtcct actgacccgc acggaggacc   2940
gcatcgtgtg gaaaacacta gccggcgacc catggataaa aacactgact gccaagtacc   3000
ctgggaattt cactgccacg atagaggagt ggcaagcaga gcatgatgcc atcatgaggc   3060
acatcttgga gagaccggac cctaccgacg tcttccagaa taaggcaaac gtgtgttggg   3120
ccaaggcttt agtgccggtg ctgaagaccg ctggcataga catgaccact gaacaatgga   3180
acactgtgga ttattttgaa acggacaaag ctcactcagc agagatagta ttgaaccaac   3240
tatgcgtgag gttctttgga ctcgatctgg actccggtct attttctgca cccactgttc   3300
cgttatccat taggaataat cactgggata actccccgtc gcctaacatg tacgggctga   3360
ataaagaagt ggtccgtcag ctctctcgca ggtacccaca actgcctcgg gcagttgcca   3420
ctggaagagt ctatgacatg aacactggta cactgcgcaa ttatgatccg cgcataaacc   3480
tagtacctgt aaacagaaga ctgcctcatg ctttagtcct ccaccataat gaacacccac   3540
agagtgactt ttcttcattc gtcagcaaat tgaagggcag aactgtcctg gtggtcgggg   3600
aaaagttgtc cgtcccaggc aaaatggttg actggttgtc agaccggcct gaggctacct   3660
tcagagctcg gctggattta ggcatcccag gtgatgtgcc caaatatgac ataatatttg   3720
ttaatgtgag gaccccatat aaataccatc actatcagca gtgtgaagac catgccatta   3780
agcttagcat gttgaccaag aaagcttgtc tgcatctgaa tcccggcgga acctgtgtca   3840
gcataggtta tggttacgct gacagggcca gcgaaagcat cattggtgct atagcgcggc   3900
agttcaagtt ttcccgggta tgcaaaccga aatcctcact tgaagagacg gaagttctgt   3960
ttgtattcat tgggtacgat cgcaaggccc gtacgcacaa ttcttacaag ctttcatcaa   4020
ccttgaccaa catttataca ggttccagac tccacgaagc cggatgtgca ccctcatatc   4080
atgtggtgcg aggggatatt gccacggcca ccgaaggagt gattataaat gctgctaaca   4140
```

-continued

```
gcaaaggaca acctggcgga ggggtgtgcg gagcgctgta taagaaattc ccggaaagct    4200
tcgatttaca gccgatcgaa gtaggaaaag cgcgactggt caaaggtgca gctaaacata    4260
tcattcatgc cgtaggacca aacttcaaca aagtttcgga ggttgaaggt gacaaacagt    4320
tggcagaggc ttatgagtcc atcgctaaga ttgtcaacga taacaattac aagtcagtag    4380
cgattccact gttgtccacc ggcatctttt ccgggaacaa agatcgacta acccaatcat    4440
tgaaccattt gctgacagct ttagacacca ctgatgcaga tgtagccata tactgcaggg    4500
acaagaaatg ggaaatgact ctcaaggaag cagtggctag gagagaagca gtggaggaga    4560
tatgcatatc cgacgactct tcagtgacag aacctgatgc agagctggtg agggtgcatc    4620
cgaagagttc tttggctgga aggaagggct acagcacaag cgatggcaaa actttctcat    4680
atttggaagg gaccaagttt caccaggcgg ccaaggatat agcagaaatt aatgccatgt    4740
ggcccgttgc aacggaggcc aatgagcagg tatgcatgta tatcctcgga gaaagcatga    4800
gcagtattag gtcgaaatgc cccgtcgaag agtcggaagc ctccacacca cctagcacgc    4860
tgccttgctt gtgcatccat gccatgactc cagaaagagt acagcgccta aaagcctcac    4920
gtccagaaca aattactgtg tgctcatcct ttccattgcc gaagtataga atcactggtg    4980
tgcagaagat ccaatgctcc cagcctatat tgttctcacc gaaagtgcct gcgtatattc    5040
atccaaggaa gtatctcgtg gaaacaccac cggtagacga gactccggag ccatcggcag    5100
agaaccaatc cacagagggg acacctgaac aaccaccact tataaccgag gatgagacca    5160
ggactagaac gcctgagccg atcatcatcg aagaggaaga agaggatagc ataagtttgc    5220
tgtcagatgg cccgacccac caggtgctgc aagtcgaggc agacattcac gggccgccct    5280
ctgtatctag ctcatcctgg tccattcctc atgcatccga ctttgatgtg gacagtttat    5340
ccatacttga caccctggag ggagctagcg tgaccagcgg ggcaacgtca gccgagacta    5400
actcttactt cgcaaagagt atggagtttc tggcgcgacc ggtgcctgcg cctcgaacag    5460
tattcaggaa ccctccacat cccgctccgc gcacaagaac accgtcactt gcacccagca    5520
gggcctgctc gagaaccagc ctagtttcca ccccgccagg cgtgaatagg gtgatcacta    5580
gagaggagct cgaggcgctt accccgtcac gcactcctag caggtcggtc tcgagaacca    5640
gcctggtctc caacccgcca ggcgtaaata gggtgattac aagagaggag tttgaggcgt    5700
tcgtagcaca acaacaatga cggtttgatg cgggtgcata catcttttcc tccgacaccg    5760
gtcaagggca tttacaacaa aaatcagtaa ggcaaacggt gctatccgaa gtggtgttgg    5820
agaggaccga attggagatt tcgtatgccc cgcgcctcga ccaagaaaaa gaagaattac    5880
tacgcaagaa attacagtta aatcccacac ctgctaacag aagcagatac cagtccagga    5940
aggtggagaa catgaaagcc ataacagcta gacgtattct gcaaggccta gggcattatt    6000
tgaaggcaga aggaaaagtg gagtgctacc gaaccctgca tcctgttcct ttgtattcat    6060
ctagtgtgaa ccgtgccttt tcaagcccca aggtcgcagt ggaagcctgt aacgccatgt    6120
tgaaagagaa ctttccgact gtggcttctt actgtattat tccagagtac gatgcctatt    6180
tggacatggt tgacggagct tcatgctgct tagacactgc cagtttttgc cctgcaaagc    6240
tgcgcagctt ccaaagaaa cactcctatt tggaacccac aatacgatcg gcagtgcctt    6300
cagcgatcca gaacacgctc cagaacgtcc tggcagctgc cacaaaaaga aattgcaatg    6360
tcacgcaaat gagagaattg cccgtattgg attcggcggc ctttaatgtg gaatgcttca    6420
agaaatatgc gtgtaataat gaatattggg aaacgtttaa agaaaacccc atcaggctta    6480
ctgaagaaaa cgtggtaaat tacattacca aattaaaagg accaaaagct gctgctcttt    6540
```

-continued

```
ttgcgaagac acataatttg aatatgttgc aggacatacc aatggacagg tttgtaatgg     6600
acttaaagag agacgtgaaa gtgactccag gaacaaaaca tactgaagaa cggcccaagg     6660
tacaggtgat ccaggctgcc gatccgctag caacagcgta tctgtgcgga atccaccgag     6720
agctggttag gagattaaat gcggtcctgc ttccgaacat tcatacactg tttgatatgt     6780
cggctgaaga ctttgacgct attatagccg agcacttcca gcctggggat tgtgttctgg     6840
aaactgacat cgcgtcgttt gataaaagtg aggacgacgc catggctctg accgcgttaa     6900
tgattctgga agacttaggt gtggacgcag agctgttgac gctgattgag gcggctttcg     6960
gcgaaatttc atcaatacat ttgcccacta aaactaaatt taaattcgga gccatgatga     7020
aatctggaat gttcctcaca ctgtttgtga acacagtcat taacattgta atcgcaagca     7080
gagtgttgag agaacggcta accggatcac catgtgcagc attcattgga gatgacaata     7140
tcgtgaaagg agtcaaatcg gacaaattaa tggcagacag gtgcgccacc tggttgaata     7200
tggaagtcaa gattatagat gctgtggtgg gcgagaaagc gccttatttc tgtggagggt     7260
ttattttgtg tgactccgtg accggcacag cgtgccgtgt ggcagacccc ctaaaaaggc     7320
tgtttaagct tggcaaacct ctggcagcag acgatgaaca tgatgatgac aggagaaggg     7380
cattgcatga agagtcaaca cgctggaacc gagtgggtat tctttcagag ctgtgcaagg     7440
cagtagaatc aaggtatgaa accgtaggaa cttccatcat agttatggcc atgactactc     7500
tagctagcag tgttaaatca ttcagctacc tgagaggggc ccctataact ctctacggct     7560
aacctgaatg gactacgaca tagtctagtc cgccaagtct agcatatggc cacccggaga     7620
aagagaggct ctggcgaagg cagaggcagc ctgcttacat gtggcgacgt ggaagagaac     7680
cccggaccta tggaccctac cgacctgagc ttcagccccg acgagatcaa caagctgatc     7740
gagacaggcc tgaacaccgt ggaatacttc accagccagc aagtgaccgg cacaagcagc     7800
ctgggcaaga acacaattcc tccaggcgtg accggcctgc tgacaaatgc tgccgaggcc     7860
aagatccaag agagcaccaa ccaccagaag ggctctgttg gaggcggagc caagcctaag     7920
aagcccagac ctaagatcgc catcgtgccc gccgacgata agacagtgcc tggcaagccc     7980
attcctaatc ctctgctggg cctcgacagc accctagca cacagacagt gctggatctg     8040
agcggcaaga cactgcctag cggcagctat aagggcgtga gctggccaa gttcggcaaa     8100 gaaaacctga tgacccggtt catcgaggaa cccagagaga ccctatcgc caccagctct     8160 cccatcgact tcaagagagg cagagacacc ggcggcttcc acagaagaga gtacagcatt     8220
ggctgggtcg gagatgaagt gaaagtgacc gagtggtgca accccagctg cagccctatt     8280
acagccgccg ctagaagatt cgagtgcacc tgtcaccagt gtcctgtgac ctgtagcgag     8340
tgcgagcggg acacatgatg agcggccgcg aattggcaag ctgcttacat agaactcgcg     8400
gcgattggca tgccgcctta aaattttttat tttatttttc ttttcttttc cgaatcggat     8460 tttgtttta atatttcaaa aaaaaaaaa aaaaaaaaa aaaaaaaaa aacgcgtcga     8520 ggggaattaa ttcttgaaga cgaaagggcc aggtggcact tttcggggaa atgtgcgcgg     8580 aaccccctatt tgtttatttt tctaaataca ttcaaatatg tatccgctca tgagacaata     8640
accctgataa atgcttcaat aatattgaaa aaggaagagt atgagtattc aacatttccg     8700
tgtcgccctt attcccttt ttgcggcatt ttgccttcct gtttttgctc acccagaaac     8760
gctggtgaaa gtaaaagatg ctgaagatca gttgggtgca cgagtgggtt acatcgaact     8820
ggatctcaac agcggtaaga tccttgagag ttttcgcccc gaagaacgtt ttccaatgat     8880
```

```
gagcacttttt aaagttctgc tatgtggcgc ggtattatcc cgtgttgacg ccgggcaaga   8940
gcaactcggt cgccgcatac actattctca gaatgacttg gttgagtact caccagtcac   9000
agaaaagcat cttacggatg gcatgacagt aagagaatta tgcagtgctg ccataaccat   9060
gagtgataac actgcggcca acttacttct gacaacgatc ggaggaccga aggagctaac   9120 cgctttttttg cacaacatgg gggatcatgt aactcgcctt gatcgttggg aaccggagct   9180
gaatgaagcc ataccaaacg acgagcgtga caccacgatg cctgtagcaa tggcaacaac   9240
gttgcgcaaa ctattaactg gcgaactact tactctagct tcccggcaac aattaataga   9300
ctggatggag gcggataaag ttgcaggacc acttctgcgc tcggcccttc cggctggctg   9360
gtttattgct gataaatctg gagccggtga gcgtgggtct cgcggtatca ttgcagcact   9420
ggggccagat ggtaagccct cccgtatcgt agttatctac acgacgggga gtcaggcaac   9480
tatggatgaa cgaaatagac agatcgctga gataggtgcc tcactgatta agcattggta   9540
actgtcagac caagtttact catatatact ttagattgat ttaaaacttc atttttaatt   9600
taaaaggatc taggtgaaga tcctttttga taatctcatg accaaaatcc cttaacgtga   9660
gttttcgttc cactgagcgt cagacccccgt agaaaagatc aaaggatctt cttgagatcc   9720 ttttttttctg cgcgtaatct gctgcttgca aacaaaaaaa ccaccgctac cagcggtggt   9780
ttgtttgccg gatcaagagc taccaactct ttttccgaag gtaactggct tcagcagagc   9840
gcagatacca aatactgtcc ttctagtgta gccgtagtta ggccaccact tcaagaactc   9900
tgtagcaccg cctacatacc tcgctctgct aatcctgtta ccagtggctg ctgccagtgg   9960
cgataagtcg tgtcttaccg ggttggactc aagacgatag ttaccggata aggcgcagcg   10020
gtcgggctga acggggggtt cgtgcacaca gcccagcttg gagcgaacga cctacaccga   10080
actgagatac ctacagcgtg agcattgaga aagcgccacg cttcccgaag ggagaaaggc   10140
ggacaggtat ccggtaagcg gcagggtcgg aacaggagag cgcacgaggg agcttccagg   10200
gggaaacgcc tggtatcttt atagtcctgt cgggtttcgc cacctctgac ttgagcgtcg   10260 attttttgtga tgctcgtcag ggggggcggag cctatggaaa aa              10302
```

<210> SEQ ID NO 38
<211> LENGTH: 10217
<212> TYPE: RNA
<213> ORGANISM: Artificial Sequence
<220> FEATURE:
<223> OTHER INFORMATION: RNA construct

<400> SEQUENCE: 38

```
augggcggcg caugagagaa gcccagacca auuaccuacc caaaauggag aaaguucacg      60
uugacaucga ggaagacagc ccauuccuca gagcuuugca gcggagcuuc ccgcaguuug     120
agguagaagc caagcagguc acugauaaug accaugcuaa ugccagagcg uuuucgcauc     180
uggcuucaaa acugaucgaa acggaggugg acccauccga cacgauccuu gacauuggaa     240
gugcgcccgc ccgcagaaug uauucuaagc acaaguauca uuguaucugu ccgaugagau     300
gugcggaaga uccggacaga uuguauaagu augcaacuaa gcugaagaaa aacuguaagg     360
aaauaacuga uaaggaauug gacaagaaaa ugaaggagcu ggccgccguc augagcgacc     420
cugaccugga aacugagacu augugccucc acgacgacga gucgugucgc uacgaagggc     480
aagucgcugu uuaccaggau guauacgcgg uugacggacc gacaagucuc uaucaccaag     540
ccaauaaggg aguuagaguc gccuacugga uaggcuuuga caccacccccu uuuaugu uua     600 agaacuuggc uggagcauau ccaucauacu cuaccaacug ggccgacgaa accguguuaa     660
```

-continued

```
cggcucguaa  cauaggccua  ugcagcucug  acguuaugga  gcggucacgu  agagggaugu      720
ccauucuuag  aaagaaguau  uugaaaccau  ccaacaaugu  ucuauucucu  guuggcucga      780
ccaucuacca  cgagaagagg  gacuuacuga  ggagcuggca  ccugccgucu  guauuucacu      840
uacguggcaa  gcaaaauuac  acaugucggu  gugagacuau  aguuaguugc  gacggguacg      900
ucguuaaaag  aauagcuauc  aguccaggcc  uguaugggaa  gccuucaggc  uaugcugcua      960
cgaugcaccg  cgagggauuc  uugugcugca  aagugacaga  cacauugaac  ggggagaggg     1020
ucucuuuucc  cgugugcacg  uaugugccag  cuacauugug  ugaccaaaug  acuggcauac     1080
uggcaacaga  ugucagugcg  gacgacgcgc  aaaaacugcu  gguugggcuc  aaccagcgua     1140
uagucgucaa  cggucgcacc  cagagaaaca  ccaauaccau  gaaaaauuac  cuuuugcccg     1200
uaguggccca  ggcauuugcu  agguggggcaa  aggaauauaa  ggaagaucaa  gaagaugaaa     1260
ggccacuagg  acuacgagau  agacaguuag  ucauggggug  uuguugggcu  uuuagaaggc     1320
acaagauaac  aucuauuuau  aagcgcccgg  auacccaaac  caucaucaaa  gugaacagcg     1380
auuuccacuc  auucgugcug  cccaggauag  gcaguaacac  auuggagauc  gggcugagaa     1440
caagaaucag  gaaaauguua  gaggagcaca  aggagccguc  accucucauu  accgccgagg     1500
acguacaaga  agcuaagugc  gcagccgaug  aggcuaagga  ggugcgugaa  gccgaggagu     1560
ugcgcgcagc  ucuaccaccu  uuggcagcug  auguugagga  gcccacucug  gaagccgaug     1620
ucgacuugau  guuacaagag  gcuggggccg  gcucagugga  gacaccucgu  ggcuugauaa     1680
agguuaccag  cuacgauggc  gaggacaaga  ucggcucuua  cgcugugcuu  ucuccgcagg     1740
cuguacucaa  gagugaaaaa  uuaucuugca  uccacccucu  cgcugaacaa  gucauaguga     1800
uaacacacuc  uggccgaaaa  gggcguuaug  ccguggaacc  auaccauggu  aaaguagugg     1860
ugccagaggg  acaugcaaua  cccguccagg  acuuucaagc  ucugagugaa  agugccacca     1920
uuguguacaa  cgaacgugag  uucguaaaca  gguaccugca  ccauauugcc  acacauggag     1980
gagcgcugaa  cacugaugaa  gaauauuaca  aaacugucaa  gcccagcgag  cacgacggcg     2040
aauaccugua  cgacaucgac  aggaaacagu  gcgucaagaa  agaacuaguc  acugggcuag     2100
ggcucacagg  cgagcuggug  gauccucccu  uccaugaauu  cgccuacgag  agucugagaa     2160
cacgaccagc  cgcuccuuac  caaguaccaa  ccauaggggu  guauggcgug  ccaggaucag     2220
gcaagucugg  caucauuaaa  agcgcaguca  ccaaaaaaga  ucuaguggug  agcgccaaga     2280
aagaaaacug  ugcagaaauu  auaagggacg  ucaagaaaau  gaaagggcug  gacgucaaug     2340
ccagaacugu  ggacucagug  cucuugaaug  gaugcaaaca  ccccguagag  acccuguaua     2400
uugacgaagc  uuuugcuugu  caugcaggua  cucucagagc  gcucauagcc  auuauaagac     2460
cuaaaaaggc  agugcucugc  ggggauccca  aacagugcgg  uuuuuuuaac  augaugugcc     2520
ugaaagugca  uuuuaaccac  gagauuugca  cacaagucuu  ccacaaaagc  aucucucgcc     2580
guugcacuaa  aucgugacu  ucggucgucu  caaccuuguu  uuacgacaaa  aaaaugagaa     2640
cgacgaaucc  gaaagagacu  aagauuguga  uugacacuac  cggcaguacc  aaaccuaagc     2700
aggacgaucu  cauucucacu  uguuucagag  guggggugaa  gcaguugcaa  auagauuaca     2760
aaggcaacga  aauaaugacg  gcagcugccu  cucaagggcu  gacccguaaa  ggugugauug     2820
ccguucggua  caagugaau  gaaaauccuc  uguacgcacc  caccucagaa  caugugaacg     2880
uccuacugac  ccgcacggag  gaccgcaucg  uguggaaaac  acuagccggc  gacccaugga     2940
uaaaaacacu  gacugccaag  uacccuggga  auuucacugc  cacgauagag  gaguggcaag     3000
```

-continued

```
cagagcauga ugccaucaug aggcacaucu uggagagacc ggacccuacc gacgucuucc   3060
agaauaaggc aaacgugugu ugggccaagg cuuuagugcc ggugcugaag accgcuggca   3120
uagacaugac cacugaacaa uggaacacug uggauuauuu ugaaacggac aaagcucacu   3180
cagcagagau aguauugaac caacuaugcg ugagguucuu uggacucgau cuggacuccg   3240
gucuauuuuc ugcacccacu guuccguuau ccauuaggaa uaaucacugg gauaacuccc   3300
cgucgccuaa cauguacggg cugaauaaag aagugguccg ucagcucucu cgcagguacc   3360
cacaacugcc ucgggcaguu gccacuggaa gagucuauga caugaacacu gguacacugc   3420
gcaauuauga uccgcgcaua aaccuaguac cuguaaacag aagacugccu caugcuuuag   3480
uccuccacca uaaugaacac ccacagagug acuuucuuc auucgucagc aaauugaagg   3540
gcagaacugu ccuggugguc ggggaaaagu uguccguccc aggcaaaaug guugacuggu   3600
ugucagaccg gccugaggcu accuucagag cucggcugga uuuaggcauc ccaggugaug   3660
ugcccaaaua ugacauaaua uuuguuaaug ugaggacccc auauaaauac caucacuauc   3720
agcaguguga agaccaugcc auuaagcuua gcaugugac caagaaagcu ugucugcauc   3780
ugaaucccgg cggaaccugu gucagcauag guuaugguua cgcugacagg gccagcgaaa   3840
gcaucauugg ugcuauagcg cggcaguuca aguuucccg gguaugcaaa ccgaaauccu   3900
cacuugaaga gacggaaguu cuguuuguau ucauugggua cgaucgcaag gcccguacgc   3960
acaauucuua caagcuuuca ucaaccuuga ccaacauuua uacagguucc agacuccacg   4020
aagccggaug ugcacccuca uaucaugugg ugcgaggggga uauugccacg gccaccgaag   4080
gagugauuau aaaaugcugcu aacagcaaag gacaaccugg cggaggggug ugcggagcgc   4140
uguauaagaa auucccggaa agcuucgauu uacagccgau cgaaguagga aaagcgcgac   4200
uggucaaagg ugcagcuaaa cauaucauuc augccguagg accaaacuuc aacaaaguuu   4260
cggagguuga aggugacaaa caguuggcag aggcuuauga guccaucgcu aagauuguca   4320
acgauaacaa uuacaaguca guagcgauuc cacuguuguc caccggcauc uuuuccggga   4380
acaaagaucg acuaacccaa ucauugaacc auuugcugac agcuuuagac accacugaug   4440
cagauguagc cauauacugc agggacaaga aaugggaaau gacucucaag gaagcagugg   4500
cuaggagaga agcaguggag gagauaugca uauccgacga cucuucagug acagaaccug   4560
augcagagcu ggugagggug cauccgaaga guucuuuggc uggaaggaag ggcuacagca   4620
caagcgaugg caaaacuuuc ucauauuugg aagggaccaa guuucaccag gcggccaagg   4680
auauagcaga aauuaaugcc auguggcccg uugcaacgga ggccaaugag cagguaugca   4740
uguauauccu cggagaaagc augagcagua uuaggucgaa augccccguc gaagagucgg   4800
aagccuccac accaccuagc acgcugccuu gcuugugcau ccaugccaug acuccagaaa   4860
gaguacagcg ccuaaaagcc ucacguccag aacaaauuac ugugugcuca uccuuuccau   4920
ugccgaagua uagaaucacu gguggugcaga agauccaaug cucccagccu auauuguucu   4980
caccgaaagu gccugcguau auucauccaa ggaaguaucu cguggaaaca ccaccgguag   5040
acgagacucc ggagccaucg gcagagaacc aauccacaga ggggacaccu gaacaaccac   5100
cacuuauaac cgaggaugag accaggacua gaacgccuga gccgaucauc aucgaagagg   5160
aagaagagga uagcauaagu uugcugucag auggcccgac ccaccagguug cugcaagucg   5220 aggcagacau ucacgggccg cccucuguau cuagcucauc cuggucccauu ccucaugcau   5280 ccgacuuuga ugugggacagu uuauccauac uugacacccu ggagggagcu agcgugacca   5340
gcggggcaac gucagccgag acuaacucuu acuucgcaaa gaguauggag uuucuggcgc   5400
```

-continued

```
gaccggugcc ugcgccucga acaguauuca ggaaccaucc acaucccgcu ccgcgcacaa    5460
gaacaccguc acuugcaccc agcagggccu gcucgagaac cagccuaguu uccaccccgc    5520
caggcgugaa uagggugauc acuagagagg agcucgaggc gcuuaccccg ucacgcacuc    5580
cuagcagguc ggucucgaga accagccugg ucuccaaccc gccaggcgua aauaggguga    5640
uuacaagaga ggaguuugag gcguucguag cacaacaaca augacgguuu gaugcggaug    5700
cauacaucuu uuccuccgac accggucaag ggcauuuaca acaaaaauca guaaggcaaa    5760
cggugcuauc cgaaguggug uuggagagga ccgaauugga gauuucguau gccccgcgcc    5820
ucgaccaaga aaaagaagaa uuacuacgca agaaauuaca guuaaauccc acaccugcua    5880
acagaagcag auaccagucc aggaaggugg agaacaugaa agccauaaca gcuagacgua    5940
uucugcaagg ccuagggcau uauuugaagg cagaaggaaa aguggagugc uaccgaaccc    6000
ugcauccugu uccuuuguau ucaucuagug ugaaccgugc cuuuucaagc cccaaggucg    6060
caguggaagc cuguaacgcc auguugaaag agaacuuucc gacugugcu ucuuacugua    6120 uuauuccaga guacgaugcc uauuuggaca ugguugacgg agcuucaugc ugcuuagaca    6180
cugccaguuu uugcccugca aagcugcgca gcuuuccaaa gaaacacucc uauuuggaac    6240
ccacaauacg aucggcagug ccuucagcga uccagaacac gcuccagaac guccuggcag    6300
cugccacaaa aagaaauugc aaugucacgc aaaugagaga auugcccgua uuggauucgg    6360
cggccuuuaa uguggaaugc uucaagaaau augcguguaa uaaugaauau ugggaaacgu    6420
uuaaagaaaa ccccaucagg cuuacugaag aaaacguggu aaauuacauu accaaauuaa    6480
aaggaccaaa agcugcugcu cuuuuugcga agacacauaa uuugaauaug uugcaggaca    6540
uaccaaugga cagguuugua auggacuuaa agagagacgu gaaagugacu ccaggaacaa    6600
aacauacuga agaacggccc aagguacagg ugauccaggc ugccgauccg cuagcaacag    6660
cguaucugug cggaauccac cgagagcugg uuaggagauu aaaugcgguc cugcuuccga    6720
acauucauac acuguuugau augucggcug aagacuuuga cgcuauuaua gccgagcacu    6780
uccagccugg ggauuguguu cuggaaacug acaucgcguc guuugauaaa agugaggacg    6840
acgccauggc ucugaccgcg uuaaugauuc uggaagacuu aggugggac gcagagcugu    6900 ugacgcugau ugaggcggcu uucggcgaaa uuucaucaau acauuugccc acuaaaacua    6960
aauuuaaauu cggagccaug augaaaucug gaauguccu cacacuguuu gugaacacag    7020
ucauuaacau uguaaucgca agcagagugu ugagagaacg gcuaaccgga ucaccaugug    7080
cagcauucau uggagaugac aauaucguga aaggagucaa aucggacaaa uuaauggcag    7140
acaggugcgc caccuggung aauauggaag ucaagauuau agaugcugug gugggcgaga    7200
aagcgccuua uuucgugga ggguuuauuu ugugugacuc cgugaccggc acagcgugcc    7260
guguggcaga cccccuaaaa aggcuguuua agcuuggcaa accucuggca gcagacgaug    7320
aacaugauga ugacaggaga agggcauugc augaagaguc aacacgcugg aaccgagugg    7380
guauucuuuc agagcugugc aaggcaguag aaucaaggua ugaaccguaa ggaacuucca    7440
ucauaguuau ggccaugacu acucuagcua gcaguguuaa aucauucagc uaccugagag    7500 gggcccuau aacucucuac ggcuaaccug aauggacuac gacauagucu aguccgccaa    7560
gucuagcaua uguauggcca ccauggaaga ugccaagaac aucaagaagg gcccugcccc    7620
auucuacccc cuggaagaug gaacagccgg cgagcagcug cacaaggcca ugaagagaua    7680
cgcccuggug cccggcacaa ucgccuucac cgaugccac aucgagugg acaucaccua    7740
```

-continued

```
cgccgaguac uucgagauga gcgugcggcu ggccgaagcu augaagcgcu acggccugaa      7800
caccaaccac cggaucgucg ugugcagcga gaacagccug caguucuuca ugcccgugcu      7860
gggcgcccug uuuaucggag uggcuguggc cccugccaac gacaucuaca acgagcgcga      7920
gcugcugaac agcaugggca ucagccagcc caccgugug uucgugucca agaagggacu       7980
gcagaaaauc cugaacgugc agaagaagcu gcccaucauc cagaaaauca ucaucaugga      8040
cagcaagacc gacuaccagg gcuuccagag cauguacacc uucgugacca gccaucugcc      8100
cccuggcuuc aacgaguacg acuucgugcc cgagagcuuc gaccgggaca agacaaucgc      8160
ccugaucaug aacagcagcg gcagcaccgg acugccuaaa ggcguggccc ugccucacag      8220
aacugccugc gugcgguuua gccacgcccg ggacccuauc uucggcaacc agaucauccc      8280
cgacaccgcc auccugagcg uggugccuuu ccaccacggc uucggcaugu ucaccacccu      8340
gggcuaccug aucugcggcu uccggguggu gcugauguac agauucgagg aagaacuguu      8400
ccugcggagc cugcaggacu acaagaucca gagcgcccug cuggugccua cccuguucag      8460
cuucuuugcc aagagcaccc ugaucgauaa guacgaccug agcaaccugc acgagaucgc      8520
cucuggcgga gccccccgu cuaaagaagu gggagaggcc guggccaagc gguuccaucu       8580
gccuggcauc agacagggcu auggccgac cgagacaacc agcgccauuc ugaucacccc       8640
cgagggcgac gauaagccug gcgccguggg aaagguggug ccauucuucg aggccaaggu      8700
gguggaccug gacaccggca agacacuggg cgugaaccag aggggcgaac ugugugugcg      8760
gggaccuaug aucaugagcg gcuacgugaa caaccccgag gccaccaacg cccugauuga      8820
caaggauggc uggcugcaca gcggcgacau ugccuacugg gacgaggacg agcacuucuu      8880
caucguggac cggcugaagu cccugaucaa guacaagggc uaccaggugg ccccagccga      8940
gcuggaaucu auccgcugc agcaccccaa caucuucgau gccggcgugg caggacugcc       9000
cgaugaugau gcuggcgaac ugccagccgc ugugguggug cuggaacacg gaaagaccau      9060
gaccgagaaa gaaaucgugg acuacgaggc cagccaagug accaccgcca agaaacugag      9120
aggcggcgug ugguuuguggg acgaggugcc aaagggccug acaggcaagc uggacgcccg      9180
gaagaucaga gagauccuga uuaaggccaa gaaaggcggc aagaucgccg uggaucggag      9240
aaagagaggc ucuggcgaag gcagaggcag ccugcuuaca ugugggcgacg uggaagagaa      9300 cccccggaccu auggacccua ccgaccgag cuucagcccc gacgagauca acaagcugau       9360
cgagacaggc cugaacaccg uggaauacuu caccagccag caagugaccg gcacaagcag      9420
ccugggcaag aacacaauuc cuccaggcgu gaccggccug cugacaaaug cugccgaggc      9480
caagauccaa gagagcacca accaccagaa gggcucuguu ggaggcggag ccaagccuaa      9540
gaagcccaga ccuaagaucg ccaucgugcc cgccgacgau aagacagugc cuggcaagcc      9600
cauuccuaau ccucugcugg gccucgacag cacccuagc acacagacag ugcuggaucu        9660
gagcggcaag acacugccua gcggcagcua uaagggcgug aagcuggcca aguucggcaa      9720
agaaaaccug augacccggu ucaucgagga acccagagag aacccuaucg ccaccagcuc      9780
ucccaucgac uucaagagag gcagagacac cggcggcuuc cacagaagag aguacagcau      9840 uggcugggguc ggagaugaag ugaaagugac cgaguggugc aacccccagcu gcagcccuau      9900 uacagccgcc gcuagaagau ucgagugcac cugucaccag ugccugugua ccguagcga         9960 gugcgagcgg gacacaugau gagcggccgc gaauuggcaa gcugcuuaca uagaacgc        10020 ggcgauuggc augccgccuu aaaauuuuua uuuuauuuuu cuuuucuuuu ccgaucgga      10080 uuuugguuuu aauauuuucaa aaaaaaaaaa aaaaaaaaaa aaaaaaaaaa aaaaaaaaaa    10140
```

```
aaaaaaaaaa aaaaaaaaaa aaaaaaaaaa aaaaaaaaaa aaaaaaaaaa aaaaaaaaaa    10200
aaaaaaaaaa aaaaaaa                                                   10217

<210> SEQ ID NO 39
<211> LENGTH: 9878
<212> TYPE: RNA
<213> ORGANISM: Artificial Sequence
<220> FEATURE:
<223> OTHER INFORMATION: the RNA construct

<400> SEQUENCE: 39
augggcggcg caugagagaa gcccagacca auuaccuacc caaaauggag aaaguucacg      60
uugacaucga ggaagacagc ccauuccuca gagcuuugca gcggagcuuc ccgcaguuug     120
agguagaagc caagcagguc acugauaaug accaugcuaa ugccagagcg uuuucgcauc     180
uggcuucaaa acugaucgaa acggaggugg acccauccga cacgauccuu gacauuggaa     240
gugcgcccgc ccgcagaaug uauucuaagc acaaguauca uuguaucugu ccgaugagau     300
gugcggaaga uccggacaga uuguauaagu augcaacuaa gcugaagaaa aacuguaagg     360
aaauaacuga uaaggaauug gacaagaaaa ugaaggagcu ggccgccguc augagcgacc     420
cugaccugga aacugagacu augugccucc acgacgacga gucgugucgc uacgaagggc     480
aagucgcugu uuaccaggau guauacgcgg uugacggacc gacaagucuc uaucaccaag     540
ccaauaaggg aguuagaguc gccuacugga uaggcuuuga caccacccu uuuauguuua     600 agaacuuggc uggagcauau ccaucauacu cuaccaacug ggccgacgaa accguguuaa     660
cggcucguaa cauaggccua ugcagcucug acguuaugga gcggucacgu agagggaugu     720
ccauucuuag aaagaaguau uugaaaccau ccaacaaugu ucuauucucu guuggcucga     780
ccaucuacca cgagaagagg gacuuacuga ggagcuggca ccugccgucu guauuucacu     840
uacguggcaa gcaaaauuac acaugucggu gugagacuau aguuaguugc gacggguacg     900
ucguuaaaag aauagcuauc aguccaggcc uguaugggaa gccuucaggc uaugcugcua     960
cgaugcaccg cgagggauuc uugugcugca aagugacaga cacauugaac ggggagaggg    1020
ucucuuuucc cguguugcacg uaugugccag cuacauugug ugaccaaaug acuggcauac    1080
uggcaacaga ugucagugcg gacgacgcgc aaaaacugcu gguugggcuc aaccagcgua    1140
uagucgucaa cggucgcacc cagagaaaca ccaauaccau gaaaaauuac cuuuugcccg    1200
uaguggccca ggcauuugcu aggugggcaa aggaauauaa ggaagaucaa gaagaugaaa    1260
ggccacuagg acuacgagau agacaguuag ucauggggug uuguugggcu uuuagaaggc    1320
acaagauaac aucuauuuau aagcgcccgg auacccaaac caucaucaaa gugaacagcg    1380
auuuccacuc auucgugcug cccaggauag gcaguaacac auuggagauc gggcugagaa    1440
caagaaucag gaaaauguua gaggagcaca aggagccguc accucucauu accgccgagg    1500
acguacaaga agcuaagugc gcagccgaug aggcuaagga ggugcgugaa gccgaggagu    1560
ugcgcgcagc ucuaccaccu uuggcagcug auguugagga gcccacucug gaagccgaug    1620
ucgacuugau guuacaagag gcuggggccg gcucagugga gacaccccgu ggcuugauaa    1680
agguuaccag cuacgauggc gaggacaaga ucggcucuua cgcugugcuu ucuccgcagg    1740
cuguacucaa gagugaaaaa uuaucuugca uccacccucu cgcugaacaa gucauaguga    1800
uaacacacuc uggccgaaaa gggcguuaug ccguggaacc auaccauggu aaaguagugg    1860
ugccagaggg acaugcaaua cccguccagg acuuucaagc ucugagugaa agugccacca    1920
```

-continued

```
uuguguacaa cgaacgugag uucguaaaca gguaccugca ccauauugcc acacauggag    1980
gagcgcugaa cacugaugaa gaauauuaca aaacugucaa gcccagcgag cacgacggcg    2040
aauaccugua cgacaucgac aggaaacagu gcgucaagaa agaacuaguc acugggcuag    2100
ggcucacagg cgagcuggug gauccucccu uccaugaauu cgccuacgag agucugagaa    2160
cacgaccagc cgcuccuuac caaguaccaa ccauaggggu guauggcgug ccaggaucag    2220
gcaagucugg caucauuaaa agcgcaguca ccaaaaaaga ucuaguggug agcgccaaga    2280 aagaaacug ugcagaaauu auaagggacg ucaagaaaau gaaagggcug gacgucaaug    2340
ccagaacugu ggacucagug cucuugaaug gaugcaaaca ccccguagag acccuguaua    2400
uugacgaagc uuuugcuugu caugcaggua cucucagagc gcucauagcc auuauaagac    2460
cuaaaaaggc agugcucugc ggggaucccaa aacagugcgg uuuuuuuaac augaugugcc    2520
ugaaagugca uuuuaaccac gagauuugca cacaagucuu ccacaaaagc aucucucgcc    2580
guugcacuaa aucugugacu ucggucgucu caaccuuguu uuacgacaaa aaaaugagaa    2640
cgacgaaucc gaaagagacu aagauuguga uugacacuac cggcaguacc aaaccuaagc    2700
aggacgaucu cauucucacu uguuucagag ggugggugaa gcaguugcaa auagauuaca    2760
aaggcaacga aauaaugacg gcagcugccu cucaagggcu gacccguaaa ggugugugug    2820
ccguucggua caaggugaau gaaaauccuc uguacgcacc caccucagaa caugugaacg    2880 uccuacgac ccgcacggag gaccgcaucg uguggaaaac acuagccggc gacccaugga    2940
uaaaaacacu gacugccaag uaccugggga uuucacugc cacgauagag gaguggcaag    3000
cagagcauga ugccaucaug aggcacaucu uggagagacc ggacccuacc gacgucuucc    3060
agaauaaggc aaacgugugu ugggccaagg cuuuagugcc ggugcugaag accgcuggca    3120
uagacaugac cacugaacaa uggaacacug uggauuauuu ugaaacggac aaagcucacu    3180
cagcagagau aguauugaac caacuaugcg ugagguucuu uggacucgau cuggacuccg    3240
gucuauuuuc ugcacccacu guuccguuau ccauuaggaa uaaucacugg gauaacucc    3300 cgucgccuaa caucuacggg cugaauaaag aaguggaccg ucagcucucu cgcagguacc    3360
cacaacugcc ucgggcaguu gccacuggaa gagucuauga caugaacacu gguacacugc    3420
gcaauuauga uccgcgcaua aaccuaguac cuguaaacag aagacugccu caugcuuuag    3480
uccuccacca uaaugaacac ccacagagug acuuuucuuc auucgucagc aaauugaagg    3540
gcagaacugu ccuggugguc ggggaaaagu uguccguccc aggcaaaaug guugacuggu    3600
ugucagaccg gccugaggcu accuucagag cucggcugga uuuaggcauc ccaggugaug    3660
ugcccaaaua ugacauaaua uuuguuaaug ugaggacccc auauaaauac caucacuauc    3720
agcaguguga agaccaugcc auuaagcuua gcauguugac caagaaagcu ugucugcauc    3780
ugaaucccgg cggaaccugu gucagcauag guuaugguua cgcugacagg gccagcgaaa    3840
gcaucauugg ugcuauagcg cggcaguuca aguuucccg gguaugcaaa ccgaaauccu    3900
cacuugaaga gacggaaguu cuguuugau ucauggggua cgaucgcaag gcccguacgc    3960
acaauucuua caagcuuuca ucaaccuuga ccaacauuua uacagguucc agacuccacg    4020
aagccggaug ugcacccuca uaucaugugg ugcgagggga uauugccacg gccaccgaag    4080
gagugauuau aaaugcugcu aacagcaaag gacaaccugg cggaggggug ugcggagcgc    4140
uguauaagaa auucccggaa agcuucgauu uacagccgau cgaaguagga aaagcgcgac    4200
uggucaaagg ugcagcuaaa cauaucauuc augccguagg accaaacuuc aacaaaguuu    4260
cggagguuga agguugacaaa caguuggcag aggcuuauga guccaucgcu aagauugca   4320
```

-continued

```
acgauaacaa uuacaaguca guagcgauuc cacuguuguc caccggcauc uuuuccggga   4380
acaaagaucg acuaacccaa ucauugaacc auuugcugac agcuuuagac accacugaug   4440
cagauguagc cauauacugc agggacaaga aaugggaaau gacucucaag gaagcagugg   4500
cuaggagaga agcaguggag gagauaugca uauccgacga cucuucagug acagaaccug   4560
augcagagcu ggugagggug cauccgaaga guucuuuggc uggaaggaag ggcuacagca   4620
caagcgaugg caaaacuuuc ucauauuugg aagggaccaa guuucaccag gcggccaagg   4680
auauagcaga aauuaaugcc auguggcccg uugcaacgga ggccaaugag cagguaugca   4740
uguauauccu cggagaaagc augagcagua uuaggucgaa augccccguc gaagagucgg   4800
aagccuccac accaccuagc acgcugccuu gcuugugcau ccaugccaug acuccagaaa   4860
gaguacagcg ccuaaaagcc ucacguccag aacaaauuac ugugugcuca uccuuuccau   4920
ugccgaagua uagaaucacu ggugugcaga agauccaaug cucccagccu auauuguucu   4980
caccgaaagu gccugcguau auucauccaa ggaaguaucu cguggaaaca ccaccgguag   5040
acgagacucc ggagccaucg gcagagaacc aauccacaga ggggacaccu gaacaaccac   5100
cacuuauaac cgaggaugag accaggacua gaacgccuga gccgaucauc aucgaagagg   5160
aagaagagga uagcauaagu uugcugucag auggcccgac ccaccaggug cugcaagucg   5220
aggcagacau ucacgggccg cccucuguau cuagcucauc cugguccauu ccucaugcau   5280
ccgacuuuga uguggacagu uuauccauac uugacacccu ggagggagcu agcgugacca   5340
gcggggcaac gucagccgag acuaacucuu acuucgcaaa gaguauggag uuucuggcgc   5400
gaccggugcc ugcgccucga acaguauuca ggaacccucc acaucccgcu ccgcgcacaa   5460
gaacaccguc acuugcaccc agcagggccu gcucgagaac cagccuaguu uccaccccgc   5520
caggcgugaa uagggugauc acuagagagg agcucgaggc gcuuaccc
g ucacgcacuc   5580 cuagcagguc ggucucgaga accagccugg ucuccaaccc gccaggcgua aauaggguga   5640
uuacaagaga ggaguuugag gcguucguag cacaacaaca augacgguuu gaugcgggug   5700
cauacaucuu uuccuccgac accggucaag ggcauuuaca acaaaaauca guaaggcaaa   5760
cggugcuauc cgaaguggug uuggagagga ccgaauugga gauuucguau gccccgcgcc   5820
ucgaccaaga aaaagaagaa uuacuacgca agaaauuaca guuaaauccc acaccugcua   5880
acagaagcag auaccagucc aggaaggugg agaacaugaa agccauaaca gcuagacgua   5940
uucugcaagg ccuagggcau uauuugaagg cagaaggaaa aguggagugc uaccgaaccc   6000
ugcauccugu uccuuuguau ucaucuagug ugaaccgugc cuuuucaagc cccaaggucg   6060
caguggaagc cuguaacgcc auguugaaag agaacuuucc gacuguggcu ucuuacugua   6120
uuauuccaga guacgaugcc uauuuggaca ugguugacgg agcuucaugc ugcuuagaca   6180
cugccaguuu uugcccugca aagcugcgca gcuuuccaaa gaaacacucc uauuuggaac   6240
ccacaauacg aucggcagug ccuucagcga uccagaacac gcuccagaac guccuggcag   6300
cugccacaaa aagaaauugc aaugucacgc aaaugagaga auugcccgua uuggauucgg   6360
cggccuuuaa uguggaaugc uucaagaaau augcguguaa uaaugaauau ugggaaacgu   6420
uuaaagaaaa ccccaucagg cuuacugaag aaaacguggu aaauuacauu accaaauuaa   6480
aaggaccaaa agcugcugcu cuuuuugcga agacacauaa uuugaauaug uugcaggaca   6540
uaccaaugga cagguuugua auggacuuaa agagagacgu gaaagugacu ccaggaacaa   6600
aacauacuga agaacggccc aagguacagg ugauccaggc ugccgauccg cuagcaacag   6660
```

-continued

```
cguaucugug cggaauccac cgagagcugg uuaggagauu aaaugcgguc cugcuuccga    6720
acauucauac acuguuugau augucggcug aagacuuuga cgcuauuaua gccgagcacu    6780
uccagccugg ggauugaguu cuggaaacug acaucgcguc guuugauaaa agugaggacg    6840
acgccauggc ucugaccgcg uuaaugauuc uggaagacuu aggguguggac gcagagcugu    6900 ugacgcugau ugaggcggcu uucggcgaaa uuucaucaau acauuugccc acuaaaacua    6960
aauuuaaauu cggagccaug augaaaucug gaauguuccu cacacuguuu gugaacacag    7020
ucauuaacau uguaaucgca agcagagugu ugagagaacg gcuaaccgga ucaccaugug    7080
cagcauucau uggagaugac aauaucguga aaggagucaa aucggacaaa uuaauggcag    7140
acaggugcgc caccugguug aauauggaag ucaagauuau agaugcugug guggggcgaga    7200 aagcgccuua uuucugugga ggguuuauuu ugugugacuc cgugaccggc acagcgugcc    7260
guguggcaga cccccuaaaa aggcuguuua agcuuggcaa accucuggca gcagacgaug    7320
aacaugauga ugacaggaga aggggcauugc augaagaguc aacacgcugg aaccgagugg    7380
guauucuuuc agagcugugc aaggcaguag aaucaaggua ugaaaccgua ggaacuucca    7440
ucauaguuau ggccaugacu acucuagcua gcaguguuaa aucauucagc uaccugagag    7500
gggccccuau aacucucuac ggcuaaccug aauggacuac gacauagucu aguccgccaa    7560
gucuagcaua uguauggcca ccauggaaga ugccaagaac aucaagaagg gcccugcccc    7620
auucuacccc cuggaagaug gaacagccgg cgagcagcug cacaaggcca ugaagagaua    7680
cgcccuggug cccggcacaa ucgccuucac cgaugcccac aucgaggugg acaucaccua    7740
cgccgaguac uucgagauga gcgugcggcu ggccgaagcu augaagcgcu acggccugaa    7800
caccaaccac cggaucgucg ugugcagcga gaacagccug caguucuuca ugcccgugcu    7860
gggcgcccug uuuaucggag uggcuguggc cccugccaac gacaucuaca cgagcgcga    7920 gcugcugaac agcaugggca ucagccagcc caccguggug uucgugucca agaagggacu    7980
gcagaaaauc cugaacgugc agaagaagcu gcccaucauc cagaaaauca ucaucaugga    8040
cagcaagacc gacuaccagg gcuuccagag cauguacacc uucgugacca gccaucugcc    8100 cccugggcuuc aacgaguacg acuucgugcc cgagagcuuc gaccgggaca agacaaucgc    8160
ccugaucaug aacagcagcg gcagcaccgg acugccuaaa ggcguggccc ugccucacag    8220
aacugccugc gugcgguuua gccacgcccg ggacccuauc uucggcaacc agaucacccc    8280
cgacaccgcc auccugagcg uggugccuuu ccaccacggc uucggcaugu ucaccacccu    8340
gggcuaccug aucugcggcu uccgggugu gcugauguac agauucgagg aagaacuguu    8400
ccugcggagc cugcaggacu acaagaucca gagcgcccug cuggugccua cccuguucag    8460
cuucuuugcc aagagcaccc ugaucgauaa guacgaccug agcaaccugc acgagaucgc    8520
cucuggcgga gccccccugu cuaaagaagu gggagaggcc guggccaagc gguuccaucu    8580
gccuggcauc agacagggcu auggccugac cgagacaacc agcgccauuc ugaucaccccc    8640 cgagggcgac gauaagccug gcgccgugggg aaaggugguu ccauucuucg aggccaaggu    8700 ggugggaccug gacaccggca agacacuggg cgugaaccag aggggcgaac ugugugugcg    8760
gggaccuaug aucaugagcg gcuacgugaa caacccccgag gccaccaacg cccugauuga    8820
caaggauggc uggcugcaca gcggcgacau ugccuacugg gacgaggacg agcacuucuu    8880 caucgugggac cggcugaagu cccugaucaa guacaagggc uaccaggugg ccccagccga    8940
gcuggaaucu auccugcugc agcaccccaa caucuucgau gccggcgugg caggacugcc    9000
cgaugaugau gcuggcgaac ugccagccgc ugugguggug cuggaacacg gaaagaccau    9060
```

-continued

```
gaccgagaaa gaaaucgugg acuacguggc cagccaagug accaccgcca agaaacugag      9120
aggcggcgug uguuugugg  acgaggugcc aaagggccug acaggcaagc uggacgcccg      9180
gaagaucaga gagauccuga uuaaggccaa gaaaggcggc aagaucgccg uggaucggag      9240
aaagagaggc ucuggcgaag gcagaggcag ccugcuuaca uguggcgacg uggaagagaa      9300
ccccggaccu auggacuacg ugcccugcu  gaaccagauu uggcagaagu accugaacag      9360
ccccuacacc accugucugu acauccccaa gccuaccgcc aaguacacac cucucgguggg     9420 cacaucucug caccccgugc uguggaauug ccagcugagc uuugccggcu acaccgaguc      9480
ugccgugaac agcacaaagg cccuggccaa acaggacgcc gcucagagaa uugccuggcu      9540
gcugcacaag gauggcggca ucccugaugg cuguagccug uaccugagac acagcagccu      9600
guucgcccag agcgaggaag aggaauccuu cagcaacuga ugagcggccg cgaauuggca      9660
agcugcuuac auagaacucg cggcgauugg caugccgccu uaaaauuuuu auuuuauuuu      9720
ucuuuucuuu uccgaaucgg auuuuguuuu uaauauuuca aaaaaaaaaa aaaaaaaaaa      9780
aaaaaaaaaa aaaaaaaaaa aaaaaaaaaa aaaaaaaaaa aaaaaaaaaa aaaaaaaaaa      9840
aaaaaaaaaa aaaaaaaaaa aaaaaaaaaa aaaaaaaa                              9878
```

```
<210> SEQ ID NO 40
<211> LENGTH: 10217
<212> TYPE: DNA
<213> ORGANISM: Artificial Sequence
<220> FEATURE:
<223> OTHER INFORMATION: nucleic acid sequence encoding the RNA
      construct

<400> SEQUENCE: 40
atgggcggcg catgagagaa gcccagacca attacctacc caaaatggag aaagttcacg        60
ttgacatcga ggaagacagc ccattcctca gagctttgca gcggagcttc ccgcagtttg       120
aggtagaagc caagcaggtc actgataatg accatgctaa tgccagagcg ttttcgcatc       180
tggcttcaaa actgatcgaa acggaggtgg acccatccga cacgatcctt gacattggaa       240
gtgcgcccgc ccgcagaatg tattctaagc acaagtatca ttgtatctgt ccgatgagat       300
gtgcggaaga tccggacaga ttgtataagt atgcaactaa gctgaagaaa aactgtaagg       360
aaataactga taaggaattg gacaagaaaa tgaaggagct ggccgccgtc atgagcgacc       420
ctgacctgga aactgagact atgtgcctcc acgacgacga gtcgtgtcgc tacgaagggc       480
aagtcgctgt ttaccaggat gtatacgcgg ttgacggacc gacaagtctc tatcaccaag       540
ccaataaggg agttagagtc gcctactgga taggctttga caccaccccct tttatgttta      600 agaacttggc tggagcatat ccatcatact ctaccaactg gccgacgaa  accgtgttaa       660 cggctcgtaa cataggccta tgcagctctg acgttatgga gcggtcacgt agagggatgt       720
ccattcttag aaagaagtat ttgaaaccat ccaacaatgt tctattctct gttggctcga       780
ccatctacca cgagaagagg gacttactga ggagctggca cctgccgtct gtatttcact       840
tacgtggcaa gcaaaattac acatgtcggt gtgagactat agttagttgc gacgggtacg       900
tcgttaaaag aatagctatc agtccaggcc tgtatgggaa gccttcaggc tatgctgcta       960
cgatgcaccg cgagggattc ttgtgctgca aagtgacaga cacattgaac gggagaggg      1020 tctctttttcc cgtgtgcacg tatgtgccag ctacattgtg tgaccaaatg actggcatac     1080
tggcaacaga tgtcagtgcg gacgacgcgc aaaaactgct ggttgggctc aaccagcgta      1140
tagtcgtcaa cggtcgcacc cagagaaaca ccaataccat gaaaaattac cttttgcccg      1200
```

```
tagtggccca ggcatttgct aggtgggcaa aggaatataa ggaagatcaa gaagatgaaa      1260
ggccactagg actacgagat agacagttag tcatggggtg ttgttgggct tttagaaggc      1320
acaagataac atctatttat aagcgcccgg atacccaaac catcatcaaa gtgaacagcg      1380
atttccactc attcgtgctg cccaggatag gcagtaacac attggagatc gggctgagaa      1440
caagaatcag gaaaatgtta gaggagcaca aggagccgtc acctctcatt accgccgagg      1500
acgtacaaga agctaagtgc gcagccgatg aggctaagga ggtgcgtgaa gccgaggagt      1560
tgcgcgcagc tctaccacct ttggcagctg atgttgagga gcccactctg gaagccgatg      1620
tcgacttgat gttacaagag gctggggccg gctcagtgga gacacctcgt ggcttgataa      1680
aggttaccag ctacgatggc gaggacaaga tcggctctta cgctgtgctt tctccgcagg      1740
ctgtactcaa gagtgaaaaa ttatcttgca tccaccctct cgctgaacaa gtcatagtga      1800
taacacactc tggccgaaaa gggcgttatg ccgtggaacc ataccatggt aaagtagtgg      1860
tgccagaggg acatgcaata cccgtccagg actttcaagc tctgagtgaa agtgccacca      1920
ttgtgtacaa cgaacgtgag ttcgtaaaca ggtacctgca ccatattgcc acacatggag      1980
gagcgctgaa cactgatgaa gaatattaca aaactgtcaa gcccagcgag cacgacggcg      2040
aatacctgta cgacatcgac aggaaacagt gcgtcaagaa agaactagtc actgggctag      2100
ggctcacagg cgagctggtg gatcctccct tccatgaatt cgcctacgag agtctgagaa      2160
cacgaccagc cgctccttac caagtaccaa ccatagggt gtatggcgtg ccaggatcag      2220
gcaagtctgg catcattaaa agcgcagtca ccaaaaaaga tctagtggtg agcgccaaga      2280
aagaaaactg tgcagaaatt ataagggacg tcaagaaaat gaaagggctg gacgtcaatg      2340
ccagaactgt ggactcagtg ctcttgaatg gatgcaaaca ccccgtagag accctgtata      2400
ttgacgaagc ttttgcttgt catgcaggta ctctcagagc gctcatagcc attataagac      2460
ctaaaaaggc agtgctctgc ggggatccca aacagtgcgg ttttttttaac atgatgtgcc      2520 tgaaagtgca ttttaaccac gagatttgca cacaagtctt ccacaaaagc atctctcgcc      2580
gttgcactaa atctgtgact tcggtcgtct caaccttgtt ttacgacaaa aaaatgagaa      2640
cgacgaatcc gaaagagact aagattgtga ttgacactac cggcagtacc aaacctaagc      2700
aggacgatct cattctcact tgtttcagag ggtgggtgaa gcagttgcaa atagattaca      2760
aaggcaacga ataatgacg gcagctgcct ctcaagggct gacccgtaaa ggtgtgtatg      2820
ccgttcggta caaggtgaat gaaaatcctc tgtacgcacc cacctcagaa catgtgaacg      2880
tcctactgac ccgcacggag gaccgcatcg tgtggaaaac actagccggc gacccatgga      2940
taaaaacact gactgccaag taccctggga atttcactgc cacgatagag gagtggcaag      3000
cagagcatga tgccatcatg aggcacatct tggagagacc ggaccctacc gacgtcttcc      3060
agaataaggc aaacgtgtgt tgggccaagg ctttagtgcc ggtgctgaag accgctggca      3120
tagacatgac cactgaacaa tggaacactg tggattattt tgaaacggac aaagctcact      3180
cagcagagat agtattgaac caactatgcg tgaggttctt tggactcgat ctggactccg      3240
gtctattttc tgcacccact gttccgttat ccattaggaa taatcactgg gataactccc      3300
cgtcgcctaa catgtacggg ctgaataaag aagtggtccg tcagctctct cgcaggtacc      3360
cacaactgcc tcgggcagtt gccactggaa gagtctatga catgaacact ggtacactgc      3420
gcaattatga tccgcgcata aacctagtac ctgtaaacag aagactgcct catgctttag      3480
tcctccacca taatgaacac ccacagagtg acttttcttc attcgtcagc aaattgaagg      3540
```

-continued

```
gcagaactgt cctggtggtc ggggaaaagt tgtccgtccc aggcaaaatg gttgactggt    3600
tgtcagaccg gcctgaggct accttcagag ctcggctgga tttaggcatc ccaggtgatg    3660
tgcccaaata tgacataata tttgttaatg tgaggacccc atataaatac catcactatc    3720
agcagtgtga agaccatgcc attaagctta gcatgttgac caagaaagct tgtctgcatc    3780
tgaatcccgg cggaacctgt gtcagcatag gttatggtta cgctgacagg gccagcgaaa    3840
gcatcattgg tgctatagcg cggcagttca agttttcccg ggtatgcaaa ccgaaatcct    3900
cacttgaaga gacggaagtt ctgtttgtat tcattgggta cgatcgcaag gcccgtacgc    3960
acaattctta caagctttca tcaaccttga ccaacattta tacaggttcc agactccacg    4020
aagccggatg tgcaccctca tatcatgtgg tgcgagggga tattgccacg gccaccgaag    4080
gagtgattat aaatgctgct aacagcaaag gacaacctgg cggaggggtg tgcggagcgc    4140
tgtataagaa attcccggaa agcttcgatt tacagccgat cgaagtagga aaagcgcgac    4200
tggtcaaagg tgcagctaaa catatcattc atgccgtagg accaaacttc aacaaagttt    4260
cggaggttga aggtgacaaa cagttggcag aggcttatga gtccatcgct aagattgtca    4320
acgataacaa ttacaagtca gtagcgattc cactgttgtc caccggcatc ttttccggga    4380
acaaagatcg actaacccaa tcattgaacc atttgctgac agctttagac accactgatg    4440
cagatgtagc catatactgc agggacaaga aatgggaaat gactctcaag gaagcagtgg    4500
ctaggagaga agcagtggag gagatatgca tatccgacga ctcttcagtg acagaacctg    4560
atgcagagct ggtgagggtg catccgaaga gttctttggc tggaaggaag ggctacagca    4620
caagcgatgg caaaactttc tcatatttgg aagggaccaa gtttcaccag gcggccaagg    4680
atatagcaga aattaatgcc atgtggcccg ttgcaacgga ggccaatgag caggtatgca    4740
tgtatatcct cggagaaagc atgagcagta ttaggtcgaa atgccccgtc gaagagtcgg    4800
aagcctccac accacctagc acgctgcctt gcttgtgcat ccatgccatg actccagaaa    4860
gagtacagcg cctaaaagcc tcacgtccag aacaaattac tgtgtgctca tcctttccat    4920
tgccgaagta tagaatcact ggtgtgcaga agatccaatg ctcccagcct atattgttct    4980
caccgaaagt gcctgcgtat attcatccaa ggaagtatct cgtggaaaca ccaccggtag    5040
acgagactcc ggagccatcg gcagagaacc aatccacaga ggggacacct gaacaaccac    5100
cacttataac cgaggatgag accaggacta gaacgcctga gccgatcatc atcgaagagg    5160
aagaagagga tagcataagt ttgctgtcag atggcccgac ccaccaggtg ctgcaagtcg    5220
aggcagacat tcacgggccg ccctctgtat ctagctcatc ctggtccatt cctcatgcat    5280
ccgactttga tgtggacagt ttatccatac ttgacacccct ggagggagct agcgtgacca    5340
gcggggcaac gtcagccgag actaactctt acttcgcaaa gagtatggag tttctggcgc    5400
gaccggtgcc tgcgcctcga acagtattca ggaaccctcc acatcccgct ccgcgcacaa    5460
gaacaccgtc acttgcaccc agcagggcct gctcgagaac cagcctagtt tccaccccgc    5520
caggcgtgaa tagggtgatc actagagagg agctcgaggc gcttacccccg tcacgcactc    5580 ctagcaggtc ggtctcgaga accagcctgg tctccaaccc gccaggcgta aatagggtga    5640
ttacaagaga ggagtttgag gcgttcgtag cacaacaaca atgacggttt gatgcgggtg    5700
catacatctt ttcctccgac accggtcaag ggcatttaca acaaaaatca gtaaggcaaa    5760
cggtgctatc cgaagtggtg ttggagagga ccgaattgga gatttcgtat gccccgcgcc    5820
tcgaccaaga aaaagaagaa ttactacgca agaaattaca gttaaatccc acacctgcta    5880
acagaagcag ataccagtcc aggaaggtgg agaacatgaa agccataaca gctagacgta    5940
```

-continued

```
ttctgcaagg cctagggcat tatttgaagg cagaaggaaa agtggagtgc taccgaaccc      6000
tgcatcctgt tcctttgtat tcatctagtg tgaaccgtgc cttttcaagc cccaaggtcg      6060
cagtggaagc ctgtaacgcc atgttgaaag agaactttcc gactgtggct tcttactgta      6120
ttattccaga gtacgatgcc tatttggaca tggttgacgg agcttcatgc tgcttagaca      6180
ctgccagttt ttgccctgca aagctgcgca gctttccaaa gaaacactcc tatttggaac      6240
ccacaatacg atcggcagtg ccttcagcga tccagaacac gctccagaac gtcctggcag      6300
ctgccacaaa aagaaattgc aatgtcacgc aaatgagaga attgcccgta ttggattcgg      6360
cggcctttaa tgtggaatgc ttcaagaaat atgcgtgtaa taatgaatat tgggaaacgt      6420
ttaaagaaaa ccccatcagg cttactgaag aaaacgtggt aaattacatt accaaattaa      6480
aaggaccaaa agctgctgct cttttttgcga agacacataa tttgaatatg ttgcaggaca      6540
taccaatgga caggtttgta atggacttaa agagagacgt gaaagtgact ccaggaacaa      6600
aacatactga agaacggccc aaggtacagg tgatccaggc tgccgatccg ctagcaacag      6660
cgtatctgtg cggaatccac cgagagctgg ttaggagatt aaatgcggtc ctgcttccga      6720
acattcatac actgtttgat atgtcggctg aagactttga cgctattata gccgagcact      6780
tccagcctgg ggattgtgtt ctggaaactg acatcgcgtc gtttgataaa agtgaggacg      6840
acgccatggc tctgaccgcg ttaatgattc tggaagactt aggtgtggac gcagagctgt      6900
tgacgctgat tgaggcggct ttcggcgaaa tttcatcaat acatttgccc actaaaacta      6960
aatttaaatt cggagccatg atgaaatctg gaatgttcct cacactgttt gtgaacacag      7020
tcattaacat tgtaatcgca agcagagtgt tgagagaacg gctaaccgga tcaccatgtg      7080
cagcattcat tggagatgac aatatcgtga aaggagtcaa atcggacaaa ttaatggcag      7140
acaggtgcgc cacctggttg aatatggaag tcaagattat agatgctgtg gtgggcgaga      7200
aagcgcctta tttctgtgga gggtttattt tgtgtgactc cgtgaccggc acagcgtgcc      7260
gtgtggcaga ccccctaaaa aggctgttta agcttggcaa acctctggca gcagacgatg      7320
aacatgatga tgacaggaga agggcattgc atgaagagtc aacacgctgg aaccgagtgg      7380
gtattctttc agagctgtgc aaggcagtag aatcaaggta tgaaaccgta ggaacttcca      7440
tcatagttat ggccatgact actctagcta gcagtgttaa atcattcagc tacctgagag      7500
gggcccctat aactctctac ggctaacctg aatggactac gacatagtct agtccgccaa      7560
gtctagcata tgtatggcca ccatggaaga tgccaagaac atcaagaagg ccctgccccc      7620
attctacccc ctggaagatg gaacagccgg cgagcagctg cacaaggcca tgaagagata      7680
cgccctggtg cccggcacaa tcgccttcac cgatgcccac atcgaggtgg acatcacccta      7740 cgccgagtac ttcgagatga gcgtgcgcgt ggccgaagct atgaagcgct acggcctgaa      7800
caccaaccac cggatcgtcg tgtgcagcga gaacagcctg cagttcttca tgcccgtgct      7860
gggcgccctg tttatcggag tggctgtggc ccctgccaac gacatctaca acgagcgcga      7920
gctgctgaac agcatgggca tcagccagcc caccgtggtg ttcgtgtcca gaaagggact      7980
gcagaaaatc ctgaacgtgc agaagaagct gcccatcatc cagaaaatca tcatcatgga      8040
cagcaagacc gactaccagg gcttccagag catgtacacc ttcgtgacca gccatctgcc      8100
ccctggcttc aacgagtacg acttcgtgcc cgagagcttc gaccgggaca agacaatcgc      8160
cctgatcatg aacagcagcg gcagcaccgg actgcctaaa ggcgtggccc tgcctcacag      8220
aactgcctgc gtgcggttta gccacgcccg ggaccctatc ttcggcaacc agatcatccc      8280
```

-continued

```
cgacaccgcc atcctgagcg tggtgccttt ccaccacggc ttcggcatgt tcaccaccct      8340
gggctacctg atctgcggct tccgggtggt gctgatgtac agattcgagg aagaactgtt      8400
cctgcggagc ctgcaggact acaagatcca gagcgccctg ctggtgccta ccctgttcag      8460
cttctttgcc aagagcaccc tgatcgataa gtacgacctg agcaacctgc acagagatcgc      8520 ctctggcgga gcccccctgt ctaaagaagt gggagaggcc gtggccaagc ggttccatct      8580
gcctggcatc agacagggct atggcctgac cgagacaacc agcgccattc tgatcacccc      8640
cgagggcgac gataagcctg cgccgtggg aaaggtggtg ccattcttcg aggccaaggt      8700
ggtggacctg acaccggca agacactggg cgtgaaccag aggggcgaac tgtgtgtgcg      8760
gggacctatg atcatgagcg gctacgtgaa caaccccgag gccaccaacg ccctgattga      8820
caaggatggc tggctgcaca gcggcgacat tgcctactgg gacgaggacg agcacttctt      8880
catcgtggac cggctgaagt ccctgatcaa gtacaagggc taccaggtgg ccccagccga      8940
gctggaatct atcctgctgc agcaccccaa catcttcgat gccggcgtgg caggactgcc      9000
cgatgatgat gctggcgaac tgccagccgc tgtggtggtg ctggaacacg aaagaccat      9060 gaccgagaaa gaaatcgtgg actacgtggc cagccaagtg accaccgcca agaaactgag      9120
aggcggcgtg gtgtttgtgg acgaggtgcc aaagggcctg acaggcaagc tggacgcccg      9180
gaagatcaga gagatcctga ttaaggccaa gaaaggcggc aagatcgccg tggatcggag      9240
aaagagaggc tctggcgaag gcagaggcag cctgcttaca tgtggcgacg tggaagagaa      9300
ccccggacct atggacccta ccgacctgag cttcagcccc gacgagatca caagctgat      9360 cgagacaggc ctgaacaccg tggaatactt caccagccag caagtgaccg gcacaagcag      9420
cctgggcaag aacacaattc ctccaggcgt gaccggcctg ctgacaaatg ctgccgaggc      9480
caagatccaa gagagcacca accaccagaa gggctctgtt ggaggcggag ccaagcctaa      9540
gaagcccaga cctaagatcg ccatcgtgcc cgccgacgat aagacagtgc ctggcaagcc      9600
cattcctaat cctctgctgg gcctcgacag caccccctagc acacagacag tgctggatct      9660
gagcggcaag acactgccta cggcagcta taagggcgtg aagctggcca agttcggcaa      9720
agaaaacctg atgacccggt tcatcgagga acccagagag aaccctatcg ccaccagctc      9780
tcccatcgac ttcaagagag gcagagacac cggcggcttc cacagaagag agtacagcat      9840
tggctgggtc ggagatgaag tgaaagtgac cgagtggtgc aacccccagct gcagccctat      9900 tacagccgcc gctagaagat tcgagtgcac ctgtcaccag tgtcctgtga cctgtagcga      9960
gtgcgagcgg gacacatgat gagcggccgc gaattggcaa gctgcttaca tagaactcgc      10020
ggcgattggc atgccgcctt aaaattttta ttttattttt cttttctttt ccgaatcgga      10080
ttttgttttt aatatttcaa aaaaaaaaaa aaaaaaaaaa aaaaaaaaaa aaaaaaaaaa      10140
aaaaaaaaaa aaaaaaaaaa aaaaaaaaaa aaaaaaaaaa aaaaaaaaaa aaaaaaaaaa      10200
aaaaaaaaaa aaaaaaa                                                        10217
```

<210> SEQ ID NO 41
<211> LENGTH: 9878
<212> TYPE: DNA
<213> ORGANISM: Artificial Sequence
<220> FEATURE:
<223> OTHER INFORMATION: nucleic acid sequence encoding RNA construct

<400> SEQUENCE: 41

```
atgggcggcg catgagagaa gcccagacca attacctacc caaaatggag aaagttcacg      60
ttgacatcga ggaagacagc ccattcctca gagctttgca gcggagcttc ccgcagtttg      120
```

```
aggtagaagc caagcaggtc actgataatg accatgctaa tgccagagcg ttttcgcatc        180
tggcttcaaa actgatcgaa acggaggtgg acccatccga cacgatcctt gacattggaa        240
gtgcgcccgc ccgcagaatg tattctaagc acaagtatca ttgtatctgt ccgatgagat        300
gtgcggaaga tccggacaga ttgtataagt atgcaactaa gctgaagaaa aactgtaagg        360
aaataactga taaggaattg gacaagaaaa tgaaggagct ggccgccgtc atgagcgacc        420
ctgacctgga aactgagact atgtgcctcc acgacgacga gtcgtgtcgc tacgaagggc        480
aagtcgctgt ttaccaggat gtatacgcgg ttgacggacc gacaagtctc tatcaccaag        540
ccaataaggg agttagagtc gcctactgga taggctttga caccacccct tttatgttta        600
agaacttggc tggagcatat ccatcatact ctaccaactg ggccgacgaa accgtgttaa        660
cggctcgtaa cataggccta tgcagctctg acgttatgga gcggtcacgt agagggatgt        720
ccattcttag aaagaagtat ttgaaaccat ccaacaatgt tctattctct gttggctcga        780
ccatctacca cgagaagagg gacttactga ggagctggca cctgccgtct gtatttcact        840
tacgtggcaa gcaaaattac acatgtcggt gtgagactat agttagttgc gacgggtacg        900
tcgttaaaag aatagctatc agtccaggcc tgtatgggaa gccttcaggc tatgctgcta        960
cgatgcaccg cgagggattc ttgtgctgca aagtgacaga cacattgaac ggggagaggg       1020
tctcttttcc cgtgtgcacg tatgtgccag ctacattgtg tgaccaaatg actggcatac       1080
tggcaacaga tgtcagtgcg gacgacgcgc aaaaactgct ggttgggctc aaccagcgta       1140
tagtcgtcaa cggtcgcacc cagagaaaca ccaataccat gaaaaattac cttttgcccg       1200
tagtggccca ggcatttgct aggtgggcaa aggaatataa ggaagatcaa gaagatgaaa       1260
ggccactagg actacgagat agacagttag tcatgggggtg ttgttgggct tttagaaggc       1320
acaagataac atctatttat aagcgcccgg atacccaaac catcatcaaa gtgaacagcg       1380
atttccactc attcgtgctg cccaggatag gcagtaacac attggagatc gggctgagaa       1440
caagaatcag gaaaatgtta gaggagcaca aggagccgtc acctctcatt accgccgagg       1500
acgtacaaga agctaagtgc gcagccgatg aggctaagga ggtgcgtgaa gccgaggagt       1560
tgcgcgcagc tctaccacct ttggcagctg atgttgagga gcccactctg gaagccgatg       1620
tcgacttgat gttacaagag gctggggccg gctcagtgga gacacctcgt ggcttgataa       1680
aggttaccag ctacgatggc gaggacaaga tcggctctta cgctgtgctt tctccgcagg       1740
ctgtactcaa gagtgaaaaa ttatcttgca tccaccctct cgctgaacaa gtcatagtga       1800
taacacactc tggccgaaaa gggcgttatg ccgtggaacc ataccatggt aaagtagtgg       1860
tgccagaggg acatgcaata cccgtccagg actttcaagc tctgagtgaa agtgccacca       1920
ttgtgtacaa cgaacgtgag ttcgtaaaca ggtacctgca ccatattgcc acacatggag       1980
gagcgctgaa cactgatgaa gaatattaca aaactgtcaa gcccagcgag cacgacggcg       2040
aatacctgta cgacatcgac aggaaacagt gcgtcaagaa agaactagtc actgggctag       2100
ggctcacagg cgagctggtg gatcctccct tccatgaatt cgcctacgag agtctgagaa       2160
cacgaccagc cgctccttac caagtaccaa ccataggggt gtatggcgtg ccaggatcag       2220
gcaagtctgg catcattaaa agcgcagtca ccaaaaaaga tctagtggtg agcgccaaga       2280
aagaaaactg tgcagaaatt ataagggacg tcaagaaaat gaaagggctg gacgtcaatg       2340
ccagaactgt ggactcagtg ctcttgaatg gatgcaaaca ccccgtagag accctgtata       2400
ttgacgaagc ttttgcttgt catgcaggta ctctcagagc gctcatagcc attataagac       2460
```

```
ctaaaaaggc agtgctctgc ggggatccca aacagtgcgg ttttttttaac atgatgtgcc   2520 tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaattctta caagctttca tcaaccttga ccaacatttta tacaggttcc agactccacg   4020
aagccggatg tgcaccctca tatcatgtgg tgcgaggggga tattgccacg gccaccgaag   4080
gagtgattat aaatgctgct aacagcaaag gacaacctgg cggaggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaactc aacaaagttt   4260 cggaggttga aggtgacaaa cagttggcag aggcttatga gtccatcgct aagattgtca   4320
acgataacaa ttacaagtca gtagcgattc cactgttgtc caccggcatc tttttccggga   4380 acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
```

-continued

```
gagtacagcg cctaaaagcc tcacgtccag aacaaattac tgtgtgctca tcctttccat      4920
tgccgaagta tagaatcact ggtgtgcaga agatccaatg ctcccagcct atattgttct      4980
caccgaaagt gcctgcgtat attcatccaa ggaagtatct cgtggaaaca ccaccggtag      5040
acgagactcc ggagccatcg gcagagaacc aatccacaga ggggacacct gaacaaccac      5100
cacttataac cgaggatgag accaggacta gaacgcctga gccgatcatc atcgaagagg      5160
aagaagagga tagcataagt ttgctgtcag atggcccgac ccaccaggtg ctgcaagtcg      5220
aggcagacat tcacgggccg ccctctgtat ctagctcatc ctggtccatt cctcatgcat      5280
ccgactttga tgtggacagt ttatccatac ttgacaccct ggaggagct agcgtgacca      5340 gcggggcaac gtcagccgag actaactctt acttcgcaaa gagtatggag tttctggcgc      5400
gaccggtgcc tgcgcctcga acagtattca ggaaccctcc acatcccgct ccgcgcacaa      5460
gaacaccgtc acttgcaccc agcagggcct gctcgagaac cagcctagtt tccaccccgc      5520
caggcgtgaa tagggtgatc actagagagg agctcgaggc gcttaccccg tcacgcactc      5580
ctagcaggtc ggtctcgaga accagcctgg tctccaaccc gccaggcgta aatagggtga      5640
ttacaagaga ggagtttgag gcgttcgtag cacaacaaca atgacggttt gatgcgggtg      5700
catacatctt ttcctccgac accggtcaag ggcatttaca acaaaaatca gtaaggcaaa      5760
cggtgctatc cgaagtggtg ttggagagga ccgaattgga gatttcgtat gccccgcgcc      5820
tcgaccaaga aaaagaagaa ttactacgca agaaattaca gttaaatccc acacctgcta      5880
acagaagcag ataccagtcc aggaaggtgg agaacatgaa agccataaca gctagacgta      5940
ttctgcaagg cctagggcat tatttgaagg cagaaggaaa agtggagtgc taccgaaccc      6000
tgcatcctgt tcctttgtat tcatctagtg tgaaccgtgc cttttcaagc cccaaggtcg      6060
cagtggaagc ctgtaacgcc atgttgaaag agaactttcc gactgtggct tcttactgta      6120
ttattccaga gtacgatgcc tatttggaca tggttgacgg agcttcatgc tgcttagaca      6180
ctgccagttt ttgccctgca aagctgcgca gctttccaaa gaaacactcc tatttggaac      6240
ccacaatacg atcggcagtg ccttcagcga tccagaacac gctccagaac gtcctggcag      6300
ctgccacaaa aagaaattgc aatgtcacgc aaatgagaga attgcccgta ttggattcgg      6360
cggcctttaa tgtggaatgc ttcaagaaat atgcgtgtaa taatgaatat tgggaaacgt      6420
ttaaagaaaa ccccatcagg cttactgaag aaaacgtggt aaattacatt accaaattaa      6480
aaggaccaaa agctgctgct ctttttgcga agacacataa tttgaatatg ttgcaggaca      6540
taccaatgga caggtttgta atggacttaa agagagacgt gaaagtgact ccaggaacaa      6600
aacatactga agaacggccc aaggtacagg tgatccaggc tgccgatccg ctagcaacag      6660
cgtatctgtg cggaatccac cgagagctgg ttaggagatt aaatgcggtc ctgcttccga      6720
acattcatac actgtttgat atgtcggctg aagactttga cgctattata gccgagcact      6780
tccagcctgg ggattgtgtt ctggaaactg acatcgcgtc gtttgataaa agtgaggacg      6840
acgccatggc tctgaccgcg ttaatgattc tggaagactt aggtgtggac gcagagctgt      6900
tgacgctgat tgaggcggct ttcggcgaaa tttcatcaat acatttgccc actaaaacta      6960
aatttaaatt cggagccatg atgaaatctg gaatgttcct cacactgttt gtgaacacag      7020
tcattaacat tgtaatcgca agcagagtgt tgagagaacg gctaaccgga tcaccatgtg      7080
cagcattcat tggagatgac aatatcgtga aaggagtcaa atcggacaaa ttaatggcag      7140
acaggtgcgc cacctggttg aatatggaag tcaagattat agatgctgtg gtgggcgaga      7200
```

-continued

```
aagcgcctta tttctgtgga gggtttattt tgtgtgactc cgtgaccggc acagcgtgcc     7260
gtgtggcaga cccctaaaa aggctgttta agcttggcaa acctctggca gcagacgatg     7320
aacatgatga tgacaggaga agggcattgc atgaagagtc aacacgctgg aaccgagtgg     7380
gtattctttc agagctgtgc aaggcagtag aatcaaggta tgaaaccgta ggaacttcca     7440
tcatagttat ggccatgact actctagcta gcagtgttaa atcattcagc tacctgagag     7500
gggcccctat aactctctac ggctaacctg aatggactac gacatagtct agtccgccaa     7560
gtctagcata tgtatggcca ccatggaaga tgccaagaac atcaagaagg ccctgcccc     7620 attctacccc ctggaagatg gaacagccgg cgagcagctg cacaaggcca tgaagagata     7680
cgccctggtg cccggcacaa tcgccttcac cgatgcccac atcgaggtgg acatcaccta     7740
cgccgagtac ttcgagatga gcgtgcggct ggccgaagct atgaagcgct acggcctgaa     7800
caccaaccac cggatcgtcg tgtgcagcga gaacagcctg cagttcttca tgcccgtgct     7860
gggcgccctg tttatcggag tggctgtggc ccctgccaac gacatctaca acgagcgcga     7920
gctgctgaac agcatgggca tcagccagcc caccgtggtg ttcgtgtcca agaagggact     7980
gcagaaaatc ctgaacgtgc agaagaagct gcccatcatc cagaaaatca tcatcatgga     8040
cagcaagacc gactaccagg gcttccagag catgtacacc ttcgtgacca gccatctgcc     8100
ccctggcttc aacgagtacg acttcgtgcc cgagagcttc gaccgggaca agacaatcgc     8160
cctgatcatg aacagcagcg gcagcaccgg actgcctaaa ggcgtggccc tgcctcacag     8220
aactgcctgc gtgcggttta gccacgcccg ggaccctatc ttcggcaacc agatcatccc     8280
cgacaccgcc atcctgagcg tggtgccttt ccaccacggc ttcggcatgt tcaccaccct     8340
gggctacctg atctgcggct tccgggtggt gctgatgtac agattcgagg aagaactgtt     8400 cctgcgggagc ctgcaggact acaagatcca gagcgccctg ctggtgccta ccctgttcag     8460
cttctttgcc aagagcaccc tgatcgataa gtacgacctg agcaacctgc acgagatcgc     8520
ctctggcgga gccccctgt ctaaagaagt gggagaggcc gtggccaagc ggttccatct     8580
gcctggcatc agacagggct atggcctgac cgagacaacc agcgccattc tgatcacccc     8640
cgagggcgac gataagcctg gcgccgtggg aaaggtggtg ccattcttcg aggccaaggt     8700
ggtggacctg gacaccggca agacactggg cgtgaaccag aggggcgaac tgtgtgtgcg     8760
gggacctatg atcatgagcg gctacgtgaa caaccccgag gccaccaacg ccctgattga     8820
caaggatggc tggctgcaca gcggcgacat tgcctactgg gacgaggacg agcacttctt     8880
catcgtggac cggctgaagt ccctgatcaa gtacaagggc taccaggtgg ccccagccga     8940
gctggaatct atcctgctgc agcacccccaa catcttcgat gccggcgtgg caggactgcc     9000
cgatgatgat gctggcgaac tgccagccgc tgtggtggtg ctggaacacg aaaagaccat     9060
gaccgagaaa gaaatcgtgg actacgtggc cagccaagtg accaccgcca agaaactgag     9120
aggcggcgtg gtgtttgtgg acgaggtgcc aaagggcctg acaggcaagc tggacgcccg     9180
gaagatcaga gagatcctga ttaaggccaa gaaaggcggc aagatcgccg tggatcggag     9240
aaagagaggc tctggcgaag gcagaggcag cctgcttaca tgtggcgacg tggaagagaa     9300
ccccggacct atggactacg tgtccctgct gaaccagatt tggcagaagt acctgaacag     9360
cccctacacc acctgtctgt acatccccaa gcctaccgcc aagtacacac tctcgtgggg     9420
cacatctctg caccccgtgc tgtggaattg ccagctgagc tttgccggct acaccgagtc     9480
tgccgtgaac agcacaaagg ccctggccaa acaggacgcc gctcagagaa ttgcctggct     9540
gctgcacaag gatggcggca tccctgatgg ctgtagcctg tacctgagac acagcagcct     9600
```

-continued

```
gttcgcccag agcgaggaag aggaatcctt cagcaactga tgagcggccg cgaattggca    9660
agctgcttac atagaactcg cggcgattgg catgccgcct taaaattttt attttatttt    9720 tctttttcttt tccgaatcgg attttgtttt taatatttca aaaaaaaaaa aaaaaaaaaa    9780
aaaaaaaaaa aaaaaaaaaa aaaaaaaaaa aaaaaaaaaa aaaaaaaaaa aaaaaaaaaa    9840
aaaaaaaaaa aaaaaaaaaa aaaaaaaaaa aaaaaaaa                              9878
```

```
<210> SEQ ID NO 42
<211> LENGTH: 588
<212> TYPE: RNA
<213> ORGANISM: human herpesvirus 2

<400> SEQUENCE: 42
```

```
gugagagacu gcuaccugau gggcuacugc cggacaagac ugggaccuag aacauggggc      60
agacugcugc agaucagcgg cggaacaugg gaugugcggc ugagaaacgc caucagagag     120
guggaagccc acuucgagcc ugccgcugaa ccugugugug aacugcccug ucugaacgcu     180
agaagauacg gcccugagug cgacgugggc aaccuggaaa caaauggcgg cagcaccagc     240
gacgacgaga uuuccgaugc caccgacagc gacgauacac uggccagcca cagcgauaca     300
gaaggcggac caucuccugc cggaagagag aauccugagu cugccucugg cggagccauu     360
gccgcuagac uggaaugcga guucggcacc uucgacugga caagcgagga aggcucucag     420
ccuuggcugu cugcuguggu ggccgauaca agcucugccg agagaagugg acuuccugcu     480
ccuggcgccu guagagcuac agaggcuccu gaaagagagg acggcugcag aaagaugcgg     540
uucccugccg ccuguccuua uccuugcggc cacacauuuc ugcggccc                   588
```

```
<210> SEQ ID NO 43
<211> LENGTH: 1191
<212> TYPE: RNA
<213> ORGANISM: human herpesvirus 1

<400> SEQUENCE: 43
```

```
gugagagacu gcuaccugau gggcuacugc cggacaagac ugggaccuag aacauggggc      60
agacugcugc agaucagcgg cggaacaugg gaugugcggc ugagaaacgc caucagagag     120
guggaagccc acuucgagcc ugccgcugaa ccugugugug aacugcccug ucugaacgcu     180
agaagauacg gcccugagug cgacgugggc aaccuggaaa caaauggcgg cagcaccagc     240
gacgacgaga uuuccgaugc caccgacagc gacgauacac uggccagcca cagcgauaca     300
gaaggcggac caucuccugc cggaagagag aauccugagu cugccucugg cggagccauu     360
gccgcuagac uggaaugcga guucggcacc uucgacugga caagcgagga aggcucucag     420
ccuuggcugu cugcuguggu ggccgauauc agagacugcu accugauggg cuacugccgg     480
gcuagacugg ccccuagaac auggugcaga cugcugcaag ugucuggcgg cacauggggc     540
augcaccuga gaaacaccau cagagaggug gaagccagau cgacgccac agccgagccu     600 gugugcaagc ugccuugucu ggaaacucgg agauacggcc ccgagugcga ccugagcaau     660
cuggaaauuc accugagcgc caccagcgac gacgagauuu cugaugccac cgaccuggaa     720
gccgccggau cugaucauac acuggccagc cagagcgaca ccgaggaugc uccaucucca     780
gugacucugg aaaccccuga gccuagagga ucucuggccg ugcgacugga agaugaguuc     840
ggcgaguucg acuggacccc ucaagaggga ucucagccuu ggcugucugc cguggugggc     900
gauacaagca gcguggaaag acccggaccu agcgauucug gugcuggcag agccgccgag     960
```

-continued

```
gauagaaagu gccuggaugg cugccggaag augcgguucu cuaccgccug uccauauccu    1020
ugcagcgaca ccuuccugcg gccuugauaa acaagcucug ccgagagaag uggacuuccu    1080
gcuccuggcg ccuguagagc uacagaggcu ccugaaagag aggacggcug cagaaagaug    1140
cgguucccug ccgccugucc uuauccuugc ggccacacau uucugcggcc c             1191
```

```
<210> SEQ ID NO 44
<211> LENGTH: 483
<212> TYPE: RNA
<213> ORGANISM: human herpesvirus 1

<400> SEQUENCE: 44
augagccaga cacagccucc agcuccaguu ggaccuggcg acccugaugu guaucugaag     60
ggcgugccaa cgccggcau gcauccuaga ggguguucaug ccccuagagg acaccccaga    120
augaucucug gcccuccuca gagaggcgac aacgaucagg cugcuggaca guguggcgau    180
agcggacugc ugagagugggg cgccgauacc acaaucagca agccaucuga ggcugugcgg    240
ccuccuacaa uccccagaac accuagagug ccccgcgagc caagagugcc uagaccuccu    300
agagagccca gagaacccag agugccaagg gcucccagag auccuagagu cccucgggac    360
ccuagggacc caagacaacc uagaucaccc agagagccuc ggagcccaag agagccaaga    420
agcccuaggg aaccccggac accaagaaca cccagggaac cuagaaccgc cagaggcagc    480
gug                                                                  483
```

```
<210> SEQ ID NO 45
<211> LENGTH: 549
<212> TYPE: RNA
<213> ORGANISM: Orf virus

<400> SEQUENCE: 45
auggccugug aaugcgccag ccugauccug gaacugcuga gaaagagcga cgacaagcug     60
cccgccaagc agaucgccaa agagcugggc aucucuaagc acgaggccaa ccggcagcug    120
uaccggcugc uggauucuga cgaagugugc ugcgaggacg gcaauccucc ucguuggbuc    180
guggaaugug ccccuagcgc ucccaccgaa gaggacgaga auagcgacac cgagccuaug    240
gaaaccgagg ccggcugcga uacacuguuu ggcggagaca ucgacaucau gacccagagc    300
gccgugaucc ggcugaaguc ccugaauccu guguccgccg ugaacgaguu cugcaugaug    360
acccaccggc cucuggaauu uugcgagaca agagccggcg gagaggauca cugccccaga    420
uucaccugua ccaucaccau cagcggcaag guggugggcug uugccgaugg cgccucuaag    480
aaacuggcca gacacaccgc cuguagcagc gcccugacaa uccugaucaa caacugcggc    540
aucagcuuc                                                            549
```

```
<210> SEQ ID NO 46
<211> LENGTH: 504
<212> TYPE: RNA
<213> ORGANISM: pestivirus type 1

<400> SEQUENCE: 46
auggaacuga ucaccaacga gcugcuguac aagaccuaca gcagaaaacc cguggggcguc     60 gaggaacccg uguaugauca gcuggcgac ccucuguuug gcgagagagg cgcuguucac    120
ccucagagca cacugaagcu gccccacaag cggggcgaaa gagaugugcc uaccaaccug    180
gccagccugc cuaagagagg cgauugcaga accggcaaua gcagaggccc uguguccggc    240
aucuaccuga aaccuggacc acuguucuac caggacuaca agggacccgu guaccacaga    300
```

```
gccccucugg aacuguuuga agagggcagc augugcgaaa ccaccaagcg gaucggaaga     360
gugaccggcu cugacggcaa gcuguaccac aucuacgugu gcaucgacgg cugcaucauc     420
aucaagagcg ccaccagauc cuaccagcgg guguucagau gggugcacaa cagacuggac     480 ugccccucugu gggucaccag cugc                                          504

<210> SEQ ID NO 47
<211> LENGTH: 666
<212> TYPE: RNA
<213> ORGANISM: Simian parainfluenza virus 5

<400> SEQUENCE: 47
auggacccua ccgaccugag cuucagcccc gacgagauca acaagcugau cgagacaggc      60
cugaacaccg uggaauacuu caccagccag caagugaccg gcacaagcag ccugggcaag     120
aacacaauuc cuccaggcgu gaccggccug cugacaaaug cugccgaggc caagauccaa     180
gagagcacca accaccagaa gggcucuguu ggaggcggag ccaagccuaa gaagcccaga     240
ccuaagaucg ccaucgugcc cgccgacgau aagacagugc cuggcaagcc cauuccuaau     300
ccucugcugg gccucgacag cacccccuagc acacagacag ugcuggaucu gagcggcaag     360
acacugccua gcggcagcua uaagggcgug aagcuggcca aguucggcaa agaaaaccug     420
augacccggu ucaucgagga acccagagag aacccuaucg ccaccagcuc ucccaucgac     480
uucaagagag gcagagacac cggcggcuuc cacagaagag aguacagcau uggcuggguc     540
ggagaugaag ugaaagugac cgaguggugc aaccccagcu gcagcccuau uacagccgcc     600
gcuagaagau ucgagugcac cugucaccag uguccuguga ccuguagcga gugcgagcgg     660
gacaca                                                               666

<210> SEQ ID NO 48
<211> LENGTH: 327
<212> TYPE: RNA
<213> ORGANISM: Middle East respiratory syndrome related coronavirus

<400> SEQUENCE: 48
auggacuacg ugcccugcu gaaccagauu uggcagaagu accugaacag ccccuacacc      60
accugucugu acauccccaa gccuaccgcc aaguacacac cucucgugggg cacaucucug     120 caccccgugc uguggaauug ccagcugagc uuugccggcu acaccgaguc ugccgugaac     180
agcacaaagg cccuggccaa acaggacgcc gcucagagaa uugccuggcu gcugcacaag     240
gauggcggca ucccugaugg cuguagccug uaccugagac acagcagccu guucgcccag     300
agcgaggaag aggaauccuu cagcaac                                        327

<210> SEQ ID NO 49
<211> LENGTH: 1143
<212> TYPE: RNA
<213> ORGANISM: Langat virus

<400> SEQUENCE: 49
guguucaagg acaaggugga caccaaggcu caagagccuc agccuggcac caagaucauc      60
augagagccg ugaacgacug gcugcuggaa cggcugguca agaaaagcag accccggaug     120
ugcagccggg aagaguuuau cgccaaagug cggagcaaug ccgcucucgg agcuuggagu     180
gacgagcaga acaaguggaa guccgccaga gaagccgugg aagaucccga guuuuggagc     240 cuggguggaag ccgagagaga gaggcaucug cagggaagau gugcccacug cguguacaac     300
```

-continued

```
augaugggca agagagagaa gaagcugggc gaguucggag uggccaaagg cagcagagcc        360
aucugguaua uguggcuggg cagccgcuuc cuggaauuug aggcccuggg cuuccugaac        420
gaggaucacu gggcuagcag agccucuucu ggugcuggcg uggaaggcau cagccugaau        480
uaucucggcu ggcaccugaa gaaacuggcc ucucugucug cggccuguu cuacgccgau         540 gauacagccg gaugggacac aaagaucacc aacgccgacc uggacgacga ggaacagauc        600
cugagauaua uggacggcga ccacaaaaag cuggccgcca ccgugcugag aaaggccuau       660
cacgccaagg ucgucagagu ggccagaccu aguagagaag gcggcugcgu gauggacauc        720
aucaccagaa gggaccagcg cggcucuggc cagguuguga cauacgcccu gaacaccauc        780
accaacauca aggugcagcu cgugcggaug auggaaggcg agggcgugau cgaaguggcc        840
gacagccaua auccucggcu gcugagagug gaaaaguggc uggaagaaca cggcgaagaa        900
cggcugagca gaaugcuggu guccggcgac gauuguguug ugcggcccgu ggacgacaga        960
uucagcaagg cccuguacuu ucugaaugac auggccaaga ccagaaagga caccggcgag       1020
ugggagccuu cuacaggcuu ugccagcugg gaagaagugc cuuucugcag ccaccacuuc       1080
cacgagcugg ucaugaagga uggcagagcc cugguggugc ccugcagaga ucaggacgaa       1140
cug                                                                     1143
```

<210> SEQ ID NO 50
<211> LENGTH: 1605
<212> TYPE: RNA
<213> ORGANISM: Artificial Sequence
<220> FEATURE:
<223> OTHER INFORMATION: nsP1 RNA sequence

<400> SEQUENCE: 50

```
auggagaaag uucacguuga caucgaggaa gacagcccau uccucagagc uuugcagcgg        60
agcuucccgc aguuugaggu agaagccaag caggucacug auaaugacca ugcuaaugcc        120
agagcguuuu cgcaucuggc uucaaaacug aucgaaacgg aggugacc auccgacacg          180 auccuugaca uuggaagugc gcccgcccgc agaauguauu cuaagcacaa guaucauugu        240
aucuguccga ugagaugugc ggaagauccg gacagauugu auaaguaugc aacuaagcug        300
aagaaaaacu guaaggaaau aacugauaag gaauuggaca agaaaaugaa ggagcuggcc        360
gccgucauga gcgacccuga ccuggaaacu gagacuaugu gccuccacga cgacgagucg        420
ugucgcuacg aagggcaagu cgcuguuuac caggauguau acgcgguuga cggaccgaca        480
agucucuauc accaagccaa uaagggaguu agagucgccu acuggauagg cuuugacacc        540
accccuuuua uguuuaagaa cuuggcugga gcauauccau cauacucuac caacugggcc        600
gacgaaaccg uguuaacggc ucguaacaua ggccuaugca gcucgacgu uauggagcgg        660 ucacguagag ggaugucau ucuuagaaag aaguauuuga aaccauccaa caauguucua        720
uucucuguug gcucgaccau cuaccacgag aagagggacu acugaggag cuggcaccug         780 ccgucuguau uucacuuacg uggcaagcaa aauuacacau gucggguga gacuauaguu        840 aguugcgacg gguacgucgu uaaaagaaua gcuaucaguc caggccugua ugggaagccu        900
ucaggcuaug cugcuacgau gcaccgcgag ggauucuugu gcugcaaagu gacagacaca        960
uugaacgggg agagggucuc uuuucccgug ugcacguaug ugccagcuac auugugugac       1020
caaaugacug gcauacuggc aacagaugu agugcggacg acgcgcaaaa acugcugguu        1080
gggcucaacc agcguauagu cgucaacggu cgcacccaga gaaacaccaa uaccaugaaa       1140
aauuaccuuu ugcccguagu ggcccaggca uuugcuaggu gggcaaagga auauaaggaa       1200
```

-continued

```
gaucaagaag augaaaggcc acuaggacua cgagauagac aguuagucau gggguguugu      1260 uggcuuuua gaaggcacaa gauaacaucu auuuauaagc gcccggauac ccaaaccauc      1320
aucaaaguga acagcgauuu ccacucauuc gugcugccca ggauaggcag uaacacauug      1380
gagaucgggc ugagaacaag aaucaggaaa auguuagagg agcacaagga gccgucaccu      1440
cucauuaccg ccgaggacgu acaagaagcu aagugcgcag ccgaugaggc uaaggaggug      1500
cgugaagccg aggaguugcg cgcagcucua ccaccuuugg cagcugaugu ugaggagccc      1560
acucuggaag ccgaugucga cuugauguua caagaggcug gggcc      1605
```

<210> SEQ ID NO 51
<211> LENGTH: 2382
<212> TYPE: RNA
<213> ORGANISM: Artificial Sequence
<220> FEATURE:
<223> OTHER INFORMATION: nsP2 RNA sequence

<400> SEQUENCE: 51

```
ggcucagugg agacaccucg uggcuugaua aagguuacca gcuacgaugg cgaggacaag      60
aucggcucuu acgcugugcu uucuccgcag gcuguacuca agagugaaaa auuaucuugc      120
auccacccuc ucgcugaaca agucauagug auaaacacacu cuggccgaaa agggcguuau      180
gccguggaac cauaccaugg uaaaguagug gugccagagg gacaugcaau acccguccag      240
gacuuucaag cucugaguga aagugccacc auuguguaca acgaacguga guucguaaac      300
agguaccugc accauauugc cacacaugga ggagcgcuga acacgaguga agaauauuac      360
aaaacuguca gcccagcga gcacgacggc gaauaccugu acgacaucga caggaaacag      420
ugcgucaaga aagaacuagu cacugggcua gggcucacag cgagcuggu ggauccuccc      480 uuccaugaau ucgccuacga gagucugaga acacgaccag ccgcuccuua ccaaguacca      540
accauagggg uguauggcgu gccaggauca ggcaagucug gcaucauuaa aagcgcaguc      600
accaaaaaag aucuaguggu gagcgccaag aaagaaaacu gugcagaaau uauuaagggac      660 gucaagaaaa ugaaagggcu ggacgucaau gccagaacug uggacucagu gcucuugaau      720
ggaugcaaac accccguaga gacccuguau auugacgaag cuuuugcuug ucaugcaggu      780
acucucagag cgcucauagc cauuauaaga ccuaaaaagg cagugcucug cgggggauccc      840 aaacagugcg guuuuuuuaa caugaugugc cugaaagugc auuuuaacca cgagauuugc      900
acacaagucu uccacaaaag caucucucgc cguugcacua aaucugugac uucggucguc      960
ucaaccuugu uuuacgacaa aaaaaugaga acgacgaauc cgaaagagac uaagauugug      1020
auugacacua ccggcaguac caaaccuaag caggacgauc ucauucucac uuguuucaga      1080 gggugggguga agcaguugca aauagauuac aaaggcaacg aaauaaugac ggcagcugcc      1140
ucucaagggc ugacccguaa aggugugauu gccguucggu acaaggugaa ugaaaauccu      1200
cuguacgcac ccaccucaga acaugugaac guccuacuga cccgcacgga ggaccgcauc      1260 gugugaaaa cacuagccgg cgacccaugg auaaaaacac ugacugccaa guacccuggg      1320
aauuucacug ccacgauaga ggaguggcaa gcagagcaug augccaucau gaggcacauc      1380
uuggagagac cggaccccuac cgacgucuuc cagaauaagg caaacgugug uugggccaag      1440
gcuuuagugc cggugcugaa gaccgcuggc auagacauga ccacugaaca auggaacacu      1500
guggauuauu uugaaacgga caaagcucac ucagcagaga uaguauugaa ccaacuaugc      1560
gugagguucu uuggacucga ucuggacucc ggucuauuuu cugcacccac uguuccguua      1620
```

-continued

```
uccauuagga auaaucacug ggauaacucc ccgucgccua acauguacgg gcugaauaaa    1680 gaagugguucc gucagcucuc ucgcaggguac ccacaacugc cucgggcagu ugccacugga   1740
agagucuaug acaugaacac ugguacacug cgcaauuaug auccgcgcau aaaccuagua     1800
ccuguaaaca gaagacugcc ucaugcuuua guccuccacc auaaugaaca cccacagagu     1860
gacuuuucuu cauucgucag caaauugaag ggcagaacug uccuggguggu cggggaaaag    1920 uuguccgucc caggcaaaau gguugacugg uugucagacc ggccugaggc uaccuucaga     1980
gcucggcugg auuuaggcau cccaggugau gugcccaaau augacauaau auuuguuaau     2040
gugaggaccc cauauaaaua ccaucacuau cagcagugug aagaccaugc cauuaagcuu     2100
agcauguuga ccaagaaagc uugucugcau cugaaucccg gcggaaccug ugucagcaua     2160
gguuaugguu acgcugacag ggccagcgaa agcaucauug gugcuauagc gcggcaguuc     2220
aaguuuuccc ggguaugcaa accgaaaucc ucacuugaag agacggaagu ucuguuugua     2280
uucauugggu acgaucgcaa ggcccguacg cacaauucuu acaagcuuuc aucaaccuug     2340
accaacauuu auacagguuc cagacuccac gaagccggau gu                        2382
```

```
<210> SEQ ID NO 52
<211> LENGTH: 1671
<212> TYPE: RNA
<213> ORGANISM: Artificial Sequence
<220> FEATURE:
<223> OTHER INFORMATION: nsP3 RNA sequence

<400> SEQUENCE: 52
gcacccucau aucauguggu gcgaggggau auugccacgg ccaccgaagg agugauuaua      60
aaugcugcua acagcaaagg acaaccuggc ggaggggugu gcggagcgcu guauaagaaa     120
uucccggaaa gcuucgauuu acagccgauc gaaguaggaa aagcgcgacu ggucaaaggu     180
gcagcuaaac auaucauuca ugccguagga ccaaacuuca caaaguuuc ggagguugaa      240 ggugacaaac aguuggcaga ggcuuaugag uccaucgcua agauugucaa cgauaacaau     300
uacaagucag uagcgauucc acuguugucc accggcaucu uuuccgggaa caaagaucga     360
cuaacccaau cauugaacca uuugcugaca gcuuuagaca ccacgaugc agauguagcc       420 auauacugca gggacaagaa augggaaaug acucucaagg aagcagguggc uaggagagaa    480 gcaguggagg agauaugcau auccgacgac ucuucaguga cagaaccuga ugcagagcug     540
gugagggugc auccgaagag uucuuuggcu ggaaggaagg gcuacagcac aagcgauggc     600
aaaacuuucu cauauuugga agggaccaag uuucaccagg cggccaagga uauagcagaa     660
auuaaugcca uguggcccgu ugcaacggag gccaaugagc agguaugcau guauauccuc     720
ggagaaagca ugagcaguau uaggucgaaa ugccccgucg aagagucgga agccuccaca     780
ccaccuagca cgcugccuug cuugugcauc caugccauga ccuccagaaag aguacagcgc     840 cuaaaagccu cacgucagaa acaaauuacu gugugcucau ccuuuccauu gccgaaguau     900
agaaucacug gugugcagaa gauccaaugc ucccagccua uauuguucuc accgaaagug     960
ccugcguaua uucauccaag gaaguaucuc gugaaacac caccgguaga cgagacuccg      1020
gagccaucgg cagagaacca auccacagag gggacaccac aacaaccacc acuuauaacc     1080
gaggaugaga ccaggacuag aacgccugag ccgaucauca ucgaagagga agaagaggau     1140
agcauaaguu ugcugucaga uggcccgacc caccagguggc ugcaagucga ggcagacauu     1200
cacgggccgc ccucuguauc uagcucaucc uggucccauuc cucaugcauc cgacuuugau     1260
guggacaguu uauccauacu ugacacccug gagggagcua gcgugaccag cgggggcaacg     1320
```

```
ucagccgaga cuaacucuua cuucgcaaag aguauggagu uucuggcgcg accggugccu      1380
gcgccucgaa caguauucag gaacccucca caucccgcuc cgcgcacaag aacaccguca      1440
cuugcaccca gcagggccug cucgagaacc agccuaguuu ccaccccgcc aggcgugaau      1500 aggugauca cuagagagga gcucgaggcg cuuaccccgu cacgcacucc uagcaggucg      1560
gucucgagaa ccagccuggu cuccaacccg ccaggcguaa auaggguugau uacaagagag     1620 gaguuugagg cguucguagc acaacaacaa ugacgguuug augcgggugc a              1671
```

```
<210> SEQ ID NO 53
<211> LENGTH: 1821
<212> TYPE: RNA
<213> ORGANISM: Artificial Sequence
<220> FEATURE:
<223> OTHER INFORMATION: nsP4 RNA sequence

<400> SEQUENCE: 53
uacaucuuuu ccuccgacac cggucaaggg cauuuacaac aaaaaucagu aaggcaaacg        60
gugcuauccg aaguggguguu ggagaggacc gaauuggaga uuucguaugc cccgcgccuc      120
gaccaagaaa aagaagaauu acuacgcaag aaauuacagu uaaaucccac accugcuaac      180
agaagcagau accaguccag gaaggguggag aacaugaaag ccauaacagc uagacguauu     240
cugcaaggcc uagggcauua uuugaaggca gaaggaaaag uggagugcua ccgaacccug      300
cauccuguuc cuuuguauuc aucuagugug aaccgugccu uuucaagccc caaggucgca      360
guggaagccu guaacgccau guugaaagag aacuuuccga cuguggcuuc uuacuguauu      420
auuccagagu acgaugccua uuuggacaug guugacggag cuucaugcug cuuagacacu      480
gccaguuuuu gcccugcaaa gcugcgcagc uuuccaaaga aacacuccua uuuggaaccc      540
acaauacgau cggcagugcc uucagcgauc cagaacacgc uccagaacgu ccuggcagcu      600
gccacaaaaa gaaauugcaa ugucacgcaa augagagaau ugcccguauu ggauucggcg      660
gccuuuaaug uggaaugcuu caagaaauau gcguguaaua augaauauug ggaaacguuu      720
aaagaaaacc ccaucaggcu uacugaagaa aacguggua auuacauuac caaauuaaaa       780
ggaccaaaag cugcugcucu uuuugcgaag acacauaauu ugaauaugu gcaggacaua       840 ccaauggaca gguuuguaau ggacuuaaag agagacguga aagugacucc aggaacaaaa      900
cauacguaag aacggcccaa gguacaggug auccaggcug ccgauccgcu agcaacagcg      960
uaucugugcg gaauccaccg agagcugguu aggagauuaa augcgguccu gcuuccgaac      1020
auucauacac uguuugauau gucggcugaa gacuuugacg cuauuauagc cgagcacuuc      1080
cagccugggg auuguguucu ggaaacugac aucgcgucgu uugauaaaag ugaggacgac      1140
gccauggcuc ugaccgcguu aaugauucg gaagacuuag guguggacgc agagcuguug      1200
acgcugauug aggcggcuuu cggcgaaauu ucaucaauac auuugcccac uaaaacuaaa      1260
uuuaaauucg gagccaugau gaaaucugga auguuccuca cacuguuugu gaacacaguc      1320
auuaacauug uaaucgcaag cagagaguug agagaacggc uaaccggauc accaugugca      1380
gcauucauug gagaugacaa uaucgugaaa ggagucaaau cggacaaauu aauggcagac      1440
aggugcgcca ccugguugaa uauggaaguc aagauuauag augcuguggu gggcgagaaa      1500
gcgccuuauu ucuguggagg guuuauuuug ugugacuccg ugaccggcac agcgugccgu      1560
guggcagacc cccuaaaaag gcuguuuaag cuuggcaaac cucuggcagc agacgaugaa      1620
caugaugaug acaggagaag ggcauugcau gaagagucaa cacgcuggaa ccgaguggu      1680
```

-continued

```
auucuuucag agcugugcaa ggcaguagaa ucaagguaug aaaccguagg aacuuccauc    1740
auaguuaugg ccaugacuac ucuagcuagc aguguuaaau cauucagcua ccugagaggg    1800
gccccuauaa cucucuacgg c                                             1821

<210> SEQ ID NO 54
<211> LENGTH: 44
<212> TYPE: RNA
<213> ORGANISM: Artificial Sequence
<220> FEATURE:
<223> OTHER INFORMATION: 5' UTR conserved sequence element

<400> SEQUENCE: 54
augggcggcg caugagagaa gcccagacca auuaccuacc caaa                      44

<210> SEQ ID NO 55
<211> LENGTH: 237
<212> TYPE: DNA
<213> ORGANISM: Severe acute respiratory syndrome coronavirus 2

<400> SEQUENCE: 55
atgatgccaa ctattttctt tgctggcata ctaattgtta cgactattgt ataccttaca     60
atagtgcaac ttcttcaatt gtcattactt caggtgatgg cacaacaagt cctatttctg    120
aacatgacta ccagattggt ggttatactg aaaaatggga atctggagca aaagactgtg    180
ttgtattaca cagttacttc acttcagact attaccagct gtactcaact caattga       237

<210> SEQ ID NO 56
<211> LENGTH: 237
<212> TYPE: RNA
<213> ORGANISM: Severe acute respiratory syndrome coronavirus 2

<400> SEQUENCE: 56
augaugccaa cuauuuucuu ugcuggcaua cuaauuguua cgacuauugu auaccuuaca     60
auagugcaac uucuucaauu gucauuacuu caggugaugg cacaacaagu ccuauuucug    120
aacaugacua ccagauuggu gguuauacug aaaaauggga aucuggagca aaagacugug    180
uuguauuaca caguuacuuc acuucagacu auuaccagcu guacucaacu caauuga       237

<210> SEQ ID NO 57
<211> LENGTH: 45
<212> TYPE: DNA
<213> ORGANISM: Artificial Sequence
<220> FEATURE:
<223> OTHER INFORMATION: 26S promoter

<400> SEQUENCE: 57
gggcccctat aactctctac ggctaacctg aatggactac gacat                    45
```

RNA CONSTRUCT

The present invention relates to RNA constructs, and particularly, although not exclusively, to RNA replicons and saRNA molecules, and to genetic constructs or vectors encoding such RNA replicons. The invention extends to the use of such RNA constructs and replicons in therapy, for example in treating diseases and/or in vaccine delivery. The invention extends to pharmaceutical compositions comprising such RNA constructs, and methods and uses thereof.

Messenger RNA (mRNA) is a promising tool for biotherapeutics. However, while mRNA therapeutics have been shown to be highly effective in small animals, the outcomes do not scale linearly when these formulations are translated in dose-escalation studies in humans. Furthermore, adverse events associated with the induction of interferon responses have been rate-limiting with respect to the increased doses of RNA likely to be effective in humans. The reason for this inconsistency is unclear, but the inventors hypothesize that inherent differences in human innate sensing pose a barrier to the translation of RNA therapeutics from the lab to the clinic. Furthermore, innate sensing of RNA has been associated with the inhibition of protein expression. To date, the main approach to overcoming the innate recognition of exogenous RNA has been to use modified ribonucleotides that are less detectable by innate sensing mechanisms. However, modified mRNA is not completely undetectable, and still results in some activation of interferon, protein silencing and reduced tolerability for human use.

Another approach has been the use of self-amplifying or saRNA vectors, which are typically based on an alphavirus backbone that have the capacity to self-amplify their own RNA by encoding polymerase activity within their non-structural proteins. Prior art methods have involved replacing the structural proteins of these vectors by a gene of interest (GOI), be it a vaccine construct, or encoding a therapeutic protein. Other versions of saRNA have been based on picornaviruses, flaviviruses, and coronaviruses. When saRNA is taken up into the cytoplasm of target cells, this leads to amplification of the RNA by the encoded polymerase machinery and very high expression levels of the GOI. As a consequence, saRNA has been shown to induce immune responses with lower doses of saRNA than mRNA (10- to 100-fold lower) and results in prolonged protein expression for up to 60 days in mice.

However, a drawback with saRNA is that it is also sensed by innate recognition, triggering antiviral responses that limit protein expression and self-amplification of these prior art saRNAs. Innate sensing of saRNA differs to that of mRNA due to its large size (typically >5000 bases) and profound secondary structure, including double stranded regions (dsRNA). Long and double stranded RNA triggers innate responses through the MDA5 ((Melanoma Differentiation-Associated protein 5) pathway. This is facilitated by the binding of PACT ((PKR activating protein) to long and dsRNA RNA promoting the oligomerization of MDA5 and subsequent triggering of a down-stream signalling cascade that inhibits replication and expression of saRNA.

Accordingly, there is a need in the art to produce new means by which RNA therapeutics may be delivered and expressed in patients, such that they are able to overcome innate immune system sensing of RNA.

The inventors have developed novel self-amplifying RNAs (saRNA) that advantageously overcome innate immune system sensing of RNA, by expressing innate inhibitor proteins that block or reduce the innate immune system machinery, resulting in improved protein expression and self-amplification.

Accordingly, in a first aspect of the invention, there is provided an RNA construct encoding (i) at least one therapeutic biomolecule; and (ii) at least one innate inhibitor protein (IIP).

RNA replicons or constructs have been postulated to be potential tools for the delivery and expression of genes of interest for vaccines and therapeutics. However, double stranded RNA (dsRNA) is detected intracellularly by innate sensing mechanisms that trigger responses, which inhibit protein translation. As a consequence, expression of genes of interest encoded in the replicon is significantly impaired and thus the therapeutic potential of RNA replicons is limited. Advantageously, the RNA constructs of the invention overcome this problem because they encode one or more innate inhibiting protein(s), i.e. IIP, which ablates the downstream inhibition of transgene expression. The induction of interferon is a downstream consequence of innate recognition, but it will be appreciated that other molecules and pathways can and are induced, and any of these will be inhibited by the one or more IIP harboured in the RNA construct. The only previously published approach to ablating the interferon response with saRNA used interferon inhibiting proteins from the vaccinia virus, E3, K3 and B18. However, in this study, the interferon inhibiting proteins were delivered and formulated as separate mRNA molecules that were combined with the saRNA. This requires the manufacture of both saRNA and mRNA and necessitates the use of 3-6 times as much vaccinia mRNA as replicon RNA construct according to the invention to ensure co-delivery into the same cells and provide any observable enhancement in protein expression. Furthermore, the kinetics of expression differ for mRNA and saRNA such that any beneficial effects of the IIPs expressed from mRNA would only be of a very short duration (up to 72 h) in comparison to the RNA constructs of the invention (up to 60 days).

Advantageously, the presence, in the RNA construct of the first aspect, of one or more IIP enables dual protein expression with the peptide or protein of interest. As opposed to delivering two different strands of RNA as described in the prior art, one encoding the peptide/protein of interest and one encoding the IIP, using the construct of the invention, only a single strand is delivered to the target cell, thereby ensuring colocalization of the RNA and the innate inhibiting protein. The IIP inhibits the innate sensing of RNA, thus enabling higher protein expression, and the IIP expression itself is self-amplified by virtue of being co-expressed on the subgenome strand with the gene of interest, i.e. the therapeutic biomolecule. As described in the examples, the RNA constructs of the invention (also known as "Stealthicons") encoding luciferase have surprisingly been shown to increase luciferase protein expression levels up to two orders of magnitude in human cell lines in vitro, and also to increase both the magnitude and duration of protein expression of luciferase compared to a conventional VEEV RNA replicon in vivo in BL/6 mice. The skilled person would readily appreciate that the luciferase reporter is truly representative of the therapeutic biomolecule, because it proves that the RNA construct is able to express in vivo the gene harboured on the RNA molecule of the invention. As such, the luciferase provides robust evidence of the proof of concept that the saRNA construct of the invention can be used to express any therapeutically active biomolecule.

The skilled person would understand that an RNA construct can also be referred to as a self-replicating RNA virus vector, or an RNA replicon. The RNA construct may be double-stranded or single-stranded. Preferably, the RNA construct comprises self-amplifying RNA (saRNA), and is preferably an saRNA construct Preferably, the RNA construct comprises or is derived from a positive stranded RNA virus selected from the group of genus consisting of: alphavirus; picornavirus; flavivirus; rubivirus; pestivirus; hepacivirus; calicivirus or coronavirus.

Suitable wild-type alphavirus sequences are well-known. Representative examples of suitable alphaviruses include Aura, Bebaru virus, Cabassou, Chikungunya virus, Eastern equine encephalomyelitis virus, Fort Morgan, Getah virus, Kyzylagach, Mayaro, Mayaro virus, Middleburg, Mucambo virus, Ndumu, Pixuna virus, Ross River virus, Semliki Forest, Sindbis virus, Tonate, Triniti, Una, Venezuelan equine encephalomyelitis, Western equine encephalomyelitis, Whataroa, and Y-62-33.

Preferably, the RNA construct comprises or is derived from a virus selected from the group of species consisting of: Venezuelan Equine Encephalitis Virus (VEEV); enterovirus 71; Encephalomyocarditis virus; Kunjin virus; and Middle East respiratory syndrome virus. Preferably, the vector is derived from VEEV.

The RNA construct comprises a sequence which encodes the at least one therapeutic biomolecule. The at least one therapeutic biomolecule may comprise or be a vaccine construct, or a therapeutic protein. The skilled person would understand that therapeutic protein relates to any protein that has therapeutic application preferably in human. Exemplary therapeutic biomolecules that can be encoded by the RNA molecule include proteins and peptides derived from pathogens, such as bacteria, viruses, fungi, protozoa/or parasites. Preferably, the protein and peptide is an antigen.

The protein and peptide derived from a virus may be a viral antigen. The viral antigen may be derived from a virus selected from the group consisting of Orthomyxoviruses; Paramyxoviridae viruses; Metapneumovirus and Morbilliviruses; Pneumoviruses; Paramyxoviruses; Poxviridae; Metapneumoviruses; Morbilliviruses; Picornaviruses; Enteroviruseses; Bunyaviruses; Phlebovirus; Nairovirus; Heparnaviruses; Togaviruses; Alphavirus; Arterivirus; Flaviviruses; Pestiviruses; Hepadnaviruses; Rhabdoviruses; Caliciviridae; Coronaviruses; Retroviruses; Reoviruses; Parvoviruses; Delta hepatitis virus (HDV); Hepatitis E virus (HEV); Human Herpesviruses and Papovaviruses.

The Orthomyxoviruses may be Influenza A, B and C. The Paramyxoviridae virus may be Pneumoviruses (RSV), Paramyxoviruses (PIV). The Metapneumovirus may be Morbilliviruses (e.g., measles). The Pneumovirus may be Respiratory syncytial virus (RSV), Bovine respiratory syncytial virus, Pneumonia virus of mice, or Turkey rhinotracheitis virus. The Paramyxovirus may be Parainkuenza virus types 1-4 (PIV), Mumps, Sendai viruses, Simian virus 5, Bovine parainkuenza virus, Nipahvirus, Henipavirus or Newcastle disease virus. The Poxviridae may be Variola vera, for example Variola major and Variola minor. The Metapneumovirus may be human metapneumovirus (hMPV) or avian metapneumoviruses (aMPV). The Morbillivirus may be measles. The Picornaviruses may be Enteroviruses, Rhinoviruses, Heparnavirus, Parechovirus, Cardioviruses and Aphthoviruses. The Enteroviruses may be Poliovirus types 1, 2 or 3, Coxsackie A virus types 1 to 22 and 24, Coxsackie B virus types 1 to 6, Echovirus (ECHO) virus) types 1 to 9, 11 to 27 and 29 to 34 or Enterovirus 68 to 71. The Bunyavirus may be California encephalitis virus.

The Phlebovirus may be Rift Valley Fever virus. The Nairovirus may be Crimean-Congo hemorrhagic fever virus. The Heparnaviruses may be Hepatitis A virus (HAV). The Togaviruses may be Rubivirus. The Flavivirus may be Tick-borne encephalitis (TBE) virus, Dengue (types 1, 2, 3 or 4) virus, Yellow Fever virus, Japanese encephalitis virus, Kyasanur Forest Virus, West Nile encephalitis virus, St. Louis encephalitis virus, Russian spring-summer encephalitis virus or Powassan encephalitis virus. The Pestivirus may be Bovine viral diarrhea (BVDV), Classical swine fever (CSFV) or Border disease (BDV). The Hepadnavirus may be Hepatitis B virus or Hepatitis C virus. The Rhabdovirus may be Lyssavirus (Rabies virus) or Vesiculovirus (VSV). The Caliciviridae may be Norwalk virus, or Norwalk-like Viruses, such as Hawaii Virus and Snow Mountain Virus. The Coronavirus may be SARS CoV-1, SARS-CoV-2, MERS, Human respiratory coronavirus, Avian infectious bronchitis (IBV), Mouse hepatitis virus (MHV), or Porcine transmissible gastroenteritis virus (TGEV). The Retrovirus may be Oncovirus, a Lentivirus or a Spumavirus. The Reovirus may be an Orthoreo virus, a Rotavirus, an Orbivirus, or a Coltivirus. The Parvovirus may be Parvovirus B 19. The Human Herpesvirus may be Herpes Simplex Viruses (HSV), Varicella-zoster virus (VZV), Epstein-Barr virus (EBV), Cytomegalovirus (CMV), Human Herpesvirus 6 (HHV6), Human Herpesvirus 7 (HHV7), or Human Herpesvirus 8 (HHV8). The Papovavirus may be Papilloma viruses, Polyomaviruses, Adenoviruess or Arenaviruses.

As shown in the examples and in FIG. 13, in a preferred embodiment, the viral antigen may be a Rabies virus antigen, preferably Rabies virus glycoprotein. In another preferred embodiment, and as shown in the examples and FIG. 29, the viral antigen may be a Coronavirus antigen. Preferably, the Coronavirus antigen is a surface glycoprotein, more preferably SARS-CoV-2 surface glycoprotein.

The protein and peptide derived from bacteria may be a bacterial antigen.

The bacterial antigen may derived from a bacterium selected from the group consisting of: *Neisseria meningitides, Streptococcus pneumoniae, Streptococcus pyogenes, Moraxella catarrhalis, Bordetella pertussis, Burkholderia* sp. {e.g., *Burkholderia mallei, Burkholderia pseudomallei* and *Burkholderia cepacia*), *Staphylococcus aureus, Haemophilus inkuenzae, Clostridium tetani* (Tetanus), *Clostridium perfringens, Clostridium botulinum, Cornynebacterium diphtheriae* (Diphtheria), *Pseudomonas aeruginosa, Legionella pneumophila, Coxiella burnetii, Brucella* sp. (e.g., *B. abortus, B. canis, B. melitensis, B. neotomae, B. ovis, B. suis* and *B. pinnipediae/Francisella* sp. (e.g., *F. novicida, F. philomiragia* and *F. tularensis*), *Streptococcus agalactiae, Neiserria gonorrhoeae, Chlamydia trachomatis, Treponema pallidum* (Syphilis), *Haemophilus ducreyi, Enterococcus faecalis, Enterococcus faecium, Helicobacter pylori, Staphylococcus saprophyticus, Yersinia enter ocolitica, E. coli, Bacillus anthracis* (anthrax), *Yersinia pestis* (plague), *Mycobacterium tuberculosis, Rickettsia, Listeria, Chlamydia pneumoniae, Vibrio cholerae, Salmonella typhi* (typhoid fever), *Borrelia burgdorfer, Porphyromonas* s and *Klebsiella* sp.

The protein and peptide derived from a fungus may be a fungal antigen.

The fungal antigen may be derived from a fungus selected from the group consisting of Dermatophytres, including: *Epidermophyton koccusum, Microsporum audouini, Microsporum canis, Microsporum distortum, Microsporum equinum, Microsporum gypsum, Microsporum nanum, Trichophyton concentricum, Trichophyton equinum, Tricho-*

*phyton gallinae, Trichophyton gypseum, Trichophyton megnini, Trichophyton mentagrophytes, Trichophyton quinckeanum, Trichophyton rubrum, Trichophyton schoenleini, Trichophyton tonsurans, Trichophyton verrucosum, T verrucosum* var. *album,* var. *discoides,* var. *ochraceum, Trichophyton violaceum,* and/or *Trichophyton faviforme;* or from *Aspergillus fumigatus, Aspergillus kavus, Aspergillus niger, Aspergillus nidulans, Aspergillus terreus, Aspergillus sydowii, Aspergillus kavatus, Aspergillus glaucus, Blastoschizomyces capitatus, Candida albicans, Candida enolase, Candida tropicalis, Candida glabrata, Candida krusei, Candida parapsilosis, Candida stellatoidea, Candida kusei, Candida parakwsei, Candida lusitaniae, Candida pseudotropicalis, Candida guilliermondi, Cladosporium carrionii, Coccidioides immitis, Blastomyces dermatidis, Cryptococcus neoformans, Geotrichum clavatum, Histoplasma capsulatum, Klebsiella pneumoniae, Microsporidia, Encephalitozoon* spp., *Septata intestinalis* and *Enterocytozoon bieneusi; Brachiola* spp, *Microsporidium* spp., *Nosema* spp., *Pleistophora* spp., *Trachipleistophora* spp., *Vittaforma* spp *Paracoccidioides brasiliensis, Pneumocystis carinii, Pythiumn insidiosum, Pityrosporum ovale, Sacharomyces cerevisae, Saccharomyces boulardii, Saccharomyces pombe, Scedosporium apiosperum, Sporothrix schenckii, Trichosporon beigelii, Toxoplasma gondii, Penicillium marneffei, Malassezia* spp., *Fonsecaea* spp., *Wangiella* spp., *Sporothrix* spp., *Basidiobolus* spp., *Conidiobolus* spp., *Rhizopus* spp, *Mucor* spp, *Absidia* spp, *Mortierella* spp, *Cunninghamella* spp, *Saksenaea* spp., *Alternaria* spp, *Curvularia* spp, *Helminthosporium* spp, *Fusarium* spp, *Aspergillus* spp, *Penicillium* spp, *Monolinia* spp, *Rhizoctonia* spp, *Paecilomyces* spp, *Pithomyces* spp, and *Cladosporium* spp.

The protein and peptide derived from a protozoan may be a protozoan antigen.

The protozoan antigen may be derived from a protozoan selected from the group consisting of: *Entamoeba histolytica, Giardia lambli, Cryptosporidium parvum, Cyclospora cayatanensis* and *Toxoplasma.*

The therapeutic biomolecule may be a protein and peptide derived from a plant. Preferably, the protein and peptide is a plant antigen. The plant antigen may be derived from *Ricinus communis.*

In another embodiment, the therapeutic biomolecule may be an immunogen or an antigen. Preferably the immunogen or an antigen is a tumour immunogen or antigen, or cancer immunogen or antigen. The tumour immunogens and antigens may be peptide-containing tumour antigens, such as a polypeptide tumour antigen or glycoprotein tumour antigens.

The tumour antigens may be (a) full length molecules associated with cancer cells, (b) homologs and modified forms of the same, including molecules with deleted, added and/or substituted portions, and (c) fragments of the same.

Suitable tumour immunogens include: class I-restricted antigens recognized by CD 8+ lymphocytes or class II-restricted antigens recognized by CD4+ lymphocytes.

The tumour antigen may be an antigen that is associated with a cancer selected from the group consisting of: a testis cancer, melanoma, lung cancer, head and neck cancer, NSCLC, breast cancer, gastrointestinal cancer, bladder cancer, colorectal cancer, pancreatic cancer, lymphoma, leukaemia, renal cancer, hepatoma, ovarian cancer, gastric cancer and prostate cancer.

The tumour antigen may be selected from:
(a) cancer-testis antigens such as NY-ESO-I, SSX2, SCPl as well as RAGE, BAGE, GAGE and MAGE family polypeptides, for example, GAGE-I, GAGE-2, MAGE- I, MAGE-2, MAGE-3, MAGE-4, MAGE-5, MAGE-6, and MAGE-12 (which can be used, for example, to address melanoma, lung, head and neck, NSCLC, breast, gastrointestinal, and bladder tumours);
(b) mutated antigens, for example, p53 (associated with various solid tumours, e.g., colorectal, lung, head and neck cancer), p21/Ras (associated with, e.g., melanoma, pancreatic cancer and colorectal cancer), CDK4 (associated with, e.g., melanoma), MUM1 (associated with, e.g., melanoma), caspase-8 (associated with, e.g., head and neck cancer), CIA 0205 (associated with, e.g., bladder cancer), HLA-A2-R1701, beta catenin (associated with, e.g., melanoma), TCR (associated with, e.g., T-cell non-Hodgkins lymphoma), BCR-abl (associated with, e.g., chronic myelogenous leukemia), triosephosphate isomerase, KIA 0205, CDC-27, and LDLR-FUT;
(c) over-expressed antigens, for example, Galectin 4 (associated with, e.g., colorectal cancer), Galectin 9 (associated with, e.g., Hodgkin's disease), proteinase 3 (associated with, e.g., chronic myelogenous leukemia), WT 1 (associated with, e.g., various leukemias), carbonic anhydrase (associated with, e.g., renal cancer), aldolase A (associated with, e.g., lung cancer), PRAME (associated with, e.g., melanoma), HER-2/neu (associated with, e.g., breast, colon, lung and ovarian cancer), alpha-fetoprotein (associated with, e.g., hepatoma), KSA (associated with, e.g., colorectal cancer), gastrin (associated with, e.g., pancreatic and gastric cancer), telomerase catalytic protein, MUC-I (associated with, e.g., breast and ovarian cancer), G-250 (associated with, e.g., renal cell carcinoma), p53 (associated with, e.g., breast, colon cancer), and carcinoembryonic antigen (associated with, e.g., breast cancer, lung cancer, and cancers of the gastrointestinal tract such as colorectal cancer);
(d) shared antigens, for example, melanoma-melanocyte differentiation antigens such as MART-1/Melan A, gplOO, MClR, melanocyte-stimulating hormone receptor, tyrosinase, tyrosinase related protein-1/TRPl and tyrosinase related protein-2/TRP2 (associated with, e.g., melanoma);
(e) prostate-associated antigens, such as PAP, PSA, PSMA, PSH-Pl, PSM-Pl, PSM-P2, associated with e.g., prostate cancer; and/or
(f) immunoglobulin idiotypes (associated with myeloma and B cell lymphomas, for example).

The therapeutic biomolecule may be a eukaryotic polypeptide. In one embodiment the eukaryotic polypeptide is a mammalian polypeptide. The mammalian polypeptide may be selected from the group consisting of: an enzyme; an enzyme inhibitor; a hormone; an immune system protein; a receptor; a binding protein; a transcription or translation factor; tumour growth suppressing protein; a structural protein and a blood protein.

The enzyme may be selected from the group consisting of: chymosin; gastric lipase; tissue plasminogen activator; streptokinase; a cholesterol biosynthetic or degradative steriodogenic enzyme; kinases; phosphodiesterases; methylases; de-methylases; dehydrogenases; cellulases; proteases; lipases; phospholipases; aromatases; cytochromes; adenylate or guanylaste cyclases and neuramidases.

The enzyme inhibitor may be tissue inhibitor of metalloproteinase (TIMP). The hormone may be growth hormone.

The immune system protein may be selected from the group consisting of: a cytokine; a chemokine; a lymphokine;

erythropoietin; an integrin; addressin; selectin; homing receptors; T cell receptors and immunoglobulins.

The cytokine may be an interleukin, for example IL-2, IL-4 and/or IL-6, colony stimulating factor (CSF), granulocyte colony stimulating factor (G-CSF), granulocyte-macrophage colony stimulating factor (GM-CSF) or tumour necrosis factor (TNF).

The chemokine may be a macrophage inflammatory protein-2 and/or a plasminogen activator.

The lymphokine may be an interferon.

The immunoglobulin may be a natural, modified or chimeric immunoglobulin or a fragment thereof. Preferably, the immunoglobulin is a chimeric immunoglobulin having dual activity such as antibody enzyme or antibody-toxin chimera.

The hormone may be selected from the group consisting of: insulin, thyroid hormone, catecholamines, gonadotrophins, trophic hormones, prolactin, oxytocin, dopamine, bovine somatotropin, leptins; growth hormones (e.g., human grown hormone), growth factors (e.g., epidermal growth factor, nerve growth factor, insulin-like growth factor and the like).

The receptor may be a steroid hormone receptor or a peptide receptor. Preferably, the receptor is a growth factor receptor.

The binding protein may be a growth factor binding protein.

The tumour growth suppressing protein may be a protein that inhibits angiogenesis.

The structural protein may be selected from the group consisting of: collagen; fibroin; fibrinogen; elastin; tubulin; actin; and myosin.

The blood protein may be selected from the group consisting of thrombin; serum albumin; Factor VII; Factor VIII; insulin; Factor IX; Factor X; tissue plasminogen activator; protein C; von Willebrand factor; antithrombin III; glucocerebrosidase; erythropoietin granulocyte colony stimulating factor (GCSF) or modified Factor VIII; and anticoagulants.

In one preferred embodiment, the therapeutic biomolecule is a cytokine which is capable of regulating lymphoid homeostasis, preferably a cytokine which is involved in and preferably induces or enhances development, priming, expansion, differentiation and/or survival of T cells. Thus, preferably, the cytokine is an interleukin. Most preferably, IL-2, IL-7, IL-12, IL-15, or IL-21.

The therapeutic biomolecule may be protein that is capable of enhancing reprogramming of somatic cells to cells having stem cell characteristics.

The protein that is capable of enhancing reprogramming of somatic cells to cells having stem cell characteristics may be selected from the group consisting of: OCT4, SOX2, NANOG, LIN28, p53, ART-4, BAGE, ss-catenin/m, Bcr-abL CAMEL, CAP-1, CASP-8, CDC27/m, CD 4/m, CEA, CLAUDIN-12, c-MYC, CT, Cyp-B, DAM, ELF2M, ETV6-AML1, G250, GAGE, GnT-V, GaplOO, HAGE, HER-2/neu, HPV-E7, HPV-E6, HAST-2, hTERT (or hTRT), LAGE, LDLR/FUT, MAGE-A, MAGE-B, MAGE-C, MART-1/Melan-A, MC1R, Myosin/m, MUC1, MUM-1, -2, -3, NA88-A, NF1, NY-ESO-1, NY-BR-1, p190 minor BCR-abL, Plac-1, Pml/RARa, PRAME, proteinase 3, PSA, PSM, RAGE, RU1 or RU2, SAGE, SART-1 or SART-3, SCGB3A2, SCP1, SCP2, SCP3, SSX, SURVIVIN, TEL/AML1, TPI/m, TRP-1, TRP-2, TRP-2/INT2, TPTE and WT, preferably WT-1.

Preferably, MAGE-A is selected from the group consisting of: MAGE-A 1, MAGE-A2, MAGE-A3, MAGE-A4, MAGE-A5, MAGE-A6, MAGE-A7, MAGE-A8, MAGE-A9, MAGE-A 10, MAGE-A 11, or MAGE-A 12

Preferably, the protein that is capable of enhancing reprogramming of somatic cells to cells having stem cell characteristics is OCT4, SOX2, LF4; c-MYC; NANOG; LIN28.

The therapeutic biomolecule may be a biomolecule that is utilised for the modification of cells ex vivo for cell-therapy indications. Thus, preferably the therapeutic biomolecule may be selected from the group consisting of an immunoglobulin, a T-cell receptor and NK receptor.

The therapeutic biomolecule may be an RNA molecule that is capable of regulating expression of endogenous host genes, for example an interfering RNA, such as small RNAs, siRNA or microRNAs.

Preferably, the RNA construct comprises a gene, which encodes the at least one innate inhibitor protein (IIP), which is capable of reducing or blocking the innate immune response to RNA. The reduction or blocking of the innate immune response to RNA is preferably achieved by the IIP by reducing or blocking recognition of RNA (preferably long RNA (which would be understood by the skilled person to mean RNA that is at least 1 kb in length) or dsRNA) by a host cell harbouring the RNA construct of the invention. More preferably, the innate inhibitor protein is an innate inhibiting protein such that it is capable of reducing or blocking the innate response to RNA, preferably the RNA of the RNA construct of the first aspect. The innate inhibitor protein may be capable of reducing or preventing the recognition of cytosolic saRNA by pattern recognition receptors leading to activation of interferon regulatory factor 3 and 7 (IRF3 and IRF7) and NF-κB transcription factors, directly triggering a range of antiviral genes (e.g. IFIT1-3, Mx1, Mx2 known to suppress saRNA expression), proinflammatory genes whose products orchestrate the innate immune response, and direct activation of canonically JN-stimulated genes (ISGs) upstream of any interferon dependent cascade. These pathways may be enhanced by the induction of type I & III interferons that provide a positive feedback loop further amplifying many of antiviral responses.

The RNA may be single stranded RNA or double stranded RNA. Preferably, the RNA is saRNA.

The at least one innate inhibitor protein may be capable of either: (i) reducing or blocking the action of Melanoma Differentiation-Associated protein 5 (MDA5), for example by preventing oligomerization of MDA5 and binding of MDA5 to RNA, and/or (ii) blocking or reducing the binding of PACT to RNA, which may also be referred to as PKR activating protein, to RNA. The skilled person would understand that these sensors transmit signals to transducing the signal to the downstream mitochondrial adaptor, mitochondrial antiviral signaling (MAVS) activating downstream cascades, including the activation of transcription factors (NF-κB, IRF-3, -7). This in turn leads to the activation of appropriate antiviral signaling responses and type-I interferon stimulated genes encoding molecules with antiviral activity including IFIT1 known to suppress saRNA expression.

The at least one innate inhibitor protein blocking the action of MDA5 may be selected from the group consisting of: paramyxovirus V protein, 3C Proteins of Coxsackievirus A16, Coxsackievirus A6, and Enterovirus D68 viruses; the VP3 protein of Birnavirus; the Accessory Protein NS6 of Porcine Deltacoronavirus; and the 2C protein of Encephalomyocarditis virus; and orthologues thereof.

Preferably, the at least one innate inhibitor protein blocking the action of MDA5 is a paramyxovirus V protein. Most preferably, the at least one innate inhibitor protein blocking the action of MDA5 is Parainfluenza virus type 5 V protein (PIV5 V).

The at least one innate inhibitor protein blocking or reducing the binding of PACT to RNA may be selected from the group consisting of: ORF4a (NS4a) of any coronavirus, ORF3b of any coronavirus, or the nucleocapsid proteins of mouse hepatitis virus and SARS (coronavirus); and orthologues thereof.

Preferably, the ORF4a (NS4a) is Middle East respiratory syndrome coronavirus MERS coronavirus (ORF4a).

Preferably, the coronavirus ORF3b is SARS-CoV2 ORF3b.

The protein, DNA and RNA sequences for each of PIV5V, ORF4a and ORF3b is provided below.

In one embodiment, the PIV5 V polypeptide is provided herein as SEQ ID No: 11, as follows:

```
                                    [SEQ ID No: 11]
MDPTDLSFSPDEINKLIETGLNTVEYFTSQQVTGTSSLGKNTIPPGVTG

LLTNAAEAKIQESTNHQKGSVGGGAKPKKPRPKIAIVPADDKTVPGKPI

PNPLLGLDSTPSTQTVLDLSGKTLPSGSYKGVKLAKFGKENLMTRFIEE

PRENPIATSSPIDFKRGRDTGGFHRREYSIGWVGDEVKVTEWCNPSCSP

ITAAARRFECTCHQCPVTCSECERDT
```

Accordingly, preferably the PIV5 V polypeptide comprises an amino acid sequence substantially as set out in SEQ ID NO: 11, or a biologically active variant or fragment thereof. Hence, the RNA construct of the first aspect preferably comprises a RNA nucleotide sequence which encodes SEQ ID No: 11, or a biologically active variant or fragment thereof.

In one embodiment, the PIV5 V polypeptide is encoded by the nucleotide sequence of SEQ ID No: 12, as follows:

```
                                    [SEQ ID No: 12]
ATGGACCCTACCGACCTGAGCTTCAGCCCCGACGAGATCAACAAGCTGA

TCGAGACAGGCCTGAACACCGTGGAATACTTCACCAGCCAGCAAGTGAC

CGGCACAAGCAGCCTGGGCAAGAACACAATTCCTCCAGGCGTGACCGGC

CTGCTGACAAATGCTGCCGAGGCCAAGATCCAAGAGAGCACCAACCACC

AGAAGGGCTCTGTTGGAGGCGGAGCCAAGCCTAAGAAGCCCAGACCTAA

GATCGCCATCGTGCCCGCCGACGATAAGACAGTGCCTGGCAAGCCCATT

CCTAATCCTCTGCTGGGCCTCGACAGCACCCCTAGCACACAGACAGTGC

TGGATCTGAGCGGCAAGACACTGCCTAGCGGCAGCTATAAGGGCGTGAA

GCTGGCCAAGTTCGGCAAAGAAAACCTGATGACCCGGTTCATCGAGGAA

CCCAGAGAGAACCCTATCGCCACCAGCTCTCCCATCGACTTCAAGAGAG

GCAGAGACACCGGCGGCTTCCACAGAAGAGAGTACAGCATTGGCTGGGT

CGGAGATGAAGTGAAAGTGACCGAGTGGTGCAACCCCAGCTGCAGCCCT

ATTACAGCCGCCGCTAGAAGATTCGAGTGCACCTGTCACCAGTGTCCTG

TGACCTGTAGCGAGTGCGAGCGGGACACA
```

Accordingly, preferably the PIV5 V polypeptide is encoded by the nucleotide sequence substantially as set out in SEQ ID NO: 12, or a variant or fragment thereof.

Thus, the RNA construct may comprise an RNA nucleotide sequence of SEQ ID No: 47, as follows:

```
                                    [SEQ ID No: 47]
AUGGACCCUACCGACCUGAGCUUCAGCCCCGACGAGAUCAACAAGCUGA

UCGAGACAGGCCUGAACACCGUGGAAUACUUCACCAGCCAGCAAGUGAC

CGGCACAAGCAGCCUGGGCAAGAACACAAUUCCUCCAGGCGUGACCGGC

CUGCUGACAAAUGCUGCCGAGGCCAAGAUCCAAGAGAGCACCAACCACC

AGAAGGGCUCUGUUGGAGGCGGAGCCAAGCCUAAGAAGCCCAGACCUAA

GAUCGCCAUCGUGCCCGCCGACGAUAAGACAGUGCCUGGCAAGCCCAUU

CCUAAUCCUCUGCUGGGGCCUCGACAGCACCCCUAGCACACAGACAGUGC

UGGAUCUGAGCGGCAAGACACUGCCUAGCGGCAGCUAUAAGGGCGUGAA

GCUGGCCAAGUUCGGCAAAGAAAACCUGAUGACCCGGUUCAUCGAGGAA

CCCAGAGAGAACCCUAUCGCCACCAGCUCUCCCAUCGACUUCAAGAGAG

GCAGAGACACCGGCGGCUUCCACAGAAGAGAGUACAGCAUUGGCUGGGU

CGGAGAUGAAGUGAAAGUGACCGAGUGGUGCAACCCCAGCUGCAGCCCU

AUUACAGCCGCCGCUAGAAGAUUCGAGUGCACCUGUCACCAGUGUCCUG

UGACCUGUAGCGAGUGCGAGCGGGACACA
```

Accordingly, therefore, preferably the RNA construct comprises an RNA nucleotide sequence substantially as set out as SEQ ID No 47 or a variant or fragment thereof.

In one embodiment, the MERS-CoV ORF4a polypeptide is provided herein as SEQ ID No: 15, as follows:

```
                                    [SEQ ID No: 15]
MDYVSLLNQIWQKYLNSPYTTCLYIPKPTAKYTPLVGTSLHPVLWNCQL

SFAGYTESAVNSTKALAKQDAAQRIAWLLHKDGGIPDGCSLYLRHSSLF

AQSEEEESFSN
```

Accordingly, preferably the MERS-CoV ORF4a polypeptide comprises an amino acid sequence substantially as set out in SEQ ID NO: 15, or a biologically active variant or fragment thereof. Hence, the RNA construct of the first aspect preferably comprises an RNA nucleotide sequence which encodes SEQ ID No: 15, or a variant or fragment thereof.

In one embodiment, the MERS-CoV ORF4a polypeptide is encoded by the nucleotide sequence of SEQ ID No: 16, as follows:

```
                                    [SEQ ID No: 16]
ATGGACTACGTGTCCCTGCTGAACCAGATTTGGCAGAAGTACCTGAACA

GCCCCTACACCACCTGTCTGTACATCCCCAAGCCTACCGCCAAGTACAC

ACCTCTCGTGGGCACATCTCTGCACCCCGTGCTGTGGAATTGCCAGCTG

AGCTTTGCCGGCTACACCGAGTCTGCCGTGAACAGCACAAAGGCCCTGG

CCAAACAGGACGCCGCTCAGAGAATTGCCTGGCTGCTGCACAAGGATGG

CGGCATCCCTGATGGCTGTAGCCTGTACCTGAGACACAGCAGCCTGTTC

GCCCAGAGCGAGGAAGAGGAATCCTTCAGCAAC
```

Accordingly, preferably the MERS-CoV ORF4a polypeptide is encoded by the nucleotide sequence substantially as set out in SEQ ID NO: 16, or a variant or fragment thereof.

Thus, the RNA construct may comprise an RNA nucleotide sequence of SEQ ID No: 48, as follows:

```
                                       [SEQ ID No: 48]
AUGGACUACGUGUCCCUGCUGAACCAGAUUUGGCAGAAGUACCUGAACA

GCCCCUACACCACCUGUCUGUACAUCCCCAAGCCUACCGCCAAGUACAC

ACCUCUCGUGGGCACAUCUCUGCACCCCGUGCUGUGGAAUUGCCAGCUG

AGCUUUGCCGGCUACACCGAGUCUGCCGUGAACAGCACAAAGGCCCUGG

CCAAACAGGACGCCGCUCAGAGAAUUGCCUGGCUGCUGCACAAGGAUGG

CGGCAUCCCUGAUGGCUGUAGCCUGUACCUGAGACACAGCAGCCUGUUC

GCCCAGAGCGAGGAAGAGGAAUCCUUCAGCAAC
```

Accordingly, therefore, preferably the RNA construct comprises an RNA nucleotide sequence substantially as set out as SEQ ID No: 48, or a variant or fragment thereof.

In one embodiment, the SARS-CoV-2 ORF3b polypeptide is provided herein as SEQ ID No: 20, as follows:

```
                                       [SEQ ID No: 20]
MMPTIFFAGILIVTTIVYLTIVQLLQLSLLQVMAQQVLFLNMTTRLVVI

LKNGNLEQKTVLYYTVTSLQTITSCTQLN
```

Accordingly, preferably the SARS-CoV-2 ORF3b polypeptide comprises an amino acid sequence substantially as set out in SEQ ID NO: 20, or a biologically active variant or fragment thereof. Hence, the RNA construct of the first aspect preferably comprises an RNA nucleotide sequence which encodes SEQ ID No: 20, or a variant or fragment thereof.

In one embodiment, the SARS-CoV-2 ORF3b polypeptide is encoded by the nucleotide sequence (Wuhan-Hu-1 Accession no. NC_045512.2; nucleotides 25814-26050) of SEQ ID No: 55, as follows:

```
                                       [SEQ ID No: 55]
ATGATGCCAACTATTTTCTTTGCTGGCATACTAATTGTTACGACTATTG

TATACCTTACAATAGTGCAACTTCTTCAATTGTCATTACTTCAGGTGAT

GGCACAACAAGTCCTATTTCTGAACATGACTACCAGATTGGTGGTTATA

CTGAAAAATGGGAATCTGGAGCAAAAGACTGTGTTGTATTACACAGTTA

CTTCACTTCAGACTATTACCAGCTGTACTCAACTCAATTGA
```

Accordingly, preferably the SARS-CoV-2 ORF3b polypeptide is encoded by the nucleotide sequence substantially as set out in SEQ ID NO: 55, or a variant or fragment thereof.

Thus, the RNA construct may comprise an RNA nucleotide sequence of SEQ ID No: 56, as follows:

```
                                       [SEQ ID No: 56]
AUGAUGCCAACUAUUUUCUUUGCUGGCAUACUAAUUGUUACGACUAUUG

UAUACCUUACAAUAGUGCAACUUCUUCAAUUGUCAUUACUUCAGGUGAU

GGCACAACAAGUCCUAUUUCUGAACAUGACUACCAGAUUGGUGGUUAUA

CUGAAAAAUGGGAAUCUGGAGCAAAAGACUGUGUUGUAUUACACAGUUA

CUUCACUUCAGACUAUUACCAGCUGUACUCAACUCAAUUGA
```

Accordingly, therefore, preferably the RNA construct comprises an RNA nucleotide sequence substantially as set out as SEQ ID No: 56, or a variant or fragment thereof.

In another embodiment, the at least one innate inhibitor protein may be capable of inhibiting pathways downstream of MDA5 activation or blocking the downstream pathways of MDA/PACT recognition of dsRNA.

The at least one innate inhibitor protein that is capable of inhibiting pathways downstream of MDA5 activation or blocking the downstream pathways of MDA/PACT recognition of dsRNA may be selected from the group consisting of: HSV-2 Us1; HSV-1 Us1; HSV-1 Us11; OV20.0L; BVDV Npro; Langat virus NS5; and Influenza NS1

The skilled person would understand that the at least one innate inhibitor protein that is capable of inhibiting pathways downstream of MDA5 activation or blocking the downstream pathways of MDA/PACT recognition of dsRNA may be used in combination with the at least one innate inhibitor protein blocking the action of MDA5 and/or the at least one innate inhibitor protein blocking or reducing the binding of PACT to RNA.

In one embodiment, the HSV-2 Us1 polypeptide is provided herein as SEQ ID No: 1, as follows:

```
                                       [SEQ ID No: 1]
VRDCYLMGYCRTRLGPRTWGRLLQISGGTWDVRLRNAIREVEAHFEPAA

EPVCELPCLNARRYGPECDVGNLETNGGSTSDDEISDAIDSDDTLASHS

DTEGGPSPAGRENPESASGGAIAARLECEFGTFDWTSEEGSQPWLSAVV

ADTSSAERSGLPAPGACRATEAPEREDGCRKMRFPAACPYPCGHTFLRP
```

Accordingly, preferably the HSV-2 Us1 polypeptide comprises an amino acid sequence substantially as set out in SEQ ID NO: 1, or a biologically active variant or fragment thereof. Hence, the RNA construct of the first aspect preferably comprises an RNA nucleotide sequence which encodes SEQ ID No: 1 or a biologically active variant or fragment thereof.

In one embodiment, the HSV-2 Us1 polypeptide is encoded by the nucleotide sequence of SEQ ID No: 2, as follows:

```
                                       [SEQ ID No: 2]
GTGAGAGACTGCTACCTGATGGGCTACTGCCGGACAAGACTGGGACCTA

GAACATGGGGCAGACTGCTGCAGATCAGCGGCGGAACATGGGATGTGCG

GCTGAGAAACGCCATCAGAGAGGTGGAAGCCCACTTCGAGCCTGCCGCT

GAACCTGTGTGTGAACTGCCCTGTCTGAACGCTAGAAGATACGGCCCTG

AGTGCGACGTGGGCAACCTGGAAACAAATGGCGGCAGCACCAGCGACGA

CGAGATTTCCGATGCCACCGACAGCGACGATACACTGGCCAGCCACAGC

GATACAGAAGGCGGACCATCTCCTGCCGGAAGAGAGAATCCTGAGTCTG

CCTCTGGCGGAGCCATTGCCGCTAGACTGGAATGCGAGTTCGGCACCTT

CGACTGGACAAGCGAGGAAGGCTCTCAGCCTTGGCTGTCTGCTGTGGTG

GCCGATACAAGCTCTGCCGAGAGAAGTGGACTTCCTGCTCCTGGCGCCT

GTAGAGCTACAGAGGCTCCTGAAAGAGAGGACGGCTGCAGAAAGATGCG

GTTCCCTGCCGCCTGTCCTTATCCTTGCGGCCACACATTTCTGCGGCCC
```

Accordingly, preferably the HSV-2 Us1 polypeptide is encoded by the nucleotide sequence substantially as set out in SEQ ID NO: 2, or a variant or fragment thereof.

Thus, the RNA construct may comprise an RNA nucleotide sequence of SEQ ID No: 42, as follows:

```
                                          [SEQ ID No: 42]
GUGAGAGACUGCUACCUGAUGGGCUACUGCCGGACAAGACUGGGACCUA

GAACAUGGGGCAGACUGCUGCAGAUCAGCGGCGGAACAUGGGAUGUGCG

GCUGAGAAACGCCAUCAGAGAGGUGGAAGCCCACUUCGAGCCUGCCGCU

GAACCUGUGUGUGAACUGCCCUGUCUGAACGCUAGAAGAUACGGCCCUG

AGUGCGACGUGGGCAACCUGGAAACAAAUGGCGGCAGCACCAGCGACGA

CGAGAUUUCCGAUGCCACCGACAGCGACGAUACACUGGCCAGCCACAGC

GAUACAGAAGGCGGACCAUCUCCUGCCGGAAGAGAGAAUCCUGAGUCUG

CCUCUGGCGGAGCCAUUGCCGCUAGACUGGAAUGCGAGUUCGGCACCUU

CGACUGGACAAGCGAGGAAGGCUCUCAGCCUUGGCUGUCUGCUGUGGUG

GCCGAUACAAGCUCUGCCGAGAGAAGUGGACUUCCUGCUCCUGGCGCCU

GUAGAGCUACAGAGGCUCCUGAAAGAGAGGACGGCUGCAGAAAGAUGCG

GUUCCCUGCCGCCUGUCCUUAUCCUUGCGGCCACACAUUUCUGCGGCCC
```

Accordingly, therefore, preferably the RNA construct comprises an RNA nucleotide sequence substantially as set out as SEQ ID No: 42, or a biologically active variant or fragment thereof.

In one embodiment, the HSV-1 Us1 polypeptide is provided herein as SEQ ID No: 3, as follows:

```
                                          [SEQ ID No: 3]
VRDCYLMGYCRTRLGPRTWGRLLQISGGTWDVRLRNAIREVEAHFEPAA

EPVCELPCLNARRYGPECDVGNLETNGGSTSDDEISDAIDSDDTLASHS

DTEGGPSPAGRENPESASGGAIAARLECEFGTFDWTSEEGSQPWLSAVV

ADIRDCYLMGYCRARLAPRTWCRLLQVSGGTWGMHLRNTIREVEARFDA

TAEPVCKLPCLETRRYGPECDLSNLEIHLSATSDDEISDATDLEAAGSD

HTLASQSDTEDAPSPVTLETPEPRGSLAVRLEDEFGEFDWTPQEGSQPW

LSAVVADTSSVERPGPSDSGAGRAAEDRKCLDGCRKMRFSTACPYPCSD

TFLRPTSSAERSGLPAPGACRATEAPEREDGCRKMRFPAACPYPCGHTF

LRP
```

Accordingly, preferably the HSV-1 Us1 polypeptide comprises an amino acid sequence substantially as set out in SEQ ID NO:3, or a biologically active variant or fragment thereof. Hence, the RNA construct of the first aspect preferably comprises an RNA nucleotide sequence which encodes SEQ ID No: 3, or a biologically active variant or fragment thereof.

In one embodiment, the HSV-1 Us1 polypeptide is encoded by the nucleotide sequence of SEQ ID No: 4, as follows:

```
                                          [SEQ ID No: 4]
ATCAGAGACTGCTACCTGATGGGCTACTGCCGGGCTAGACTGGC

CCCTAGAACATGGTGCAGACTGCTGCAAGTGTCTGGCGGCACAT

GGGGCATGCACCTGAGAAACACCATCAGAGAGGTGGAAGCCAGA

TTCGACGCCACAGCCGAGCCTGTGTGCAAGCTGCCTTGTCTGGA
```

```
                             -continued
AACTCGGAGATACGGCCCCGAGTGCGACCTGAGCAATCTGGAAA

TTCACCTGAGCGCCACCAGCGACGACGAGATTTCTGATGCCACC

GACCTGGAAGCCGCCGGATCTGATCATACACTGGCCAGCCAGAG

CGACACCGAGGATGCTCCATCTCCAGTGACTCTGGAAACCCCTG

AGCCTAGAGGATCTCTGGCCGTGCGACTGGAAGATGAGTTCGGC

GAGITCGACTGGACCCCTCAAGAGGGATCTCAGCCTTGGCTGTC

TGCCGTGGTGGCCGATACAAGCAGCGTGGAAAGACCCGGACCTA

GCGATTCTGGTGCTGGCAGAGCCGCCGAGGATAGAAAGTGCCTG

GATGGCTGCCGGAAGATGCGGTTCTCTACCGCCTGTCCATATCC

TTGCAGCGACACCTTCCTGCGGCCT
```

Accordingly, preferably the HSV-1 Us1 polypeptide is encoded by the nucleotide sequence substantially as set out in SEQ ID NO: 4, or a variant or fragment thereof.

Thus, the RNA construct may comprise an RNA nucleotide sequence of SEQ ID No: 43, as follows:

```
                                          [SEQ ID No: 43]
GUGAGAGACUGCUACCUGAUGGGCUACUGCCGGACAAGACUGGG

ACCUAGAACAUGGGGCAGACUGCUGCAGAUCAGCGGCGGAACAU

GGGAUGUGCGGCUGAGAAACGCCAUCAGAGAGGUGGAAGCCCAC

UUCGAGCCUGCCGCUGAACCUGUGUGUGAACUGCCCUGUCUGAA

CGCUAGAAGAUACGGCCCUGAGUGCGACGUGGGCAACCUGGAAA

CAAAUGGCGGCAGCACCAGCGACGACGAGAUUUCCGAUGCCACC

GACAGCGACGAUACACUGGCCAGCCACAGCGAUACAGAAGGCGG

ACCAUCUCCUGCCGGAAGAGAGAAUCCUGAGUCUGCCUCUGGCG

GAGCCAUUGCCGCUAGACUGGAAUGCGAGUUCGGCACCUUCGAC

UGGACAAGCGAGGAAGGCUCUCAGCCUUGGCUGUCUGCUGUGGU

GGCCGAUAUCAGAGACUGCUACCUGAUGGGCUACUGCCGGGCUA

GACUGGCCCCUAGAACAUGGUGCAGACUGCUGCAAGUGUCUGGC

GGCACAUGGGGCAUGCACCUGAGAAACACCAUCAGAGAGGUGGA

AGCCAGAUUCGACGCCACAGCCGAGCCUGUGUGCAAGCUGCCUU

GUCUGGAAACUCGGAGAUACGGCCCCGAGUGCGACCUGAGCAAU

CUGGAAAUUCACCUGAGCGCCACCAGCGACGACGAGAUUUCUGA

UGCCACCGACCUGGAAGCCGCCGGAUCUGAUCAUACACUGGCCA

GCCAGAGCGACACCGAGGAUGCUCCAUCUCCAGUGACUCUGGAA

ACCCCUGAGCCUAGAGGAUCUCUGGCCGUGCGACUGGAAGAUGA

GUUCGGCGAGUUCGACUGGACCCCUCAAGAGGGAUCUCAGCCUU

GGCUGUCUGCCGUGGUGGCCGAUACAAGCAGCGUGGAAAGACCC

GGACCUAGCGAUUCUGGUGCUGGCAGAGCCGCCGAGGAUAGAAA

GUGCCUGGAUGGCUGCCGGAAGAUGCGGUUCUCUACCGCCUGUC

CAUAUCCUUGCAGCGACACCUUCCUGCGGCCUUGAUAAACAAGC

UCUGCCGAGAGAAGUGGACUUCCUGCUCCUGGCGCCUGUAGAGC

UACAGAGGCUCCUGAAAGAGAGGACGGCUGCAGAAAGAUGCGGU
```

-continued

```
UCCCUGCCGCCUGUCCUUAUCCUUGCGGCCACACAUUUCUGCGG

CCC
```

Accordingly, therefore, preferably the RNA construct comprises an RNA nucleotide sequence substantially as set out as SEQ ID No: 43, or a variant or fragment thereof.

In one embodiment, the HSV-1 Us11 polypeptide is provided herein as SEQ ID No: 5, as follows:

```
                                       [SEQ ID No: 5]
MSQTQPPAPVGPGDPDVYLKGVPSAGMHPRGVHAPRGHPRMISG

PPQRGDNDQAAGQCGDSGLLRVGADTTISKPSEAVRPPTIPRTP

RVPREPRVPRPPREPREPRVPRAPRDPRVPRDPRDPRQPRSPRE

PRSPREPRSPREPRTPRTPREPRTARGSV
```

Accordingly, preferably the HSV-1 Us11 polypeptide comprises an amino acid sequence substantially as set out in SEQ ID NO: 5, or a biologically active variant or fragment thereof. Hence, the RNA construct of the first aspect preferably comprises a RNA nucleotide sequence which encodes SEQ ID No: 5, or a variant or fragment thereof.

In one embodiment, the HSV-1 Us11 polypeptide is encoded by the nucleotide sequence of SEQ ID No: 6, as follows:

```
                                       [SEQ ID No: 6]
ATGAGCCAGACACAGCCTCCAGCTCCAGTTGGACCTGGCGACCC

TGATGTGTATCTGAAGGGCGTGCCAAGCGCCGGCATGCATCCTA

GAGGTGTTCATGCCCCTAGAGGACACCCCAGAATGATCTCTGGC

CCTCCTCAGAGAGGCGACAACGATCAGGCTGCTGGACAGTGTGG

CGATAGCGGACTGCTGAGAGTGGGCGCCGATACCACAATCAGCA

AGCCATCTGAGGCTGTGCGGCCTCCTACAATCCCCAGAACACCT

AGAGTGCCCCGCGAGCCAAGAGTGCCTAGACCTCCTAGAGAGCC

CAGAGAACCCAGAGTGCCAAGGGCTCCCAGAGATCCTAGAGTCC

CTCGGGACCCTAGGGACCCAAGACAACCTAGATCACCCAGAGAG

CCTCGGAGCCCAAGAGAGCCAAGAAGCCCTAGGGAACCCCGGAC

ACCAAGAACACCCAGGGAACCTAGAACCGCCAGAGGCAGCGTG
```

Accordingly, preferably the HSV-1 Us11 polypeptide is encoded by the nucleotide sequence substantially as set out in SEQ ID NO: 6, or a variant or fragment thereof.

Thus, the RNA construct may comprise an RNA nucleotide sequence of SEQ ID No: 44, as follows:

```
                                      [SEQ ID No: 44]
AUGAGCCAGACACAGCCUCCAGCUCCAGUUGGACCUGGCGACCC

UGAUGUGUAUCUGAAGGGCGUGCCAAGCGCCGGCAUGCAUCCUA

GAGGUGUUCAUGCCCCUAGAGGACACCCCAGAAUGAUCUCUGGC

CCUCCUCAGAGAGGCGACAACGAUCAGGCUGCUGGACAGUGUGG

CGAUAGCGGACUGCUGAGAGUGGGCGCCGAUACCACAAUCAGCA

AGCCAUCUGAGGCUGUGCGGCCUCCUACAAUCCCCAGAACACCU
```

-continued

```
AGAGUGCCCCGCGAGCCAAGAGUGCCUAGACCUCCUAGAGAGCC

CAGAGAACCCAGAGUGCCAAGGGCUCCCAGAGAUCCUAGAGUCC

CUCGGGACCCUAGGGACCCAAGACAACCUAGAUCACCCAGAGAG

CCUCGGAGCCCAAGAGAGCCAAGAAGCCCUAGGGAACCCCGGAC

ACCAAGAACACCCAGGGAACCUAGAACCGCCAGAGGCAGCGUG
```

Accordingly, therefore, preferably the RNA construct comprises an RNA nucleotide sequence substantially as set out as SEQ ID No: 44 or a variant or fragment thereof.

In one embodiment, the OV20.0L polypeptide is provided herein as SEQ ID No: 7, as follows:

```
                                       [SEQ ID No: 7]
MACECASLILELLRKSDDKLPAKQIAKELGISKHEANRQLYRLL

DSDEVCCEDGNPPRWFVECAPSAPTEEDENSDTEPMETEAGCDT

LFGGDIDIMTQSAVIRLKSLNPVSAVNEFCMMTHRPLEFCETRA

GGEDHCPRFTCTITISGKVVAVADGASKKLARHTACSSALTILI

NNCGISF
```

Accordingly, preferably the OV20.0L polypeptide comprises an amino acid sequence substantially as set out in SEQ ID NO: 7, or a biologically active variant or fragment thereof. Hence, the RNA construct of the first aspect preferably comprises a RNA nucleotide sequence which encodes SEQ ID No: 7 or a variant or fragment thereof.

In one embodiment, the OV20.0L polypeptide is encoded by the nucleotide sequence of SEQ ID No: 8, as follows:

```
                                       [SEQ ID No: 8]
ATGGCCTGTGAATGCGCCAGCCTGATCCTGGAACTGCTGAGAAA

GAGCGACGACAAGCTGCCCGCCAAGCAGATCGCCAAAGAGCTGG

GCATCTCTAAGCACGAGGCCAACCGGCAGCTGTACCGGCTGCTG

GATTCTGACGAAGTGTGCTGCGAGGACGGCAATCCTCCTCGTTG

GTTCGTGGAATGTGCCCCTAGCGCTCCCACCGAAGAGGACGAGA

ATAGCGACACCGAGCCTATGGAAACCGAGGCCGGCTGCGATACA

CTGTTTGGCGGAGACATCGACATCATGACCCAGAGCGCCGTGAT

CCGGCTGAAGTCCCTGAATCCTGTGTCCGCCGTGAACGAGTTCT

GCATGATGACCCACCGGCCTCTGGAATTTTGCGAGACAAGAGCC

GGCGGAGAGGATCACTGCCCCAGATTCACCTGTACCATCACCAT

CAGCGGCAAGGTGGTGGCTGTTGCCGATGGCGCCTCTAAGAAAC

TGGCCAGACACACCGCCTGTAGCAGCGCCCTGACAATCCTGATC

AACAACTGCGGCATCAGCTTC
```

Accordingly, preferably the OV20.0L polypeptide is encoded by the nucleotide sequence substantially as set out in SEQ ID NO: 8, or a variant or fragment thereof.

Thus, the RNA construct may comprise an RNA nucleotide sequence of SEQ ID No: 45, as follows:

```
                                      [SEQ ID No: 45]
AUGGCCUGUGAAUGCGCCAGCCUGAUCCUGGAACUGCUGAGAAA

GAGCGACGACAAGCUGCCCGCCAAGCAGAUCGCCAAAGAGCUGG

GCAUCUCUAAGCACGAGGCCAACCGGCAGCUGUACCGGCUGCUG

GAUUCUGACGAAGUGUGCUGCGAGGACGGCAAUCCUCCUCGUUG

GUUCGUGGAAUGUGCCCCUAGCGCUCCCACCGAAGAGGACGAGA

AUAGCGACACCGAGCCUAUGGAAACCGAGGCCGGCUGCGAUACA

CUGUUUGGCGGAGACAUCGACAUCAUGACCCAGAGCGCCGUGAU

CCGGCUGAAGUCCCUGAAUCCUGUGUCCGCCGUGAACGAGUUCU

GCAUGAUGACCCACCGGCCUCUGGAAUUUUGCGAGACAAGAGCC

GGCGGAGAGGAUCACUGCCCCAGAUUCACCUGUACCAUCACCAU

CAGCGGCAAGGUGGUGGCUGUUGCCGAUGGCGCCUCUAAGAAAC

UGGCCAGACACACCGCCUGUAGCAGCGCCCUGACAAUCCUGAUC

AACAACUGCGGCAUCAGCUUC
```

Accordingly, therefore, preferably the RNA construct comprises an RNA nucleotide sequence substantially as set out as SEQ ID No: 45, or a variant or fragment thereof.

In one embodiment, the BVDV Npro polypeptide is provided herein as SEQ ID No: 9, as follows:

```
                                      [SEQ ID No: 9]
MELITNELLYKTYKQKPVGVEEPVYDQAGDPLFGERGAVHPQST

LKLPHKRGERDVPTNLASLPKRGDCRTGNSRGPVSGIYLKPGPL

FYQDYKGPVYHRAPLELFEEGSMCETTKRIGRVTGSDGKLYHIY

VCIDGCIIKSATRSYQRVFRWVHNRLDCPLWVTSC
```

Accordingly, preferably the BVDV Npro polypeptide comprises an amino acid sequence substantially as set out in SEQ ID NO: 9, or a biologically active variant or fragment thereof. Hence, the RNA construct of the first aspect preferably comprises a RNA nucleotide sequence which encodes SEQ ID No: 9 or a variant or fragment thereof.

In one embodiment, the BVDV Npro polypeptide is encoded by the nucleotide sequence of SEQ ID No: 10, as follows:

```
                                      [SEQ ID No: 10]
ATGGAACTGATCACCAACGAGCTGCTGTACAAGACCTACAAGCA

GAAACCCGTGGGCGTCGAGGAACCCGTGTATGATCAAGCTGGCG

ACCCTCTGTTTGGCGAGAGAGGCGCTGTTCACCCTCAGAGCACA

CTGAAGCTGCCCCACAAGCGGGGCGAAAGAGATGTGCCTACCAA

CCTGGCCAGCCTGCCTAAGAGAGGCGATTGCAGAACCGGCAATA

GCAGAGGCCCTGTGTCCGGCATCTACCTGAAACCTGGACCACTG

TTCTACCAGGACTACAAGGGACCCGTGTACCACAGAGCCCCTCT

GGAACTGTTTGAAGAGGGCAGCATGTGCGAAACCACCAAGCGGA

TCGGAAGAGTGACCGGCTCTGACGGCAAGCTGTACCACATCTAC
```

```
-continued
GTGTGCATCGACGGCTGCATCATCATCAAGAGCGCCACCAGATC

CTACCAGCGGGTGTTCAGATGGGTGCACAACAGACTGGACTGCC

CTCTGTGGGTCACCAGCTGC
```

Accordingly, preferably the BVDV Npro polypeptide is encoded by the nucleotide sequence substantially as set out in SEQ ID NO: 10, or a variant or fragment thereof.

Thus, the RNA construct may comprise an RNA nucleotide sequence of SEQ ID No: 46, as follows:

```
                                      [SEQ ID No: 46]
GTGTTCAAGGACAAGGTGGACACCAAGGCTCAAGAGCCTCAGCC

TGGCACCAAGATCATCATGAGAGCCGTGAACGACTGGCTGCTGG

AACGGCTGGTCAAGAAAAGCAGACCCCGGATGTGCAGCCGGGAA

GAGTTTATCGCCAAAGTGCGGAGCAATGCCGCTCTCGGAGCTTG

GAGTGACGAGCAGAACAAGTGGAAGTCCGCCAGAGAAGCCGTGG

AAGATCCCGAGTTTTGGAGCCTGGTGGAAGCCGAGAGAGAGAGG

CATCTGCAGGGAAGATGTGCCCACTGCGTGTACAACATGATGGG

CAAGAGAGAGAAGAAGCTGGGCGAGTTCGGGAGTGGCCAAAGGCA

GCAGAGCCATCTGGTATATGTGGCTGGGCAGCCGCTTCCTGGAA

TTTGAGGCCCTGGGCTTCCTGAACGAGGATCACTGGGCTAGCAG

AGCCTCTTCTGGTGCTGGCGTGGAAGGCATCAGCCTGAATTATC

TCGGCTGGCACCTGAAGAAACTGGCCTCTCTGTCTGGCGGCCTG

TTCTACGCCGATGATACAGCCGGATGGGACACAAAGATCACCAA

CGCCGACCTGGACGACGAGGAACAGATCCTGAGATATATGGACG

GCGACCACAUGGAACUGAUCACCAACGAGCUGCUGUACAAGACC

UACAAGCAGAAACCCGUGGGCGUCGAGGAACCCGUGUAUGAUCA

AGCUGGCGACCCUCUGUUUGGCGAGAGAGGCGCUGUUCACCCUC

AGAGCACACUGAAGCUGCCCCACAAGCGGGGCGAAAGAGAUGUG

CCUACCAACCUGGCCAGCCUGCCUAAGAGAGGCGAUUGCAGAAC

CGGCAAUAGCAGAGGCCCUGUGUCCGGCAUCUACCUGAAACCUG

GACCACUGUUCUACCAGGACUACAAGGGACCCGUGUACCACAGA

GCCCCUCUGGAACUGUUUGAAGAGGGCAGCAUGUGCGAAACCAC

CAAGCGGAUCGGAAGAGUGACCGGCUCUGACGGCAAGCUGUACC

ACAUCUACGUGUGCAUCGACGGCUGCAUCAUCAUCAAGAGCGCC

ACCAGAUCCUACCAGCGGGUGUUCAGAUGGGUGCACAACAGACU

GGACUGCCCUCUGUGGGUCACCAGCUGC
```

Accordingly, therefore, preferably the RNA construct comprises an RNA nucleotide sequence substantially as set out as SEQ ID No: 46, or a variant or fragment thereof.

In one embodiment, the Langat NS5 polypeptide is provided herein as SEQ ID No: 17, as follows:

```
                                      [SEQ ID No: 17]
VFKDKVDTKAQEPQPGTKIIMRAVNDWLLERLVKKSRPRMCSRE

EFIAKVRSNAALGAWSDEQNKWKSAREAVEDPEFWSLVEAERER
```

-continued

```
HLQGRCAHCVYNMMGKREKKLGEFGVAKGSRAIWYMWLGSRFLE

FEALGFLNEDHWASRASSGAGVEGISLNYLGWHLKKLASLSGGL

FYADDTAGWDTKITNADLDDEEQILRYMDGDHKKLAATVLRKAY

HAKVVRVARPSREGGCVMDIITRRDQRGSGQVVTYALNTITNIK

VQLVRMMEGEGVIEVADSHNPRLLRVEKWLEEHGEERLSRMLVS

GDDCWRPVDDRFSKALYFLNDMAKTRKDTGEWEPSTGFASWEEV

PFCSHHFHELVMKDGRALWPCRDQDEL
```

Accordingly, preferably the Langat NS5 polypeptide comprises an amino acid sequence substantially as set out in SEQ ID NO: 17, or a biologically active variant or fragment thereof. Hence, the RNA construct of the first aspect preferably comprises a RNA nucleotide sequence which encodes SEQ ID No: 17, or a variant or fragment thereof.

In one embodiment, the Langat NS5 polypeptide is encoded by the nucleotide sequence of SEQ ID No: 18, as follows:

[SEQ ID No: 18]
```
GTGTTCAAGGACAAGGTGGACACCAAGGCTCAAGAGCCTCAGCC

TGGCACCAAGATCATCATGAGAGCCGTGAACGACTGGCTGCTGG

AACGGCTGGTCAAGAAAAGCAGACCCCGGATGTGCAGCCGGGAA

GAGTTTATCGCCAAAGTGCGGAGCAATGCCGCTCTCGGAGCTTG

GAGTGACGAGCAGAACAAGTGGAAGTCCGCCAGAGAAGCCGTGG

AAGATCCCGAGTTTTGGAGCCTGGTGGAAGCCGAGAGAGAGAGG

CATCTGCAGGGAAGATGTGCCCACTGCGTGTACAACATGATGGG

CAAGAGAGAGAAGAAGCTGGGCGAGTTCGGAGTGGCCAAAGGCA

GCAGAGCCATCTGGTATATGTGGCTGGGCAGCCGCTTCCTGGAA

TTTGAGGCCCTGGGCTTCCTGAACGAGGATCACTGGGCTAGCAG

AGCCTCTTCTGGTGCTGGCGTGGAAGGCATCAGCCTGAATTATC

TCGGCTGGCACCTGAAGAAACTGGCCTCTCTGTCTGGCGGCCTG

TTCTACGCCGATGATACAGCCGGATGGGACACAAAGATCACCAA

CGCCGACCTGGACGACGAGGAACAGATCCTGAGATATATGGACG

GCGACCACAAAAAGCTGGCCGCCACCGTGCTGAGAAAGGCCTAT

CACGCCAAGGTCGTCAGAGTGGCCAGACCTAGTAGAGAAGGCGG

CTGCGTGATGGACATCATCACCAGAAGGGACCAGCGCGGCTCTG

GCCAGGTTGTGACATACGCCCTGAACACCATCACCAACATCAAG

GTGCAGCTCGTGCGGATGATGGAAGGCGAGGGCGTGATCGAAGT

GGCCGACAGCCATAATCCTCGGCTGCTGAGAGTGGAAAAGTGGC

TGGAAGAACACGGCGAAGAACGGCTGAGCAGAATGCTGGTGTCC

GGCGACGATTGTGTTGTGCGGCCCGTGGACGACAGATTCAGCAA

GGCCCTGTACTTTCTGAATGACATGGCCAAGACCAGAAAGGACA

CCGGCGAGTGGGAGCCTTCTACAGGCTTTGCCAGCTGGGAAGAA

GTGCCTTTCTGCAGCCACCACTTCCACGAGCTGGTCATGAAGGA

TGGCAGAGCCCTGGTGGTGCCCTGCAGAGATCAGGACGAACTG
```

Accordingly, preferably the Langat NS5 polypeptide is encoded by the nucleotide sequence substantially as set out in SEQ ID NO: 18, or a variant or fragment thereof.

Thus, the RNA construct may comprise an RNA nucleotide sequence of SEQ ID No: 49, as follows:

[SEQ ID No: 49]
```
GUGUUCAAGGACAAGGUGGACACCAAGGCUCAAGAGCCUCAGCC

UGGCACCAAGAUCAUCAUGAGAGCCGUGAACGACUGGCUGCUGG

AACGGCUGGUCAAGAAAAGCAGACCCCGGAUGUGCAGCCGGGAA

GAGUUUAUCGCCAAAGUGCGGAGCAAUGCCGCUCUCGGAGCUUG

GAGUGACGAGCAGAACAAGUGGAAGUCCGCCAGAGAAGCCGUGG

AAGAUCCCGAGUUUUGGAGCCUGGUGGAAGCCGAGAGAGAGAGG

CAUCUGCAGGGAAGAUGUGCCCACUGCGUGUACAACAUGAUGGG

CAAGAGAGAGAAGAAGCUGGGCGAGUUCGGAGUGGCCAAAGGCA

GCAGAGCCAUCUGGUAUAUGUGGCUGGGCAGCCGCUUCCUGGAA

UUUGAGGCCCUGGGCUUCCUGAACGAGGAUCACUGGGCUAGCAG

AGCCUCUUCUGGUGCUGGCGUGGAAGGCAUCAGCCUGAAUUAUC

UCGGCUGGCACCUGAAGAAACUGGCCUCUCUGUCUGGCGGCCUG

UUCUACGCCGAUGAUACAGCCGGAUGGGACACAAAGAUCACCAA

CGCCGACCUGGACGACGAGGAACAGAUCCUGAGAUAUAUGGACG

GCGACCACAAAAAGCUGGCCGCCACCGUGCUGAGAAAGGCCUAU

CACGCCAAGGUCGUCAGAGUGGCCAGACCUAGUAGAGAAGGCGG

CUGCGUGAUGGACAUCAUCACCAGAAGGGACCAGCGCGGCUCUG

GCCAGGUUGUGACAUACGCCCUGAACACCAUCACCAACAUCAAG

GUGCAGCUCGUGCGGAUGAUGGAAGGCGAGGGCGUGAUCGAAGU

GGCCGACAGCCAUAAUCCUCGGCUGCUGAGAGUGGAAAAGUGGC

UGGAAGAACACGGCGAAGAACGGCUGAGCAGAAUGCUGGUGUCC

GGCGACGAUUGUGUUGUGCGGCCCGUGGACGACAGAUUCAGCAA

GGCCCUGUACUUUCUGAAUGACAUGGCCAAGACCAGAAAGGACA

CCGGCGAGUGGGAGCCUUCUACAGGCUUUGCCAGCUGGGAAGAA

GUGCCUUUCUGCAGCCACCACUUCCACGAGCUGGUCAUGAAGGA

UGGCAGAGCCCUGGUGGUGCCCUGCAGAGAUCAGGACGAACUG
```

Accordingly, therefore, preferably the RNA construct comprises an RNA nucleotide sequence substantially as set out as SEQ ID No: 49 or a variant or fragment thereof.

In one embodiment, the Influenza NS1 polypeptide (Accession number DQ508893) is provided herein as SEQ ID No: 13, as follows:

[SEQ ID No: 13]
```
MDSNTVSSFQVDCFLWHVRKQVADQELGDAPFLDRLRRDQKSLK

GRGSTLGLNIETATCVGKQIVERILKEESDEAFRMTMASALASR

YLTDMTIEEMSRDWFMLMPKQKVAGPLCVRMDQAIMDKNIILKA

NFSVIFDRLETLTLLRAFTEEGAIVGEISPLPSLPGHTNEDVKN
```

-continued

AIGVLIGGLEWNDNTVRVSETLQRFAWRSSNENGGPPLTPTQKR

KMAGKIRSEV

Accordingly, preferably the Influenza NS1 polypeptide comprises an amino acid sequence substantially as set out in SEQ ID NO: 13, or a biologically active variant or fragment thereof. Hence, the RNA construct of the first aspect preferably comprises a RNA nucleotide sequence which encodes SEQ ID No: 13, or a variant or fragment thereof.

In one embodiment, the Influenza NS1 polypeptide is encoded by the nucleotide sequence of SEQ ID No: 14, as follows:

[SEQ ID No: 14]
atggattccaacactgtgtcaagotttcaggtaga ttgottcctttggcatgtccgcaaacaagttgcag accaagagctaggtgatgccccattccttgatcgg cttcgccgagatcagaagtccctaaagggaagagg cagcactctcggtctgaacatcgaaacagccacct gtgttggaaagcaaatagtagagaggattctgaag gaagaatccgatgaggcatttagaatgaccatggc ctccgcacttgottcgcgatacctaactgacatga ctattgaagagatgtcaagggactggttcatgctc atgcccaagcagaaagtggcaggccctotttgtgt cagaatggaccaggcgataatggataagaacatca tactgaaagcgaatttcagtgtgattttttgaccgg ttggagactctgacattactaagggctttcaccga agagggagcaattgttggcgaaatttcaccattgc cttctcttccaggacatactaatgaggatgtcaaa aatgcaattggggtoctcatcgggggacttgaatg gaatgataacacagttcgagtctctgaaactctac agagattcgcttggagaagcagtaatgagaatggg ggacctccactcactccaacacagaaacggaaaat ggcgggaaaaattaggtcagaagtttga Accordingly, preferably the Influenza NS1 polypeptide is encoded by the nucleotide sequence substantially as set out in SEQ ID NO: 14, or a variant or fragment thereof.

Thus, the RNA construct may comprise an RNA nucleotide sequence of SEQ ID No: 19, as follows:

[SEQ ID No: 19]
auggauuccaacacugugucaagcuuucagguaga uugcuuccuuuggcauguccgcaaacaaguugcag accaagagcuaggugaugccccauuccuugaucgg cuucgccgagaucagaaguhccuaaagggaagagg cagcacucucggucugaacaucgaaacagccaccu guguuggaaagcaaauaguagagaggauucugaag -continued
gaagaauccgaugaggcauuuagaaugaccauggc cuccgcacuugcuucgcgauaccuaacugacauga cuauugaagagaugucaagggacugguucaugcuc augcccaagcagaaaguggcaggcccucuuugugu cagaauggaccaggcgauaauggauaagaacauca uacugaaagcgaauuucagugugauuuuugaccgg uuggagacucugacauuacuaagggcuuucaccga agagggagcaauuguuggcgaaauuucaccauugc cuucucuuccaggacauacuaaugaggaugucaaa aaugcaauuggggucaucaucggggggacuugaaug gaaugauaacacaguucgagucucugaaacucuac agagauucgcuuggagaagcaguaaugagaauggg ggaccuccacucacuccaacacagaaacggaaaau ggcgggaaaaauuaggucagaaguuuga Accordingly, therefore, preferably the RNA construct comprises an RNA nucleotide sequence substantially as set out as SEQ ID No: 19, or a variant or fragment thereof.

Preferably, the innate inhibitor protein is selected from the group consisting of HSV-2 Us1; HSV-1 Us11; OV20.0L; BVDV Npro, PIV5 V; MERS-CoV ORF4a; SARS-CoV-2 ORF3b; Langat virus NS5 and Influenza NS1.

Preferably, the innate inhibitor protein is selected from the group consisting of HSV-2 Us1; HSV-1 Us11; OV20.0L; BVDV Npro, PIV5 V; MERS-CoV ORF4a; and Langat virus NS5.

Preferably, the innate inhibitor protein is selected from the group consisting of HSV-2 Us1; HSV-1 Us11; OV20.0L; BVDV Npro, PIV5 V; and MERS-CoV ORF4a.

As described in the Examples, through a process of screening a wide range of IIPs, the inventors identified two highly potent IIPs that were surprisingly able to significantly enhance saRNA expression in vitro and in vivo: Parainfluenza virus type 5 V protein (PIV-5), an inhibitor of MDA5 activation and Middle East respiratory syndrome (MERS) coronavirus ORF4a, and inhibitor of PACT/MDA activation. The inventors have utilized these two novel IIPs, PIV-5 and MERS-CoV ORF4a, which have not previously been used to mitigate innate sensing of replicon RNA. The inventors have shown that these constructs can be the next-generation RNA replicons that will enable higher efficacy of RNA vaccines and therapeutics in humans. The inventors believe that they will have significant utility, whether expressed in alphavirus, picornaviruses, flaviviruses, or coronaviruses replicons.

Thus, most preferably, the innate inhibitor protein is PIV-5 and/or MERS-CoV ORF4a, which the skilled person would understand may also be referred to as NS4a.

Such constructs display many advantages over those described in the prior art, including:

i) insertion of PIV-5 and ORF4a proteins directly into the VEEV replicon, enabling dual protein expression of the VPII protein and the gene of interest;

ii) as opposed to delivering two different strands of RNA, one encoding the gene of interest (GOI), i.e. the therapeutic biomolecule, and one encoding the IIP, a single strand is delivered thus ensuring colocalization of the RNA and the innate inhibiting protein;

iii) the IIP inhibits innate sensing of RNA, thus enabling higher protein expression;

iv) the IIP expression itself is self-amplified by virtue of being co-expressed on the sub genome strand with the GOI; and/or v) an increase in both the magnitude and duration of protein expression compared to conventional VEEV RNA replicon constructs.

The sequence encoding the at least one innate inhibitor protein may be disposed anywhere within the RNA construct or replicon sequence, such that the sequence encoding the at least one peptide or protein of interest may be disposed 5' or 3' to the sequence encoding the at least one innate inhibitor protein.

However, preferably the sequence encoding the at least one peptide or protein of interest is disposed 5' to the sequence encoding the at least one innate inhibitor protein.

Preferably, the RNA construct according to the first aspect comprises at least one promoter, either genomic or subgenomic. Preferably, the promoter is a sub genomic promoter.

The skilled person would understand that the sub genomic promotor relates to a promoter that is operably linked to the sequences encoding the at least one therapeutic biomolecule and the at least one innate inhibitor protein, such that it enables the transcription the nucleotide sequence encoding the therapeutic biomolecule and the at least one innate inhibitor protein.

Preferably, the sub genomic promoter is 26S, which is provided herein as SEQ ID No: 57, as follows:

[SEQ ID No: 57]
GGGCCCCTATAACTCTCTACGGCTAACCTGAATGGACTACGACAT

Accordingly, preferably the promoter (preferably, a sub genomic promoter) is as substantially as set out in SEQ ID NO: 57, or a variant or fragment thereof.

In one embodiment, the same promotor is operably linked to the sequence encoding the at least one peptide or protein of interest and the sequence encoding the at least one innate inhibitor.

The inventor's design, wherein both the GOI (i.e. the therapeutic biomolecule) and IIPs are encoded in a single strand, advantageously enables the use of much smaller doses of RNA, because it ensures that the protein is being expressed in the same cell that is sensing the RNA, and can also be replicated, therefore having the additional aspect of amplification of the innate inhibitory component.

Thus, in one embodiment, the promoter is disposed 5' of the sequence encoding the peptide or protein of interest (i.e. the therapeutic biomolecule) and the sequence encoding the at least one innate inhibitor protein such that the promoter is operably linked to both sequences.

In another embodiment, a first promotor is operably linked to the sequence encoding the at least one peptide or protein of interest (i.e. the therapeutic biomolecule) and a second promotor is operably linked the sequence encoding the at least one innate inhibitor protein.

The RNA construct may encode at least two, three, four or five IIPs. In embodiments in which there is more than one sequence encoding an innate inhibitor protein, a single promotor may be operably linked to all sequences encoding an innate inhibitor protein.

Alternatively, a promotor may be linked to each of the at least one other sequence encoding an innate inhibitor protein such that each innate inhibitor protein is operably linked to a separate promoter. In this embodiment, the separate promoters may comprise the same promotor sequence or different promoter sequences. In another embodiment, different promotors are operably linked to each sequence encoding an innate inhibitor protein.

The RNA construct may further comprise a linker sequence disposed between the sequence encoding the at least one peptide or protein of interest (i.e. the therapeutic biomolecule) and the sequence encoding the at least one innate inhibitor protein.

In one embodiment, the linker sequence comprises a sequence that encodes a peptide spacer that is configured to be digested to thereby separate the at least one therapeutic biomolecule encoded by the gene of interest and the at least one innate inhibitor protein. Therefore, preferably the spacer sequence is disposed between the sequence encoding the at least one peptide or protein of interest and the sequence encoding at least one innate inhibitor protein.

As such, the spacer sequence is preferably a cleavable peptide, for example a 2A peptide. Suitable 2A peptides include the porcine teschovirus-12A (P2A)-ATNFSLLKQAGDVEENPGP (SEQ ID No: 21), thosea asigna virus 2A (T2A)-QCTNYALLKLAGDVESNPGP (SEQ ID No: 22), equine rhinitis A virus 2A (E2A), and Foot and mouth disease virus 2A (F2A) VKQTLNFDLLKLAGDVESNPGP (SEQ ID No: 23). Preferably, the 2A peptide is thosea asigna virus 2A (T2A).

In another embodiment, the cleavable peptide is a self-cleaving peptide. Preferably, the self-cleaving peptide is a furin/2A peptide. The furin sequence may be disposed 3' or 5' of the 2A sequence. Preferably, however, the furin sequence is disposed 5' of the 2A sequence, and preferably with a GSG spacer disposed between the furin and 2A sequence.

The skilled person would appreciate that furin is a ubiquitous calcium-dependent proprotein convertase located in the secretory pathway (mainly in the golgi and trans-golgi network) that cleaves precursor proteins at a specific recognition sequence—canonically R-X-R/K/X-R (SEQ ID No: 24), and cleaving the proprotein after the final R. Thus, in one embodiment the furin sequence is R-X-R/K/X-R. However, preferably, the furin sequence is the optimised sequence RRRRRR (SEQ ID No: 25) a GSG sequence. Preferably, the GSG spacer is disposed 3' of the furin sequence and 5' of the 2A sequence.

Thus, preferably, the spacer sequence is the furin/T2A, as provided by NCBI Reference Sequence: GenBank: AAC97195.1, and provided herein as SEQ ID No: 26, as follows:

[SEQ ID No: 26]
RRRRRRGSGEGRGSLLTCGDVEENPGP

Hence, preferably the spacer sequence comprises an amino acid sequence substantially as set out in SEQ ID NO: 26, or a variant or fragment thereof.

In embodiments in which the RNA construct or replicon comprises more than one sequence encoding an innate inhibiting protein, the replicon may have linker sequences disposed between each sequence encoding an innate inhibitor protein, or only between some IIPs.

In one embodiment, the at least one sequence encoding the therapeutic biomolecule and the at least one innate inhibitor protein may be separated by a stop codon followed by an internal ribosome entry site (IRES) sequence capable of initiating translation of the downstream sequence. Typical IRES sequences include those such as the IRES sequence of encephalomyocarditis virus or vascular endothelial growth factor and type 1 collagen-inducible protein (VCIP), and would be known to those skilled in the Art. Therefore, preferably the IRES sequence is disposed between the sequence encoding the at least one peptide or protein of interest and the sequence encoding at least one innate inhibitor protein. Where multiple sequences encoding at least one innate inhibitor protein are used, spacer sequences may include combinations of known cleavage sequences and/or IRES sequences.

In another embodiment, the sequence encoding the at least one therapeutic biomolecule and the at least one innate inhibitor protein may be separated by a stop codon followed by a second subgenomic promotor sequence capable of initiating transcription of the downstream sequence.

The RNA construct may encode at least one non-structural protein (NSP), disposed 5' or 3' of the sequence encoding the at least one peptide or protein of interest and the at least one innate inhibiting protein. Preferably, the sequence encoding the at least one NSP is disposed 5' of the sequences encoding the peptide or protein of interest and the at least one innate inhibiting protein. Thus, preferably the sequence encoding the at least one NSP is disposed at the 5' end of the RNA construct.

The at least one non-structural protein, which is encoded by the RNA construct, may be the RNA polymerase nsP4. Preferably, the construct encodes nsP1, nsP2, nsP3 and nsP4. The skilled person would understand that nsP1 is the viral capping enzyme and membrane anchor of the replication complex (RC), while nsP2 is an RNA helicase and the protease responsible for the ns polyprotein processing. nsP3 interacts with several host proteins and may modulate protein poly- and mono-ADP-ribosylation, and nsP4 is the core viral RNA-dependent RNA polymerase.

In one embodiment, nsP1 is provided herein as SEQ ID No: 27, as follows:

```
                                  [SEQ ID No: 27]
MEKVHVDIEEDSPFLRALQRSFPQFEVEAKQVTDN

DHANARAFSHLASKLIETEVDPSDTILDIGSAPAR

RMYSKHKYHCICPMRCAEDPDRLYKYATKLKKNCK

EITDKELDKKMKELAAVMSDPDLETETMCLHDDES

CRYEGQVAVYQDVYAVDGPTSLYHQANKGVRVAYW

IGFDTTPFMFKNLAGAYPSYSTNWADETVLTARNI

GLCSSDVMERSRRGMSILRKKYLKPSNNVLFSVGS

TIYHEKRDLLRSWHLPSVFHLRGKQNYTCRCETIV

SCDGYVVKRIAISPGLYGKPSGYAATMHREGFLCC

KVTDTLNGERVSFPVCTYVPATLCDQMTGILATDV

SADDAQKLLVGLNQRIVVNGRTQRNTNTMKNYLLP

VVAQAFARWAKEYKEDQEDERPLGLRDRQLVMGCC

WAFRRHKITSIYKRPDTQTIIKVNSDFHSFVLPRI

GSNTLEIGLRTRIRKMLEEHKEPSPLITAEDVQEA

KCAADEAKEVREAEELRAALPPLAADVEEPTLEAD

VDLMLQEAGA
```

Accordingly, nsP1 preferably comprises an amino acid sequence as substantially as set out in SEQ ID No: 27, or a biologically active variant or fragment thereof.

In one embodiment, nsP1 is encoded by a nucleotide sequence a defined in SEQ ID No: 28, as follows:

```
                                  [SEQ ID No: 28]
ATGGAGAAAGTTCACGTTGACATCGAGGAAGACAG

CCCATTCCTCAGAGCTTTGCAGCGGAGCTTCCCGC

AGTTTGAGGTAGAAGCCAAGCAGGTCACTGATAAT

GACCATGCTAATGCCAGAGCGTTTTCGCATCTGGC

TTCAAAACTGATCGAAACGGAGGTGGACCCATCCG

ACACGATCCTTGACATTGGAAGTGCGCCCGCCCGC

AGAATGTATTCTAAGCACAAGTATCATTGTATCTG

TCCGATGAGATGTGCGGAAGATCCGGACAGATTGT

ATAAGTATGCAACTAAGCTGAAGAAAAACTGTAAG

GAAATAACTGATAAGGAATTGGACAAGAAAATGAA

GGAGCTGGCCGCCGTCATGAGCGACCCTGACCTGG

AAACTGAGACTATGTGCCTCCACGACGACGAGTCG

TGTCGCTACGAAGGGCAAGTCGCTGTTTACCAGGA

TGTATACGCGGTTGACGGACCGACAAGTCTCTATC

ACCAAGCCAATAAGGGAGTTAGAGTCGCCTACTGG

ATAGGCTTTGACACCACCCCTTTTATGTTTAAGAA

CTTGGCTGGAGCATATCCATCATACTCTACCAACT

GGGCCGACGAAACCGTGTTAACGGCTCGTAACATA

GGCCTATGCAGCTCTGACGTTATGGAGCGGTCACG

TAGAGGGATGTCCATTCTTAGAAAGAAGTATTTGA

AACCATCCAACAATGTTCTATTCTCTGTTGGCTCG

ACCATCTACCACGAGAAGAGGGACTTACTGAGGAG

CTGGCACCTGCCGTCTGTATTTCACTTACGTGGCA

AGCAAAATTACACATGTCGGTGTGAGACTATAGTT

AGTTGCGACGGGTACGTCGTTAAAAGAATAGCTAT

CAGTCCAGGCCTGTATGGGAAGCCTTCAGGCTATG

CTGCTACGATGCACCGCGAGGGATTCTTGTGCTGC

AAAGTGACAGACACATTGAACGGGGAGAGGGTCTC

TTTTCCCGTGTGCACGTATGTGCCAGCTACATTGT

GTGACCAAATGACTGGCATACTGGCAACAGATGTC

AGTGCGGACGACGCGCAAAAACTGCTGGTTGGGCT

CAACCAGCGTATAGTCGTCAACGGTCGCACCCAGA

GAAACACCAATACCATGAAAAATTACCTTTTGCCC

GTAGTGGCCCAGGCATTTGCTAGGTGGGCAAAGGA

ATATAAGGAAGATCAAGAAGATGAAAGGCCACTAG

GACTACGAGATAGACAGTTAGTCATGGGGTGTTGT

TGGGCTTTTAGAAGGCACAAGATAACATCTATTTA

TAAGCGCCCGGATACCCAAACCATCATCAAAGTGA
```

-continued

ACAGCGATTTCCACTCATTCGTGCTGCCCAGGATA

GGCAGTAACACATTGGAGATCGGGCTGAGAACAAG

AATCAGGAAAATGTTAGAGGAGCACAAGGAGCCGT

CACCTCTCATTACCGCCGAGGACGTACAAGAAGCT

AAGTGCGCAGCCGATGAGGCTAAGGAGGTGCGTGA

AGCCGAGGAGTTGCGCGCAGCTCTACCACCTTTGG

CAGCTGATGTTGAGGAGCCCACTCTGGAAGCCGAT

GTCGACTTGATGTTACAAGAGGCTGGGGCC

Accordingly, nsP1 is preferably encoded by a nucleotide sequence as substantially as set out in SEQ ID No: 28, or a variant or fragment thereof.

Accordingly, therefore, preferably the RNA construct comprises an RNA nucleotide sequence substantially as set out as SEQ ID No 50 or a variant or fragment thereof.

[SEQ ID No: 50]

AUGGAGAAAGUUCACGUUGACAUCGAGGAAGACAG

CCCAUUCCUCACAGCUUUGCAGCGGAGCUUCCCGC

AGUUUGAGGUAGAAGCCAAGCAGGUCACUGAUAAU

GACCAUGCUAAUGCCAGAGCGUUUUCGCAUCUGGC

UUCAAAACUGAUCGAAACGGAGGUGGACCCAUCCG

ACACGAUCCUUGACAUUGGAAGUGCGCCCGCCCGC

AGAAUGUAUUCUAAGCACAAGUAUCAUUGUAUCUG

UCCGAUGAGAUGUGCGGAAGAUCCGGACAGAUUGU

AUAAGUAUGCAACUAAGCUGAAGAAAAACUGUAAG

GAAAUAACUGAUAAGGAAUUGGACAAGAAAAUGAA

GGAGCUGGCCGCCGUCAUGAGCGACCCUGACCUGG

AAACUGAGACUAUGUGCCUCCACGACGACGAGUCG

UGUCGCUACGAAGGGCAAGUCGCUGUUUACCAGGA

UGUAUACGCGGUUGACGGACCGACAAGUCUCUAUC

ACCAAGCCAAUAAGGGAGUUAGAGUCGCCUACUGG

AUAGGCUUUGACACCACCCCUUUUAUGUUUAAGAA

CUUGGCUGGAGCAUAUCCAUCAUACUCUACCAACU

GGGCCGACGAAACCGUGUUAACGGCUCGUAACAUA

GGCCUAUGCAGCUCUGACGUUAUGGAGCGGUCACG

UAGAGGGAUGUCCAUUCUUAGAAAGAAGUAUUUGA

AACCAUCCAACAAUGUUCUAUUCUCUGUUGGCUCG

ACCAUCUACCACGAGAAGAGGGACUUACUGAGGAG

CUGGCACCUGCCGUCUGUAUUUCACUUACGUGGCA

AGCAAAAUUACACAUGUCGGUGUGAGACUAUAGUU

AGUUGCGACGGGUACGUCGUUAAAAGAAUAGCUAU

CAGUCCAGGCCUGUAUGGGAAGCCUUCAGGCUAUG

CUGCUACGAUGCACCGCGAGGGAUUCUUGUGCUGC

-continued

AAAGUGACAGACACAUUGAACGGGGAGAGGGUCUC

UUUUCCCGUGUGCACGUAUGUGCCAGCUACAUUGU

GUGACCAAAUGACUGGCAUACUGGCAACAGAUGUC

AGUGCGGACGACGCGCAAAAACUGCUGGUUGGGCU

CAACCAGCGUAUAGUCGUCAACGGUCGCACCCAGA

GAAACACCAAUACCAUGAAAAAUUACCUUUUGCCC

GUAGUGGCCCAGGCAUUUGCUAGGUGGGCAAAGGA

AUAUAAGGAAGAUCAAGAAGAUGAAAGGCCACUAG

GACUACGAGAUAGACAGUUAGUCAUGGGGUGUUGU

UGGGCUUUUAGAAGGCACAAGAUAACAUCUAUUUA

UAAGCGCCCGGAUACCCAAACCAUCAUCAAAGUGA

ACAGCGAUUUCCACUCAUUCGUGCUGCCCAGGAUA

GGCAGUAACACAUUGGAGAUCGGGCUGAGAACAAG

AAUCAGGAAAAUGUUAGAGGAGCACAAGGAGCCGU

CACCUCUCAUUACCGCCGAGGACGUACAAGAAGCU

AAGUGCGCAGCCGAUGAGGCUAAGGAGGUGCGUGA

AGCCGAGGAGUUGCGCGCAGCUCUACCACCUUUGG

CAGCUGAUGUUGAGGAGCCCACUCUGGAAGCCGAU

GUCGACUUGAUGUUACAAGAGGCUGGGGCC

In one embodiment, nsP2 is provided herein as SEQ ID No: 29, as follows:

[SEQ ID No: 29]

GSVETPRGLIKVTSYDGEDKIGSYAVLSPQAVLKS

EKLSCIHPLAEQVIVITHSGRKGRYAVEPYHGKVV

VPEGHAIPVQDFQALSESATIVYNEREFVNRYLHH

IATHGGALNTDEEYYKTVKPSEHDGEYLYDIDRKQ

CVKKELVTGLGLTGELVDPPFHEFAYESLRTRPAA

PYQVPTIGVYGVPGSGKSGIIKSAVTKKDLVVSAK

KENCAEIIRDVKKMKGLDVNARTVDSVLLNGCKHP

VETLYIDEAFACHAGTLRALIAIIRPKKAVLCGDP

KQCGFFNMMCLKVHFNHEICTQVFHKSISRRCTKS

VTSVVSTLFYDKKMRTTNPKETKIVIDTTGSTKPK

QDDLILTCFRGWVKQLQIDYKGNEIMTAAASQGLT

RKGVYAVRYKVNENPLYAPTSEHVNVLLTRTEDRI

VWKTLAGDPWIKTLTAKYPGNFTATIEEWQAEHDA

IMRHILERPDPTDVFQNKANVCNAKALVPVLKTAG

IDMTTEQWNTVDYFETDKAHSAEIVLNQLCVRFFG

LDLDSGLFSAPTVPLSIRNNHWDNSPSPNMYGLNK

EVVRQLSRRYPQLPRAVATGRVYDMNTGTLRNYDP

RINLVPVNRRLPHALVLHHNEHPQSDFSSFVSKLK

GRTVLVVGEKLSVPGKMVDWLSDRPEATFRARLDL

-continued

GIPGDVPKYDIIFVNVRTPYKYHHYQQCEDHAIKL

SMLTKKACLHLNPGGTCVSIGYGYADRASESIIGA

IARQFKFSRVCKPKSSLEETEVLFVFIGYDRKART

HNSYKLSSTLTNIYTGSRLHEAGC

Accordingly, nsP2 preferably comprises an amino acid sequence as substantially as set out in SEQ ID No: 29, or a biologically active variant or fragment thereof.

In one embodiment, nsP2 is encoded by a nucleotide sequence a defined in SEQ ID No: 30, as follows:

[SEQ ID No: 30]

GGCTCAGTGGAGACACCTCGTGGCTTGATAAAGGT

TACCAGCTACGATGGCGAGGACAAGATCGGCTCTT

ACGCTGTGCTTTCTCCGCAGGCTGTACTCAAGAGT

GAAAAATTATCTTGCATCCACCCTCTCGCTGAACA

AGTCATAGTGATAACACACTCTGGCCGAAAAGGGC

GTTATGCCGTGGAACCATACCATGGTAAAGTAGTG

GTGCCAGAGGGACATGCAATACCCGTCCAGGACTT

TCAAGCTCTGAGTGAAAGTGCCACCATTGTGTACA

ACGAACGTGAGTTCGTAAACAGGTACCTGCACCAT

ATTGCCACACATGGAGGAGCGCTGAACACTGATGA

AGAATATTACAAAACTGTCAAGCCCAGCGAGCACG

ACGGCGAATACCTGTACGACATCGACAGGAAACAG

TGCGTCAAGAAAGAACTAGTCACTGGGCTAGGGCT

CACAGGCGAGCTGGTGGATCCTCCCTTCCATGAAT

TCGCCTACGAGAGTCTGAGAACACGACCAGCCGCT

CCTTACCAAGTACCAACCATAGGGGTGTATGGCGT

GCCAGGATCAGGCAAGTCTGGCATCATTAAAAGCG

CAGTCACCAAAAAAGATCTAGTGGTGAGCGCCAAG

AAAGAAAACTGTGCAGAAATTATAAGGGACGTCAA

GAAAATGAAAGGGCTGGACGTCAATGCCAGAACTG

TGGACTCAGTGCTCTTGAATGGATGCAAACACCCC

GTAGAGACCCTGTATATTGACGAAGCTTTTGCTTG

TCATGCAGGTACTCTCAGAGCGCTCATAGCCATTA

TAAGACCTAAAAAGGCAGTGCTCTGCGGGGATCCC

AAACAGTGCGGTTTTTTTAACATGATGTGCCTGAA

AGTGCATTTTAACCACGAGATTTGCACACAAGTCT

TCCACAAAAGCATCTCTCGCCGTTGCACTAAATCT

GTGACTTCGGTCGTCTCAACCTTGTTTTACGACAA

AAAAATGAGAACGACGAATCCGAAAGAGACTAAGA

TTGTGATTGACACTACCGGCAGTACCAAACCTAAG

CAGGACGATCTCATTCTCACTTGTTTCAGAGGGTG

-continued

GGTGAAGCAGTTGCAAATAGATTACAAAGGCAACG

AAATAATGACGGCAGCTGCCTCTCAAGGGCTGACC

CGTAAAGGTGTGTATGCCGTTCGGTACAAGGTGAA

TGAAAATCCTCTGTACGCACCCACCTCAGAACATG

TGAACGTCCTACTGACCCGCACGGAGGACCGCATC

GTGTGGAAAACACTAGCCGGCGACCCATGGATAAA

AACACTGACTGCCAAGTACCCTGGGAATTTCACTG

CCACGATAGAGGAGTGGCAAGCAGAGCATGATGCC

ATCATGAGGCACATCTTGGAGAGACCGGACCCTAC

CGACGTCTTCCAGAATAAGGCAAACGTGTGTTGGG

CCAAGGCTTTAGTGCCGGTGCTGAAGACCGCTGGC

ATAGACATGACCACTGAACAATGGAACACTGTGGA

TTATTTTGAAACGGACAAAGCTCACTCAGCAGAGA

TAGTATTGAACCAACTATGCGTGAGGTTCTTTGGA

CTCGATCTGGACTCCGGTCTATTTTCTGCACCCAC

TGTTCCGTTATCCATTAGGAATAATCACTGGGATA

ACTCCCCGTCGCCTAACATGTACGGGCTGAATAAA

GAAGTGGTCCGTCAGCTCTCTCGCAGGTACCCACA

ACTGCCTCGGGCAGTTGCCACTGGAAGAGTCTATG

ACATGAACACTGGTACACTGCGCAATTATGATCCG

CGCATAAACCTAGTACCTGTAAACAGAAGACTGCC

TCATGCTTTAGTCCTCCACCATAATGAACACCCAC

AGAGTGACTTTTCTTCATTCGTCAGCAAATTGAAG

GGCAGAACTGTCCTGGTGGTCGGGGAAAAGTTGTC

CGTCCCAGGCAAAATGGTTGACTGGTTGTCAGACC

GGCCTGAGGCTACCTTCAGAGCTCGGCTGGATTTA

GGCATCCCAGGTGATGTGCCCAAATATGACATAAT

ATTTGTTAATGTGAGGACCCCATATAAATACCATC

ACTATCAGCAGTGTGAAGACCATGCCATTAAGCTT

AGCATGTTGACCAAGAAAGCTTGTCTGCATCTGAA

TCCCGGCGGAACCTGTGTCAGCATAGGTTATGGTT

ACGCTGACAGGGCCAGCGAAAGCATCATTGGTGCT

ATAGCGCGGCAGTTCAAGTTTTCCCGGGTATGCAA

ACCGAAATCCTCACTTGAAGAGACGGAAGTTCTGT

TTGTATTCATTGGGTACGATCGCAAGGCCCGTACG

CACAATTCTTACAAGCTTTCATCAACCTTGACCAA

CATTTATACAGGTTCCAGACTCCACGAAGCCGGAT

GT

Accordingly, preferably nsP2 is encoded by a nucleotide sequence as substantially as set out in SEQ ID No: 30, or a variant or fragment thereof.

Thus, the RNA construct may comprise SEQ ID No 51, as follows:

[SEQ ID No: 51]
GGCUCAGUGGAGACACCUCGUGGCUUGAUAAAGGU

UACCAGCUACGAUGGCGAGGACAAGAUCGGCUCUU

ACGCUGUGCUUUCUCCGCAGGCUGUACUCAAGAGU

GAAAAAUUAUCUUGCAUCCACCCUCUCGCUGAACA

AGUCAUAGUGAUAACACACUCUGGCCGAAAAGGGC

GUUAUGCCGUGGAACCAUACCAUGGUAAAGUAGUG

GUGCCAGAGGGACAUGCAAUACCCGUCCAGGACUU

UCAAGCUCUGAGUGAAAGUGCCACCAUUGUGUACA

ACGAACGUGAGUUCGUAAACAGGUACCUGCACCAU

AUUGCCACACAUGGAGGAGCGCUGAACACUGAUGA

AGAAUAUUACAAAACUGUCAAGCCCAGCGAGCACG

ACGGCGAAUACCUGUACGACAUCGACAGGAAACAG

UGCGUCAAGAAAGAACUAGUCACUGGGCUAGGGCU

CACAGGCGAGCUGGUGGAUCCUCCCUUCCAUGAAU

UCGCCUACGAGAGUCUGAGAACACGACCAGCCGCU

CCUUACCAAGUACCAACCAUAGGGGGUGUAUGGCGU

GCCAGGAUCAGGCAAGUCUGGCAUCAUUAAAAGCG

CAGUCACCAAAAAAGAUCUAGUGGUGAGCGCCAAG

AAAGAAAACUGUGCAGAAAUUAUAAGGGACGUCAA

GAAAAUGAAAGGGCUGGACGUCAAUGCCAGAACUG

UGGACUCAGUGCUCUUGAAUGGAUGCAAACACCCC

GUAGAGACCCUGUAUAUUGACGAAGCUUUUGCUUG

UCAUGCAGGUACUCUCAGAGCGCUCAUAGCCAUUA

UAAGACCUAAAAAGGCAGUGCUCUGCGGGGAUCCC

AAACAGUGCGGUUUUUUUAACAUGAUGUGCCUGAA

AGUGCAUUUUAACCACGAGAUUUGCACACAAGUCU

UCCACAAAAGCAUCUCUCGCCGUUGCACUAAAUCU

GUGACUUCGGUCGUCUCAACCUUGUUUUUACGACAA

AAAAUGAGAACGACGAAUCCGAAAGAGACUAAGA

UUGUGAUUGACACUACCGGCAGUACCAAACCUAAG

CAGGACGAUCUCAUUCUCACUUGUUUCAGAGGGUG

GGUGAAGCAGUUGCAAAUAGAUUACAAAGGCAACG

AAAUAAUGACGGCAGCUGCCUCUCAAGGGCUGACC

CGUAAAGGUGUGUAUGCCGUUCGGUACAAGGUGAA

UGAAAAUCCUCUGUACGCACCCACCUCGAACAUG

UGAACGUCCUACUGACCCGCACGGAGGACCGCAUC

GUGUGGAAAACACUAGCCGGCGACCCAUGGAUAAA

AACACUGACUGCCAAGUACCCUGGGAAUUUCACUG

-continued
CCACGAUAGAGGAGUGGCAAGCAGAGCAUGAUGCC

AUCAUGAGGCACAUCUUGGAGAGACCGGACCCUAC

CGACGUCUUCCAGAAUAAGGCAAACGUGUGUUGGG

CCAAGGCUUUAGUGCCGGUGCUGAAGACCGCUGGC

AUAGACAUGACCACUGAACAAUGGAACACUGUGGA

UUAUUUUGAAACGGACAAAGCUCACUCAGCAGAGA

UAGUAUUGAACCAACUAUGCGUGAGGUUCUUUGGA

CUCGAUCUGGACUCCGGUCUAUUUUCUGCACCCAC

UGUUCCGUUAUCCAUUAGGAAUAAUCACUGGGAUA

ACUCCCCGUCGCCUAACAUGUACGGGCUGAAUAAA

GAAGUGGUCCGUCAGCUCUCUCGCAGGUACCCACA

ACUGCCUCGGGCAGUUGCCACUGGAAGAGUCUAUG

ACAUGAACACUGGUACACUGCGCAAUUAUGAUCCG

CGCAUAAACCUAGUACCUGUAAACAGAAGACUGCC

UCAUGCUUUAGUCCUCCACCAUAAUGAACACCCAC

AGAGUGACUUUUCUUCAUUCGUCAGCAAAUUGAAG

GGCAGAACUGUCCUGGUGGUCGGGGAAAAGUUGUC

CGUCCCAGGCAAAAUGGUUGACUGGUUGUCAGACC

GGCCUGAGGCUACCUUCAGAGCUCGGCUGGAUUUA

GGCAUCCCAGGUGAUGUGCCCAAAUAUGACAUAAU

AUUUGUUAAUGUGAGGACCCCAUAUAAAUACCAUC

ACUAUCAGCAGUGUGAAGACCAUGCCAUUAAGCUU

AGCAUGUUGACCAAGAAAGCUUGUCUGCAUCUGAA

UCCCGGCGGAACCUGUGUCAGCAUAGGUUAUGGUU

ACGCUGACAGGGCCAGCGAAAGCAUCAUUGGUGCU

AUAGCGCGGCAGUUCAAGUUUUCCCGGGUAUGCAA

ACCGAAAUCCUCACUUGAAGAGACGGAAGUUCUGU

UUGUAUUCAUUGGGUACGAUCGCAAGGCCCGUACG

CACAAUUCUUACAAGCUUUCAUCAACCUUGACCAA

CAUUUAUACAGGUUCCAGACUCCACGAAGCCGGAU

GU

Accordingly, therefore, preferably the RNA construct comprises an RNA nucleotide sequence substantially as set out as SEQ ID No 51 or a variant or fragment thereof.

In one embodiment, nsP3 is provided herein as SEQ ID No: 31, as follows:

[SEQ ID No: 31]
APSYHVVRGDIATATEGVIINAANSKGQPGGGVCG

ALYKKFPESFDLQPIEVGKARLVKGAAKHIIHAVG

PNFNKVSEVEGDKQLAEAYESIAKIVNDNNYKSVA

IPLLSTGIFSGNKDRLTQSLNHLLTALDTTDADVA

IYCRDKKWEMTLKEAVARREAVEEICISODSSVTE

-continued

PDAELVRVHPKSSLAGRKGYSTSDGKTFSYLEGTK

FHQAAKDIAEINAMWPVATEANEQVCMYILGESAS

SIRSKCPVEESEASTPPSTLPCLCIHAMTPERVQR

LKASRPEQITVCSSFPLPKYRITGVQKIQCSQPIL

FSPKVPAYIHPRKYLVETPPVDETPEPSAENQSTE

GTPEQPPLITEDETRTRTPEPIIIEEEEEDSISLL

SDGPTHQVLQVEADIHGPPSVSSSSWSIPHASDFD

VDSLSILDTLEGASVTSGATSAETNSYFAKSMEFL

ARPVPAPRTVFRNPPHPAPRTRIPSLAPSRACSRT

SLVSTPPGVNRVITREELEALTPSRTPSRSVSRTS

LVSNPPGVNRVITREEFEAFVAQQQRFDAGA

Accordingly, preferably nsP3 comprises an amino acid sequence as substantially as set out in SEQ ID No: 31, or a biologically active variant or fragment thereof.

In one embodiment, nsP3 is encoded by a nucleotide sequence a defined in SEQ ID No: 32, as follows:

[SEQ ID No: 32]
GCACCCTCAIATCATGTGGTGCGAGGGGATATTGC

CACGGCCACCGAAGGAGTGATTATAAATGCTGCTA

ACAGCAAAGGACAACCTGGCGGAGGGGTGTGCGGA

GCGCTGTATAAGAAATTCCCGGAAAGCTTCGATTT

ACAGCCGATCGAAGTAGGAAAAGCGCGACTGGTCA

AAGGTGCAGCTAAACATATCATTCATGCCGTAGGA

CCAAACTTCAACAAAGTTTCGGAGGTTGAAGGTGA

CAAACAGTTGGCAGAGGCTTATGAGTCCATCGCTA

AGATTGTCAACGATAACAATTACAAGTCAGTAGCG

ATTCCACTGTTGTCCACCGGCATCTTTTCCGGGAA

CAAAGATCGACTAACCCAATCATTGAACCATTTGC

TGACAGCTTTAGACACCACTGATGCAGATGTAGCC

ATATACTGCAGGGACAAGAAATGGGAAATGACTCT

CAAGGAAGCAGTGGCTAGGAGAGAAGCAGTGGAGG

AGATATGCATATCCGACGACTCTTCAGTGACAGAA

CCTGATGCAGAGCTGGTGAGGGTGCATCCGAAGAG

TTCTTTGGCTGGAAGGAAGGGCTACAGCACAAGCG

ATGGCAAAACTTTCTCATATTTGGAAGGGACCAAG

TTTCACCAGGCGGCCAAGGATATAGCAGAAATTAA

TGCCATGTGGCCCGTTGCAACGGAGGCCAATGAGC

AGGTATGCATGTATATCCTCGGAGAAAGCATGAGC

AGTATTAGGTCGAAATGCCCCGTCGAAGAGTCGGA

AGCCTCCACACCACCTAGCACGCTGCCTTGCTTGT

GCATCCATGCCATGACTCCAGAAAGAGTACAGCGC

-continued
CTAAAAGCCTCACGTCCAGAACAAATTACTGTGTG

CTCATCCTTTCCATTGCCGAAGTATAGAATCACTG

GTGTGCAGAAGATCCAATGCTCCCAGCCTATATTG

TTCTCACCGAAAGTGCCTGCGTATATTCATCCAAG

GAAGTATCTCGTGGAAACACCACCGGTAGACGAGA

CTCCGGAGCCATCGGCAGAGAACCAATCCACAGAG

GGGACACCTGAACAACCACCACTTATAACCGAGGA

TGAGACCAGGACTAGAACGCCTGAGCCGATCATCA

TCGAAGAGGAAGAAGAGGATAGCATAAGTTTGCTG

TCAGATGGCCCGACCCACCAGGTGCTGCAAGTCGA

GGCAGACATTCACGGGCCGCCCTCTGTATCTAGCT

CATCCTGGTCCATTCCTCATGCATCCGACTTTGAT

GTGGACAGTTTATCCATACTTGACACCCTGGAGGG

AGCTAGCGTGACCAGCGGGGCAACGTCAGCCGAGA

CTAACTCTTACTTCGCAAAGAGTATGGAGTTTCTG

GCGCGACCGGTGCCTGCGCCTCGAACAGTATTCAG

GAACCCTCCACATCCCGCTCCGCGCACAAGAACAC

CGTCACTTGCACCCAGCAGGGCCTGCTCGAGAACC

AGCCTAGTTTCCACCCCGCCAGGCGTGAATAGGGT

GATCACTAGAGAGGAGCTCGAGGCGCTTACCCCGT

CACGCACTCCTAGCAGGTCGGTCTCGAGAACCAGC

CTGGTCTCCAACCCGCCAGGCGTAAATAGGGTGAT

TACAAGAGAGGAGTTTGAGGCGTTCGTAGCACAAC

AACAATGACGGTTTGATGCGGGTGCA

Accordingly, preferably nsP3 is encoded by a nucleotide sequence as substantially as set out in SEQ ID No: 32, or a variant or fragment thereof.

Thus, the RNA construct may comprise SEQ ID No 52, as follows:

[SEQ ID No: 52]
GCACCCUCAUAUCAUGUGGUGCGAGGGGAUAUUGC

CACGGCCACCGAAGGAGUGAUUAUAAAUGCUGCUA

ACAGCAAAGGACAACCUGGCGGAGGGGUGUGCGGA

GCGCUGUAUAAGAAAUUCCCGGAAAGCUUCGAUUU

ACAGCCGAUCGAAGUAGGAAAAGCGCGACUGGUCA

AAGGUGCAGCUAAACAUAUCAUUCAUGCCGUAGGA

CCAAACUUCAACAAAGUUUCGGAGGUUGAAGGUGA

CAAACAGUUGGCAGAGGCUUAUGAGUCCAUCGCUA

AGAUUGUCAACGAUAACAAUUACAAGUCAGUAGCG

AUUCCACUGUUGUCCACCGGCAUCUUUUCCGGGAA

CAAAGAUCGACUAACCCAAUCAUUGAACCAUUUGC

UGACAGCUUUAGACACCACUGAUGCAGAUGUAGCC

-continued

AUAUACUGCAGGGACAAGAAAUGGGAAAUGACUCU

CAAGGAAGCAGUGGCUAGGAGAGAAGCAGUGGAGG

AGAUAUGCAUAUCCGACGACUCUUCAGUGACAGAA

CCUGAUGCAGAGCUGGUGAGGGUGCAUCCGAAGAG

UUCUUUGGCUGGAAGGAAGGGCUACAGCACAAGCG

AUGGCAAAACUUUCUCAUAUUUGGAAGGGACCAAG

UUUCACCAGGCGGCCAAGGAUAUAGCAGAAAUUAA

UGCCAUGUGGCCCGUUGCAACGGAGGCCAAUGAGC

AGGUAUGCAUGUAUAUCCUCGGAGAAAGCAUGAGC

AGUAUUAGGUCGAAAUGCCCCGUCGAAGAGUCGGA

AGCCUCCACACCACCUAGCACGCUGCCUUGCUUGU

GCAUCCAUGCCAUGACUCCAGAAAGAGUACAGCGC

CUAAAAGCCUCACGUCCAGAACAAAUUACUGUGUG

CUCAUCCUUUCCAUUGCCGAAGUAUAGAAUCACUG

GUGUGCAGAAGAUCCAAUGCUCCCAGCCUAUAUUG

UUCUCACCGAAAGUGCCUGCGUAUAUUCAUCCAAG

GAAGUAUCUCGUGGAAACACCACCGGUAGACGAGA

CUCCGGAGCCAUCGGCAGAGAACCAAUCCACAGAG

GGGACACCUGAACAACCACCACUUAUAACCGAGGA

UGAGACCAGGACUAGAACGCCUGAGCCGAUCAUCA

UCGAAGAGGAAGAAGAGGAUAGCAUAAGUUUGCUG

UCAGAUGGCCCGACCCACCAGGUGCUGCAAGUCGA

GGCAGACAUUCACGGGCCGCCCUCUGUAUCUAGCU

CAUCCUGGUCCAUUCCUCAUGCAUCCGACUUUGAU

GUGGACAGUUUAUCCAUACUUGACACCCUGGAGGG

AGCUAGCGUGACCAGCGGGGCAACGUCAGCCGAGA

CUAACUCUUACUUCGCAAAGAGUAUGGAGUUUCUG

GCGCGACCGGUGCCUGCGCCUCGAACAGUAUUCAG

GAACCCUCCACAUCCCGCUCCGCGCACAAGAACAC

CGUCACUUGCACCCAGCAGGGCCUGCUCGAGAACC

AGCCUAGUUUCCACCCCGCCAGGCGUGAAUAGGGU

GAUCACUAGAGAGGAGCUCGAGGCGCUUACCCCGU

CACGCACUCCUAGCAGGUCGGUCUCGAGAACCAGC

CUGGUCUCCAACCCGCCAGGCGUAAAUAGGGUGAU

UACAAGAGAGGAGUUUGAGGCGUUCGUAGCACAAC

AACAAUGACGGUUUGAUGCGGGUGCA

Accordingly, therefore, preferably the RNA construct comprises an RNA nucleotide sequence substantially as set out as SEQ ID No 52 or a variant or fragment thereof. In one embodiment, nsP4 is provided herein as SEQ ID No: 33, as follows:

[SEQ ID No: 33]

YIFSSDTGQGHLQQKSVRQTVLSEVVLERTELEIS

YAPRLDQEKEELLRKKLQLNPTPANRSRYQSRKVE

NMKAITARRILQGLGHYLKAEGKVECYRTLHPVPL

YSSSVNRAFSSPKVAVEACNAMLKENFPTVASYCI

IPEYDAYLDMVDGASCCLDTASFCPAKLRSFPKKH

SYLEPTIRSAVPSAIQNTLQNVLAAATKRNCNVTQ

MRELPVLDSAAFNVECFKKYACNNEYWETFKENPI

RLTEENVVNYITKLKGPKAAALFAKTHNLNMLQDI

PMDRFVMDLKRDVKVTPGTKHTEERPKVQVIQAAD

PLATAYLCGIHRELVRRLNAVLLPNIHTLFDMSAE

DFDAIIAEHFQPGDCVLETDIASFDKSEDDAMALT

ALMILEDLGVDAELLTLIEAAFGEISSIHLPTKTK

FKFGAMMKSGMFLTLFVNTVINIVIASRVLRERLT

GSPCAAFIGDDNIVKGVKSDKLMADRCATWLNMEV

KIIDAVVGEKAPYFCGGFILCDSVTGTACRVADPL

KRLFKLGKPLAADDEHDDDRRRALHEESTRWNRVG

ILSELCKAVESRYETVGTSIIVMAMTTLASSVKSF

SYLRGAPITLYG

Accordingly, preferably nsP4 comprises an amino acid sequence as substantially as set out in SEQ ID No: 33, or a biologically active variant or fragment thereof.

In one embodiment, nsP4 is encoded by a nucleotide sequence a defined in SEQ ID No: 34, as follows:

[SEQ ID No: 34]

TACATCTTTTCCTCCGACACCGGTCAAGGGCATTT

ACAACAAAAATCAGTAAGGCAAACGGTGCTATCCG

AAGTGGTGTTGGAGAGGACCGAATTGGAGATTTCG

TATGCCCCGCGCCTCGACCAAGAAAAAGAAGAATT

ACTACGCAAGAAATTACAGTTAAATCCCACACCTG

CTAACAGAAGCAGATACCAGTCCAGGAAGGTGGAG

AACATGAAAGCCATAACAGCTAGACGTATTCTGCA

AGGCCTAGGGCATTATTTGAAGGCAGAAGGAAAAG

TGGAGTGCTACCGAACCCTGCATCCTGTTCCTTTG

TATTCATCTAGTGTGAACCGTGCCTTTTCAAGCCC

CAAGGTCGCAGTGGAAGCCTGTAACGCCATGTTGA

AAGAGAACTTTCCGACTGTGGCTTCTTACTGTATT

ATTCCAGAGTACGATGCCTATTTGGACATGGTTGA

CGGAGCTTCATGCTGCTTAGACACTGCCAGTTTTT

GCCCTGCAAAGCTGCGCAGCTTTCCAAAGAAACAC

TCCTATTTGGAACCCACAATACGATCGGCAGTGCC

TTCAGCGATCCAGAACACGCTCCAGAACGTCCTGG

-continued

```
CAGCTGCCACAAAAAGAAATTGCAATGTCACGCAA

ATGAGAGAATTGCCCGTATTGGATTCGGCGGCCTT

TAATGTGGAATGCTTCAAGAAATATGCGTGTAATA

ATGAATATTGGGAAACGTTTAAAGAAAACCCCATC

AGGCTTACTGAAGAAACGTGGTAAATTACATTAC

CAAATTAAAAGGACCAAAAGCTGCTGCTCTTTTTG

CGAAGACACATAATTTGAATATGTTGCAGGACATA

CCAATGGACAGGTTTGTAATGGACTTAAAGAGAGA

CGTGAAAGTGACTCCAGGAACAAAACATACTGAAG

AACGGCCCAAGGTACAGGTGATCCAGGCTGCCGAT

CCGCTAGCAACAGCGTATCTGTGCGGAATCCACCG

AGAGCTGGTTAGGAGATTAAATGCGGTCCTGCTTC

CGAACATTCATACACTGTTTGATATGTCGGCTGAA

GACTTTGACGCTATTATAGCCGAGCACTTCCAGCC

TGGGGATTGTGTTCTGGAAACTGACATCGCGTCGT

TTGATAAAAGTGAGGACGACGCCATGGCTCTGACC

GCGTTAATGATTCTGGAAGACTTAGGTGTGGACGC

AGAGCTGTTGACGCTGATTGAGGCGGCTTTCGGCG

AAATTTCATCAATACATTTGCCCACTAAAACTAAA

TTTAAATTCGGAGCCATGATGAAATCTGGAATGTT

CCTCACACTGTTTGTGAACACAGTCATTAACATTG

TAATCGCAAGCAGAGTGTTGAGAGAACGGCTAACC

GGATCACCATGTGCAGCATTCATTGGAGATGACAA

TATCGTGAAAGGAGTCAAATCGGACAAATTAATGG

CAGACAGGTGCGCCACCTGGTTGAATATGGAAGTC

AAGATTATAGATGCTGTGGTGGGCGAGAAAGCGCC

TTATTTCTGTGGAGGGTTTATTTTGTGTGACTCCG

TGACCGGCACAGCGTGCCGTGTGGCAGACCCCCTA

AAAAGGCTGTTTAAGCTTGGCAAACCTCTGGCAGC

AGACGATGAACATGATGATGACAGGAGAAGGGCAT

TGCATGAAGAGTCAACACGCTGGAACCGAGTGGGT

ATTCTTTCAGAGCTGTGCAAGGCAGTAGAATCAAG

GTATGAAACCGTAGGAACTTCCATCATAGTTATGG

CCATGACTACTCTAGCTAGCAGTGTTAAATCATTC

AGCTACCTGAGAGGGGCCCCTATAACTCTCTACGG

C
```

Accordingly, preferably nsP4 is encoded by a nucleotide sequence as substantially as set out in SEQ ID No: 34, or a variant or fragment thereof.

Thus, the RNA construct may comprise SEQ ID No 53, as follows:

[SEQ ID No: 53]
```
UACAUCUUUUCCUCCGACACCGGUCAAGGGCAUUUACAA

CAAAAAUCAGUAAGGCAAACGGUGCUAUCCGAAGUGGUG

UUGGAGAGGACCGAAUUGGAGAUUUCGUAUGCCCCGCGC

CUCGACCAAGAAAAAGAAGAAUUACUACGCAAGAAAUUA

CAGUUAAAUCCCACACCUGCUAACAGAAGCAGAUACCAG

UCCAGGAAGGUGGAGAACAUGAAAGCCAUAACAGCUAGA

CGUAUUCUGCAAGGCCUAGGGCAUUAUUUGAAGGCAGAA

GGAAAAGUGGAGUGCUACCGAACCCUGCAUCCUGUUCCU

UUGUAUUCAUCUAGUGUGAACCGUGCCUUUUCAAGCCCC

AAGGUCGCAGUGGAAGCCUGUAACGCCAUGUUGAAAGAG

AACUUUCCGACUGUGGCUUCUUACUGUAUUAUUCCAGAG

UACGAUGCCUAUUUGGACAUGGUUGACGGAGCUUCAUGC

UGCUUAGACACUGCCAGUUUUUGCCCUGCAAAGCUGCGC

AGCUUUCCAAAGAAACACUCCUAUUUGGAACCCACAAUA

CGAUCGGCAGUGCCUUCAGCGAUCCAGAACACGCUCCAG

AACGUCCUGGCAGCUGCCACAAAAAGAAAUUGCAAUGUC

ACGCAAAUGAGAGAAUUGCCCGUAUUGGAUUCGGCGGCC

UUUAAUGUGGAAUGCUUCAAGAAAUAUGCGUGUAAUAAU

GAAUAUUGGGAAACGUUUAAAGAAAACCCCAUCAGGCUU

ACUGAAGAAACGUGGUAAAUUACAUUACCAAAUUAAAA

GGACCAAAAGCUGCUGCUCUUUUUGCGAAGACACAUAAU

UUGAAUAUGUUGCAGGACAUACCAAUGGACAGGUUUGUA

AUGGACUUAAAGAGAGACGUGAAAGUGACUCCAGGAACA

AAACAUACUGAAGAACGGCCCAAGGUACAGGUGAUCCAG

GCUGCCGAUCCGCUAGCAACAGCGUAUCUGUGCGGAAUC

CACCGAGAGCUGGUUAGGAGAUUAAAUGCGGUCCUGCUU

CCGAACAUUCAUACACUGUUUGAUAUGUCGGCUGAAGAC

UUUGACGCUAUUAUAGCCGAGCACUUCCAGCCUGGGGAU

UGUGUUCUGGAAACUGACAUCGCGUCGUUUGAUAAAAGU

GAGGACGACGCCAUGGCUCUGACCGCGUUAAUGAUUCUG

GAAGACUUAGGUGUGGACGCAGAGCUGUUGACGCUGAUU

GAGGCGGCUUUCGGCGAAAUUUCAUCAAUACAUUUGCCC

ACUAAAACUAAAUUUAAAUUCGGAGCCAUGAUGAAAUCU

GGAAUGUUCCUCACACUGUUUGUGAACACAGUCAUUAAC

AUUGUAAUCGCAAGCAGAGUGUUGAGAGAACGGCUAACC

GGAUCACCAUGUGCAGCAUUCAUUGGAGAUGACAAUAUC

GUGAAAGGAGUCAAAUCGGACAAAUUAAUGGCAGACAGG

UGCGCCACCUGGUUGAAUAUGGAAGUCAAGAUUAUAGAU
```

```
                    -continued
GCUGUGGUGGGCGAGAAAGCGCCUUAUUUCUGUGGAGGG

UUUAUUUUGUGUGACUCCGUGACCGGCACAGCGUGCCGU

GUGGCAGACCCCCUAAAAAGGCUGUUUAAGCUUGGCAAA

CCUCUGGCAGCAGACGAUGAACAUGAUGAUGACAGGAGA

AGGGCAUUGCAUGAAGAGUCAACACGCUGGAACCGAGUG

GGUAUUCUUUCAGAGCUGUGCAAGGCAGUAGAAUCAAGG

UAUGAAACCGUAGGAACUUCCAUCAUAGUUAUGGCCAUG

ACUACUCUAGCUAGCAGUGUUAAAUCAUUCAGCUACCUG

AGAGGGGCCCCUAUAACUCUCUACGGC
```

Accordingly, therefore, preferably the RNA construct comprises an RNA nucleotide sequence substantially as set out as SEQ ID No 53 or a variant or fragment thereof.

Preferably, together with proteins present in a host cell, the non-structural proteins encoded by the RNA construct of the invention form an enzyme complex that is required for genome replication and transcription of the sequences encoding the at least one peptide or protein of interest and the at least one innate inhibitor protein. For example, the one or more non-structural protein may encode a polymerase to enable the construct to amplify the nucleotide sequences encoding the at least one peptide or protein of interest and the at least one innate inhibitor protein.

The host cell may be a eukaryotic or prokaryotic host cell. Preferably, the host cell is a eukaryotic host cell. More preferably, the host cell is a mammalian host cell.

The RNA construct may further comprise a promoter disposed 5' of the at least one non-structural protein, such that the promoter is operably linked to sequence encoding the at least one non-structural protein and enables expression of the at least one non-structural protein in a host cell.

Preferably, the promoter comprises a 5' UTR conserved sequence element, which may be referred to herein as SEQ ID No: 54, as follows:

```
                              [SEQ ID No: 54]
  AUGGGCGGCGCAUGAGAGAAGCCCAGACCAAUUACCUACCCAAA
```

Accordingly, preferably the UTR is disposed 5' of the at least one non-structural protein and comprises a nucleotide sequence substantially as set out in SEQ ID No: 54, or a fragment or variant thereof.

Preferably, the replicon comprises a polyA tail. Preferably, the polyA tail is disposed at the 3' end of the replicon. The replicon may further comprise a 5' cap. In the context of the present invention, the term "5'-cap" includes a 5'-cap analog that resembles the RNA cap structure and is modified to possess the ability to stabilize RNA and/or enhance translation of RNA if attached thereto, preferably in vivo and/or in a cell.

An RNA with a 5'-cap may be achieved by in vitro transcription of a DNA template in presence of said 5'-cap, wherein said 5'-cap is co-transcriptionally incorporated into the generated RNA strand, or the RNA may be generated, for example, by in vitro transcription, and the 5'-cap may be attached to the RNA post-transcriptionally using capping enzymes, for example, capping enzymes of vaccinia virus. In capped RNA, the 3' position of the first base of a (capped) RNA molecule is linked to the 5' position of the subsequent base of the RNA molecule ("second base") via a phosphodiester bond.

In one embodiment, the RNA construct comprises, preferably 5' to 3', a promoter, a sequence encoding at least one therapeutic biomolecule, a spacer sequence, and at least one sequence encoding an innate inhibitor protein.

In another embodiment, the RNA construct comprises, preferably 5' to 3', a promoter, a sequence encoding at least one non-structural protein, a sub genomic promoter, a sequence encoding at least one therapeutic biomolecule, a spacer sequence, and at least one sequence encoding an innate inhibitor protein.

In yet another embodiment, the RNA construct comprises, preferably 5' to 3', a promoter, a sequence encoding at least one non-structural protein, a sub genomic promoter, a sequence encoding at least one therapeutic biomolecule, a spacer sequence, at least one sequence encoding an innate inhibitor protein, and a polyA tail.

In another embodiment, the RNA construct comprises, preferably 5' to 3', a promoter, a sequence encoding at least one non-structural protein, a sub genomic promoter, a sequence encoding at least one therapeutic biomolecule, a spacer sequence, at least one sequence encoding an innate inhibitor protein, optionally a spacer sequence between each at least one sequence encoding an innate inhibitor protein, and a polyA tail.

In one embodiment, the RNA construct comprises, preferably 5' to 3', a 5' cap, a promoter, a sequence encoding at least one non-structural protein, a sub genomic promoter, a sequence encoding at least one therapeutic biomolecule, a spacer sequence, at least one sequence encoding an innate inhibitor protein, optionally a spacer sequence between each at least one sequence encoding an innate inhibitor protein, and a polyA tail.

In one embodiment, the RNA construct comprises, preferably 5' to 3', a 5' cap, a promoter, a sequence encoding at least one non-structural protein, a spacer, at least one sequence encoding an innate inhibitor protein, a sub genomic promoter, a sequence encoding at least one therapeutic biomolecule and a polyA tail.

In one embodiment, the RNA construct comprises, preferably 5' to 3', a 5' cap, a promoter, a sequence encoding at least one non-structural protein, a spacer, at least one sequence encoding an innate inhibitor protein, a sub genomic promoter, a sequence encoding at least one therapeutic biomolecule, a spacer sequence, a sequence encoding at least one an innate inhibitor protein, optionally a spacer sequence between each sequence encoding at least one innate inhibitor protein, and a polyA tail.

The V protein of PIV5 is thought to directly bind to MDA5 preventing oligomerization, while ORF4a is thought to block the binding of PACT to dsRNA. The inventors incorporated these protein-encoding genes into saRNA following the gene of interest (GOI) (i.e. the therapeutic biomolecule), separated by a T2A cleavage site, to generate constructs that are advantageously able to bypass innate sensing mechanisms. Pairing the GOI and IIPs into a single open reading frame that is cleaved by endogenous proteases (T2A) upon expression, maximize expression of both within the same cells at a set ratio with the same kinetics.

Accordingly, preferably, the RNA construct comprises, 5' to 3', a 5' cap, a promoter comprising a 51 nucleotide conserved sequence element, nsP1, nsP2, nsP3v, nsP4, the sub genomic promoter 26S, a sequence encoding a therapeutic biomolecule, a T2A spacer sequence, a sequence encoding PIV5 V and/or MERS-CoV ORF4a and a polyA tail.

In one embodiment, therefore, the RNA construct may comprise or consist of SEQ ID No: 38 as follows:

```
                                       [SEQ ID No: 38]
AUGGGCGGCGCAUGAGAGAAGCCCAGACCAAUUACCUACCCAAAA

UGGAGAAAGUUCACGUUGACAUCGAGGAAGACAGCCCAUUCCUC

AGAGCUUUGCAGCGGAGCUUCCCGCAGUUUGAGGUAGAAGCCAA

GCAGGUCACUGAUAAUGACCAUGCUAAUGCCAGAGCGUUUUCGC

AUCUGGCUUCAAAACUGAUCGAAACGGAGGUGGACCCAUCCGAC

ACGAUCCUUGACAUUGGAAGUGCGCCCGCCCGCAGAAUGUAUUC

UAAGCACAAGUAUCAUUGUAUCUGUCCGAUGAGAUGUGCGGAAG

AUCCGGACAGAUUGUAUAAGUAUGCAACUAAGCUGAAGAAAAAC

UGUAAGGAAAUAACUGAUAAGGAAUUGGACAAGAAAAUGAAGGA

GCUGGCCGCCGUCAUGAGCGACCCUGACCUGGAAACUGAGACUA

UGUGCCUCCACGACGACGAGUCGUGUCGCUACGAAGGGCAAGUC

GCUGUUUACCAGGAUGUAUACGCGGUUGACGGACCGACAAGUCU

CUAUCACCAAGCCAAUAAGGGAGUUAGAGUCGCCUACUGGAUAG

GCUUUGACACCACCCCUUUUAUGUUUUAAGAACUUGGCUGGAGCA

UAUCCAUCAUACUCUACCAACUGGGCCGACGAAACCGUGUUAAC

GGCUCGUAACAUAGGCCUAUGCAGCUCUGACGUUAUGGAGCGGU

CACGUAGAGGGAUGUCCAUUCUUAGAAAGAAGUAUUUGAAACCA

UCCAACAAUGUUCUAUUCUCUGUUGGCUCGACCAUCUACCACGA

GAAGAGGGACUUACUGAGGAGCUGGCACCUGCCGUCUGUAUUUC

ACUUACGUGGCAAGCAAAAUUACACAUGUCGGUGUGAGACUAUA

GUUAGUUGCGACGGGUACGUCGUUAAAAGAAUAGCUAUCAGUCC

AGGCCUGUAUGGGAAGCCUUCAGGCUAUGCUGCUACGAUGCACC

GCGAGGGAUUCUUGUGCUGCAAAGUGACAGACACAUUGAACGGG

GAGAGGGUCUCUUUUCCCGUGUGCACGUAUGUGCCAGCUACAUU

GUGUGACCAAAUGACUGGCAUACUGGCAACAGAUGUCAGUGCGG

ACGACGCGCAAAAACUGCUGGUUGGGCUCAACCAGCGUAUAGUC

GUCAACGGUCGCACCCAGAGAAACACCAAUACCAUGAAAAAUUA

CCUUUUGCCCGUAGUGGCCCAGGCAUUUGCUAGGUGGGCAAAGG

AAUAUAAGGAAGAUCAAGAAGAUGAAAGGCCACUAGGACUACGA

GAUAGACAGUUAGUCAUGGGGUGUUGUUGGGCUUUUAGAAGGCA

CAAGAUAACAUCUAUUUAUAAGCGCCCGGAUACCCAAACCAUCA

UCAAAGUGAACAGCGAUUUCCACUCAUUCGUGCUGCCCAGGAUA

GGCAGUAACACAUUGGAGAUCGGGCUGAGAACAAGAAUCAGGAA

AAUGUUAGAGGAGCACAAGGAGCCGUCACCUCUCAUUACCGCCG

AGGACGUACAAGAAGCUAAGUGCGCGACCGAUGAGGCUAAGGAG

GUGCGUGAAGCCGAGGAGUUGCGCGCAGCUCUACCACCUUUGGC

AGCUGAUGUUGAGGAGCCCACUCUGGAAGCCGAUGUCGACUUGA

UGUUACAAGAGGCUGGGGCCGGCUCAGUGGAGACACCUCGUGGC
```

-continued
```
UUGAUAAAGGUUACCAGCUACGAUGGCGAGGACAAGAUCGGCUC

UUACGCUGUGCUUUCUCCGCAGGCUGUACUCAAGAGUGAAAAAU

UAUCUUGCAUCCACCCUCUCGCUGAACAAGUCAUAGUGAUAACA

CACUCUGGCCGAAAAGGGCGUUAUGCCGUGGAACCAUACCAUGG

UAAAGUAGUGGUGCCAGAGGGACAUGCAAUACCCGUCCAGGACU

UUCAAGCUCUGAGUGAAAGUGCCACCAUUGUGUACAACGAACGU

GAGUUCGUAAACAGGUACCUGCACCAUAUUGCCACACAUGGAGG

AGCGCUGAACACUGAUGAAGAAUAUUACAAAACUGUCAAGCCCA

GCGAGCACGACGGCGAAUACCUGUACGACAUCGACAGGAAACAG

UGCGUCAAGAAAGAACUAGUCACUGGGCUAGGGCUCACAGGCGA

GCUGGUGGAUCCUCCCUUCCAUGAAUUCGCCUACGAGAGUCUGA

GAACACGACCAGCCGCUCCUUACCAAGUACCAACCAUAGGGGUG

UAUGGCGUGCCAGGAUCAGGCAAGUCUGGCAUCAUUAAAAGCGC

AGUCACCAAAAAAGAUCUAGUGGUGAGCGCCAAGAAAGAAAACU

GUGCAGAAAUUAUAAGGGACGUCAAGAAAAUGAAAGGGCUGGAC

GUCAAUGCCAGAACUGUGGACUCAGUGCUCUUGAAUGGAUGCAA

ACACCCCGUAGAGACCCGUAUAUUGACGAAGCUUUUGCUUGUC

AUGCAGGUACUCUCAGAGCGCUCAUAGCCAUUAUAAGACCUAAA

AAGGCAGUGCUCUGCGGGGAUCCCAAACAGUGCGGUUUUUUUAA

CAUGAUGUGCCUGAAAGUGCAUUUUAACCACGAGAUUUGCACAC

AAGUCUUCCACAAAAGCAUCUCUCGCCGUUGCACUAAAUCUGUG

ACUUCGGUCGUCUCAACCUUGUUUUUACGACAAAAAAAUGAGAAC

GACGAAUCCGAAAGAGACUAAGAUUGUGAUUGACACUACCGGCA

GUACCAAACCUAAGCAGGACGAUCUCAUUCUCACUUGUUUCAGA

GGGUGGGUGAAGCAGUUGCAAAUAGAUUACAAAGGCAACGAAAU

AAUGACGGCAGCUGCCUCUCAAGGGCUGACCCGUAAAGGUGUGU

AUGCCGUUCGGUACAAGGUGAAUGAAAAUCCUCUGUACGCACCC

ACCUCAGAACAUGUGAACGUCCUACUGACCCGCACGGAGGACCG

CAUCGUGUGGAAAACACUAGCCGGCGACCCAUGGAUAAAAACAC

UGACUGCCAAGUACCCUGGGAAUUUCACUGCCACGAUAGAGGAG

UGGCAAGCAGAGCAUGAUGCCAUCAUGAGGCACAUCUUGGAGAG

ACCGGACCCUACCGACGUCUUCCAGAAUAAGGCAAACGUGUGUU

GGGCCAAGGCUUUAGUGCCGGUGCUGAAGACCGCUGGCAUAGAC

AUGACCACUGAACAAUGGAACACUGUGGAUUAUUUUGAAACGGA

CAAAGCUCACUCAGCAGAGAUAGUAUUGAACCAACUAUGCGUGA

GGUUCUUUGGACUCGAUCUGGACUCCGGUCUAUUUUCUGCACCC

ACUGUUCCGUUAUCCAUUAGGAAUAAUCACUGGGAUAACUCCCC

GUCGCCUAACAUGUACGGGCUGAAUAAAGAAGUGGUCCGUCAGC

UCUCUCGCAGGUACCCACAACUGCCUCGGGCAGUUGCCACUGGA

AGAGUCUAUGACAUGAACACUGGUACACUGCGCAAUUAUGAUCC

GCGCAUAAACCUAGUACCUGUAAACAGAAGACUGCCUCAUGCUU
```

-continued

UAGUCCUCCACCAUAAUGAACACCCACAGAGUGACUUUUCUUCA

UUCGUCAGCAAAUUGAAGGGCAGAACUGUCCUGGUGGUCGGGGA

AAAGUUGUCCGUCCCAGGCAAAAUGGUUGACUGGUUGUCAGACC

GGCCUGAGGCUACCUUCAGAGCUCGGCUGGAUUUAGGCAUCCCA

GGUGAUGUGCCCAAAUAUGACAUAAUAUUUGUUAAUGUGAGGAC

CCCAUAUAAAUACCAUCACUAUCAGCAGUGUGAAGACCAUGCCA

UUAAGCUUAGCAUGUUGACCAAGAAAGCUUGUCUGCAUCUGAAU

CCCGGCGGAACCUGUGUCAGCAUAGGUUAUGGUUACGCUGACAG

GGCCAGCGAAAGCAUCAUUGGUGCUAUAGCGCGGCAGUUCAAGU

UUUCCCGGGUAUGCAAACCGAAAUCCUCACUUGAAGAGACGGAA

GUUCUGUUUGUAUUCAUUGGGUACGAUCGCAAGGCCCGUACGCA

CAAUUCUUACAAGCUUUCAUCAACCUUGACCAACAUUUAUACAG

GUUCCAGACUCCACGAAGCCGGAUGUGCACCCUCAUAUCAUGUG

GUGCGAGGGGAUAUUGCCACGGCCACCGAAGGAGUGAUUAUAAA

UGCUGCUAACAGCAAAGGACAACCUGGCGGAGGGGUGUGCGGAG

CGCUGUAUAAGAAAUUCCCGGAAAGCUUCGAUUUACAGCCGAUC

GAAGUAGGAAAAGCGCGACUGGUCAAAGGUGCAGCUAAACAUAU

CAUUCAUGCCGUAGGACCAAACUUCAACAAAGUUUCGGAGGUUG

AAGGUGACAAACAGUUGGCAGAGGCUUAUGAGUCCAUCGCUAAG

AUUGUCAACGAUAACAAUUACAAGUCAGUAGCGAUUCCACUGUU

GUCCACCGGCAUCUUUUCCGGGAACAAAGAUCGACUAACCCAAU

CAUUGAACCAUUUGCUGACAGCUUUAGACACCACUGAUGCAGAU

GUAGCCAUAUACUGCAGGGACAAGAAAUGGGAAAUGACUCUCAA

GGAAGCAGUGGCUAGGAGAGAAGCAGUGGAGGAGAUAUGCAUAU

CCGACGACUCUUCAGUGACAGAACCUGAUGCAGAGCUGGUGAGG

GUGCAUCCGAAGAGUUCUUUGGCUGGAAGGAAGGGCUACAGCAC

AAGCGAUGGCAAAACUUUCUCAUAUUUGGAAGGGACCAAGUUUC

ACCAGGCGGCCAAGGAUAUAGCAGAAAUUAAUGCCAUGUGGCCC

GUUGCAACGGAGGCCAAUGAGCAGGUAUGCAUGUAUAUCCUCGG

AGAAAGCAUGAGCAGUAUUAGGUCGAAAUGCCCCGUCGAAGAGU

CGGAAGCCUCCACACCACCUAGCACGCUGCCUUGCUUGUGCAUC

CAUGCCAUGACUCCAGAAAGAGUACAGCGCCUAAAAGCCUCACG

UCCAGAACAAAUUACUGUGUGCUCAUCCUUUCCAUUGCCGAAGU

AUAGAAUCACUGGUGUGCAGAAGAUCCAAUGCUCCCAGCCUAUA

UUGUUCUCACCGAAAGUGCCUGCGUAUAUUCAUCCAAGGAAGUA

UCUCGUGGAAACACCACCGGUAGACGAGACUCCGGAGCCAUCGG

CAGAGAACCAAUCCACAGAGGGGACACCUGAACAACCACCACUU

AUAACCGAGGAUGAGACCAGGACUAGAACGCCUGAGCCGAUCAU

CAUCGAAGAGGAAGAAGAGGAUAGCAUAAGUUUUGCGUCUCAGAUG

GCCCGACCCACCAGGUGCUGCAAGUCGAGGCAGACAUUCACGGG

-continued

CCGCCCUCUGUAUCUAGCUCAUCCUGGUCCAUUCCUCAUGCAUC

CGACUUUGAUGUGGACAGUUUAUCCAUACUUGACACCCUGGAGG

GAGCUAGCGUGACCAGCGGGGCAACGUCAGCCGAGACUAACUCU

UACUUCGCAAAGAGUAUGGAGUUUCUGGCGCGACCGGUGCCUGC

GCCUCGAACAGUAUUCAGGAACCCUCCACAUCCCGCUCCGCGCA

CAAGAACACCGUCACUUGCACCCAGCAGGGCCUGCUCGAGAACC

AGCCUAGUUUCCACCCCGCCAGGCGUGAAUAGGGUGAUCACUAG

AGAGGAGCUCGAGGCGCUUACCCCGUCACGCACUCCUAGCAGGU

CGGUCUCGAGAACCAGCCUGGUCUCCAACCCGCCAGGCGUAAAU

AGGGUGAUUACAAGAGAGGAGUUUGAGGCGUUCGUAGCACAACA

ACAAUGACGGUUUGAUGCGGGUGCAUACAUCUUUUCCUCCGACA

CCGGUCAAGGGCAUUUACAACAAAAAUCAGUAAGGCAAACGGUG

CUAUCCGAAGUGGUGUUGGAGAGGACCGAAUUGGAGAUUUCGUA

UGCCCCGCGCCUCGACCAAGAAAAAGAAGAAUUACUACGCAAGA

AAUUACAGUUAAAUCCCACACCUGCUAACAGAAGCAGAUACCAG

UCCAGGAAGGUGGAGAACAUGAAAGCCAUAACAGCUAGACGUAU

UCUGCAAGGCCUAGGGCAUUAUUUGAAGGCAGAAGGAAAAGUGG

AGUGCUACCGAACCCUGCAUCCUGUUCCUUUGUAUUCAUCUAGU

GUGAACCUGCCUUUUCAAGCCCCAAGGUCGCAGUGGAAGCCUG

UAACGCCAUGUUGAAAGAGAACUUUCCGACUGUGGCUUCUUACU

GUAUUAUUCCAGAGUACGAUGCCUAUUGGACAUGGUUGACGGA

GCUUCAUGCUGCUUAGACACUGCCAGUUUUUGCCCUGCAAAGCU

GCGCAGCUUUCCAAAGAAACACUCCUAUUUGGAACCCACAAUAC

GAUCGGCAGUGCCUUCAGCGAUCCAGAACACGCUCCAGAACGUC

CUGGCAGCUGCCACAAAAAGAAAUUGCAAUGUCACGCAAAUGAG

AGAAUUGCCCGUAUUGGAUUCGGCGGCCUUUAAUGUGGAAUGCU

UCAAGAAAUAUGCGUGUAAUAAUGAAUAUUGGGAAACGUUUAAA

GAAAACCCCAUCAGGCUUACUGAAGAAAACGUGGUAAAUUACAU

UACCAAAUUAAAAGGACCAAAAGCUGCUGCUCUUUUUGCGAAGA

CACAUAAUUUGAAUAUGUUGCAGGACAUACCAAUGGACAGGUUU

GUAAUGGACUUAAAGAGAGACGUGAAAGUGACUCCAGGAACAAA

ACAUACUGAAGAACGGCCCAAGGUACAGGUGAUCCAGGCUGCCG

AUCCGCUAGCAACAGCGUAUCUGUGCGGAAUCCACCGAGAGCUG

GUUAGGAGAUUAAAUGCGGUCCUGCUUCCGAACAUUCAUACACU

GUUUGAUAUGUCGGCUGAAGACUUUGACGCUAUUAUAGCCGAGC

ACUUCCAGCCUGGGGAUUGUGUUCUGGAAACUGACAUCGCGUCG

UUUGAUAAAAGUGAGGACGACGCCAUGGCUCUGACCGCGUUAAU

GAUUCUGGAAGACUUAGGUGUGGACGCAGAGCUGUUGACGCUGA

UUGAGGCGGCUUUCGGCGAAAUUUCAUCAAUACAUUUGCCCACU

AAAACUAAAUUUAAAUUCGGAGCCAUGAUGAAAUCUGGAAUGUU

CCUCACACUGUUUGUGAACACAGUCAUUAACAUUGUAAUCGCAA

-continued

```
GCAGAGUGUUGAGAGAACGGCUAACCGGAUCACCAUGUGCAGCA

UUCAUUGGAGAUGACAAUAUCGUGAAAGGAGUCAAAUCGGACAA

AUUAAUGGCAGACAGGUGCGCCACCUGGUUGAAUAUGGAAGUCA

AGAUUAUAGAUGCUGUGGUGGGCGAGAAAGCGCCUUAUUUCUGU

GGAGGGUUUAUUUUGUGUGACUCCGUGACCGGCACAGCGUGCCG

UGUGGCAGACCCCCUAAAAAGGCUGUUUAAGCUUGGCAAACCUC

UGGCAGCAGACGAUGAACAUGAUGAUGACAGGAGAAGGGCAUUG

CAUGAAGAGUCAACACGCUGGAACCGAGUGGGUAUUCUUUCAGA

GCUGUGCAAGGCAGUAGAAUCAAGGUAUGAAACCGUAGGAACUU

CCAUCAUAGUUAUGGCCAUGACUACUCUAGCUAGCAGUGUUAAA

UCAUUCAGCUACCUGAGAGGGGCCCCUAUAACUCUCUACGGCUA

ACCUGAAUGGACUACGACAUAGUCUAGUCCGCCAAGUCUAGCAU

AUGUAUGGCCACCAUGGAAGAUGCCAAGAACAUCAAGAAGGGCC

CUGCCCCAUUCUACCCCCUGGAAGAUGGAACAGCCGGCGAGCAG

CUGCACAAGGCCAUGAAGAGAUACGCCCUGGUGCCCGGCACAAU

CGCCUUCACCGAUGCCCACAUCGAGGUGGACAUCACCUACGCCG

AGUACUUCGAGAUGAGCGUGCGGCUGGCCGAAGCUAUGAAGCGC

UACGGCCUGAACACCAACCACCGGAUCGUCGUGUGCAGCGAGAA

CAGCCUGCAGUUCUUCAUGCCCGUGCUGGGCGCCCUGUUUAUCG

GAGUGGCUGUGGCCCCUGCCAACGACAUCUACAACGAGCGCGAG

CUGCUGAACAGCAUGGGCAUCAGCCAGCCCACCGUGGUGUUCGU

GUCCAAGAAGGGACUGCAGAAAAAUCCUGAACGUGCAGAAGAAGC

UGCCCAUCAUCCAGAAAAUCAUCAUCAUGGACAGCAAGACCGAC

UACCAGGGCUUCCAGAGCAUGUACACCUUCGUGACCAGCCAUCU

GCCCCCUGGCUUCAACGAGUACGACUUCGUGCCCGAGAGCUUCG

ACCGGGACAAGACAAUCGCCCUGAUCAUGAACAGCAGCGGCAGC

ACCGGACUGCCUAAAGGCGUGGCCCUGCCUCACAGAACUGCCUG

CGUGCGGUUUAGCCACGCCCGGGACCCUAUCUUCGGCAACCAGA

UCAUCCCCGACACCGCCAUCCUGAGCGUGGUGCCCUUUCCACCAC

GGCUUCGGCAUGUUCACCACCCUGGGCUACCUGAUCUGCGGCUU

CCGGGUGGUGCUGAUGUACAGAUUCGAGGAAGAACUGUUCCUGC

GGAGCCUGCAGGACUACAAGAUCCAGAGCGCCCUGCUGGUGCCU

ACCCUGUUCAGCUUCUUUGCCAAGAGCACCCUGAUCGAUAAGUA

CGACCUGAGCAACCUGCACGAGAUCGCCUCUGGCGGAGCCCCCC

UGUCUAAAGAAGUGGGGAGAGGCCGUGGCCAAGCGGUUCCAUCUG

CCUGGCAUCAGACAGGGCUAUGGCCUGACCGAGACAACCAGCGC

CAUUCUGAUCACCCCCGAGGGCGACGAUAAGCCUGGCGCCGUGG

GAAAGGUGGUGCCAUUCUUCGAGGCCAAGGUGGUGGACCUGGAC

ACCGGCAAGACACUGGGCGUGAACCAGAGGGGCGAACUGUGUGU

GCGGGGACCUAUGAUCAUGAGCGGCUACGUGAACAACCCCGAGG
```

-continued

```
CCACCAACGCCCUGAUUGACAAGGAUGGCUGGCUGCACAGCGGC

GACAUUGCCUACUGGGACGAGGACGAGCACUUCUUCAUCGUGGA

CCGGCUGAAGUCCCUGAUCAAGUACAAGGGCUACCAGGUGGCCC

CAGCCGAGCUGGAAUCUAUCCUGCUGCAGCACCCCAACAUCUUC

GAUGCCGGCGUGGCAGGACUGCCCGAUGAUGAUGCUGGCGAACU

GCCAGCCGCUGUGGUGGUGCUGGAACACGGAAAGACCAUGACCG

AGAAAGAAAUCGUGGACUACGUGGCCAGCCAAGUGACCACCGCC

AAGAAACUGAGAGGCGGCGUGGGUGUUUGUGGACGAGGUGCCAAA

GGGCCUGACAGGCAAGCUGGACGCCCGGAAGAUCAGAGAGAUCC

UGAUUAAGGCCAAGAAAGGCGGCAAGAUCGCCGUGGAUCGGAGA

AAGAGAGGCUCUGGCGAAGGCAGAGGCAGCCUGCUUACAUGUGG

CGACGUGGAAGAGAACCCCGGACCUAUGGACCCUACCGACCUGA

GCUUCAGCCCCGACGAGAUCAACAAGCUGAUCGAGACAGGCCUG

AACACCGUGGAAUACUUCACCAGCCAGCAAGUGACCGGCACAAG

CAGCCUGGGCAAGAACACAAUUCCUCCAGGCGUGACCGGCCUGC

UGACAAAUGCUGCCGAGGCCAAGAUCCAAGAGAGCACCAACCAC

CAGAAGGGCUCUGUUGGAGGCGGAGCCAAGCCUAAGAAGCCCAG

ACCUAAGAUCGCCAUCGUGCCCGCCGACGAUAAGACAGUGCCUG

GCAAGCCCAUUCCUAAUCCUCUGCUGGGCCUCGACAGCACCCCU

AGCACACAGACAGUGCUGGAUCUGAGCGGCAAGACACUGCCUAG

CGGCAGCUAUAAGGGCGUGAAGCUGGCCAAGUUCGGCAAAGAAA

ACCUGAUGACCCGGUUCAUCGAGGAACCCAGAGAGAACCCUAUC

GCCACCAGCUCUCCCAUCGACUUCAAGAGAGGCAGAGACACCGG

CGGCUUCCACAGAAGAGAGUACAGCAUUGGCUGGGUCGGAGAUG

AAGUGAAAGUGACCGAGUGGUGCAACCCCAGCUGCAGCCCUAUU

ACAGCCGCCGCUAGAAGAUUCGAGUGCACCUGUCACCAGUGUCC

UGUGACCUGUAGCGAGUGCGAGCGGGACACAUGAUGAGCGGCCG

CGAAUUGGCAAGCUGCUUACAUAGAACUCGCGGCGAUUGGCAUG

CCGCCUUAAAAUUUUUAUUUUAUUUUUCUUUUCUUUUCCGAAUC

GGAUUUUGUUUUUAAUAUUUCAAAAAAAAAAAAAAAAAAAAAAA

AAAAAAAAAAAAAAAAAAAAAAAAAAAAAAAAAAAAAAAAAAAA

AAAAAAAAAAAAAAAAAAAAAAAAAAAAAAAAAAAAAAAAAAAA

AAAAAAAA
```

Accordingly, preferably the RNA construct comprises a nucleotide sequence substantially as set out in SEQ ID No: 38, or a fragment or variant thereof.

In another embodiment, the RNA construct may comprise or consist of SEQ ID No: 39, as follows:

[SEQ ID No: 39]
```
AUGGGCGGCGCAUGAGAGAAGCCCAGACCAAUUACCUACCCAAA

AUGGAGAAAGUUCACGUUGACAUCGAGGAAGACAGCCCAUUCCU

CAGAGCUUUGCAGCGGAGCUUCCCGCAGUUUGAGGGUAGAAGCCA
```

-continued

AGCAGGUCACUGAUAAUGACCAUGCUAAUGCCAGAGCGUUUUCG

CAUCUGGCUUCAAAACUGAUCGAAACGGAGGUGGACCCAUCCGA

CACGAUCCUUGACAUUGGAAGUGCGCCCGCCCGCAGAAUGUAUU

CUAAGCACAAGUAUCAUUGUAUCUGUCCGAUGAGAUGUGCGGAA

GAUCCGGACAGAUUGUAUAAGUAUGCAACUAAGCUGAAGAAAAA

CUGUAAGGAAAUAACUGAUAAGGAAUUGGACAAGAAAAUGAAGG

AGCUGGCCGCCGUCAUGAGCGACCCUGACCUGGAAACUGAGACU

AUGUGCCUCCACGACGACGAGUCGUGUCGCUACGAAGGGCAAGU

CGCUGUUUACCAGGAUGUAUACGCGGUUGACGGACCGACAAGUC

UCUAUCACCAAGCCAAUAAGGGAGUUAGAGUCGCCUACUGGAUA

GGCUUUGACACCACCCCUUUUAUGUUUAAGAACUUGGCUGGAGC

AUAUCCAUCAUACUCUACCAACUGGGCCGACGAAACCGUGUUAA

CGGCUCGUAACAUAGGCCUAUGCAGCUCUGACGUUAUGGAGCGG

UCACGUAGAGGGAUGUCCAUUCUUAGAAAGAAGUAUUUGAAACC

AUCCAACAAUGUUCUAUUCUCUGUUGGCUCGACCAUCUACCACG

AGAAGAGGGACUUACUGAGGAGCUGGCACCUGCCGUCUGUAUUU

CACUUACGUGGCAAGCAAAAUUACACAUGUCGGUGUGAGACUAU

AGUUAGUUGCGACGGGUACGUCGUUAAAAGAAUAGCUAUCAGUC

CAGGCCUGUAUGGGAAGCCUUCAGGCUAUGCUGCUACGAUGCAC

CGCGAGGGAUUCUUGUGCUGCAAAGUGACAGACACAUUGAACGG

GGAGAGGGUCUCUUUUCCCGUGUGCACGUAUGUGCCAGCUACAU

UGUGUGACCAAAUGACUGGCAUACUGGCAACAGAUGUCAGUGCG

GACGACGCGCAAAAACUGCUGGUUGGGCUCAACCAGCGUAUAGU

CGUCAACGGUCGCACCCAGAGAAACACCAAUACCAUGAAAAAUU

ACCUUUUGCCCGUAGUGGCCCAGGCAUUUGCUAGGUGGGCAAAG

GAAUAUAAGGAAGAUCAAGAAGAUGAAAGGCCACUAGGACUACG

AGAUAGACAGUUAGUCAUGGGGUGUUGUUGGGCUUUUAGAAGGC

ACAAGAUAACAUCUAUUUAUAAGCGCCCGGAUACCCAAACCAUC

AUCAAAGUGAACAGCGAUUUCCACUCAUUCGUGCUGCCCAGGAU

AGGCAGUAACACAUUGGAGAUCGGGCUGAGAACAAGAAUCAGGA

AAAUGUUAGAGGAGCACAAGGAGCCGUCACCUCUCAUUACCGCC

GAGGACGUACAAGAAGCUAAGUGCGCAGCCGAUGAGGCUAAGGA

GGUGCGUGAAGCCGAGGAGUUGCGCGCAGCUCUACCACCUUUGG

CAGCUGAUGUUGAGGAGCCCACUCUGGAAGCCGAUGUCGACUUG

AUGUUACAAGAGGCUGGGGCCGGCUCAGUGGAGACACCUCGUGG

CUUGAUAAAGGUUACCAGCUACGAUGGCGAGGACAAGAUCGGCU

CUUACGCUGUGCUUUCUCCGCAGGCUGUACUCAAGAGUGAAAAA

UUAUCUUGCAUCCACCCUCUCGCUGAACAAGUCAUAGUGAUAAC

ACACUCUGGCCGAAAAGGGCGUUAUGCCUGUGGAACCAUACCAUG

GUAAAGUAGUGGUGCCAGAGGGACAUGCAAUACCCGUCCAGGAC

-continued

UUUCAAGCUCUGAGUGAAAGUGCCACCAUUGUGUACAACGAACG

UGAGUUCGUAAACAGGUACCUGCACCAUAUUGCCACACAUGGAG

GAGCGCUGAACACUGAUGAAGAAUAUUACAAAACUGUCAAGCCC

AGCGAGCACGACGGCGAAUACCUGUACGACAUCGACAGGAAACA

GUGCGUCAAGAAAGAACUAGUCACUGGGCUAGGGCUCACAGGCG

AGCUGGUGGAUCCUCCCUUCCAUGAAUUCGCCUACGAGAGUCUG

AGAACACGACCAGCCGCUCCUUACCAAGUACCAACCAUAGGGGU

GUAUGGCGUGCCAGGAUCAGGCAAGUCUGGCAUCAUUAAAAGCG

CAGUCACCAAAAAAGAUCUAGUGGUGAGCGCCAAGAAAGAAAAC

UGUGCAGAAAUUAUAAGGGACGUCAAGAAAAUGAAAGGGCUGGA

CGUCAAUGCCAGAACUGUGGACUCAGUGCUCUUGAAUGGAUGCA

AACACCCCGUAGAGACCCUGUAUAUUGACGAAGCUUUUGCUUGU

CAUGCAGGUACUCUCAGAGCGCUCUAGAGCCAUUAUAAGACCUAA

AAAGGCAGUGCUCUGCGGGGAUCCCAAACAGUGCGGUUUUUUUA

ACAUGAUGUGCCUGAAAGUGCAUUUUAACCACGAGAUUUGCACA

CAAGUCUUCCACAAAAGCAUCUCUCGCCGUUGCACUAAAUCUGU

GACUUCGGUCGUCUCAACCUUGUUUUACGACAAAAAAAUGAGAA

CGACGAAUCCGAAAGAGACUAAGAUUGUGAUUGACACUACCGGC

AGUACCAAACCUAAGCAGGACGAUCUCAUUCUCACUUGUUUCAG

AGGGUGGGUGAAGCAGUUGCAAAUAGAUUACAAAGGCAACGAAA

UAAUGACGGCAGCUGCCUCUCAAGGGCUGACCCGUAAAGGUGUG

UAUGCCGUUCGGUACAAGGUGAAUGAAAAUCCUCUGUACGCACC

CACCUCGAACAUGUGAACGUCCUACUGACCCGCACGGAGGACC

GCAUCGUGUGGAAAACACUAGCCGGCGACCCAUGGAUAAAAACA

CUGACUGCCAAGUACCCUGGGGAAUUUCACUGCCACGAUAGAGGA

GUGGCAAGCAGAGCAUGAUGCCAUCAUGAGGCACAUCUUGGAGA

GACCGGACCCUACCGACGUCUUCCAGAAUAAGGCAAACGUGUGU

UGGGCCAAGGCUUUAGUGCCGGUGCUGAAGACCGCUGGCAUAGA

CAUGACCACUGAACAAUGGAACACUGUGGAUUAUUUUGAAACGG

ACAAAGCUCACUCAGCAGAGAUAGUAUUGAACCAACUAUGCGUG

AGGUUCUUUGGACUCGAUCUGGACUCCGGUCUAUUUUCUGCACC

CACUGUUCCGUUAUCCAUUAGGAAUAAUCACUGGGAUAACUCCC

CGUCGCCUAACAUGUACGGGCUGAAUAAAGAAGUGGUCCGUCAG

CUCUCUCGCAGGUACCCACAACUGCCUCGGGCAGUUGCCACUGG

AAGAGUCUAUGACAUGAACACUGGUACACUGCGCAAUUAUGAUC

CGCGCAUAAACCUAGUACCUGUAAACAGAAGACUGCCUCAUGCU

UUAGUCCUCCACCAUAAUGAACACCCACAGAGUGACUUUUCUUC

AUUCGUCAGCAAAUUGAAGGGCAGAACUGUCCUGGUGGUCGGGG

AAAAGUUGUCCGUCCCAGGCAAAAUGGUUGACUGGUUGUCAGAC

CGGCCUGAGGCUACCUUCAGAGCUCGGCUGGAUUUAGGCAUCCC

AGGUGAUGUGCCCAAAUAUGACAUAAUAUUUGUUAAUGUGAGGA

-continued

CCCCAUAUAAAUACCAUCACUAUCAGCAGUGUGAAGACCAUGCC

AUUAAGCUUAGCAUGUUGACCAAGAAAGCUUGUCUGCAUCUGAA

UCCCGGCGGAACCUGUGUCAGCAUAGGUUAUGGUUACGCUGACA

GGGCCAGCGAAAGCAUCAUUGGUGCUAUAGCGCGGCAGUUCAAG

UUUUCCCGGGUAUGCAAACCGAAAUCCUCACUUGAAGAGACGGA

AGUUCUGUUUGUAUUCAUUGGGUACGAUCGCAAGGCCCGUACGC

ACAAUUCUUACAAGCUUUCAUCAACCUUGACCAACAUUUAUACA

GGUUCCAGACUCCACGAAGCCGGAUGUGCACCCUCAUAUCAUGU

GGUGCGAGGGGAUAUUGCCACGGCCACCGAAGGAGUGAUUAUAA

AUGCUGCUAACAGCAAAGGACAACCUGGCGGAGGGGUGUGCGGA

GCGCUGUAUAAGAAAUUCCCGGAAAGCUUCGAUUUACAGCCGAU

CGAAGUAGGAAAAGCGCGACUGGUCAAAGGUGCAGCUAAACAUA

UCAUUCAUGCCGUAGGACCAAACUUCAACAAAGUUUCGGAGGUU

GAAGGUGACAAACAGUUGGCAGAGGCUUAUGAGUCCAUCGCUAA

GAUUGUCAACGAUAACAAUUACAAGUCAGUAGCGAUUCCACUGU

UGUCCACCGGCAUCUUUUCCGGGAACAAAGAUCGACUAACCCAA

UCAUUGAACCAUUUGCUGACAGCUUUAGACACCACUGAUGCAGA

UGUAGCCAUAUACUGCAGGGACAAGAAAUGGGAAAUGACUCUCA

AGGAAGCAGUGGCUAGGAGAGAAGCAGUGGAGGAGAUAUGCAUA

UCCGACGACUCUUCAGUGACAGAACCUGAUGCAGAGCUGGUGAG

GGUGCAUCCGAAGAGUUCUUUGGCUGGAAGGAAGGGCUACAGCA

CAAGCGAUGGCAAAACUUUCUCAUAUUUGGAAGGGACCAAGUUU

CACCAGGCGGCCAAGGAUAUAGCAGAAAUUAAUGCCAUGUGGCC

CGUUGCAACGCGAGGCCAAUGAGCAGGUAUGCAUGUAUAUCCUCG

GAGAAAGCAUGAGCAGUAUUAGGUCGAAAUGCCCCGUCGAAGAG

UCGGAAGCCUCCACACCACCUAGCACGCUGCCUUGCUUGUGCAU

CCAUGCCAUGACUCCAGAAAGAGUACAGCGCCUAAAAGCCUCAC

GUCCAGAACAAAUUACUGUGUGCUCAUCCUUUCCAUUGCCGAAG

UAUAGAAUCACUGGUGUGCAGAAGAUCCAAUGCUCCCAGCCUAU

AUUGUUCUCACCGAAAGUGCCUGCGUAUAUUCAUCCAAGGAAGU

AUCUCGUGGAAACACCACCGGUAGACGAGACUCCGGAGCCAUCG

GCAGAGAACCAAUCCACAGAGGGGACACCUGAACAACCACCACU

UAUAACCGAGGAUGAGACCAGGACUAGAACGCCUGAGCCGAUCA

UCAUCGAAGAGGAAGAAGAGGAUAGCAUAAGUUUGCUGUCAGAU

GGCCCGACCCACCAGGUGCUGCAAGUCGAGGCAGACAUUCACGG

GCCGCCCUCUGUAUCUAGCUCAUCCUGGUCCAUUCCUCAUGCAU

CCGACUUUGAUGUGGCAGUUUAUCCAUACUUGACACCCUGGAG

GGAGCUAGCGUGACCAGCGGGGCAACGUCAGCCGAGACUAACUC

UUACUUCGCAAAGAGUAUGGAGUUUCGGGCGCGACCGGUGCCUG

CGCCUCGAACAGUAUUCAGGAACCCUCCACAUCCCGCUCCGCGC

-continued

ACAAGAACACCGUCACUUGCACCCAGCAGGGCCUGCUCGAGAAC

CAGCCUAGUUUCCACCCCGCCAGGCGUGAAUAGGGUGAUCACUA

GAGAGGAGCUCGAGGCGCUUACCCCGUCACGCACUCCUAGCAGG

UCGGUCUCGAGAACCAGCCUGGUCUCCAACCCGCCAGGCGUAAA

UAGGGUGAUUACAAGAGAGGAGUUUGAGGCGUUCGUAGCACAAC

AACAAUGACGGUUUGAUGCGGGUGCAUACAUCUUUUCCUCCGAC

ACCGGUCAAGGGCAUUUACAACAAAAAUCAGUAAGGCAAACGGU

GCUAUCCGAAGUGGUGUUGGAGAGGACCGAAUUGGAGAUUUCGU

AUGCCCCGCGCCUCGACCAAGAAAAAGAAGAAUUACUACGCAAG

AAAUUACAGUUAAAUCCCACACCUGCUAACAGAAGCAGAUACCA

GUCCAGGAAGGUGGAGAACAUGAAAGCCAUAACAGCUAGACGUA

UUCUGCAAGGCCUAGGGCAUUAUUUGAAGGCAGAAGGAAAAGUG

GAGUGCUACCGAACCCUGCAUCCUGUUCCUUUGUAUUCAUCUAG

UGUGAACCGUGCCUUUUCAAGCCCCAAGGUCGCAGUGGAAGCCU

GUAACGCCAUGUUGAAAGAGAACUUUCCGACUGUGGCUUCUUAC

UGUAUUAUUCCAGAGUACGAUGCCUAUUUGGACAUGGUUGACGG

AGCUUCAUGCUGCUUAGACACUGCCAGUUUUUGCCCUGCAAAGC

UGCGCAGCUUUCCAAAGAAACACUCCUAUUUGGAACCCACAAUA

CGAUCGGCAGUGCCUUCAGCGAUCCAGAACACGCUCCAGAACGU

CCUGGCAGCUGCCACAAAAAGAAAUUGCAAUGUCACGCAAAUGA

GAGAAUUGCCCGUAUUGGAUUCGGCGGCCUUUAAUGUGGAAUGC

UUCAAGAAAUAUGCGUGUAAUAAUGAAUAUUGGGAAACGUUUAA

AGAAAACCCCAUCAGGCUUACUGAAGAAAACGUGGUAAAUUACA

UUACCAAAUUAAAAGGACCAAAAGCUGCUGCUCUUUUUGCGAAG

ACACAUAAUUUGAAUAUGUUGCAGGACAUACCAAUGGACAGGUU

UGUAAUGGACUUAAAGAGAGACGUGAAAGUGACUCCAGGAACAA

AACAUACUGAAGAACGGCCCAAGGUACAGGUGAUCCAGGCUGCC

GAUCCGCUAGCAACAGCGUAUCUGUGCGGAAUCCACCGAGAGCU

GGUUAGGAGAUUAAAUGCGGUCCUGCUUCCGAACAUUCAUACAC

UGUUUGAUAUGUCGGCUGAAGACUUUGACGCUAUUAUAGCCGAG

CACUUCCAGCCUGGGGAUUGUGUUUCGGAAACUGACAUCGCGUC

GUUUGAUAAAGUGAGGACGACGCCAUGGCUCUGACCGCGUUAA

UGAUUCUGGAAGACUUAGGUGUGGACGCAGAGCUGUUGACGCUG

AUUGAGGCGGCUUUCGGCGAAAUUUCAUCAAUACAUUUGCCCAC

UAAAACUAAAUUUAAAUUCGGAGCCAUGAUGAAAUCUGGAAUGU

UCCUCACACUGUUUGUGAACACAGUCAUUAACAUUGUAAUCGCA

AGCAGAGUGUUGAGAGAACGGCUAACCGGAUCACCAUGUGCAGC

AUUCAUUGGAGAUGACAAUAUCGUGAAAGGAGUCAAAUCGGACA

AAUUAAUGGCAGACAGGUGCGCCACCUGGUUGAAUAUGGAAGUC

AAGAUUAUAGAUGCUGUGGUGGGGCGAGAAAGCGCCUUAUUUCUG

UGGAGGGUUUAUUUUGUGUGACUCCGUGACCGGCACAGCGUGCC

-continued

GUGUGGCAGACCCCCUAAAAAGGCUGUUUAAGCUUGGCAAACCU

CUGGCAGCAGACGAUGAACAUGAUGAUGACAGGAGAAGGGCAUU

GCAUGAAGAGUCAACACGCUGGAACCGAGUGGGUAUUCUUUCAG

AGCUGUGCAAGGCAGUAGAAUCAAGGUAUGAAACCGUAGGAACU

UCCAUCAUAGUUAUGGCCAUGACUACUCUAGCUAGCAGUGUUAA

AUCAUUCAGCUACCUGAGAGGGGCCCCUAUAACUCUCUACGGCU

AACCUGAAUGGACUACGACAUAGUCUAGUCCGCCAAGUCUAGCA

UAUGUAUGGCCACCAUGGAAGAUGCCAAGAACAUCAAGAAGGGC

CCUGCCCCAUUCUACCCCCUGGAAGAUGGAACAGCCGGCGAGCA

GCUGCACAAGGCCAUGAAGAGAUACGCCCUGGUGCCCGGCACAA

UCGCCUUCACCGAUGCCCACAUCGAGGUGGACAUCACCUACGCC

GAGUACUUCGAGAUGAGCGUGCGGCUGGCCGAAGCUAUGAAGCG

CUACGGCCUGAACACCAACCACCGGAUCGUCGUGUGCAGCGAGA

ACAGCCUGCAGUUCUUCAUGCCCGUGCUGGGCGCCCUGUUUAUC

GGAGUGGCUGUGGCCCCUGCCAACGACAUCUACAACGAGCGCGA

GCUGCUGAACAGCAUGGGCAUCAGCCAGCCCACCGUGGUGUUCG

UGUCCAAGAAGGGACUGCAGAAAAUCCUGAACGUGCAGAAGAAG

CUGCCCAUCAUCCAGAAAAUCAUCAUCAUGGACAGCAAGACCGA

CUACCAGGGCUUCCAGAGCAUGUACACCUUCGUGACCAGCCAUC

UGCCCCCUGGCUUCAACGAGUACGACUUCGUGCCCGAGAGCUUC

GACCGGGACAAGACAAUCGCCCUGAUCAUGAACAGCAGCGGCAG

CACCGGACUGCCUAAAGGCGUGGCCCUGCCUCACAGAACUGCCU

GCGUGCGGUUUAGCCACGCCCGGGACCCUAUCUUCGGCAACCAG

AUCAUCCCCGACACCGCCAUCCUGAGCGUGGUGCCUUUCCACCA

CGGCUUCGGCAUGUUCACCACCCUGGGCUACCUGAUCUGCGGCU

UCCGGGUGGUGCUGAUGUACAGAUUCGAGGAAGAACUGUUCCUG

CGGAGCCUGCAGGACUACAAGAUCCAGAGCGCCCUGCUGGUGCC

UACCCUGUUCAGCUUCUUUGCCAAGAGCACCCUGAUCGAUAAGU

ACGACCUGAGCAACCUGCACGAGAUCGCCUCUGGCGGAGCCCCC

CUGUCUAAAGAAGUGGGAGAGGCCGUGGCCAAGCGGUUCCAUCU

GCCUGGCAUCAGACAGGGCUAUGGCCUGACCGAGACAACCAGCG

CCAUUCUGAUCACCCCCGAGGGCGACGAUAAGCCUGGCGCCGUG

GGAAAGGUGGUGCCAUUCUUCGAGGCCAAGGUGGUGGACCUGGA

CACCGGCAAGACACUGGGCGUGAACCAGAGGGGCGAACUGUGUG

UGCGGGGACCUAUGAUCAUGAGCGGCUACGUGAACAACCCCGAG

GCCACCAACGCCCUGAUUGACAAGGAUGGCUGGCUGCACAGCGG

CGACAUUGCCUACUGGGACGAGGACGAGCACUUCUUCAUCGUGG

ACCGGCUGAAGUCCCUGAUCAAGUACAAGGGCUACCAGGUGGCC

CCAGCCGAGCUGGAAUCUAUCCUGCUGCAGCACCCCAACAUCUU

CGAUGCCGGCGUGGCAGGACUGCCCGAUGAUGAUGCUGGCGAAC

-continued

UGCCAGCCGCUGUGGUGGUGCUGGAACACGGAAAGACCAUGACC

GAGAAAGAAAUCGUGGACUACGUGGCCAGCCAAGUGACCACCGC

CAAGAAACUGAGAGGCGGCGUGGUGUUUGUGGACGAGGUGCCAA

AGGGCCUGACAGGCAAGCUGGACGCCCGGAAGAUCAGAGAGAUC

CUGAUUAAGGCCAAGAAAGGCGGCAAGAUCGCCGUGGAUCGGAG

AAAGAGAGGCUCUGGCGAAGGCAGAGGCAGCCUGCUUACAUGUG

GCGACGUGGAAGAGAACCCCGGACCUAUGGACUACGUGUCCCUG

CUGAACCAGAUUUGGCAGAAGUACCUGAACAGCCCCUACACCAC

CUGUCUGUACAUCCCCAAGCCUACCGCCAAGUACACACCUCUCG

UGGGCACAUCUCUGCACCCCGUGCUGUGGAAUUGCCAGCUGAGC

UUUGCCGGCUACACCGAGUCUGCCGUGAACAGCACAAAGGCCCU

GGCCAAACAGGACGCCGCUCAGAGAAUUGCCUGGCUGCUGCACA

AGGAUGGCGGCAUCCCUGAUGGCUGUAGCCUGUACCUGAGACAC

AGCAGCCUGUUCGCCCAGAGCGAGGAAGAGGAAUCCUUCAGCAA

CUGAUGAGCGGCCGCGAAUUGGCAAGCUGCUUACAUAGAACUCG

CGGCGAUUGGCAUGCCGCCUUAAAAUUUUUAUUUUAUUUUUCUU

UUCUUUUCCGAAUCGGAUUUUGUUUUUAAUAUUUCAAAAAAAAA

AAAAAAAAAAAAAAAAAAAAAAAAAAAAAAAAAAAAAAAAAAAA

AAAAAAAAAAAAAAAAAAAAAAAAAAAAAAAAAAAAAAAAAAAA

AAAAAAAAAAAAAAAAAAAAA

Accordingly, preferably the RNA construct comprises a nucleotide sequence substantially as set out in SEQ ID No: 39, or a fragment or variant thereof.

In a second aspect of the invention, there is provided a nucleic acid sequence encoding the RNA construct of the first aspect.

In one embodiment, the nucleic acid sequence may comprise or consist of SEQ ID No: 40, as follows:

[SEQ ID No: 40]

ATGGGCGGCGCATGAGAGAAGCCCAGACCAATTACCTACCCAAA

ATGGAGAAAGTTCACGTTGACATCGAGGAAGACAGCCCATTCCT

CAGAGCTTTGCAGCGGAGCTTCCCGCAGTTTGAGGTAGAAGCCA

AGCAGGTCACTGATAATGACCATGCTAATGCCAGAGCGTTTTCG

CATCTGGCTTCAAAACTGATCGAAACGGAGGTGGACCCATCCGA

CACGATCCTTGACATTGGAAGTGCGCCCGCCCGCAGAATGTATT

CTAAGCACAAGTATCATTGTATCTGTCCGATGAGATGTGCGGAA

GATCCGGACAGATTGTATAAGTATGCAACTAAGCTGAAGAAAAA

CTGTAAGGAAATAACTGATAAGGAATTGGACAAGAAAATGAAGG

AGCTGGCCGCCGTCATGAGCGACCCTGACCTGGAAACTGAGACT

ATGTGCCTCCACGACGACGAGTCGTGTCGCTACGAAGGGCAAGT

CGCTGTTTACCAGGATGTATACGCGGTTGACGGACCGACAAGTC

TCTATCACCAAGCCAATAAGGGAGTTAGAGTCGCCTACTGGATA

GGCTTTGACACCACCCCTTTTATGTTTAAGAACTTGGCTGGAGC

-continued

ATATCCATCATACTCTACCAACTGGGCCGACGAAACCGTGTTAA

CGGCTCGTAACATAGGCCTATGCAGCTCTGACGTTATGGAGCGG

TCACGTAGAGGGATGTCCATTCTTAGAAAGAAGTATTTGAAACC

ATCCAACAATGTTCTATTCTCTGTTGGCTCGACCATCTACCACG

AGAAGAGGGACTTACTGAGGAGCTGGCACCTGCCGTCTGTATTT

CACTTACGTGGCAAGCAAAATTACACATGTCGGTGTGAGACTAT

AGTTAGTTGCGACGGGTACGTCGTTAAAGAATAGCTATCAGTC

CAGGCCTGTATGGGAAGCCTTCAGGCTATGCTGCTACGATGCAC

CGCGAGGGATTCTTGTGCTGCAAAGTGACAGACACATTGAACGG

GGAGAGGGTCTCTTTTCCCGTGTGCACGTATGTGCCAGCTACAT

TGTGTGACCAAATGACTGGCATACTGGCAACAGATGTCAGTGCG

GACGACGCGCAAAAACTGCTGGTTGGGCTCAACCAGCGTATAGT

CGTCAACGGTCGCACCCAGAGAAACACCAATACCATGAAAAATT

ACCTTTTGCCCGTAGTGGCCCAGGCATTTGCTAGGTGGGCAAAG

GAATATAAGGAAGATCAAGAAGATGAAAGGCCACTAGGACTACG

AGATAGACAGTTAGTCATGGGGTGTTGTTGGGCTTTTAGAAGGC

ACAAGATAACATCTATTTATAAGCGCCCGGATACCCAAACCATC

ATCAAAGTGAACAGCGATTTCCACTCATTCGTGCTGCCCAGGAT

AGGCAGTAACACATTGGAGATCGGGCTGAGAACAAGAATCAGGA

AAATGTTAGAGGAGCACAAGGAGCCGTCACCTCTCATTACCGCC

GAGGACGTACAAGAAGCTAAGTGCGCAGCCGATGAGGCTAAGGA

GGTGCGTGAAGCCGAGGAGTTGCGCGCAGCTCTACCACCTTTGG

CAGCTGATGTTGAGGAGCCCACTCTGGAAGCCGATGTCGACTTG

ATGTTACAAGAGGCTGGGGCCGGCTCAGTGGAGACACCTCGTGG

CTTGATAAAGGTTACCAGCTACGATGGCGAGGACAAGATCGGCT

CTTACGCTGTGCTTTCTCCGCAGGCTGTACTCAAGAGTGAAAAA

TTATCTTGCATCCACCCTCTCGCTGAACAAGTCATAGTGATAAC

ACACTCTGGCCGAAAAGGGCGTTATGCCGTGGAACCATACCATG

GTAAAGTAGTGGTGCCAGAGGGACATGCAATACCCGTCCAGGAC

TTTCAAGCTCTGAGTGAAAGTGCCACCATTGTGTACAACGAACG

TGAGTTCGTAAACAGGTACCTGCACCATATTGCCACACATGGAG

GAGCGCTGAACACTGATGAAGAATATTACAAAACTGTCAAGCCC

AGCGAGCACGACGGCGAATACCTGTACGACATCGACAGGAAACA

GTGCGTCAAGAAGAACTAGTCACTGGGCTAGGGCTCACAGGCG

AGCTGGTGGATCCTCCCTTCCATGAATTCGCCTACGAGAGTCTG

AGAACACGACCAGCCGCTCCTTACCAAGTACCAACCATAGGGGT

GTATGCGTGCCAGGATCAGGCAAGTCTGGCATCATTAAAAGCG

CAGTCACCAAAAAAGATCTAGTGGTGAGCGCCAAGAAAGAAAC

TGTGCAGAAATTATAAGGGACGTCAAGAAAATGAAAGGGCTGGA

CGTCAATGCCAGAACTGTGGACTCAGTGCTCTTGAATGGATGCA

AACACCCCGTAGAGACCCTGTATATTGACGAAGCTTTTGCTTGT

-continued

CATGCAGGTACTCTCAGAGCGCTCATAGCCATTATAAGACCTAA

AAAGGCAGTGCTCTGCGGGGATCCCAAACAGTGCGGTTTTTTTA

ACATGATGTGCCTGAAAGTGCATTTTAACCACGAGATTTGCACA

CAAGTCTTCCACAAAAGCATCTCTCGCCGTTGCACTAAATCTGT

GACTTCGGTCGTCTCAACCTTGTTTTACGACAAAAAAATGAGAA

CGACGAATCCGAAAGAGACTAAGATTGTGATTGACACTACCGGC

AGTACCAAACCTAAGCAGGACGATCTCATTCTCACTTGTTTCAG

AGGGTGGGTGAAGCAGTTGCAAATAGATTACAAAGGCAACGAAA

TAATGACGGCAGCTGCCTCTCAAGGGCTGACCCGTAAAGGTGTG

TATGCCGTTCGGTACAAGGTGAATGAAAATCCTCTGTACGCACC

CACCTCAGAACATGTGAACGTCCTACTGACCCGCACGGAGGACC

GCATCGTGTGGAAAACACTAGCCGGCGACCCATGGATAAAAACA

CTGACTGCCAAGTACCCTGGGAATTTCACTGCCACGATAGAGGA

GTGGCAAGCAGAGCATGATGCCATCATGAGGCACATCTTGGAGA

GACCGGACCCTACCGACGTCTTCCAGAATAAGGCAAACGTGTGT

TGGGCCAAGGCTTTAGTGCCGGTGCTGAAGACCGCTGGCATAGA

CATGACCACTGAACAATGGAACACTGTGGATTATTTTGAAACGG

ACAAAGCTCACTCAGCAGAGATAGTATTGAACCAACTATGCGTG

AGGTTCTTTGGACTCGATCTGGACTCCGGTCTATTTTCTGCACC

CACTGTTCCGTTATCCATTAGGAATAATCACTGGGATAACTCCC

CGTCGCCTAACATGTACGGGCTGAATAAAGAAGTGGTCCGTCAG

CTCTCTCGCAGGTACCCACAACTGCCTCGGGCAGTTGCCACTGG

AAGAGTCTATGACATGAACACTGGTACACTGCGCAATTATGATC

CGCGCATAAACCTAGTACCTGTAAACAGAAGACTGCCTCATGCT

TTAGTCCTCCACCATAATGAACACCCACAGAGTGACTTTTCTTC

ATTCGTCAGCAAATTGAAGGGCAGAACTGTCCTGGTGGTCGGGG

AAAAGTTGTCCGTCCCAGGCAAAATGGTTGACTGGTTGTCAGAC

CGGCCTGAGGCTACCTTCAGAGCTCGGCTGGATTTAGGCATCCC

AGGTGATGTGCCCAAATATGACATAATATTTGTTAATGTGAGGA

CCCCATATAAATACCATCACTATCAGCAGTGTGAAGACCATGCC

ATTAAGCTTAGCATGTTGACCAAGAAAGCTTGTCTGCATCTGAA

TCCCGGCGGAACCTGTGTCAGCATAGGTTATGGTTACGCTGACA

GGGCCAGCGAAAGCATCATTGGTGCTATAGCGCGGCAGTTCAAG

TTTTCCCGGGTATGCAAACCGAAATCCTCACTTGAAGAGACGGA

AGTTCTGTTTGTATTCATTGGGTACGATCGCAAGGCCCGTACGC

ACAATTCTTACAAGCTTTCATCAACCTTGACCAACATTTATACA

GGTTCCAGACTCCACGAAGCCGGATGTGCACCCTCATATCATGT

GGTGCGAGGGGATATTGCCACGGCCACCGAAGGAGTGATTATAA

ATGCTGCTAACAGCAAAGGACAACCTGGCGGAGGGGTGTGCGGA

GCGCTGTATAAGAAATTCCCGGAAAGCTTCGATTTACAGCCGAT

-continued

```
CGAAGTAGGAAAAGCGCGACTGGTCAAAGGTGCAGCTAAACATA

TCATTCATGCCGTAGGACCAAACTTCAACAAAGTTTCGGAGGTT

GAAGGTGACAAACAGTTGGCAGAGGCTTATGAGTCCATCGCTAA

GATTGTCAACGATAACAATTACAAGTCAGTAGCGATTCCACTGT

TGTCCACCGGCATCTTTTCCGGGAACAAAGATCGACTAACCCAA

TCATTGAACCATTTGCTGACAGCTTTAGACACCACTGATGCAGA

TGTAGCCATATACTGCAGGGACAAGAAATGGGAAATGACTCTCA

AGGAAGCAGTGGCTAGGAGAGAAGCAGTGGAGGAGATATGCATA

TCCGACGACTCTTCAGTGACAGAACCTGATGCAGAGCTGGTGAG

GGTGCATCCGAAGAGTTCTTTGGCTGGAAGGAAGGGCTACAGCA

CAAGCGATGGCAAAACTTTCTCATATTTGGAAGGGACCAAGTTT

CACCAGGCGGCCAAGGATATAGCAGAAATTAATGCCATGTGGCC

CGTTGCAACGGAGGCCAATGAGCAGGTATGCATGTATATCCTCG

GAGAAAGCATGAGCAGTATTAGGTCGAAATGCCCCGTCGAAGAG

TCGGAAGCCTCCACACCACCTAGCACGCTGCCTTGCTTGTGCAT

CCATGCCATGACTCCAGAAAGAGTACAGCGCCTAAAAGCCTCAC

GTCCAGAACAAATTACTGTGTGCTCATCCTTTCCATTGCCGAAG

TATAGAATCACTGGTGTGCAGAAGATCCAATGCTCCCAGCCTAT

ATTGTTCTCACCGAAAGTGCCTGCGTATATTCATCCAAGGAAGT

ATCTCGTGGAAACACCACCGGTAGACGAGACTCCGGAGCCATCG

GCAGAGAACCAATCCACAGAGGGGACACCTGAACAACCACCACT

TATAACCGAGGATGAGACCAGGACTAGAACGCCTGAGCCGATCA

TCATCGAAGAGGAAGAAGAGGATAGCATAAGTTTGCTGTCAGAT

GGCCCGACCCACCAGGTGCTGCAAGTCGAGGCAGACATTCACGG

GCCGCCCTCTGTATCTAGCTCATCCTGGTCCATTCCTCATGCAT

CCGACTTTGATGTGGACAGTTTATCCATACTTGACACCCTGGAG

GGAGCTAGCGTGACCAGCGGGGCAACGTCAGCCGAGACTAACTC

TTACTTCGCAAAGAGTATGGAGTTTCTGGCGCGACCGGTGCCTG

CGCCTCGAACAGTATTCAGGAACCCTCCACATCCCGCTCCGCGC

ACAAGAACACCGTCACTTGCACCCAGCAGGGCCTGCTCGAGAAC

CAGCCTAGTTTCCACCCCGCCAGGCGTGAATAGGGTGATCACTA

GAGAGGAGCTCGAGGCGCTTACCCCGTCACGCACTCCTAGCAGG

TCGGTCTCGAGAACCAGCCTGGTCTCCAACCCGCCAGGCGTAAA

TAGGGTGATTACAAGAGAGGAGTTTGAGGCGTTCGTAGCACAAC

AACAATGACGGTTTGATGCGGGTGCATACATCTTTTCCTCCGAC

ACCGGTCAAGGGCATTTACAACAAAAATCAGTAAGGCAAACGGT

GCTATCCGAAGTGGTGTTGGAGAGGACCGAATTGGAGATTTCGT

ATGCCCCGCGCCTCGACCAAGAAAAAGAAGAATTACTACGCAAG

AAATTACAGTTAAATCCCACACCTGCTAACAGAAGCAGATACCA

GTCCAGGAAGGTGGAGAACATGAAAGCCATAACAGCTAGACGTA

TTCTGCAAGGCCTAGGGCATTATTTGAAGGCAGAAGGAAAAGTG
```

-continued

```
GAGTGCTACCGAACCCTGCATCCTGTTCCTTTGTATTCATCTAG

TGTGAACCGTGCCTTTTCAAGCCCCAAGGTCGCAGTGGAAGCCT

GTAACGCCATGTTGAAAGAGAACTTTCCGACTGTGGCTTCTTAC

TGTATTATTCCAGAGTACGATGCCTATTTGGACATGGTTGACGG

AGCTTCATGCTGCTTAGACACTGCCAGTTTTTGCCCTGCAAAGC

TGCGCAGCTTTCCAAAGAAACACTCCTATTTGGAACCCACAATA

CGATCGGCAGTGCCTTCAGCGATCCAGAACACGCTCCAGAACGT

CCTGGCAGCTGCCACAAAAAGAAATTGCAATGTCACGCAAATGA

GAGAATTGCCCGTATTGGATTCGGCGGCCTTTAATGTGGAATGC

TTCAAGAAATATGCGTGTAATAATGAATATTGGGAAACGTTTAA

AGAAAACCCCATCAGGCTTACTGAAGAAAACGTGGTAAATTACA

TTACCAAATTAAAAGGACCAAAAGCTGCTGCTCTTTTTGCGAAG

ACACATAATTTGAATATGTTGCAGGACATACCAATGGACAGGTT

TGTAATGGACTTAAAGAGAGACGTGAAAGTGACTCCAGGAACAA

AACATACTGAAGAACGGCCCAAGGTACAGGTGATCCAGGCTGCC

GATCCGCTAGCAACAGCGTATCTGTGCGGAATCCACCGAGAGCT

GGTTAGGAGATTAAATGCGGTCCTGCTTCCGAACATTCATACAC

TGTTTGATATGTCGGCTGAAGACTTTGACGCTATTATAGCCGAG

CACTTCCAGCCTGGGGATTGTGTTCTGGAAACTGACATCGCGTC

GTTTGATAAAAGTGAGGACGACGCCATGGCTCTGACCGCGTTAA

TGATTCTGGAAGACTTAGGTGTGGACGCAGAGCTGTTGACGCTG

ATTGAGGCGGCTTTCGGCGAAATTTCATCAATACATTTGCCCAC

TAAAACTAAATTTAAATTCGGAGCCATGATGAAATCTGGAATGT

TCCTCACACTGTTTGTGAACACAGTCATTAACATTGTAATCGCA

AGCAGAGTGTTGAGAGAACGGCTAACCGGATCACCATGTGCAGC

ATTCATTGGAGATGACAATATCGTGAAAGGAGTCAAATCGGACA

AATTAATGGCAGACAGGTGCGCCACCTGGTTGAATATGGAAGTC

AAGATTATAGATGCTGTGGTGGGCGAGAAAGCGCCTTATTTCTG

TGGAGGGTTTATTTTGTGTGACTCCGTGACCGGCACAGCGTGCC

GTGTGGCAGACCCCCTAAAAAGGCTGTTTAAGCTTGGCAAACCT

CTGGCAGCAGACGATGAACATGATGATGACAGGAGAAGGGCATT

GCATGAAGAGTCAACACGCTGGAACCGAGTGGGTATTCTTTCAG

AGCTGTGCAAGGCAGTAGAATCAAGGTATGAAACCGTAGGAACT

TCCATCATAGTTATGGCCATGACTACTCTAGCTAGCAGTGTTAA

ATCATTCAGCTACCTGAGAGGGGCCCCTATAACTCTCTACGGCT

AACCTGAATGGACTACGACATAGTCTAGTCCGCCAAGTCTAGCA

TATGTATGGCCACCATGGAAGATGCCAAGAACATCAAGAAGGGC

CCTGCCCCATTCTACCCCCTGGAAGATGGAACAGCCGGCGAGCA

GCTGCACAAGGCCATGAAGAGATACGCCCTGGTGCCCGGCACAA

TCGCCTTCACCGATGCCCACATCGAGGTGGACATCACCTACGCC
```

-continued

```
GAGTACTTCGAGATGAGCGTGCGGCTGGCCGAAGCTATGAAGCG

CTACGGCCTGAACACCAACCACCGGATCGTCGTGTGCAGCGAGA

ACAGCCTGCAGTTCTTCATGCCCGTGCTGGGCGCCCTGTTTATC

GGAGTGGCTGTGGCCCCTGCCAACGACATCTACAACGAGCGCGA

GCTGCTGAACAGCATGGGCATCAGCCAGCCCACCGTGGTGTTCG

TGTCCAAGAAGGGACTGCAGAAAATCCTGAACGTGCAGAAGAAG

CTGCCCATCATCCAGAAAATCATCATCATGGACAGCAAGACCGA

CTACCAGGGCTTCCAGAGCATGTACACCTTCGTGACCAGCCATC

TGCCCCCTGGCTTCAACGAGTACGACTTCGTGCCCGAGAGCTTC

GACCGGGACAAGACAATCGCCCTGATCATGAACAGCAGCGGCAG

CACCGGACTGCCTAAAGGCGTGGCCCTGCCTCACAGAACTGCCT

GCGTGCGGTTTAGCCACGCCCGGGACCCTATCTTCGGCAACCAG

ATCATCCCCGACACCGCCATCCTGAGCGTGGTGCCTTTCCACCA

CGGCTTCGGCATGTTCACCACCCTGGGCTACCTGATCTGCGGCT

TCCGGGTGGTGCTGATGTACAGATTCGAGGAAGAACTGTTCCTG

CGGAGCCTGCAGGACTACAAGATCCAGAGCGCCCTGCTGGTGCC

TACCCTGTTCAGCTTCTTTGCCAAGAGCACCCTGATCGATAAGT

ACGACCTGAGCAACCTGCACGAGATCGCCTCTGGCGGAGCCCCC

CTGTCTAAAGAAGTGGGAGAGGCCGTGGCCAAGCGGTTCCATCT

GCCTGGCATCAGACAGGGCTATGGCCTGACCGAGACAACCAGCG

CCATTCTGATCACCCCCGAGGGCGACGATAAGCCTGGCGCCGTG

GGAAAGGTGGTGCCATTCTTCGAGGCCAAGGTGGTGGACCTGGA

CACCGGCAAGACACTGGGCGTGAACCAGAGGGGCGAACTGTGTG

TGCGGGGACCTATGATCATGAGCGGCTACGTGAACAACCCCGAG

GCCACCAACGCCCTGATTGACAAGGATGGCTGGCTGCACAGCGG

CGACATTGCCTACTGGGACGAGGACGAGCACTTCTTCATCGTGG

ACCGGCTGAAGTCCCTGATCAAGTACAAGGGCTACCAGGTGGCC

CCAGCCGAGCTGGAATCTATCCTGCTGCAGCACCCCAACATCTT

CGATGCCGGCGTGGCAGGACTGCCCGATGATGATGCTGGCGAAC

TGCCAGCCGCTGTGGTGGTGCTGGAACACGGAAAGACCATGACC

GAGAAAGAAATCGTGGACTACGTGGCCAGCCAAGTGACCACCGC

CAAGAAACTGAGAGGCGGCGTGGTGTTTGTGGACGAGGTGCCAA

AGGGCCTGACAGGCAAGCTGGACGCCCGGAAGATCAGAGAGATC

CTGATTAAGGCCAAGAAAGGCGGCAAGATCGCCGTGGATCGGAG

AAAGAGAGGCTCTGGCGAAGGCAGAGGCAGCCTGCTTACATGTG

GCGACGTGGAAGAGAACCCCGGACCTATGGACCCTACCGACCTG

AGCTTCAGCCCCGACGAGATCAACAAGCTGATCGAGACAGGCCT

GAACACCGTGGAATACTTCACCAGCCAGCAAGTGACCGGCACAA

GCAGCCTGGGCAAGAACACAATTCCTCCAGGCGTGACCGGCCTG

CTGACAAATGCTGCCGAGGCCAAGATCCAAGAGAGCACCAACCA

CCAGAAGGGCTCTGTTGGAGGCGGAGCCAAGCCTAAGAAGCCCA
```

-continued

```
GACCTAAGATCGCCATCGTGCCCGCCGACGATAAGACAGTGCCT

GGCAAGCCCATTCCTAATCCTCTGCTGGGCCTCGACAGCACCCC

TAGCACACAGACAGTGCTGGATCTGAGCGGCAAGACACTGCCTA

GCGGCAGCTATAAGGGCGTGAAGCTGGCCAAGTTCGGCAAAGAA

AACCTGATGACCCGGTTCATCGAGGAACCCAGAGAGAACCCTAT

CGCCACCAGCTCTCCCATCGACTTCAAGAGAGGCAGAGACACCG

GCGGCTTCCACAGAAGAGAGTACAGCATTGGCTGGGTCGGAGAT

GAAGTGAAAGTGACCGAGTGGTGCAACCCCAGCTGCAGCCCTAT

TACAGCCGCCGCTAGAAGATTCGAGTGCACCTGTCACCAGTGTC

CTGTGACCTGTAGCGAGTGCGAGCGGGACACATGATGAGCGGCC

GCGAATTGGCAAGCTGCTTACATAGAACTCGCGGCGATTGGCAT

GCCGCCTTAAAATTTTTATTTTATTTTTCTTTTCTTTTCCGAAT

CGGATTTTGTTTTTAATATTTCAAAAAAAAAAAAAAAAAAAAAA

AAAAAAAAAAAAAAA
```

Accordingly, preferably the nucleic acid sequence comprises a nucleotide sequence substantially as set out in SEQ ID No: 40, or a fragment or variant thereof.

In one embodiment, the nucleic acid sequence may comprise or consist of SEQ ID No: 41, as follows:

[SEQ ID No: 41]
```
ATGGGCGGCGCATGAGAGAAGCCCAGACCAATTACCTACCCAAA

ATGGAGAAAGTTCACGTTGACATCGAGGAAGACAGCCCATTCCT

CAGAGCTTTGCAGCGGAGCTTCCCGCAGTTTGAGGTAGAAGCCA

AGCAGGTCACTGATAATGACCATGCTAATGCCAGAGCGTTTTCG

CATCTGGCTTCAAAACTGATCGAAACGGAGGTGGACCCATCCGA

CACGATCCTTGACATTGGAAGTGCGCCCGCCCGCGAATGTATT

CTAAGCACAAGTATCATTGTATCTGTCCGATGAGATGTGCGGAA

GATCCGGACAGATTGTATAAGTATGCAACTAAGCTGAAGAAAAA

CTGTAAGGAAATAACTGATAAGGAATTGGACAAGAAAATGAAGG

AGCTGGCCGCCGTCATGAGCGACCCTGACCTGGAAACTGAGACT

ATGTGCCTCCACGACGACGAGTCGTGTCGCTACGAAGGGCAAGT

CGCTGTTTACCAGGATGTATACGCGGTTGACGGACCGACAAGTC

TCTATCACCAAGCCAATAAGGGAGTTAGAGTCGCCTACTGGATA

GGCTTTGACACCACCCCTTTTATGTTTAAGAACTTGGCTGGAGC

ATATCCATCATACTCTACCAACTGGGCCGACGAAACCGTGTTAA

CGGCTCGTAACATAGGCCTATGCAGCTCTGACGTTATGGAGCGG

TCACGTAGAGGGATGTCCATTCTTAGAAAGAAGTATTTGAAACC

ATCCAACAATGTTCTATTCTCTGTTGGCTCGACCATCTACCACG

AGAAGAGGGACTTACTGAGGAGCTGGCACCTGCCGTCTGTATTT

CACTTACGTGGCAAGCAAAATTACACATGTCGGTGTGAGACTAT

AGTTAGTTGCGACGGGTACGTCGTTAAAAGAATAGCTATCAGTC
```

-continued

CAGGCCTGTATGGGAAGCCTTCAGGCTATGCTGCTACGATGCAC

CGCGAGGGATTCTTGTGCTGCAAAGTGACAGACACATTGAACGG

GGAGAGGGTCTCTTTTCCCGTGTGCACGTATGTGCCAGCTACAT

TGTGTGACCAAATGACTGGCATACTGGCAACAGATGTCAGTGCG

GACGACGCGCAAAAACTGCTGGTTGGGCTCAACCAGCGTATAGT

CGTCAACGGTCGCACCCAGAGAAACACCAATACCATGAAAAATT

ACCTTTTGCCCGTAGTGGCCCAGGCATTTGCTAGGTGGGCAAAG

GAATATAAGGAAGATCAAGAAGATGAAAGGCCACTAGGACTACG

AGATAGACAGTTAGTCATGGGGTGTTGTTGGGCTTTTAGAAGGC

ACAAGATAACATCTATTTATAAGCGCCCGGATACCCAAACCATC

ATCAAAGTGAACAGCGATTTCCACTCATTCGTGCTGCCCAGGAT

AGGCAGTAACACATTGGAGATCGGGCTGAGAACAAGAATCAGGA

AAATGTTAGAGGAGCACAAGGAGCCGTCACCTCTCATTACCGCC

GAGGACGTACAAGAAGCTAAGTGCGCAGCCGATGAGGCTAAGGA

GGTGCGTGAAGCCGAGGAGTTGCGCGCAGCTCTACCACCTTTGG

CAGCTGATGTTGAGGAGCCCACTCTGGAAGCCGATGTCGACTTG

ATGTTACAAGAGGCTGGGGCCGGCTCAGTGGAGACACCTCGTGG

CTTGATAAAGGTTACCAGCTACGATGGCGAGGACAAGATCGGCT

CTTACGCTGTGCTTTCTCCGCAGGCTGTACTCAAGAGTGAAAAA

TTATCTTGCATCCACCCTCTCGCTGAACAAGTCATAGTGATAAC

ACACTCTGGCCGAAAAGGGCGTTATGCCGTGGAACCATACCATG

GTAAAGTAGTGGTGCCAGAGGGACATGCAATACCCGTCCAGGAC

TTTCAAGCTCTGAGTGAAAGTGCCACCATTGTGTACAACGAACG

TGAGTTCGTAAACAGGTACCTGCACCATATTGCCACACATGGAG

GAGCGCTGAACACTGATGAAGAATATTACAAAACTGTCAAGCCC

AGCGAGCACGACGGCGAATACCTGTACGACATCGACAGGAAACA

GTGCGTCAAGAAGAACTAGTCACTGGGCTAGGGCTCACAGGCG

AGCTGGTGGATCCTCCCTTCCATGAATTCGCCTACGAGAGTCTG

AGAACACGACCAGCCGCTCCTTACCAAGTACCAACCATAGGGGT

GTATGGCGTGCCAGGATCAGGCAAGTCTGGCATCATTAAAAGCG

CAGTCACCAAAAAAGATCTAGTGGTGAGCGCCAAGAAAGAAAC

TGTGCAGAAATTATAAGGGACGTCAAGAAAATGAAAGGGCTGGA

CGTCAATGCCAGAACTGTGGACTCAGTGCTCTTGAATGGATGCA

AACACCCCGTAGAGACCCTGTATATTGACGAAGCTTTTGCTTGT

CATGCAGGTACTCTCAGAGCGCTCATAGCCATTATAAGACCTAA

AAAGGCAGTGCTCTGCGGGGATCCCAAACAGTGCGGTTTTTTTA

ACATGATGTGCCTGAAAGTGCATTTTAACCACGAGATTTGCACA

CAAGTCTTCCACAAAAGCATCTCTCGCCGTTGCACTAAATCTGT

GACTTCGGTCGTCTCAACCTTGTTTTACGACAAAAAAATGAGAA

CGACGAATCCGAAAGAGACTAAGATTGTGATTGACACTACCGGC

AGTACCAAACCTAAGCAGGACGATCTCATTCTCACTTGTTTCAG

-continued

AGGGTGGGTGAAGCAGTTGCAAATAGATTACAAAGGCAACGAAA

TAATGACGGCAGCTGCCTCTCAAGGGCTGACCCGTAAAGGTGTG

TATGCCGTTCGGTACAAGGTGAATGAAAATCCTCTGTACGCACC

CACCTCAGAACATGTGAACGTCCTACTGACCCGCACGGAGGACC

GCATCGTGTGGAAAACACTAGCCGGCGACCCATGGATAAAAACA

CTGACTGCCAAGTACCCTGGGAATTTCACTGCCACGATAGAGGA

GTGGCAAGCAGAGCATGATGCCATCATGAGGCACATCTTGGAGA

GACCGGACCCTACCGACGTCTTCCAGAATAAGGCAAACGTGTGT

TGGGCCAAGGCTTTAGTGCCGGTGCTGAAGACCGCTGGCATAGA

CATGACCACTGAACAATGGAACACTGTGGATTATTTTGAAACGG

ACAAAGCTCACTCAGCAGAGATAGTATTGAACCAACTATGCGTG

AGGTTCTTTGGACTCGATCTGGACTCCGGTCTATTTTCTGCACC

CACTGTTCCGTTATCCATTAGGAATAATCACTGGGATAACTCCC

CGTCGCCTAACATGTACGGGCTGAATAAAGAAGTGGTCCGTCAG

CTCTCTCGCAGGTACCCACAACTGCCTCGGGCAGTTGCCACTGG

AAGAGTCTATGACATGAACACTGGTACACTGCGCAATTATGATC

CGCGCATAAACCTAGTACCTGTAAACAGAAGACTGCCTCATGCT

TTAGTCCTCCACCATAATGAACACCCACAGAGTGACTTTTCTTC

ATTCGTCAGCAAATTGAAGGGCAGAACTGTCCTGGTGGTCGGGG

AAAAGTTGTCCGTCCCAGGCAAAATGGTTGACTGGTTGTCAGAC

CGGCCTGAGGCTACCTTCAGAGCTCGGCTGGATTTAGGCATCCC

AGGTGATGTGCCCAAATATGACATAATATTTGTTAATGTGAGGA

CCCCATATAAATACCATCACTATCAGCAGTGTGAAGACCATGCC

ATTAAGCTTAGCATGTTGACCAAGAAAGCTTGTCTGCATCTGAA

TCCCGGCGGAACCTGTGTCAGCATAGGTTATGGTTACGCTGACA

GGGCCAGCGAAAGCATCATTGGTGCTATAGCGCGGCAGTTCAAG

TTTTCCCGGGTATGCAAACCGAAATCCTCACTTGAAGAGACGGA

AGTTCTGTTTGTATTCATTGGGTACGATCGCAAGGCCCGTACGC

ACAATTCTTACAAGCTTTCATCAACCTTGACCAACATTTATACA

GGTTCCAGACTCCACGAAGCCGGATGTGCACCCTCATATCATGT

GGTGCGAGGGGATATTGCCACGGCCACCGAAGGAGTGATTATAA

ATGCTGCTAACAGCAAAGGACAACCTGGCGGAGGGGTGTGCGGA

GCGCTGTATAAGAAATTCCCGGAAAGCTTCGATTTACAGCCGAT

CGAAGTAGGAAAAGCGCGACTGGTCAAAGGTGCAGCTAAACATA

TCATTCATGCCGTAGGACCAAACTTCAACAAAGTTTCGGAGGTT

GAAGGTGACAAACAGTTGGCAGAGGCTTATGAGTCCATCGCTAA

GATTGTCAACGATAACAATTACAAGTCAGTAGCGATTCCACTGT

TGTCCACCGGCATCTTTTCCGGGAACAAAGATCGACTAACCCAA

TCATTGAACCATTTGCTGACAGCTTTAGACACCACTGATGCAGA

TGTAGCCATATACTGCAGGGACAAGAAATGGGAAATGACTCTCA

-continued

AGGAAGCAGTGGCTAGGAGAGAAGCAGTGGAGGAGATATGCATA

TCCGACGACTCTTCAGTGACAGAACCTGATGCAGAGCTGGTGAG

GGTGCATCCGAAGAGTTCTTTGGCTGGAAGGAAGGGCTACAGCA

CAAGCGATGGCAAAACTTTCTCATATTTGGAAGGGACCAAGTTT

CACCAGGCGGCCAAGGATATAGCAGAAATTAATGCCATGTGGCC

CGTTGCAACGGAGGCCAATGAGCAGGTATGCATGTATATCCTCG

GAGAAAGCATGAGCAGTATTAGGTCGAAATGCCCCGTCGAAGAG

TCGGAAGCCTCCACACCACCTAGCACGCTGCCTTGCTTGTGCAT

CCATGCCATGACTCCAGAAAGAGTACAGCGCCTAAAAGCCTCAC

GTCCAGAACAAATTACTGTGTGCTCATCCTTTCCATTGCCGAAG

TATAGAATCACTGGTGTGCAGAAGATCCAATGCTCCCAGCCTAT

ATTGTTCTCACCGAAAGTGCCTGCGTATATTCATCCAAGGAAGT

ATCTCGTGGAAACACCACCGGTAGACGAGACTCCGGAGCCATCG

GCAGAGAACCAATCCACAGAGGGGACACCTGAACAACCACCACT

TATAACCGAGGATGAGACCAGGACTAGAACGCCTGAGCCGATCA

TCATCGAAGAGGAAGAAGAGGATAGCATAAGTTTGCTGTCAGAT

GGCCCGACCCACCAGGTGCTGCAAGTCGAGGCAGACATTCACGG

GCCGCCCTCTGTATCTAGCTCATCCTGGTCCATTCCTCATGCAT

CCGACTTTGATGTGGACAGTTTATCCATACTTGACACCCTGGAG

GGAGCTAGCGTGACCAGCGGGGCAACGTCAGCCGAGACTAACTC

TTACTTCGCAAAGAGTATGGAGTTTCTGGCGCGACCGGTGCCTG

CGCCTCGAACAGTATTCAGGAACCCTCCACATCCCGCTCCGCGC

ACAAGAACACCGTCACTTGCACCCAGCAGGGCCTGCTCGAGAAC

CAGCCTAGTTTCCACCCCGCCAGGCGTGAATAGGGTGATCACTA

GAGAGGAGCTCGAGGCGCTTACCCCGTCACGCACTCCTAGCAGG

TCGGTCTCGAGAACCAGCCTGGTCTCCAACCCGCCAGGCGTAAA

TAGGGTGATTACAAGAGAGGAGTTTGAGGCGTTCGTAGCACAAC

AACAATGACGGTTTGATGCGGGTGCATACATCTTTTCCTCCGAC

ACCGGTCAAGGGCATTTACAACAAAAATCAGTAAGGCAAACGGT

GCTATCCGAAGTGGTGTTGGAGAGGACCGAATTGGAGATTTCGT

ATGCCCCGCGCCTCGACCAAGAAAAAGAAGAATTACTACGCAAG

AAATTACAGTTAAATCCCACACCTGCTAACAGAAGCAGATACCA

GTCCAGGAAGGTGGAGAACATGAAAGCCATAACAGCTAGACGTA

TTCTGCAAGGCCTAGGGCATTATTTGAAGGCAGAAGGAAAAGTG

GAGTGCTACCGAACCCTGCATCCTGTTCCTTTGTATTCATCTAG

TGTGAACCGTGCCTTTTCAAGCCCCAAGGTCGCAGTGGAAGCCT

GTAACGCCATGTTGAAAGAGAACTTTCCGACTGTGGCTTCTTAC

TGTATTATTCCAGAGTACGATGCCTATTTGGACATGGTTGACGG

AGCTTCATGCTGCTTAGACACTGCCAGTTTTTGCCCTGCAAAGC

TGCGCAGCTTTCCAAAGAAACACTCCTATTTGGAACCCACAATA

CGATCGGCAGTGCCTTCAGCGATCCAGAACACGCTCCAGAACGT

-continued

CCTGGCAGCTGCCACAAAAAGAAATTGCAATGTCACGCAAATGA

GAGAATTGCCCGTATTGGATTCGGCGGCCTTTAATGTGGAATGC

TTCAAGAAATATGCGTGTAATAATGAATATTGGGAAACGTTTAA

AGAAAACCCCATCAGGCTTACTGAAGAAAACGTGGTAAATTACA

TTACCAAATTAAAAGGACCAAAAGCTGCTGCTCTTTTTGCGAAG

ACACATAATTTGAATATGTTGCAGGACATACCAATGGACAGGTT

TGTAATGGACTTAAAGAGAGACGTGAAAGTGACTCCAGGAACAA

AACATACTGAAGAACGGCCCAAGGTACAGGTGATCCAGGCTGCC

GATCCGCTAGCAACAGCGTATCTGTGCGGAATCCACCGAGAGCT

GGTTAGGAGATTAAATGCGGTCCTGCTTCCGAACATTCATACAC

TGTTTGATATGTCGGCTGAAGACTTTGACGCTATTATAGCCGAG

CACTTCCAGCCTGGGGATTGTGTTCTGGAAACTGACATCGCGTC

GTTTGATAAAAGTGAGGACGACGCCATGGCTCTGACCGCGTTAA

TGATTCTGGAAGACTTAGGTGTGGACGCAGAGCTGTTGACGCTG

ATTGAGGCGGCTTTCGGCGAAATTTCATCAATACATTTGCCCAC

TAAAACTAAATTTAAATTCGGAGCCATGATGAAATCTGGAATGT

TCCTCACACTGTTTGTGAACACAGTCATTAACATTGTAATCGCA

AGCAGAGTGTTGAGAGAACGGCTAACCGGATCACCATGTGCAGC

ATTCATTGGAGATGACAATATCGTGAAAGGAGTCAAATCGGACA

AATTAATGGCAGACAGGTGCGCCACCTGGTTGAATATGGAAGTC

AAGATTATAGATGCTGTGGTGGGCGAGAAAGCGCCTTATTTCTG

TGGAGGGTTTATTTTGTGTGACTCCGTGACCGGCACAGCGTGCC

GTGTGGCAGACCCCCTAAAAAGGCTGTTTAAGCTTGGCAAACCT

CTGGCAGCAGACGATGAACATGATGATGACAGGAGAAGGGCATT

GCATGAAGAGTCAACACGCTGGAACCGAGTGGGTATTCTTTCAG

AGCTGTGCAAGGCAGTAGAATCAAGGTATGAAACCGTAGGAACT

TCCATCATAGTTATGGCCATGACTACTCTAGCTAGCAGTGTTAA

ATCATTCAGCTACCTGAGAGGGGCCCCTATAACTCTCTACGGCT

AACCTGAATGGACTACGACATAGTCTAGTCCGCCAAGTCTAGCA

TATGTATGGCCACCATGGAAGATGCCAAGAACATCAAGAAGGGC

CCTGCCCCATTCTACCCCCTGGAAGATGGAACAGCCGGCGAGCA

GCTGCACAAGGCCATGAAGAGATACGCCCTGGTGCCCGGCACAA

TCGCCTTCACCGATGCCCACATCGAGGTGGACATCACCTACGCC

GAGTACTTCGAGATGAGCGTGCGGCTGGCCGAAGCTATGAAGCG

CTACGGCCTGAACACCAACCACCGGATCGTCGTGTGCAGCGAGA

ACAGCCTGCAGTTCTTCATGCCCGTGCTGGGCGCCCTGTTTATC

GGAGTGGCTGTGGCCCCTGCCAACGACATCTACAACGAGCGCGA

GCTGCTGAACAGCATGGGCATCAGCCAGCCCACCGTGGTGTTCG

TGTCCAAGAAGGGACTGCAGAAAATCCTGAACGTGCAGAAGAAG

CTGCCCATCATCCAGAAAATCATCATCATGGACAGCAAGACCGA

-continued

```
CTACCAGGGCTTCCAGAGCATGTACACCTTCGTGACCAGCCATC

TGCCCCCTGGCTTCAACGAGTACGACTTCGTGCCCGAGAGCTTC

GACCGGGACAAGACAATCGCCCTGATCATGAACAGCAGCGGCAG

CACCGGACTGCCTAAAGGCGTGGCCCTGCCTCACAGAACTGCCT

GCGTGCGGTTTAGCCACGCCCGGGACCCTATCTTCGGCAACCAG

ATCATCCCCGACACCGCCATCCTGAGCGTGGTGCCTTTCCACCA

CGGCTTCGGCATGTTCACCACCCTGGGCTACCTGATCTGCGGCT

TCCGGGTGGTGCTGATGTACAGATTCGAGGAAGAACTGTTCCTG

CGGAGCCTGCAGGACTACAAGATCCAGAGCGCCCTGCTGGTGCC

TACCCTGTTCAGCTTCTTTGCCAAGAGCACCCTGATCGATAAGT

ACGACCTGAGCAACCTGCACGAGATCGCCTCTGGCGGAGCCCCC

CTGTCTAAAGAAGTGGGAGAGGCCGTGGCCAAGCGGTTCCATCT

GCCTGGCATCAGACAGGGCTATGGCCTGACCGAGACAACCAGCG

CCATTCTGATCACCCCCGAGGGCGACGATAAGCCTGGCGCCGTG

GGAAAGGTGGTGCCATTCTTCGAGGCCAAGGTGGTGGACCTGGA

CACCGGCAAGACACTGGGCGTGAACCAGAGGGGCGAACTGTGTG

TGCGGGGACCTATGATCATGAGCGGCTACGTGAACAACCCCGAG

GCCACCAACGCCCTGATTGACAAGGATGGCTGGCTGCACAGCGG

CGACATTGCCTACTGGGACGAGGACGAGCACTTCTTCATCGTGG

ACCGGCTGAAGTCCCTGATCAAGTACAAGGGCTACCAGGTGGCC

CCAGCCGAGCTGGAATCTATCCTGCTGCAGCACCCCAACATCTT

CGATGCCGGCGTGGCAGGACTGCCCGATGATGATGCTGGCGAAC

TGCCAGCCGCTGTGGTGGTGCTGGAACACGGAAAGACCATGACC

GAGAAAGAAATCGTGGACTACGTGGCCAGCCAAGTGACCACCGC

CAAGAAACTGAGAGGCGGCGTGGTGTTTGTGGACGAGGTGCCAA

AGGGCCTGACAGGCAAGCTGGACGCCCGGAAGATCAGAGAGATC

CTGATTAAGGCCAAGAAAGGCGGCAAGATCGCCGTGGATCGGAG

AAAGAGAGGCTCTGGCGAAGGCAGAGGCAGCCTGCTTACATGTG

GCGACGTGGAAGAGAACCCCGGACCTATGGACTACGTGTCCCTG

CTGAACCAGATTTGGCAGAAGTACCTGAACAGCCCCTACACCAC

CTGTCTGTACATCCCCAAGCCTACCGCCAAGTACACACCTCTCG

TGGGCACATCTCTGCACCCCGTGCTGTGGAATTGCCAGCTGAGC

TTTGCCGGCTACACCGAGTCTGCCGTGAACAGCACAAAGGCCCT

GGCCAAACAGGACGCCGCTCAGAGAATTGCCTGGCTGCTGCACA

AGGATGGCGGCATCCCTGATGGCTGTAGCCTGTACCTGAGACAC

AGCAGCCTGTTCGCCCAGAGCGAGGAAGAGGAATCCTTCAGCAA

CTGATGAGCGGCCGCGAATTGGCAAGCTGCTTACATAGAACTCG

CGGCGATTGGCATGCCGCCTTAAAATTTTTATTTTATTTTTCTT

TTCTTTTCCGAATCGGATTTTGTTTTTAATATTTCAAAAAAAA

AAAAAAAAAAAAAAAAAAAAAAAAAAAAAAAAA
```

Accordingly, preferably the nucleic acid sequence comprises a nucleotide sequence substantially as set out in SEQ ID No: 41, or a fragment or variant thereof.

In a third aspect, there is provided an expression cassette comprising a nucleic acid sequence according to the second aspect.

The nucleic acid sequences of the invention are preferably harboured in a recombinant vector, for example a recombinant vector for delivery into a host cell of interest to enable production of the RNA construct.

Accordingly, in a fourth aspect, there is provided a recombinant vector comprising the expression cassette according to the third aspect.

In one embodiment, the vector may comprise the nucleic acid sequence of SEQ ID No: 35, as follows, where "GOI" represents the position of the therapeutic biomolecule encoding sequence:

```
                                          [SEQ ID No: 35]
CGCCAGCAACGCGAGCTCTAATACGACTCACTATAGATGGGCGG

CGCATGAGAGAAGCCCAGACCAATTACCTACCCAAAATGGAGAA

AGTTCACGTTGACATCGAGGAAGACAGCCCATTCCTCAGAGCTT

TGCAGCGGAGCTTCCCGCAGTTTGAGGTAGAAGCCAAGCAGGTC

ACTGATAATGACCATGCTAATGCCAGAGCGTTTTCGCATCTGGC

TTCAAAACTGATCGAAACGGAGGTGGACCCATCCGACACGATCC

TTGACATTGGAAGTGCGCCCGCCCGCAGAATGTATTCTAAGCAC

AAGTATCATTGTATCTGTCCGATGAGATGTGCGGAAGATCCGGA

CAGATTGTATAAGTATGCAACTAAGCTGAAGAAAAACTGTAAGG

AAATAACTGATAAGGAATTGGACAAGAAAATGAAGGAGCTGGCC

GCCGTCATGAGCGACCCTGACCTGGAAACTGAGACTATGTGCCT

CCACGACGACGAGTCGTGTCGCTACGAAGGGCAAGTCGCTGTTT

ACCAGGATGTATACGCGGTTGACGGACCGACAAGTCTCTATCAC

CAAGCCAATAAGGGAGTTAGAGTCGCCTACTGGATAGGCTTTGA

CACCACCCCTTTTATGTTTAAGAACTTGGCTGGAGCATATCCAT

CATACTCTACCAACTGGGCCGACGAAACCGTGTTAACGGCTCGT

AACATAGGCCTATGCAGCTCTGACGTTATGGAGCGGTCACGTAG

AGGGATGTCCATTCTTAGAAAGAAGTATTTGAAACCATCCAACA

ATGTTCTATTCTCTGTTGGCTCGACCATCTACCACGAGAAGAGG

GACTTACTGAGGAGCTGGCACCTGCCGTCTGTATTTCACTTACG

TGGCAAGCAAAATTACACATGTCGGTGTGAGACTATAGTTAGTT

GCGACGGGTACGTCGTTAAAAGAATAGCTATCAGTCCAGGCCTG

TATGGGAAGCCTTCAGGCTATGCTGCTACGATGCACCGCGAGGG

ATTCTTGTGCTGCAAAGTGACAGACACATTGAACGGGGAGAGGG

TCTCTTTTCCCGTGTGCACGTATGTGCCAGCTACATTGTGTGAC

CAAATGACTGGCATACTGGCAACAGATGTCAGTGCGGACGACGC

GCAAAAACTGCTGGTTGGGCTCAACCAGCGTATAGTCGTCAACG

GTCGCACCCAGAGAAACACCAATACCATGAAAAATTACCTTTTG

CCCGTAGTGGCCCAGGCATTTGCTAGGTGGGCAAAGGAATATAA
```

65

-continued

```
GGAAGATCAAGAAGATGAAAGGCCACTAGGACTACGAGATAGAC

AGTTAGTCATGGGGTGTTGTTGGGCTTTTAGAAGGCACAAGATA

ACATCTATTTATAAGCGCCCGGATACCCAAACCATCATCAAAGT

GAACAGCGATTTCCACTCATTCGTGCTGCCCAGGATAGGCAGTA

ACACATTGGAGATCGGGCTGAGAACAAGAATCAGGAAAATGTTA

GAGGAGCACAAGGAGCCGTCACCTCTCATTACCGCCGAGGACGT

ACAAGAAGCTAAGTGCGCAGCCGATGAGGCTAAGGAGGTGCGTG

AAGCCGAGGAGTTGCGCGCAGCTCTACCACCTTTGGCAGCTGAT

GTTGAGGAGCCCACTCTGGAAGCCGATGTCGACTTGATGTTACA

AGAGGCTGGGGCCGGCTCAGTGGAGACACCTCGTGGCTTGATAA

AGGTTACCAGCTACGATGGCGAGGACAAGATCGGCTCTTACGCT

GTGCTTTCTCCGCAGGCTGTACTCAAGAGTGAAAAATTATCTTG

CATCCACCCTCTCGCTGAACAAGTCATAGTGATAACACACTCTG

GCCGAAAAGGGCGTTATGCCGTGGAACCATACCATGGTAAAGTA

GTGGTGCCAGAGGGACATGCAATACCCGTCCAGGACTTTCAAGC

TCTGAGTGAAAGTGCCACCATTGTGTACAACGAACGTGAGTTCG

TAAACAGGTACCTGCACCATATTGCCACACATGGAGGAGCGCTG

AACACTGATGAAGAATATTACAAAACTGTCAAGCCCAGCGAGCA

CGACGGCGAATACCTGTACGACATCGACAGGAAACAGTGCGTCA

AGAAAGAACTAGTCACTGGGCTAGGGCTCACAGGCGAGCTGGTG

GATCCTCCCTTCCATGAATTCGCCTACGAGAGTCTGAGAACACG

ACCAGCCGCTCCTTACCAAGTACCAACCATAGGGGTGTATGGCG

TGCCAGGATCAGGCAAGTCTGGCATCATTAAAAGCGCAGTCACC

AAAAAAGATCTAGTGGTGAGCGCCAAGAAAGAAAACTGTGCAGA

AATTATAAGGGACGTCAAGAAAATGAAAGGGCTGGACGTCAATG

CCAGAACTGTGGACTCAGTGCTCTTGAATGGATGCAAACACCCC

GTAGAGACCCTGTATATTGACGAAGCTTTTGCTTGTCATGCAGG

TACTCTCAGAGCGCTCATAGCCATTATAAGACCTAAAAAGGCAG

TGCTCTGCGGGGATCCCAAACAGTGCGGTTTTTTTAACATGATG

TGCCTGAAAGTGCATTTTAACCACGAGATTTGCACACAAGTCTT

CCACAAAAGCATCTCTCGCCGTTGCACTAAATCTGTGACTTCGG

TCGTCTCAACCTTGTTTTACGACAAAAAAATGAGAACGACGAAT

CCGAAAGAGACTAAGATTGTGATTGACACTACCGGCAGTACCAA

ACCTAAGCAGGACGATCTCATTCTCACTTGTTTCAGAGGGTGGG

TGAAGCAGTTGCAAATAGATTACAAAGGCAACGAAATAATGACG

GCAGCTGCCTCTCAAGGGCTGACCCGTAAAGGTGTGTATGCCGT

TCGGTACAAGGTGAATGAAAATCCTCTGTACGCACCCACCTCAG

AACATGTGAACGTCCTACTGACCCGCACGGAGGACCGCATCGTG

TGGAAAACACTAGCCGGCGACCCATGGATAAAAACACTGACTGC

CAAGTACCCTGGGAATTTCACTGCCACGATAGAGGAGTGGCAAG
```

66

-continued

```
CAGAGCATGATGCCATCATGAGGCACATCTTGGAGAGACCGGAC

CCTACCGACGTCTTCCAGAATAAGGCAAACGTGTGTTGGGCCAA

GGCTTTAGTGCCGGTGCTGAAGACCGCTGGCATAGACATGACCA

CTGAACAATGGAACACTGTGGATTATTTTGAAACGGACAAAGCT

CACTCAGCAGAGATAGTATTGAACCAACTATGCGTGAGGTTCTT

TGGACTCGATCTGGACTCCGGTCTATTTTCTGCACCCACTGTTC

CGTTATCCATTAGGAATAATCACTGGGATAACTCCCCGTCGCCT

AACATGTACGGGCTGAATAAAGAAGTGGTCCGTCAGCTCTCTCG

CAGGTACCCACAACTGCCTCGGGCAGTTGCCACTGGAAGAGTCT

ATGACATGAACACTGGTACACTGCGCAATTATGATCCGCGCATA

AACCTAGTACCTGTAAACAGAAGACTGCCTCATGCTTTAGTCCT

CCACCATAATGAACACCCACAGAGTGACTTTTCTTCATTCGTCA

GCAAATTGAAGGGCAGAACTGTCCTGGTGGTCGGGGAAAAGTTG

TCCGTCCCAGGCAAAATGGTTGACTGGTTGTCAGACCGGCCTGA

GGCTACCTTCAGAGCTCGGCTGGATTTAGGCATCCCAGGTGATG

TGCCCAAATATGACATAATATTTGTTAATGTGAGGACCCCATAT

AAATACCATCACTATCAGCAGTGTGAAGACCATGCCATTAAGCT

TAGCATGTTGACCAAGAAAGCTTGTCTGCATCTGAATCCCGGCG

GAACCTGTGTCAGCATAGGTTATGGTTACGCTGACAGGGCCAGC

GAAAGCATCATTGGTGCTATAGCGCGGCAGTTCAAGTTTTCCCG

GGTATGCAAACCGAAATCCTCACTTGAAGAGACGGAAGTTCTGT

TTGTATTCATTGGGTACGATCGCAAGGCCCGTACGCACAATTCT

TACAAGCTTTCATCAACCTTGACCAACATTTATACAGGTTCCAG

ACTCCACGAAGCCGGATGTGCACCCTCATATCATGTGGTGCGAG

GGGATATTGCCACGGCCACCGAAGGAGTGATTATAAATGCTGCT

AACAGCAAAGGACAACCTGGCGGAGGGGTGTGCGGAGCGCTGTA

TAAGAAATTCCCGGAAAGCTTCGATTTACAGCCGATCGAAGTAG

GAAAAGCGCGACTGGTCAAAGGTGCAGCTAAACATATCATTCAT

GCCGTAGGACCAAACTTCAACAAAGTTTCGGAGGTTGAAGGTGA

CAAACAGTTGGCAGAGGCTTATGAGTCCATCGCTAAGATTGTCA

ACGATAACAATTACAAGTCAGTAGCGATTCCACTGTTGTCCACC

GGCATCTTTTCCGGGAACAAAGATCGACTAACCCAATCATTGAA

CCATTTGCTGACAGCTTTAGACACCACTGATGCAGATGTAGCCA

TATACTGCAGGGACAAGAAATGGGAAATGACTCTCAAGGAAGCA

GTGGCTAGGAGAAGCAGTGGAGGAGATATGCATATCCGACGA

CTCTTCAGTGACAGAACCTGATGCAGAGCTGGTGAGGGTGCATC

CGAAGAGTTCTTTGGCTGGAAGGAAGGGCTACAGCACAAGCGAT

GGCAAAACTTTCTCATATTTGGAAGGGACCAAGTTTCACCAGGC

GGCCAAGGATATAGCAGAAATTAATGCCATGTGGCCCGTTGCAA

CGGAGGCCAATGAGCAGGTATGCATGTATATCCTCGGAGAAAGC

ATGAGCAGTATTAGGTCGAAATGCCCCGTCGAAGAGTCGGAAGC
```

-continued

CTCCACACCACCTAGCACGCTGCCTTGCTTGTGCATCCATGCCA

TGACTCCAGAAAGAGTACAGCGCCTAAAAGCCTCACGTCCAGAA

CAAATTACTGTGTGCTCATCCTTTCCATTGCCGAAGTATAGAAT

CACTGGTGTGCAGAAGATCCAATGCTCCCAGCCTATATTGTTCT

CACCGAAAGTGCCTGCGTATATTCATCCAAGGAAGTATCTCGTG

GAAACACCACCGGTAGACGAGACTCCGGAGCCATCGGCAGAGAA

CCAATCCACAGAGGGGACACCTGAACAACCACCACTTATAACCG

AGGATGAGACCAGGACTAGAACGCCTGAGCCGATCATCATCGAA

GAGGAAGAAGAGGATAGCATAAGTTTGCTGTCAGATGGCCCGAC

CCACCAGGTGCTGCAAGTCGAGGCAGACATTCACGGGCCGCCCT

CTGTATCTAGCTCATCCTGGTCCATTCCTCATGCATCCGACTTT

GATGTGGACAGTTTATCCATACTTGACACCCTGGAGGGAGCTAG

CGTGACCAGCGGGGCAACGTCAGCCGAGACTAACTCTTACTTCG

CAAAGAGTATGGAGTTTCTGGCGCGACCGGTGCCTGCGCCTCGA

ACAGTATTCAGGAACCCTCCACATCCCGCTCCGCGCACAAGAAC

ACCGTCACTTGCACCCAGCAGGGCCTGCTCGAGAACCAGCCTAG

TTTCCACCCCGCCAGGCGTGAATAGGGTGATCACTAGAGAGGAG

CTCGAGGCGCTTACCCCGTCACGCACTCCTAGCAGGTCGGTCTC

GAGAACCAGCCTGGTCTCCAACCCGCCAGGCGTAAATAGGGTGA

TTACAAGAGAGGAGTTTGAGGCGTTCGTAGCACAACAACAATGA

CGGTTTGATGCGGGTGCATACATCTTTTCCTCCGACACCGGTCA

AGGGCATTTACAACAAAAATCAGTAAGGCAAACGGTGCTATCCG

AAGTGGTGTTGGAGAGGACCGAATTGGAGATTTCGTATGCCCCG

CGCCTCGACCAAGAAAAGAAGAATTACTACGCAAGAAATTACA

GTTAAATCCCACACCTGCTAACAGAAGCAGATACCAGTCCAGGA

AGGTGGAGAACATGAAAGCCATAACAGCTAGACGTATTCTGCAA

GGCCTAGGGCATTATTTGAAGGCAGAAGGAAAAGTGGAGTGCTA

CCGAACCCTGCATCCTGTTCCTTTGTATTCATCTAGTGTGAACC

GTGCCTTTTCAAGCCCCAAGGTCGCAGTGGAAGCCTGTAACGCC

ATGTTGAAAGAGAACTTTCCGACTGTGGCTTCTTACTGTATTAT

TCCAGAGTACGATGCCTATTTGGACATGGTTGACGGAGCTTCAT

GCTGCTTAGACACTGCCAGTTTTTGCCCTGCAAAGCTGCGCAGC

TTTCCAAAGAAACACTCCTATTTGGAACCCACAATACGATCGGC

AGTGCCTTCAGCGATCCAGAACACGCTCCAGAACGTCCTGGCAG

CTGCCACAAAAAGAAATTGCAATGTCACGCAAATGAGAGAATTG

CCCGTATTGGATTCGGCGGCCTTTAATGTGGAATGCTTCAAGAA

ATATGCGTGTAATAATGAATATTGGGAAACGTTTAAAGAAAACC

CCATCAGGCTTACTGAAGAAACGTGGTAAATTACATTACCAAA

TTAAAAGGACCAAAAGCTGCTGCTCTTTTTGCGAAGACACATAA

TTTGAATATGTTGCAGGACATACCAATGGACAGGTTTGTAATGG

-continued

ACTTAAAGAGAGACGTGAAAGTGACTCCAGGAACAAAACATACT

GAAGAACGGCCCAAGGTACAGGTGATCCAGGCTGCCGATCCGCT

AGCAACAGCGTATCTGTGCGGAATCCACCGAGAGCTGGTTAGGA

GATTAAATGCGGTCCTGCTTCCGAACATTCATACACTGTTTGAT

ATGTCGGCTGAAGACTTTGACGCTATTATAGCCGAGCACTTCCA

GCCTGGGGATTGTGTTCTGGAAACTGACATCGCGTCGTTTGATA

AAAGTGAGGACGACGCCATGGCTCTGACCGCGTTAATGATTCTG

GAAGACTTAGGTGTGGACGCAGAGCTGTTGACGCTGATTGAGGC

GGCTTTCGGCGAAATTTCATCAATACATTTGCCCACTAAAACTA

AATTTAAATTCGGAGCCATGATGAAATCTGGAATGTTCCTCACA

CTGTTTGTGAACACAGTCATTAACATTGTAATCGCAAGCAGAGT

GTTGAGAGAACGGCTAACCGGATCACCATGTGCAGCATTCATTG

GAGATGACAATATCGTGAAAGGAGTCAAATCGGACAAATTAATG

GCAGACAGGTGCGCCACCTGGTTGAATATGGAAGTCAAGATTAT

AGATGCTGTGGTGGGCGAGAAAGCGCCTTATTTCTGTGGAGGGT

TTATTTTGTGTGACTCCGTGACCGGCACAGCGTGCCGTGTGGCA

GACCCCCTAAAAAGGCTGTTTAAGCTTGGCAAACCTCTGGCAGC

AGACGATGAACATGATGATGACAGGAGAAGGGCATTGCATGAAG

AGTCAACACGCTGGAACCGAGTGGGTATTCTTTCAGAGCTGTGC

AAGGCAGTAGAATCAAGGTATGAAACCGTAGGAACTTCCATCAT

AGTTATGGCCATGACTACTCTAGCTAGCAGTGTTAAATCATTCA

GCTACCTGAGAGGGGCCCCTATAACTCTCTACGGCTAACCTGAA

TGGACTACGACATAGTCTAGTCCGCCAAGTCTAGCATATGGCCA

CC- - - - - - - - - - - - - - - GOI - - -

- - - - - - - - - - - - - -

TGATGAGCGGCCGCGAA

TTGGCAAGCTGCTTACATAGAACTCGCGGCGATTGGCATGCCGC

CTTAAAATTTTTATTTTATTTTTCTTTTCTTTTCCGAATCGGAT

TTTGTTTTTAATATTTCAAAAAAAAAAAAAAAAAAAAAAAAAAA

AAAAAAAACGCGTCGAGGGGAATTAATTCTTGAAGACGAAAGGG

CCAGGTGGCACTTTTCGGGGAAATGTGCGCGGAACCCCTATTTG

TTTATTTTTCTAAATACATTCAAATATGTATCCGCTCATGAGAC

AATAACCCTGATAAATGCTTCAATAATATTGAAAAAGGAAGAGT

ATGAGTATTCAACATTTCCGTGTCGCCCTTATTCCCTTTTTTGC

GGCATTTTGCCTTCCTGTTTTTGCTCACCCAGAAACGCTGGTGA

AAGTAAAAGATGCTGAAGATCAGTTGGGTGCACGAGTGGGTTAC

ATCGAACTGGATCTCAACAGCGGTAAGATCCTTGAGAGTTTTCG

CCCCGAAGAACGTTTTCCAATGATGAGCACTTTTAAAGTTCTGC

TATGTGGCGCGGTATTATCCCGTGTTGACGCCGGGCAAGAGCAA

CTCGGTCGCCGCATACACTATTCTCAGAATGACTTGGTTGAGTA

CTCACCAGTCACAGAAAAGCATCTTACGGATGGCATGACAGTAA

-continued

```
GAGAATTATGCAGTGCTGCCATAACCATGAGTGATAACACTGCG

GCCAACTTACTTCTGACAACGATCGGAGGACCGAAGGAGCTAAC

CGCTTTTTTGCACAACATGGGGGATCATGTAACTCGCCTTGATC

GTTGGGAACCGGAGCTGAATGAAGCCATACCAAACGACGAGCGT

GACACCACGATGCCTGTAGCAATGGCAACAACGTTGCGCAAACT

ATTAACTGGCAACTACTTACTCTAGCTTCCCGGCAACAATTAA

TAGACTGGATGGAGGCGGATAAAGTTGCAGGACCACTTCTGCGC

TCGGCCCTTCCGGCTGGCTGGTTTATTGCTGATAAATCTGGAGC

CGGTGAGCGTGGGTCTCGCGGTATCATTGCAGCACTGGGGCCAG

ATGGTAAGCCCTCCCGTATCGTAGTTATCTACACGACGGGGAGT

CAGGCAACTATGGATGAACGAAATAGACAGATCGCTGAGATAGG

TGCCTCACTGATTAAGCATTGGTAACTGTCAGACCAAGTTTACT

CATATATACTTTAGATTGATTTAAAACTTCATTTTTAATTTAAA

AGGATCTAGGTGAAGATCCTTTTTGATAATCTCATGACCAAAAT

CCCTTAACGTGAGTTTTCGTTCCACTGAGCGTCAGACCCCGTAG

AAAAGATCAAAGGATCTTCTTGAGATCCTTTTTTTCTGCGCGTA

ATCTGCTGCTTGCAAACAAAAAAACCACCGCTACCAGCGGTGGT

TTGTTTGCCGGATCAAGAGCTACCAACTCTTTTTCCGAAGGTAA

CTGGCTTCAGCAGAGCGCAGATACCAAATACTGTCCTTCTAGTG

TAGCCGTAGTTAGGCCACCACTTCAAGAACTCTGTAGCACCGCC

TACATACCTCGCTCTGCTAATCCTGTTACCAGTGGCTGCTGCCA

GTGGCGATAAGTCGTGTCTTACCGGGTTGGACTCAAGACGATAG

TTACCGGATAAGGCGCAGCGGTCGGGCTGAACGGGGGGTTCGTG

CACACAGCCCAGCTTGGAGCGAACGACCTACACCGAACTGAGAT

ACCTACAGCGTGAGCATTGAGAAAGCGCCACGCTTCCCGAAGGG

AGAAAGGCGGACAGGTATCCGGTAAGCGGCAGGGTCGGAACAGG

AGAGCGCACGAGGGAGCTTCCAGGGGGAAACGCCTGGTATCTTT

ATAGTCCTGTCGGGTTTCGCCACCTCTGACTTGAGCGTCGATTT

TTGTGATGCTCGTCAGGGGGGCGGAGCCTATGGAAAAA
```

Accordingly, preferably the vector comprises the nucleotide sequence substantially as set out in SEQ ID NO: 35, or a variant or fragment thereof.

In an embodiment in which the vector comprises a nucleic acid sequence that encodes an RNA construct comprising MERS-CoV ORF4a the vector may comprise the nucleic acid sequence of SEQ ID No: 36, as follows, where "GOI" represents the position of the therapeutic biomolecule encoding sequence:

[SEQ ID No: 36]
```
CGCCAGCAACGCGAGCTCTAATACGACTCACTATAGATGGGCGG

CGCATGAGAGAAGCCCAGACCAATTACCTACCCAAAATGGAGAA

AGTTCACGTTGACATCGAGGAAGACAGCCCATTCCTCAGAGCTT

TGCAGCGGAGCTTCCCGCAGTTTGAGGTAGAAGCCAAGCAGGTC
```

-continued

```
ACTGATAATGACCATGCTAATGCCAGAGCGTTTTCGCATCTGGC

TTCAAAACTGATCGAAACGGAGGTGGACCCATCCGACACGATCC

TTGACATTGGAAGTGCGCCCGCCCGCAGAATGTATTCTAAGCAC

AAGTATCATTGTATCTGTCCGATGAGATGTGCGGAAGATCCGGA

CAGATTGTATAAGTATGCAACTAAGCTGAAGAAAAACTGTAAGG

AAATAACTGATAAGGAATTGGACAAGAAAATGAAGGAGCTGGCC

GCCGTCATGAGCGACCCTGACCTGGAAACTGAGACTATGTGCCT

CCACGACGACGAGTCGTGTCGCTACGAAGGGCAAGTCGCTGTTT

ACCAGGATGTATACGCGGTTGACGGACCGACAAGTCTCTATCAC

CAAGCCAATAAGGGAGTTAGAGTCGCCTACTGGATAGGCTTTGA

CACCACCCCTTTTATGTTTAAGAACTTGGCTGGAGCATATCCAT

CATACTCTACCAACTGGGCCGACGAAACCGTGTTAACGGCTCGT

AACATAGGCCTATGCAGCTCTGACGTTATGGAGCGGTCACGTAG

AGGGATGTCCATTCTTAGAAAGAAGTATTTGAAACCATCCAACA

ATGTTCTATTCTCTGTTGGCTCGACCATCTACCACGAGAAGAGG

GACTTACTGAGGAGCTGGCACCTGCCGTCTGTATTTCACTTACG

TGGCAAGCAAAATTACACATGTCGGTGTGAGACTATAGTTAGTT

GCGACGGGTACGTCGTTAAAAGAATAGCTATCAGTCCAGGCCTG

TATGGGAAGCCTTCAGGCTATGCTGCTACGATGCACCGCGAGGG

ATTCTTGTGCTGCAAAGTGACAGACACATTGAACGGGGAGAGGG

TCTCTTTTCCCGTGTGCACGTATGTGCCAGCTACATTGTGTGAC

CAAATGACTGGCATACTGGCAACAGATGTCAGTGCGGACGACGC

GCAAAAACTGCTGGTTGGGCTCAACCAGCGTATAGTCGTCAACG

GTCGCACCCAGAGAAACACCAATACCATGAAAAATTACCTTTTG

CCCGTAGTGGCCCAGGCATTTGCTAGGTGGGCAAAGGAATATAA

GGAAGATCAAGAAGATGAAAGGCCACTAGGACTACGAGATAGAC

AGTTAGTCATGGGGTGTTGTTGGGCTTTTAGAAGGCACAAGATA

ACATCTATTTATAAGCGCCCGGATACCCAAACCATCATCAAAGT

GAACAGCGATTTCCACTCATTCGTGCTGCCCAGGATAGGCAGTA

ACACATTGGAGATCGGGCTGAGAACAAGAATCAGGAAAATGTTA

GAGGAGCACAAGGAGCCGTCACCTCTCATTACCGCCGAGGACGT

ACAAGAAGCTAAGTGCGCAGCCGATGAGGCTAAGGAGGTGCGTG

AAGCCGAGGAGTTGCGCGCAGCTCTACCACCTTTGGCAGCTGAT

GTTGAGGAGCCCACTCTGGAAGCCGATGTCGACTTGATGTTACA

AGAGGCTGGGGCCGGCTCAGTGGAGACACCTCGTGGCTTGATAA

AGGTTACCAGCTACGATGGCGAGGACAAGATCGGCTCTTACGCT

GTGCTTTCTCCGCAGGCTGTACTCAAGAGTGAAAAATTATCTTG

CATCCACCCTCTCGCTGAACAAGTCATAGTGATAACACACTCTG

GCCGAAAAGGGCGTTATGCCGTGGAACCATACCATGGTAAAGTA

GTGGTGCCAGAGGGACATGCAATACCCGTCCAGGACTTTCAAGC

TCTGAGTGAAAGTGCCACCATTGTGTACAACGAACGTGAGTTCG
```

-continued

```
TAAACAGGTACCTGCACCATATTGCCACACATGGAGGAGCGCTG

AACACTGATGAAGAATATTACAAAACTGTCAAGCCCAGCGAGCA

CGACGGCGAATACCTGTACGACATCGACAGGAAACAGTGCGTCA

AGAAAGAACTAGTCACTGGGCTAGGGCTCACAGGCGAGCTGGTG

GATCCTCCCTTCCATGAATTCGCCTACGAGAGTCTGAGAACACG

ACCAGCCGCTCCTTACCAAGTACCAACCATAGGGGTGTATGGCG

TGCCAGGATCAGGCAAGTCTGGCATCATTAAAAGCGCAGTCACC

AAAAAAGATCTAGTGGTGAGCGCCAAGAAAGAAAACTGTGCAGA

AATTATAAGGGACGTCAAGAAAATGAAAGGGCTGGACGTCAATG

CCAGAACTGTGGACTCAGTGCTCTTGAATGGATGCAAACACCCC

GTAGAGACCCTGTATATTGACGAAGCTTTTGCTTGTCATGCAGG

TACTCTCAGAGCGCTCATAGCCATTATAAGACCTAAAAAGGCAG

TGCTCTGCGGGGATCCCAAACAGTGCGGTTTTTTTAACATGATG

TGCCTGAAAGTGCATTTTAACCACGAGATTTGCACACAAGTCTT

CCACAAAAGCATCTCTCGCCGTTGCACTAAATCTGTGACTTCGG

TCGTCTCAACCTTGTTTTACGACAAAAAAATGAGAACGACGAAT

CCGAAAGAGACTAAGATTGTGATTGACACTACCGGCAGTACCAA

ACCTAAGCAGGACGATCTCATTCTCACTTGTTTCAGAGGGTGGG

TGAAGCAGTTGCAAATAGATTACAAAGGCAACGAAATAATGACG

GCAGCTGCCTCTCAAGGGCTGACCCGTAAAGGTGTGTATGCCGT

TCGGTACAAGGTGAATGAAAATCCTCTGTACGCACCCACCTCAG

AACATGTGAACGTCCTACTGACCCGCACGGAGGACCGCATCGTG

TGGAAAACACTAGCCGGCGACCCATGGATAAAAACACTGACTGC

CAAGTACCCTGGGAATTTCACTGCCACGATAGAGGAGTGGCAAG

CAGAGCATGATGCCATCATGAGGCACATCTTGGAGAGACCGGAC

CCTACCGACGTCTTCCAGAATAAGGCAAACGTGTGTTGGGCCAA

GGCTTTAGTGCCGGTGCTGAAGACCGCTGGCATAGACATGACCA

CTGAACAATGGAACACTGTGGATTATTTTGAAACGGACAAAGCT

CACTCAGCAGAGATAGTATTGAACCAACTATGCGTGAGGTTCTT

TGGACTCGATCTGGACTCCGGTCTATTTTCTGCACCCACTGTTC

CGTTATCCATTAGGAATAATCACTGGGATAACTCCCCGTCGCCT

AACATGTACGGGCTGAATAAAGAAGTGGTCCGTCAGCTCTCTCG

CAGGTACCCACAACTGCCTCGGGCAGTTGCCACTGGAAGAGTCT

ATGACATGAACACTGGTACACTGCGCAATTATGATCCGCGCATA

AACCTAGTACCTGTAAACAGAAGACTGCCTCATGCTTTAGTCCT

CCACCATAATGAACACCCACAGAGTGACTTTTCTTCATTCGTCA

GCAAATTGAAGGGCAGAACTGTCCTGGTGGTCGGGGAAAAGTTG

TCCGTCCCAGGCAAAATGGTTGACTGGTTGTCAGACCGGCCTGA

GGCTACCTTCAGAGCTCGGCTGGATTTAGGCATCCCAGGTGATG

TGCCCAAATATGACATAATATTTGTTAATGTGAGGACCCCATAT
```

-continued

```
AAATACCATCACTATCAGCAGTGTGAAGACCATGCCATTAAGCT

TAGCATGTTGACCAAGAAAGCTTGTCTGCATCTGAATCCCGGCG

GAACCTGTGTCAGCATAGGTTATGGTTACGCTGACAGGGCCAGC

GAAAGCATCATTGGTGCTATAGCGCGGCAGTTCAAGTTTTCCCG

GGTATGCAAACCGAAATCCTCACTTGAAGAGACGGAAGTTCTGT

TTGTATTCATTGGGTACGATCGCAAGGCCCGTACGCACAATTCT

TACAAGCTTTCATCAACCTTGACCAACATTTATACAGGTTCCAG

ACTCCACGAAGCCGGATGTGCACCCTCATATCATGTGGTGCGAG

GGGATATTGCCACGGCCACCGAAGGAGTGATTATAAATGCTGCT

AACAGCAAAGGACAACCTGGCGGAGGGGTGTGCGGAGCGCTGTA

TAAGAAATTCCCGGAAAGCTTCGATTTACAGCCGATCGAAGTAG

GAAAAGCGCGACTGGTCAAAGGTGCAGCTAAACATATCATTCAT

GCCGTAGGACCAAACTTCAACAAAGTTTCGGAGGTTGAAGGTGA

CAAACAGTTGGCAGAGGCTTATGAGTCCATCGCTAAGATTGTCA

ACGATAACAATTACAAGTCAGTAGCGATTCCACTGTTGTCCACC

GGCATCTTTTCCGGGAACAAAGATCGACTAACCCAATCATTGAA

CCATTTGCTGACAGCTTTAGACACCACTGATGCAGATGTAGCCA

TATACTGCAGGGACAAGAAATGGGAAATGACTCTCAAGGAAGCA

GTGGCTAGGAGAGAAGCAGTGGAGGAGATATGCATATCCGACGA

CTCTTCAGTGACAGAACCTGATGCAGAGCTGGTGAGGGTGCATC

CGAAGAGTTCTTTGGCTGGAAGGAAGGGCTACAGCACAAGCGAT

GGCAAAACTTTCTCATATTTGGAAGGGACCAAGTTTCACCAGGC

GGCCAAGGATATAGCAGAAATTAATGCCATGTGGCCCGTTGCAA

CGGAGGCCAATGAGCAGGTATGCATGTATATCCTCGGAGAAAGC

ATGAGCAGTATTAGGTCGAAATGCCCCGTCGAAGAGTCGGAAGC

CTCCACACCACCTAGCACGCTGCCTTGCTTGTGCATCCATGCCA

TGACTCCAGAAAGAGTACAGCGCCTAAAAGCCTCACGTCCAGAA

CAAATTACTGTGTGCTCATCCTTTCCATTGCCGAAGTATAGAAT

CACTGGTGTGCAGAAGATCCAATGCTCCCAGCCTATATTGTTCT

CACCGAAAGTGCCTGCGTATATTCATCCAAGGAAGTATCTCGTG

GAAACACCACCGGTAGACGAGACTCCGGAGCCATCGGCAGAGAA

CCAATCCACAGAGGGGACACCTGAACAACCACCACTTATAACCG

AGGATGAGACCAGGACTAGAACGCCTGAGCCGATCATCATCGAA

GAGGAAGAAGAGGATAGCATAAGTTTGCTGTCAGATGGCCCGAC

CCACCAGGTGCTGCAAGTCGAGGCAGACATTCACGGGCCGCCCT

CTGTATCTAGCTCATCCTGGTCCATTCCTCATGCATCCGACTTT

GATGTGGACAGTTTATCCATACTTGACACCCTGGAGGGAGCTAG

CGTGACCAGCGGGGCAACGTCAGCCGAGACTAACTCTTACTTCG

CAAAGAGTATGGAGTTTCTGGCGCGACCGGTGCCTGCGCCTCGA

ACAGTATTCAGGAACCCTCCACATCCCGCTCCGCGCACAAGAAC

ACCGTCACTTGCACCCAGCAGGGCCTGCTCGAGAACCAGCCTAG
```

-continued

TTTCCACCCCGCCAGGCGTGAATAGGGTGATCACTAGAGAGGAG

CTCGAGGCGCTTACCCCGTCACGCACTCCTAGCAGGTCGGTCTC

GAGAACCAGCCTGGTCTCCAACCCGCCAGGCGTAAATAGGGTGA

TTACAAGAGAGGAGTTTGAGGCGTTCGTAGCACAACAACAATGA

CGGTTTGATGCGGGTGCATACATCTTTTCCTCCGACACCGGTCA

AGGGCATTTACAACAAAAATCAGTAAGGCAAACGGTGCTATCCG

AAGTGGTGTTGGAGAGGACCGAATTGGAGATTTCGTATGCCCCG

CGCCTCGACCAAGAAAAAGAAGAATTACTACGCAAGAAATTACA

GTTAAATCCCACACCTGCTAACAGAAGCAGATACCAGTCCAGGA

AGGTGGAGAACATGAAAGCCATAACAGCTAGACGTATTCTGCAA

GGCCTAGGGCATTATTTGAAGGCAGAAGGAAAAGTGGAGTGCTA

CCGAACCCTGCATCCTGTTCCTTTGTATTCATCTAGTGTGAACC

GTGCCTTTTCAAGCCCCAAGGTCGCAGTGGAAGCCTGTAACGCC

ATGTTGAAAGAGAACTTTCCGACTGTGGCTTCTTACTGTATTAT

TCCAGAGTACGATGCCTATTTGGACATGGTTGACGGAGCTTCAT

GCTGCTTAGACACTGCCAGTTTTTGCCCTGCAAAGCTGCGCAGC

TTTCCAAAGAAACACTCCTATTTGGAACCCACAATACGATCGGC

AGTGCCTTCAGCGATCCAGAACACGCTCCAGAACGTCCTGGCAG

CTGCCACAAAAAGAAATTGCAATGTCACGCAAATGAGAGAATTG

CCCGTATTGGATTCGGCGGCCTTTAATGTGGAATGCTTCAAGAA

ATATGCGTGTAATAATGAATATTGGGAAACGTTTAAAGAAAACC

CCATCAGGCTTACTGAAGAAAACGTGGTAAATTACATTACCAAA

TTAAAAGGACCAAAAGCTGCTGCTCTTTTTGCGAAGACACATAA

TTTGAATATGTTGCAGGACATACCAATGGACAGGTTTGTAATGG

ACTTAAAGAGAGACGTGAAAGTGACTCCAGGAACAAAACATACT

GAAGAACGGCCCAAGGTACAGGTGATCCAGGCTGCCGATCCGCT

AGCAACAGCGTATCTGTGCGGAATCCACCGAGAGCTGGTTAGGA

GATTAAATGCGGTCCTGCTTCCGAACATTCATACACTGTTTGAT

ATGTCGGCTGAAGACTTTGACGCTATTATAGCCGAGCACTTCCA

GCCTGGGGATTGTGTTCTGGAAACTGACATCGCGTCGTTTGATA

AAAGTGAGGACGACGCCATGGCTCTGACCGCGTTAATGATTCTG

GAAGACTTAGGTGTGGACGCAGAGCTGTTGACGCTGATTGAGGC

GGCTTTCGGCGAAATTTCATCAATACATTTGCCCACTAAAACTA

AATTTAAATTCGGAGCCATGATGAAATCTGGAATGTTCCTCACA

CTGTTTGTGAACACAGTCATTAACATTGTAATCGCAAGCAGAGT

GTTGAGAGAACGGCTAACCGGATCACCATGTGCAGCATTCATTG

GAGATGACAATATCGTGAAAGGAGTCAAATCGGACAAATTAATG

GCAGACAGGTGCGCCACCTGGTTGAATATGGAAGTCAAGATTAT

AGATGCTGTGGTGGGCGAGAAAGCGCCTTATTTCTGTGGAGGGT

TTATTTTGTGTGACTCCGTGACCGGCACAGCGTGCCGTGTGGCA

-continued

GACCCCCTAAAAAGGCTGTTTAAGCTTGGCAAACCTCTGGCAGC

AGACGATGAACATGATGATGACAGGAGAAGGGCATTGCATGAAG

AGTCAACACGCTGGAACCGAGTGGGTATTCTTTCAGAGCTGTGC

AAGGCAGTAGAATCAAGGTATGAAACCGTAGGAACTTCCATCAT

AGTTATGGCCATGACTACTCTAGCTAGCAGTGTTAAATCATTCA

GCTACCTGAGAGGGGCCCCTATAACTCTCTACGGCTAACCTGAA

TGGACTACGACATAGTCTAGTCCGCCAAGTCTAGCATATGGCCA

CC- - - - - - - - - - - - - - - GOI - - -

- - - - - - - - - - - - - -

CGGAGAAAGAGAGGCTC

TGGCGAAGGCAGAGGCAGCCTGCTTACATGTGGCGACGTGGAAG

AGAACCCCGGACCTATGGACTACGTGTCCCTGCTGAACCAGATT

TGGCAGAAGTACCTGAACAGCCCCTACACCACCTGTCTGTACAT

CCCCAAGCCTACCGCCAAGTACACACCTCTCGTGGGCACATCTC

TGCACCCCGTGCTGTGGAATTGCCAGCTGAGCTTTGCCGGCTAC

ACCGAGTCTGCCGTGAACAGCACAAAGGCCCTGGCCAAACAGGA

CGCCGCTCAGAGAATTGCCTGGCTGCTGCACAAGGATGGCGGCA

TCCCTGATGGCTGTAGCCTGTACCTGAGACACAGCAGCCTGTTC

GCCCAGAGCGAGGAAGAGGAATCCTTCAGCAACTGATGAGCGGC

CGCGAATTGGCAAGCTGCTTACATAGAACTCGCGGCGATTGGCA

TGCCGCCTTAAAATTTTTATTTTATTTTTCTTTTCTTTTCCGAA

TCGGATTTTGTTTTTAATATTTCAAAAAAAAAAAAAAAAAAAAA

AAAAAAAAAAAAAACGCGTCGAGGGGAATTAATTCTTGAAGACG

AAAGGGCCAGGTGGCACTTTTCGGGGAAATGTGCGCGGAACCCC

TATTTGTTTATTTTTCTAAATACATTCAAATATGTATCCGCTCA

TGAGACAATAACCCTGATAAATGCTTCAATAATATTGAAAAAGG

AAGAGTATGAGTATTCAACATTTCCGTGTCGCCCTTATTCCCTT

TTTTGCGGCATTTTGCCTTCCTGTTTTTGCTCACCCAGAAACGC

TGGTGAAAGTAAAAGATGCTGAAGATCAGTTGGGTGCACGAGTG

GGTTACATCGAACTGGATCTCAACAGCGGTAAGATCCTTGAGAG

TTTTCGCCCCGAAGAACGTTTTCCAATGATGAGCACTTTTAAAG

TTCTGCTATGTGGCGCGGTATTATCCCGTGTTGACGCCGGGCAA

GAGCAACTCGGTCGCCGCATACACTATTCTCAGAATGACTTGGT

TGAGTACTCACCAGTCACAGAAAAGCATCTTACGGATGGCATGA

CAGTAAGAGAATTATGCAGTGCTGCCATAACCATGAGTGATAAC

ACTGCGGCCAACTTACTTCTGACAACGATCGGAGGACCGAAGGA

GCTAACCGCTTTTTTGCACAACATGGGGGATCATGTAACTCGCC

TTGATCGTTGGGAACCGGAGCTGAATGAAGCCATACCAAACGAC

GAGCGTGACACCACGATGCCTGTAGCAATGGCAACAACGTTGCG

CAAACTATTAACTGGCGAACTACTTACTCTAGCTTCCCGGCAAC

AATTAATAGACTGGATGGAGGCGGATAAAGTTGCAGGACCACTT

CTGCGCTCGGCCCTTCCGGCTGGCTGGTTTATTGCTGATAAATC

TGGAGCCGGTGAGCGTGGGTCTCGCGGTATCATTGCAGCACTGG

GGCCAGATGGTAAGCCCTCCCGTATCGTAGTTATCTACACGACG

GGGAGTCAGGCAACTATGGATGAACGAAATAGACAGATCGCTGA

GATAGGTGCCTCACTGATTAAGCATTGGTAACTGTCAGACCAAG

TTTACTCATATATACTTTAGATTGATTTAAAACTTCATTTTTAA

TTTAAAAGGATCTAGGTGAAGATCCTTTTTGATAATCTCATGAC

CAAAATCCCTTAACGTGAGTTTTCGTTCCACTGAGCGTCAGACC

CCGTAGAAAAGATCAAAGGATCTTCTTGAGATCCTTTTTTTCTG

CGCGTAATCTGCTGCTTGCAAACAAAAAAACCACCGCTACCAGC

GGTGGTTTGTTTGCCGGATCAAGAGCTACCAACTCTTTTTCCGA

AGGTAACTGGCTTCAGCAGAGCGCAGATACCAAATACTGTCCTT

CTAGTGTAGCCGTAGTTAGGCCACCACTTCAAGAACTCTGTAGC

ACCGCCTACATACCTCGCTCTGCTAATCCTGTTACCAGTGGCTG

CTGCCAGTGGCGATAAGTCGTGTCTTACCGGGTTGGACTCAAGA

CGATAGTTACCGGATAAGGCGCAGCGGTCGGGCTGAACGGGGGG

TTCGTGCACACAGCCCAGCTTGGAGCGAACGACCTACACCGAAC

TGAGATACCTACAGCGTGAGCATTGAGAAAGCGCCACGCTTCCC

GAAGGGAGAAAGGCGGACAGGTATCCGGTAAGCGGCAGGGTCGG

AACAGGAGAGCGCACGAGGGAGCTTCCAGGGGGAAACGCCTGGT

ATCTTTATAGTCCTGTCGGGTTTCGCCACCTCTGACTTGAGCGT

CGATTTTTGTGATGCTCGTCAGGGGGCGGAGCCTATGGAAAAA

In an embodiment in which the vector comprises a nucleic acid sequence that encodes an RNA construct comprising PIV5, the vector may comprise the nucleic acid sequence of SEQ ID No: 37, as follows, where "GOI" represents the position of the sequence encoding the therapeutic biomolecule:

[SEQ ID No: 37]
CGCCAGCAACGCGAGCTCTAATACGACTCACTATAGATGGGCGG

CGCATGAGAGAAGCCCAGACCAATTACCTACCCAAAATGGAGAA

AGTTCACGTTGACATCGAGGAAGACAGCCCATTCCTCAGAGCTT

TGCAGCGGAGCTTCCCGCAGTTTGAGGTAGAAGCCAAGCAGGTC

ACTGATAATGACCATGCTAATGCCAGAGCGTTTTCGCATCTGGC

TTCAAAACTGATCGAAACGGAGGTGGACCCATCCGCACGATCC

TTGACATTGGAAGTGCGCCCGCCCGCAGAATGTATTCTAAGCAC

AAGTATCATTGTATCTGTCCGATGAGATGTGCGGAAGATCCGGA

CAGATTGTATAAGTATGCAACTAAGCTGAAGAAAAACTGTAAGG

AAATAACTGATAAGGAATTGGACAAGAAAATGAAGGAGCTGGCC

GCCGTCATGAGCGACCCTGACCTGGAAACTGAGACTATGTGCCT

CCACGACGACGAGTCGTGTCGCTACGAAGGGCAAGTCGCTGTTT

ACCAGGATGTATACGCGGTTGACGGACCGACAAGTCTCTATCAC

CAAGCCAATAAGGGAGTTAGAGTCGCCTACTGGATAGGCTTTGA

CACCACCCCTTTTATGTTTAAGAACTTGGCTGGAGCATATCCAT

CATACTCTACCAACTGGGCCGACGAAACCGTGTTAACGGCTCGT

AACATAGGCCTATGCAGCTCTGACGTTATGGAGCGGTCACGTAG

AGGGATGTCCATTCTTAGAAAGAAGTATTTGAAACCATCCAACA

ATGTTCTATTCTCTGTTGGCTCGACCATCTACCACGAGAAGAGG

GACTTACTGAGGAGCTGGCACCTGCCGTCTGTATTTCACTTACG

TGGCAAGCAAAATTACACATGTCGGTGTGAGACTATAGTTAGTT

GCGACGGGTACGTCGTTAAAAGAATAGCTATCAGTCCAGGCCTG

TATGGGAAGCCTTCAGGCTATGCTGCTACGATGCACCGCGAGGG

ATTCTTGTGCTGCAAAGTGACAGACACATTGAACGGGGAGAGGG

TCTCTTTTCCCGTGTGCACGTATGTGCCAGCTACATTGTGTGAC

CAAATGACTGGCATACTGGCAACAGATGTCAGTGCGGACGACGC

GCAAAAACTGCTGGTTGGGCTCAACCAGCGTATAGTCGTCAACG

GTCGCACCCAGAGAAACACCAATACCATGAAAAATTACCTTTTG

CCCGTAGTGGCCCAGGCATTTGCTAGGTGGGCAAAGGAATATAA

GGAAGATCAAGAAGATGAAAGGCCACTAGGACTACGAGATAGAC

AGTTAGTCATGGGGTGTTGTTGGGCTTTTAGAAGGCACAAGATA

ACATCTATTTATAAGCGCCCGGATACCCAAACCATCATCAAAGT

GAACAGCGATTTCCACTCATTCGTGCTGCCCAGGATAGGCAGTA

ACACATTGGAGATCGGGCTGAGAACAAGAATCAGGAAAATGTTA

GAGGAGCACAAGGAGCCGTCACCTCTCATTACCGCCGAGGACGT

ACAAGAAGCTAAGTGCGCAGCCGATGAGGCTAAGGAGGTGCGTG

AAGCCGAGGAGTTGCGCGCAGCTCTACCACCTTTGGCAGCTGAT

GTTGAGGAGCCCACTCTGGAAGCCGATGTCGACTTGATGTTACA

AGAGGCTGGGGCCGGCTCAGTGGAGACACCTCGTGGCTTGATAA

AGGTTACCAGCTACGATGGCGAGGACAAGATCGGCTCTTACGCT

GTGCTTTCTCCGCAGGCTGTACTCAAGAGTGAAAAATTATCTTG

CATCCACCCTCTCGCTGAACAAGTCATAGTGATAACACACTCTG

GCCGAAAAGGGCGTTATGCCGTGGAACCATACCATGGTAAAGTA

GTGGTGCCAGAGGGACATGCAATACCCGTCCAGGACTTTCAAGC

TCTGAGTGAAAGTGCCACCATTGTGTACAACGAACGTGAGTTCG

TAAACAGGTACCTGCACCATATTGCCACACATGGAGGAGCGCTG

AACACTGATGAAGAATATTACAAAACTGTCAAGCCCAGCGAGCA

CGACGGCGAATACCTGTACGACATCGACAGGAAACAGTGCGTCA

AGAAGAACTAGTCACTGGGCTAGGGCTCACAGGCGAGCTGGTG

GATCCTCCCTTCCATGAATTCGCCTACGAGAGTCTGAGAACACG

ACCAGCCGCTCCTTACCAAGTACCAACCATAGGGGTGTATGGCG

TGCCAGGATCAGGCAAGTCTGGCATCATTAAAAGCGCAGTCACC

AAAAAAGATCTAGTGGTGAGCGCCAAGAAAGAAAACTGTGCAGA

-continued

```
AATTATAAGGGACGTCAAGAAAATGAAAGGGCTGGACGTCAATG

CCAGAACTGTGGACTCAGTGCTCTTGAATGGATGCAAACACCCC

GTAGAGACCCTGTATATTGACGAAGCTTTTGCTTGTCATGCAGG

TACTCTCAGAGCGCTCATAGCCATTATAAGACCTAAAAAGGCAG

TGCTCTGCGGGGATCCCAAACAGTGCGGTTTTTTTAACATGATG

TGCCTGAAAGTGCATTTTAACCACGAGATTTGCACACAAGTCTT

CCACAAAAGCATCTCTCGCCGTTGCACTAAATCTGTGACTTCGG

TCGTCTCAACCTTGTTTTACGACAAAAAAATGAGAACGACGAAT

CCGAAAGAGACTAAGATTGTGATTGACACTACCGGCAGTACCAA

ACCTAAGCAGGACGATCTCATTCTCACTTGTTTCAGAGGGTGGG

TGAAGCAGTTGCAAATAGATTACAAAGGCAACGAAATAATGACG

GCAGCTGCCTCTCAAGGGCTGACCCGTAAAGGTGTGTATGCCGT

TCGGTACAAGGTGAATGAAAATCCTCTGTACGCACCCACCTCAG

AACATGTGAACGTCCTACTGACCCGCACGGAGGACCGCATCGTG

TGGAAAACACTAGCCGGCGACCCATGGATAAAAACACTGACTGC

CAAGTACCCTGGGAATTTCACTGCCACGATAGAGGAGTGGCAAG

CAGAGCATGATGCCATCATGAGGCACATCTTGGAGAGACCGGAC

CCTACCGACGTCTTCCAGAATAAGGCAAACGTGTGTTGGGCCAA

GGCTTTAGTGCCGGTGCTGAAGACCGCTGGCATAGACATGACCA

CTGAACAATGGAACACTGTGGATTATTTTGAAACGGACAAAGCT

CACTCAGCAGAGATAGTATTGAACCAACTATGCGTGAGGTTCTT

TGGACTCGATCTGGACTCCGGTCTATTTTCTGCACCCACTGTTC

CGTTATCCATTAGGAATAATCACTGGGATAACTCCCCGTCGCCT

AACATGTACGGGCTGAATAAAGAAGTGGTCCGTCAGCTCTCTCG

CAGGTACCCACAACTGCCTCGGGCAGTTGCCACTGGAAGAGTCT

ATGACATGAACACTGGTACACTGCGCAATTATGATCCGCGCATA

AACCTAGTACCTGTAAACAGAAGACTGCCTCATGCTTTAGTCCT

CCACCATAATGAACACCCACAGAGTGACTTTTCTTCATTCGTCA

GCAAATTGAAGGGCAGAACTGTCCTGGTGGTCGGGGAAAAGTTG

TCCGTCCCAGGCAAAATGGTTGACTGGTTGTCAGACCGGCCTGA

GGCTACCTTCAGAGCTCGGCTGGATTTAGGCATCCCAGGTGATG

TGCCCAAATATGACATAATATTTGTTAATGTGAGGACCCCATAT

AAATACCATCACTATCAGCAGTGTGAAGACCATGCCATTAAGCT

TAGCATGTTGACCAAGAAAGCTTGTCTGCATCTGAATCCCGGCG

GAACCTGTGTCAGCATAGGTTATGGTTACGCTGACAGGGCCAGC

GAAAGCATCATTGGTGCTATAGCGCGGCAGTTCAAGTTTTCCCG

GGTATGCAAACCGAAATCCTCACTTGAAGAGACGGAAGTTCTGT

TTGTATTCATTGGGTACGATCGCAAGGCCCGTACGCACAATTCT

TACAAGCTTTCATCAACCTTGACCAACATTTATACAGGTTCCAG

ACTCCACGAAGCCGGATGTGCACCCTCATATCATGTGGTGCGAG

GGGATATTGCCACGGCCACCGAAGGAGTGATTATAAATGCTGCT
```

-continued

```
AACAGCAAAGGACAACCTGGCGGAGGGGTGTGCGGAGCGCTGTA

TAAGAAATTCCCGGAAAGCTTCGATTTACAGCCGATCGAAGTAG

GAAAAGCGCGACTGGTCAAAGGTGCAGCTAAACATATCATTCAT

GCCGTAGGACCAAACTTCAACAAAGTTTCGGAGGTTGAAGGTGA

CAAACAGTTGGCAGAGGCTTATGAGTCCATCGCTAAGATTGTCA

ACGATAACAATTACAAGTCAGTAGCGATTCCACTGTTGTCCACC

GGCATCTTTTCCGGGAACAAAGATCGACTAACCCAATCATTGAA

CCATTTGCTGACAGCTTTAGACACCACTGATGCAGATGTAGCCA

TATACTGCAGGGACAAGAAATGGGAAATGACTCTCAAGGAAGCA

GTGGCTAGGAGAGAAGCAGTGGAGGAGATATGCATATCCGACGA

CTCTTCAGTGACAGAACCTGATGCAGAGCTGGTGAGGGTGCATC

CGAAGAGTTCTTTGGCTGGAAGGAAGGGCTACAGCACAAGCGAT

GGCAAAACTTTCTCATATTTGGAAGGGACCAAGTTTCACCAGGC

GGCCAAGGATATAGCAGAAATTAATGCCATGTGGCCCGTTGCAA

CGGAGGCCAATGAGCAGGTATGCATGTATATCCTCGGAGAAAGC

ATGAGCAGTATTAGGTCGAAATGCCCCGTCGAAGAGTCGGAAGC

CTCCACACCACCTAGCACGCTGCCTTGCTTGTGCATCCATGCCA

TGACTCCAGAAAGAGTACAGCGCCTAAAAGCCTCACGTCCAGAA

CAAATTACTGTGTGCTCATCCTTTCCATTGCCGAAGTATAGAAT

CACTGGTGTGCAGAAGATCCAATGCTCCCAGCCTATATTGTTCT

CACCGAAAGTGCCTGCGTATATTCATCCAAGGAAGTATCTCGTG

GAAACACCACCGGTAGACGAGACTCCGGAGCCATCGGCAGAGAA

CCAATCCACAGAGGGGACACCTGAACAACCACCACTTATAACCG

AGGATGAGACCAGGACTAGAACGCCTGAGCCGATCATCATCGAA

GAGGAAGAAGAGGATAGCATAAGTTTGCTGTCAGATGGCCCGAC

CCACCAGGTGCTGCAAGTCGAGGCAGACATTCACGGGCCGCCCT

CTGTATCTAGCTCATCCTGGTCCATTCCTCATGCATCCGACTTT

GATGTGGACAGTTTATCCATACTTGACACCCTGGAGGGAGCTAG

CGTGACCAGCGGGGCAACGTCAGCCGAGACTAACTCTTACTTCG

CAAAGAGTATGGAGTTTCTGGCGCGACCGGTGCCTGCGCCTCGA

ACAGTATTCAGGAACCCTCCACATCCCGCTCCGCGCACAAGAAC

ACCGTCACTTGCACCCAGCAGGGCCTGCTCGAGAACCAGCCTAG

TTTTCCACCCCGCCAGGCGTGAATAGGGTGATCACTAGAGAGGAG

CTCGAGGCGCTTACCCCGTCACGCACTCCTAGCAGGTCGGTCTC

GAGAACCAGCCTGGTCTCCAACCCGCCAGGCGTAAATAGGGTGA

TTACAAGAGAGGAGTTTGAGGCGTTCGTAGCACAACAACAATGA

CGGTTTGATGCGGGTGCATACATCTTTTCCTCCGACACCGGTCA

AGGGCATTTACAACAAAAATCAGTAAGGCAAACGGTGCTATCCG

AAGTGGTGTTGGAGAGGACCGAATTGGAGATTTCGTATGCCCCG

CGCCTCGACCAAGAAAAAGAAGAATTACTACGCAAGAAATTACA
```

-continued

GTTAAATCCCACACCTGCTAACAGAAGCAGATACCAGTCCAGGA

AGGTGGAGAACATGAAAGCCATAACAGCTAGACGTATTCTGCAA

GGCCTAGGGCATTATTTGAAGGCAGAAGGAAAAGTGGAGTGCTA

CCGAACCCTGCATCCTGTTCCTTTGTATTCATCTAGTGTGAACC

GTGCCTTTTCAAGCCCCAAGGTCGCAGTGGAAGCCTGTAACGCC

ATGTTGAAAGAGAACTTTCCGACTGTGGCTTCTTACTGTATTAT

TCCAGAGTACGATGCCTATTTGGACATGGTTGACGGAGCTTCAT

GCTGCTTAGACACTGCCAGTTTTTGCCCTGCAAAGCTGCGCAGC

TTTCCAAAGAAACACTCCTATTTGGAACCCACAATACGATCGGC

AGTGCCTTCAGCGATCCAGAACACGCTCCAGAACGTCCTGGCAG

CTGCCACAAAAAGAAATTGCAATGTCACGCAAATGAGAGAATTG

CCCGTATTGGATTCGGCGGCCTTTAATGTGGAATGCTTCAAGAA

ATATGCGTGTAATAATGAATATTGGGAAACGTTTAAAGAAAACC

CCATCAGGCTTACTGAAGAAAACGTGGTAAATTACATTACCAAA

TTAAAAGGACCAAAAGCTGCTGCTCTTTTTGCGAAGACACATAA

TTTGAATATGTTGCAGGACATACCAATGGACAGGTTTGTAATGG

ACTTAAAGAGAGACGTGAAAGTGACTCCAGGAACAAAACATACT

GAAGAACGGCCCAAGGTACAGGTGATCCAGGCTGCCGATCCGCT

AGCAACAGCGTATCTGTGCGGAATCCACCGAGAGCTGGTTAGGA

GATTAAATGCGGTCCTGCTTCCGAACATTCATACACTGTTTGAT

ATGTCGGCTGAAGACTTTGACGCTATTATAGCCGAGCACTTCCA

GCCTGGGGATTGTGTTCTGGAAACTGACATCGCGTCGTTTGATA

AAAGTGAGGACGACGCCATGGCTCTGACCGCGTTAATGATTCTG

GAAGACTTAGGTGTGGACGCAGAGCTGTTGACGCTGATTGAGGC

GGCTTTCGGCGAAATTTCATCAATACATTTGCCCACTAAAACTA

AATTTAAATTCGGAGCCATGATGAAATCTGGAATGTTCCTCACA

CTGTTTGTGAACACAGTCATTAACATTGTAATCGCAAGCAGAGT

GTTGAGAGAACGGCTAACCGGATCACCCATGTGCAGCATTCATTG

GAGATGACAATATCGTGAAAGGAGTCAAATCGGACAAATTAATG

GCAGACAGGTGCGCCACCTGGTTGAATATGGAAGTCAAGATTAT

AGATGCTGTGGTGGGCGAGAAAGCGCCTTATTTCTGTGGAGGGT

TTATTTTGTGTGACTCCGTGACCGGCACAGCGTGCCGTGTGGCA

GACCCCCTAAAAAGGCTGTTTAAGCTTGGCAAACCTCTGGCAGC

AGACGATGAACATGATGATGACAGGAGAAGGGCATTGCATGAAG

AGTCAACACGCTGGAACCGAGTGGGTATTCTTTCAGAGCTGTGC

AAGGCAGTAGAATCAAGGTATGAAACCGTAGGAACTTCCATCAT

AGTTATGGCCATGACTACTCTAGCTAGCAGTGTTAAATCATTCA

-continued

GCTACCTGAGAGGGGCCCCTATAACTCTCTACGGCTAACCTGAA

TGGACTACGACATAGTCTAGTCCGCCAAGTCTAGCATATGGCCA

CC- - - - - - - - - - - - - - - - GOI - - -

- - - - - - - - - - - - - - -

CGGAGAAAGAGAGGCTC

TGGCGAAGGCAGAGGCAGCCTGCTTACATGTGGCGACGTGGAAG

AGAACCCCGGACCTATGGACCCTACCGACCTGAGCTTCAGCCCC

GACGAGATCAACAAGCTGATCGAGACAGGCCTGAACACCGTGGA

ATACTTCACCAGCCAGCAAGTGACCGGCACAAGCAGCCTGGGCA

AGAACACAATTCCTCCAGGCGTGACCGGCCTGCTGACAAATGCT

GCCGAGGCCAAGATCCAAGAGAGCACCAACCACCAGAAGGGCTC

TGTTGGAGGCGGAGCCAAGCCTAAGAAGCCCAGACCTAAGATCG

CCATCGTGCCCGCCGACGATAAGACAGTGCCTGGCAAGCCCATT

CCTAATCCTCTGCTGGGCCTCGACAGCACCCCTAGCACACAGAC

AGTGCTGGATCTGAGCGGCAAGACACTGCCTAGCGGCAGCTATA

AGGGCGTGAAGCTGGCCAAGTTCGGCAAAGAAAACCTGATGACC

CGGTTCATCGAGGAACCCAGAGAGAACCCTATCGCCACCAGCTC

TCCCATCGACTTCAAGAGAGGCAGAGACACCGGCGGCTTCCACA

GAAGAGAGTACAGCATTGGCTGGGTCGGAGATGAAGTGAAAGTG

ACCGAGTGGTGCAACCCCAGCTGCAGCCCTATTACAGCCGCCGC

TAGAAGATTCGAGTGCACCTGTCACCAGTGTCCTGTGACCTGTA

GCGAGTGCGAGCGGGACACATGATGAGCGGCCGCGAATTGGCAA

GCTGCTTACATAGAACTCGCGGCGATTGGCATGCCGCCTTAAAA

TTTTTATTTTATTTTTCTTTTCTTTTCCGAATCGGATTTTGTTT

TTAATATTTCAAAAAAAAAAAAAAAAAAAAAAAAAAAAAAAAAA

ACGCGTCGAGGGGAATTAATTCTTGAAGACGAAAGGGCCAGGTG

GCACTTTTCGGGGAAATGTGCGCGGAACCCCTATTTGTTTATTT

TTCTAAATACATTCAAATATGTATCCGCTCATGAGACAATAACC

CTGATAAATGCTTCAATAATATTGAAAAAGGAAGAGTATGAGTA

TTCAACATTTCCGTGTCGCCCTTATTCCCTTTTTTGCGGCATTT

TGCCTTCCTGTTTTTGCTCACCCAGAAACGCTGGTGAAAGTAAA

AGATGCTGAAGATCAGTTGGGTGCACGAGTGGGTTACATCGAAC

TGGATCTCAACAGCGGTAAGATCCTTGAGAGTTTTCGCCCCGAA

GAACGTTTTCCAATGATGAGCACTTTTAAAGTTCTGCTATGTGG

CGCGGTATTATCCCGTGTTGACGCCGGGCAAGAGCAACTCGGTC

GCCGCATACACTATTCTCAGAATGACTTGGTTGAGTACTCACCA

GTCACAGAAAAGCATCTTACGGATGGCATGACAGTAAGAGAATT

ATGCAGTGCTGCCATAACCATGAGTGATAACACTGCGGCCAACT

TACTTCTGACAACGATCGGAGGACCGAAGGAGCTAACCGCTTTT

TTGCACAACATGGGGGATCATGTAACTCGCCTTGATCGTTGGGA

```
-continued
ACCGGAGCTGAATGAAGCCATACCAAACGACGAGCGTGACACCA

CGATGCCTGTAGCAATGGCAACAACGTTGCGCAAACTATTAACT

GGCGAACTACTTACTCTAGCTTCCCGGCAACAATTAATAGACTG

GATGGAGGCGGATAAAGTTGCAGGACCACTTCTGCGCTCGGCCC

TTCCGGCTGGCTGGTTTATTGCTGATAAATCTGGAGCCGGTGAG

CGTGGGTCTCGCGGTATCATTGCAGCACTGGGGCCAGATGGTAA

GCCCTCCCGTATCGTAGTTATCTACACGACGGGGAGTCAGGCAA

CTATGGATGAACGAAATAGACAGATCGCTGAGATAGGTGCCTCA

CTGATTAAGCATTGGTAACTGTCAGACCAAGTTTACTCATATAT

ACTTTAGATTGATTTAAAACTTCATTTTTAATTTAAAAGGATCT

AGGTGAAGATCCTTTTTGATAATCTCATGACCAAAATCCCTTAA

CGTGAGTTTTCGTTCCACTGAGCGTCAGACCCCGTAGAAAAGAT

CAAAGGATCTTCTTGAGATCCTTTTTTTCTGCGCGTAATCTGCT

GCTTGCAAACAAAAAAACCACCGCTACCAGCGGTGGTTTGTTTG

CCGGATCAAGAGCTACCAACTCTTTTTCCGAAGGTAACTGGCTT

CAGCAGAGCGCAGATACCAAATACTGTCCTTCTAGTGTAGCCGT

AGTTAGGCCACCACTTCAAGAACTCTGTAGCACCGCCTACATAC

CTCGCTCTGCTAATCCTGTTACCAGTGGCTGCTGCCAGTGGCGA

TAAGTCGTGTCTTACCGGGTTGGACTCAAGACGATAGTTACCGG

ATAAGGCGCAGCGGTCGGGCTGAACGGGGGGTTCGTGCACACAG

CCCAGCTTGGAGCGAACGACCTACACCGAACTGAGATACCTACA

GCGTGAGCATTGAGAAAGCGCCACGCTTCCCGAAGGGAGAAAGG

CGGACAGGTATCCGGTAAGCGGCAGGGTCGGAACAGGAGAGCGC

ACGAGGGAGCTTCCAGGGGGAAACGCCTGGTATCTTTATAGTCC

TGTCGGGTTTCGCCACCTCTGACTTGAGCGTCGATTTTTGTGAT

GCTCGTCAGGGGGGCGGAGCCTATGGAAAAA
```

Accordingly, preferably the vector comprises the nucleotide sequence substantially as set out in SEQ ID NO: 37, or a variant or fragment thereof.

The saRNA constructs of the invention may be made using a DNA plasmid, which is shown in FIG. 7 or 8, as a template. RNA copies may then be made by in vitro transcription using a polymerase, such as T7 polymerase, and the T7 promoter is shown upstream of the saRNA in the plasmid map in FIG. 7 or 8. Hence, the saRNA constructs of the first aspect may be made using the DNA plasmid having a nucleic acid sequence as set out in any one of SEQ ID No: 35-37, or a variant or fragment thereof, which is shown in FIG. 7 or 8, as the template. Of course, it will be appreciated that other RNA polymerases could be used instead of T7 polymerase, for example the SP6 or the T3 polymerase, in which case the saRNA construct may comprise the SP6 or T3 promoter instead.

The vector of the fourth aspect encoding the RNA construct of the first aspect may for example be a plasmid, cosmid or phage and/or be a viral vector. Such recombinant vectors are highly useful in the delivery systems of the invention for transforming cells with the nucleotide sequences. The nucleotide sequences may preferably be a DNA sequence, and it is this DNA sequence which encodes the RNA sequence forming the RNA construct of the first aspect.

Recombinant vectors encoding the RNA construct of the first aspect may also include other functional elements. For example, they may further comprise a variety of other functional elements including a suitable promoter for initiating transgene expression upon introduction of the vector in a host cell. For instance, the vector is preferably capable of autonomously replicating in the nucleus of the host cell, such as a bacterial cell. In this case, elements which induce or regulate DNA replication may be required in the recombinant vector. Alternatively, the recombinant vector may be designed such that it integrates into the genome of a host cell. In this case, DNA sequences which favour targeted integration (e.g. by homologous recombination) are envisaged. Suitable promoters may include the SV40 promoter, CMV, EF1a, PGK, viral long terminal repeats, as well as inducible promoters, such as the Tetracycline inducible system, as examples.

The cassette or vector may also comprise a terminator, such as the Beta globin, SV40 polyadenylation sequences or synthetic polyadenylation sequences. The recombinant vector may also comprise a promoter or regulator or enhancer to control expression of the nucleic acid as required.

The vector may also comprise DNA coding for a gene that may be used as a selectable marker in the cloning process, i.e. to enable selection of cells that have been transfected or transformed, and to enable the selection of cells harbouring vectors incorporating heterologous DNA. For example, ampicillin, neomycin, puromycin or chloramphenicol resistance is envisaged. The vectors shown in FIGS. 7 and 8 include an ampicillin resistant marker, which is useful for selecting the plasmid in bacteria. Alternatively, the selectable marker gene may be in a different vector to be used simultaneously with the vector containing the transgene(s). The cassette or vector may also comprise DNA involved with regulating expression of the nucleotide sequence, or for targeting the expressed polypeptide to a certain part of the host cell.

Purified vector may be inserted directly into a host cell by suitable means, e.g. direct endocytotic uptake. The vector may be introduced directly into a host cell (e.g. a eukaryotic or prokaryotic cell) by transfection, infection, electroporation, microinjection, cell fusion, protoplast fusion or ballistic bombardment. Alternatively, vectors of the invention may be introduced directly into a host cell using a particle gun.

The nucleic acid molecule may (but not necessarily) be one, which becomes incorporated in the DNA of the host cell. Undifferentiated cells may be stably transformed leading to the production of genetically modified daughter cells (in which case regulation of expression in the subject may be required e.g. with specific transcription factors or gene activators). Alternatively, the delivery system may be designed to favour unstable or transient transformation of differentiated cells. When this is the case, regulation of expression may be less important because expression of the DNA molecule will stop when the transformed cells die or stop expressing the protein.

Alternatively, the delivery system may provide the nucleic acid molecule to the host cell without it being incorporated in a vector. For instance, the nucleic acid molecule may be incorporated within a liposome or virus particle. Alternatively a "naked" nucleic acid molecule may be inserted into a host cell by a suitable means e.g. direct endocytotic uptake.

In a fifth aspect, there is provided a pharmaceutical composition comprising the RNA construct of the first aspect, the nucleic acid sequence of the second aspect, the expression cassette of the third aspect or the vector of the fourth aspect, and a pharmaceutically acceptable vehicle.

In a sixth aspect, there is provided a process for making the pharmaceutical composition according to the fifth aspect, the method comprising contacting the RNA construct of the first aspect, the nucleic acid sequence of the second aspect, the expression cassette of the third aspect or the vector of the fourth aspect, with a pharmaceutically acceptable vehicle.

In an seventh aspect, there is provided a method of preparing the RNA construct of the first aspect, the method comprising:

a) i) introducing, into a host cell, the vector of the fourth aspect; and ii) culturing the host cell under conditions to result in the production of the RNA construct of the first aspect; or b) transcribing the RNA construct from the vector according to the fourth aspect.

The host cell of step a) may be a eukaryotic or prokaryotic host cell. Preferably, the host cell is a eukaryotic host cell. More preferably, the host cell is a mammalian host cell such as Human embryonic kidney 293 cells or Chinese hamster ovary (CHO) cells. Step (b) may be performed in vitro or in vivo, preferably in vitro.

Suitable methods of in vitro transcription are well known in the art and would be known to those skilled in the art. For example, as described in Molecular Cloning, A Laboratory Manual, 2nd edition. (1989) editor C Nolan, Cold Spring Harbor Laboratory Press.

The RNA replicon of the first aspect is particularly suitable for therapy.

While the inventors envisaged that the RNA construct of the first aspect would be generated by in vitro transcription for in vivo use in therapy, those experienced in the art will recognise that the RNA construct can be generated in vivo in a subject for therapy, by in vivo delivery of the nucleic acid according to the second aspect, the expression cassette according to the third aspect, the vector according to the fourth aspect to a subject.

Hence, according to an eighth aspect, there is provided a RNA construct according to the first aspect, the nucleic acid according to the second aspect, the expression cassette according to the third aspect, the vector according to the fourth aspect or the pharmaceutical composition according to the fifth aspect, for use as a medicament or in therapy.

In a ninth aspect of the invention, there is provided a RNA construct according to the first aspect, the nucleic acid according to the second aspect, the expression cassette according to the third aspect, the vector according to the fourth aspect or the pharmaceutical composition according to the fifth aspect, for use in the prevention, amelioration or treatment of a protozoan, fungal, bacterial or viral infection.

The protozoan, fungal, bacterial or viral infection may be an infection of a protozoa, fungus, bacterium or virus as defined in the first aspect.

In a tenth aspect of the invention, there is provided a RNA construct according to the first aspect, the nucleic acid according to the second aspect, the expression cassette according to the third aspect, the vector according to the fourth aspect or the pharmaceutical composition according to the fifth aspect, for use in the prevention, amelioration or treatment of cancer.

The cancer may be as defined in the first aspect.

In an eleventh aspect of the invention, there is provided a method for treating a protozoan, fungal, bacterial or viral infection, the method comprising administering, to a subject in need thereof, a therapeutically effective amount of the RNA construct according to the first aspect, the nucleic acid according to the second aspect, the expression cassette according to the third aspect, the vector according to the fourth aspect or the pharmaceutical composition according to the fifth aspect.

The protozoan, fungal, bacterial or viral infection to be treated may be an infection of a protozoa, fungus, bacterium or virus as defined in the first aspect.

In a twelfth aspect of the invention, there is provided a method for treating cancer, the method comprising administering, to a subject in need thereof, a therapeutically effective amount of the RNA construct according to the first aspect, the nucleic acid according to the second aspect, the expression cassette according to the third aspect, the vector according to the fourth aspect or the pharmaceutical composition according to the fifth aspect.

The cancer to be treated may be as defined in the first aspect.

The RNA construct described herein provides an effective means of vaccinating a subject against a viral infection and cancer.

Accordingly, in a thirteenth aspect of the invention, there is provided a vaccine comprising the RNA construct according to the first aspect, the nucleic acid according to the second aspect, the expression cassette according to the third aspect, the vector according to the fourth aspect or the pharmaceutical composition according to the fifth aspect.

Preferably, the vaccine comprises a suitable adjuvant.

The adjuvant may be an encoded molecular adjuvant that is encoded in the RNA construct sequence of the first aspect, the nucleic acid according to the second aspect, the expression cassette according to the third aspect, the vector according to the fourth aspect or the pharmaceutical composition according to the fifth aspect, or as adjuvant incorporated into a delivery formulation.

The encoded molecular adjuvant may encode a cytokine, for example IL-12, GM-CSF, IL-2, IFN-g, or an effector protein such as CD40L, Flt-3 or microbial protein, e.g. flagellin or cholera toxin B.

The adjuvant incorporated into a delivery formulation may be selected form the group consisting of a bacterial lipopeptide, lipoprotein and lipoteichoic acid; mycobacterial lipoglycan; yeast zymosan, porin, Lipopolysaccharide, Lipid A, monophosphoryl lipid A (MPL), Flagellin, CpG DNA, hemozoin, Saponins (Quil-A, QS-21, Tomatine, ISCOM, ISCOMATRIX™), squalene based emulsions, polymers such as PEI, Carbopol, lipid nanoparticles and bacterial toxins (CT, LT).

In a fourteenth aspect of the invention, there is provided an RNA construct according to the first aspect, the nucleic acid according to the second aspect, the expression cassette according to the third aspect, the vector according to the fourth aspect or the pharmaceutical composition according to the fifth aspect, for use in stimulating an immune response in a subject.

The immune response may be stimulated against a protozoa, bacterium, virus, fungus or cancer as per the antigens defined in the first aspect.

According to a fifteenth aspect, there is provided an RNA construct according to the first aspect, the nucleic acid according to the second aspect, the expression cassette according to the third aspect, the vector according to the fourth aspect or the pharmaceutical composition according to the fifth aspect, for use in stem cell therapy.

Stem cell therapy may relate to the reprogramming somatic cells to cells having stem cell characteristics.

Somatic cells may be reprogrammed by delivering one or more proteins that are capable of enhancing reprogramming of somatic cells to cells having stem cell characteristics as defined in the first aspect.

According to a sixteenth aspect, there is provided a method of modifying a cell ex vivo or in vitro, comprising delivering, to the cell, the RNA construct according to the first aspect, the nucleic acid according to the second aspect, the expression cassette according to the third aspect, the vector according to the fourth aspect or the pharmaceutical composition according to the fifth aspect.

Preferably, the method is performed ex vivo.

The cell may be a eukaryotic or prokaryotic cell. Preferably, the cell is a eukaryotic cell. More preferably, the cell is a mammalian host cell. Most preferably, the cell is a human cell.

Preferably, the modified cell is suitable for cell-therapy indications.

In a seventeenth aspect, there is provided a modified cell obtained from, or obtainable by, the method of the sixteenth aspect.

In an eighteenth aspect, there is provided the modified cell of the seventeenth aspect, for use in therapy, optionally cell therapy.

It will be appreciated that the RNA construct according to the first aspect, the nucleic acid according to the second aspect, the expression cassette according to the third aspect, the vector according to the fourth aspect or the pharmaceutical composition according to the fifth aspect (herein known as the active agents) may be used in a medicament, which may be used as a monotherapy (i.e. use of the active agent), for treating, ameliorating, or preventing disease or vaccination. Alternatively, the active agents according to the invention may be used as an adjunct to, or in combination with, known therapies for treating, ameliorating, or preventing disease.

The RNA construct, nucleic acid sequence, expression cassette, vector or pharmaceutical composition of the invention may be combined in compositions having a number of different forms depending, in particular, on the manner in which the composition is to be used. Thus, for example, the composition may be in the form of a powder, tablet, capsule, liquid, ointment, cream, gel, hydrogel, aerosol, spray, micellar solution, transdermal patch, liposome suspension, polyplex, emulsion, lipid nanoparticles (with RNA on the surface or encapsulated) or any other suitable form that may be administered to a person or animal in need of treatment or vaccination. It will be appreciated that the vehicle of medicaments according to the invention should be one which is well-tolerated by the subject to whom it is given.

The RNA construct, nucleic acid sequence, expression cassette, vector or pharmaceutical composition of the invention may also be incorporated within a slow- or delayed-release device. Such devices may, for example, be inserted on or under the skin, and the medicament may be released over weeks or even months. The device may be located at least adjacent the treatment site. Such devices may be particularly advantageous when long-term treatment with the genetic construct or the recombinant vector is required and which would normally require frequent administration (e.g. at least daily injection).

In a preferred embodiment, however, medicaments according to the invention may be administered to a subject by injection into the blood stream, muscle, skin or directly into a site requiring treatment. Most preferably, the medicaments, including the RNA construct, are injected into muscle. Injections may be intravenous (bolus or infusion) or subcutaneous (bolus or infusion), or intradermal (bolus or infusion), or intramuscular (bolus or infusion).

It will be appreciated that the amount of RNA construct, nucleic acid sequence, expression cassette, vector or pharmaceutical composition that is required is determined by its biological activity and bioavailability, which in turn depends on the mode of administration, the physiochemical properties of the RNA construct, nucleic acid sequence, expression cassette, vector or pharmaceutical composition and whether it is being used as a monotherapy or in a combined therapy. The frequency of administration will also be influenced by the half-life of the active agent within the subject being treated. Optimal dosages to be administered may be determined by those skilled in the art, and will vary with the particular the RNA construct, nucleic acid sequence, expression cassette, vector or pharmaceutical composition in use, the strength of the pharmaceutical composition, the mode of administration, and the type and advancement of the viral infection. Additional factors depending on the particular subject being treated will result in a need to adjust dosages, including subject age, weight, gender, diet, and time of administration.

Generally, a daily dose of between 0.001 µg/kg of body weight and 10 mg/kg of body weight, or between 0.01 µg/kg of body weight and 1 mg/kg of body weight, of the RNA construct, nucleic acid sequence, expression cassette, vector or pharmaceutical composition of the invention may be used for treating, ameliorating, or preventing a disease, depending upon the active agent used.

Daily doses may be given as a single administration (e.g. a single daily injection or inhalation of a nasal spray). Alternatively, the RNA construct, nucleic acid sequence, expression cassette, vector or pharmaceutical composition may require administration twice or more times during a day. As an example, the RNA construct, nucleic acid sequence, expression cassette, vector or pharmaceutical composition may be administered as two (or more depending upon the severity of the disease being treated) daily doses of between 0.07 µg and 700 mg (i.e. assuming a body weight of 70 kg). A patient receiving treatment may take a first dose upon waking and then a second dose in the evening (if on a two dose regime) or at 3- or 4-hourly intervals thereafter. Alternatively, a slow release device may be used to provide optimal doses of the RNA construct, nucleic acid sequence, expression cassette, vector or pharmaceutical composition according to the invention to a patient without the need to administer repeated doses.

Preferably, however, the RNA construct, nucleic acid sequence, expression cassette, vector or pharmaceutical composition according to the invention may be given as a weekly dose, and more preferably a fortnightly dose.

Known procedures, such as those conventionally employed by the pharmaceutical industry (e.g. in vivo experimentation, clinical trials, etc.), may be used to form specific formulations of the RNA construct, nucleic acid sequence, expression cassette or vector according to the invention and precise therapeutic regimes (such as daily doses of the agents and the frequency of administration).

A "subject" may be a vertebrate, mammal, or domestic animal. Hence, compositions and medicaments according to the invention may be used to treat any mammal, for example livestock (e.g. a horse), pets, or may be used in other veterinary applications. Most preferably, however, the subject is a human being.

A "therapeutically effective amount" of the RNA construct, nucleic acid sequence, expression cassette, vector or pharmaceutical composition is any amount which, when administered to a subject, is the amount of the aforementioned that is needed to ameliorate, prevent or treat any given disease.

For example, the RNA construct, nucleic acid sequence, expression cassette, vector or pharmaceutical composition of the invention may be used may be from about 0.0001 mg to about 800 mg, and preferably from about 0.001 mg to about 500 mg. It is preferred that the amount of the replicon, nucleic acid sequence, expression cassette, vector or pharmaceutical composition is an amount from about 0.01 mg to about 250 mg, and most preferably from about 0.01 mg to about 1 mg. Preferably, the RNA construct, nucleic acid sequence, expression cassette, vector or pharmaceutical composition according to the invention is administered at a dose of 1-200 g.

A "pharmaceutically acceptable vehicle" as referred to herein, is any known compound or combination of known compounds that are known to those skilled in the art to be useful in formulating pharmaceutical compositions.

In one embodiment, the pharmaceutically acceptable vehicle may be a solid, and the composition may be in the form of a powder or tablet. A solid pharmaceutically acceptable vehicle may include one or more substances which may also act as flavouring agents, lubricants, solubilisers, suspending agents, dyes, fillers, glidants, compression aids, inert binders, sweeteners, preservatives, dyes, coatings, or tablet-disintegrating agents. The vehicle may also be an encapsulating material. In powders, the vehicle is a finely divided solid that is in admixture with the finely divided active agents according to the invention. In tablets, the active agent (e.g. RNA construct, nucleic acid sequence, expression cassette, vector or pharmaceutical composition according to the invention) may be mixed with a vehicle having the necessary compression properties in suitable proportions and compacted in the shape and size desired. The powders and tablets preferably contain up to 99% of the active agents. Suitable solid vehicles include, for example calcium phosphate, magnesium stearate, talc, sugars, lactose, dextrin, starch, gelatin, cellulose, polyvinylpyrrolidine, low melting waxes and ion exchange resins. In another embodiment, the pharmaceutical vehicle may be a gel and the composition may be in the form of a cream or the like.

However, the pharmaceutical vehicle may be a liquid, and the pharmaceutical composition is in the form of a solution. Liquid vehicles are used in preparing solutions, suspensions, emulsions, syrups, elixirs and pressurized compositions. The RNA construct, nucleic acid sequence, expression cassette, vector or pharmaceutical composition according to the invention may be dissolved or suspended in a pharmaceutically acceptable liquid vehicle such as water, an organic solvent, a mixture of both or pharmaceutically acceptable oils or fats. The liquid vehicle can contain other suitable pharmaceutical additives such as solubilisers, emulsifiers, buffers, preservatives, sweeteners, flavouring agents, suspending agents, thickening agents, colours, viscosity regulators, stabilizers or osmo-regulators. Suitable examples of liquid vehicles for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the vehicle can also be an oily ester such as ethyl oleate and isopropyl myristate. Sterile liquid vehicles are useful in sterile liquid form compositions for parenteral administration. The liquid vehicle for pressurized compositions can be a halogenated hydrocarbon or other pharmaceutically acceptable propellant.

Liquid pharmaceutical compositions, which are sterile solutions or suspensions, can be utilized by, for example, subcutaneous, intradermal, intrathecal, epidural, intraperitoneal, intravenous and particularly intramuscular injection. The nucleic acid sequence, or expression cassette of the invention may be prepared as a sterile solid composition that may be dissolved or suspended at the time of administration using sterile water, saline, or other appropriate sterile injectable medium.

The RNA construct, nucleic acid sequence, expression cassette, vector or pharmaceutical composition of the invention may be administered orally in the form of a sterile solution or suspension containing other solutes or suspending agents (for example, enough saline or glucose to make the solution isotonic), bile salts, acacia, gelatin, sorbitan monoleate, polysorbate 80 (oleate esters of sorbitol and its anhydrides copolymerized with ethylene oxide) and the like. The RNA construct, nucleic acid sequence, expression cassette, vector or pharmaceutical composition according to the invention can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

It will be appreciated that the invention extends to any nucleic acid or peptide or variant, derivative or analogue thereof, which comprises substantially the amino acid or nucleic acid sequences of any of the sequences referred to herein, including variants or fragments thereof. The terms "substantially the amino acid/nucleotide/peptide sequence", "variant" and "fragment", can be a sequence that has at least 40% sequence identity with the amino acid/nucleotide/peptide sequences of any one of the sequences referred to herein, for example 40% identity with the sequence identified as SEQ ID Nos: 1-55 and so on.

Amino acid/polynucleotide/polypeptide sequences with a sequence identity which is greater than 65%, more preferably greater than 70%, even more preferably greater than 75%, and still more preferably greater than 80% sequence identity to any of the sequences referred to are also envisaged. Preferably, the amino acid/polynucleotide/polypeptide sequence has at least 85% identity with any of the sequences referred to, more preferably at least 90% identity, even more preferably at least 92% identity, even more preferably at least 95% identity, even more preferably at least 97% identity, even more preferably at least 98% identity and, most preferably at least 99% identity with any of the sequences referred to herein.

The skilled technician will appreciate how to calculate the percentage identity between two amino acid/polynucleotide/polypeptide sequences. In order to calculate the percentage identity between two amino acid/polynucleotide/polypeptide sequences, an alignment of the two sequences must first be prepared, followed by calculation of the sequence identity value. The percentage identity for two sequences may take different values depending on:— (i) the method used to align the sequences, for example, ClustalW, BLAST, FASTA, Smith-Waterman (implemented in different programs), or structural alignment from 3D comparison; and (ii) the parameters used by the alignment method, for example, local vs global alignment, the pair-score matrix used (e.g. BLOSUM62, PAM250, Gonnet etc.), and gap-penalty, e.g. functional form and constants.

Having made the alignment, there are many different ways of calculating percentage identity between the two sequences. For example, one may divide the number of identities by: (i) the length of shortest sequence; (ii) the length of alignment; (iii) the mean length of sequence; (iv) the number of non-gap positions; or (v) the number of equivalenced positions excluding overhangs. Furthermore, it will be appreciated that percentage identity is also strongly length dependent. Therefore, the shorter a pair of sequences is, the higher the sequence identity one may expect to occur by chance.

Hence, it will be appreciated that the accurate alignment of protein or DNA sequences is a complex process. The popular multiple alignment program ClustalW (Thompson et al., 1994, Nucleic Acids Research, 22, 4673-4680; Thompson et al., 1997, Nucleic Acids Research, 24, 4876-4882) is a preferred way for generating multiple alignments of proteins or DNA in accordance with the invention. Suitable parameters for ClustalW may be as follows: For DNA alignments: Gap Open Penalty=15.0, Gap Extension Penalty=6.66, and Matrix=Identity. For protein alignments: Gap Open Penalty=10.0, Gap Extension Penalty=0.2, and Matrix=Gonnet. For DNA and Protein alignments: END-GAP=−1, and GAPDIST=4. Those skilled in the art will be aware that it may be necessary to vary these and other parameters for optimal sequence alignment.

Preferably, calculation of percentage identities between two amino acid/polynucleotide/polypeptide sequences may then be calculated from such an alignment as (N/T)*100, where N is the number of positions at which the sequences share an identical residue, and T is the total number of positions compared including gaps and either including or excluding overhangs. Preferably, overhangs are included in the calculation. Hence, a most preferred method for calculating percentage identity between two sequences comprises (i) preparing a sequence alignment using the ClustalW program using a suitable set of parameters, for example, as set out above; and (ii) inserting the values of N and T into the following formula:— Sequence Identity=(N/T)*100.

Alternative methods for identifying similar sequences will be known to those skilled in the art. For example, a substantially similar nucleotide sequence will be encoded by a sequence which hybridizes to DNA sequences or their complements under stringent conditions. By stringent conditions, the inventors mean the nucleotide hybridises to filter-bound DNA or RNA in 3× sodium chloride/sodium citrate (SSC) at approximately 45° C. followed by at least one wash in 0.2×SSC/0.1% SDS at approximately 20-65° C. Alternatively, a substantially similar polypeptide may differ by at least 1, but less than 5, 10, 20, 50 or 100 amino acids from the sequences shown in, for example, SEQ ID Nos:1 to 57.

Due to the degeneracy of the genetic code, it is clear that any nucleic acid sequence described herein could be varied or changed without substantially affecting the sequence of the protein encoded thereby, to provide a functional variant thereof. Suitable nucleotide variants are those having a sequence altered by the substitution of different codons that encode the same amino acid within the sequence, thus producing a silent (synonymous) change. Other suitable variants are those having homologous nucleotide sequences but comprising all, or portions of, sequence, which are altered by the substitution of different codons that encode an amino acid with a side chain of similar biophysical properties to the amino acid it substitutes, to produce a conservative change. For example, small non-polar, hydrophobic amino acids include glycine, alanine, leucine, isoleucine, valine, proline, and methionine. Large non-polar, hydrophobic amino acids include phenylalanine, tryptophan and tyrosine. The polar neutral amino acids include serine, threonine, cysteine, asparagine and glutamine. The positively charged (basic) amino acids include lysine, arginine and histidine. The negatively charged (acidic) amino acids include aspartic acid and glutamic acid. It will therefore be appreciated which amino acids may be replaced with an amino acid having similar biophysical properties, and the skilled technician will know the nucleotide sequences encoding these amino acids.

All of the features described herein (including any accompanying claims, abstract and drawings), and/or all of the steps of any method or process so disclosed, may be combined with any of the above aspects in any combination, except combinations where at least some of such features and/or steps are mutually exclusive.

For a better understanding of the invention, and to show how embodiments of the same may be carried into effect, reference will now be made, by way of example, to the accompanying Figures, in which:—

FIG. 1 shows a schematic of one embodiment of a self-amplifying RNA replicon or construct based on the Venezuelan Equine Encephalitis Virus (VEEV) backbone. The so-called 'Stealthicon' vector is an saRNA replicon/construct encoding Non-structural Proteins (NSP1-4), and an innate inhibitory protein (IIP), which is upstream or downstream of the GOI (Gene of Interest).

FIG. 2 shows that genome replication results in dsRNA, which is recognized by the sensor molecules MDA5 and PACT. These sensors transmit signals to activate downstream cascades, including the activation of transcription factors (NF-κB, IRF-3, -7), restriction factors which directly inhibit RNA amplification and protein expression (dotted line). Expression of PIV-V or ORF4a block innate recognition of dsRNA by MDA5 and PACT preventing the activation of the downstream cascade that limits replicon RNA amplification and protein expression from the synthetic RNA.

FIG. 3 shows a) screening of IIP-encoding VEEV replicons in vitro. Cells were transfected with two batches of RNA containing luciferase as a reporter protein and assess for protein expression after 24 hours. HeLa and MRC5 are known to have more intact IFN expression pathways compared to HEK and b) Data for FIG. 3a shown as fold change in expression relative to wild type.

FIG. 7 shows the construct map of one embodiment of an expression vector encoding the RNA construct comprising GOI-MERS-CoV ORF4a.

Figure 9:
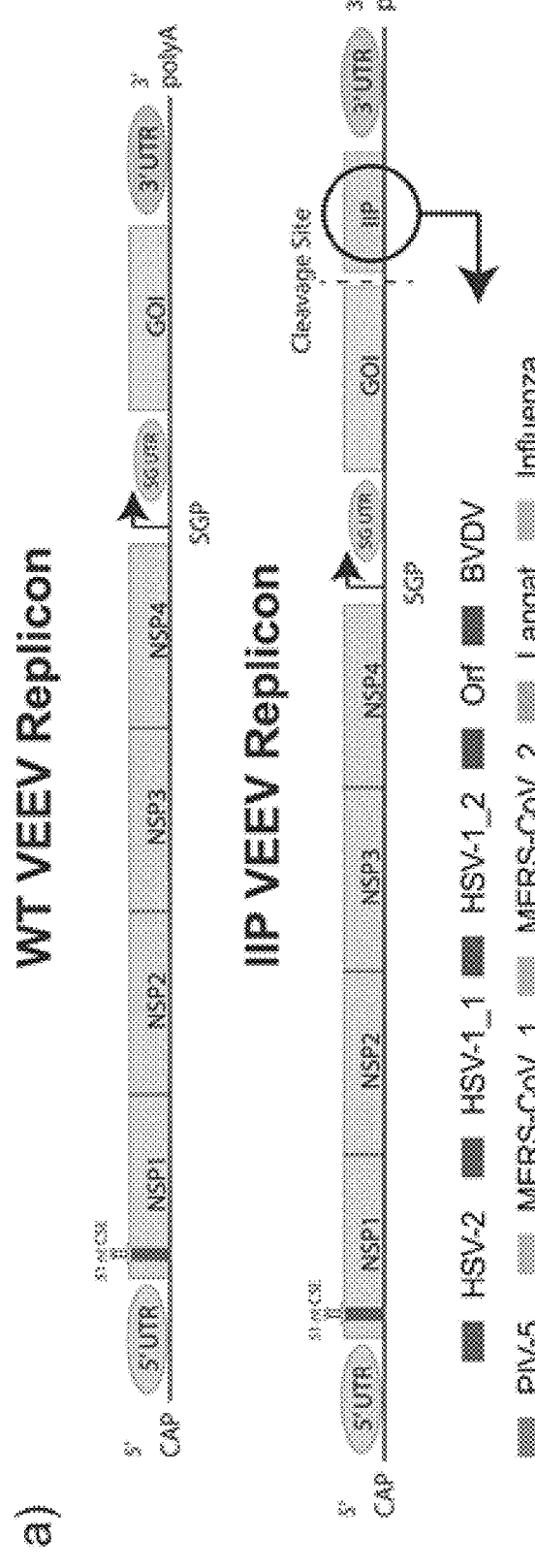
Figure 9:
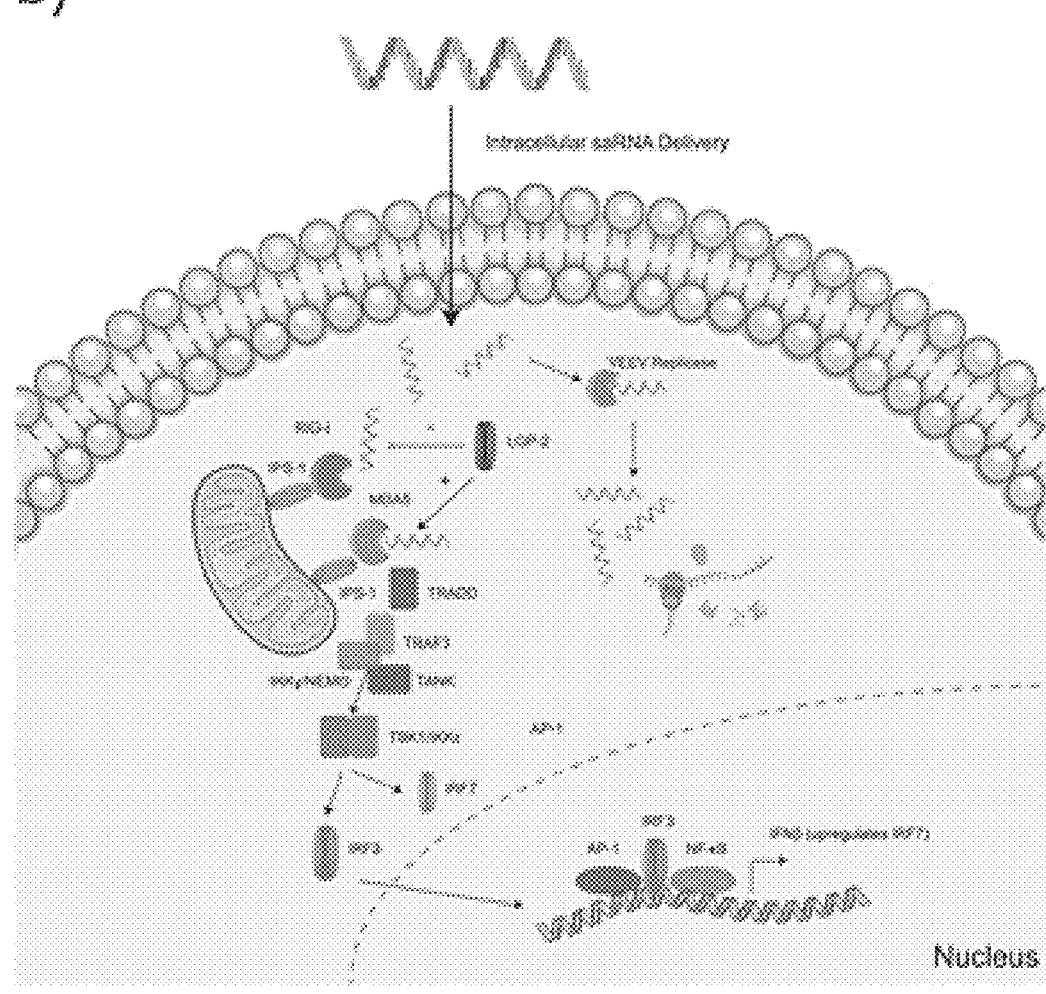
Figure 9:
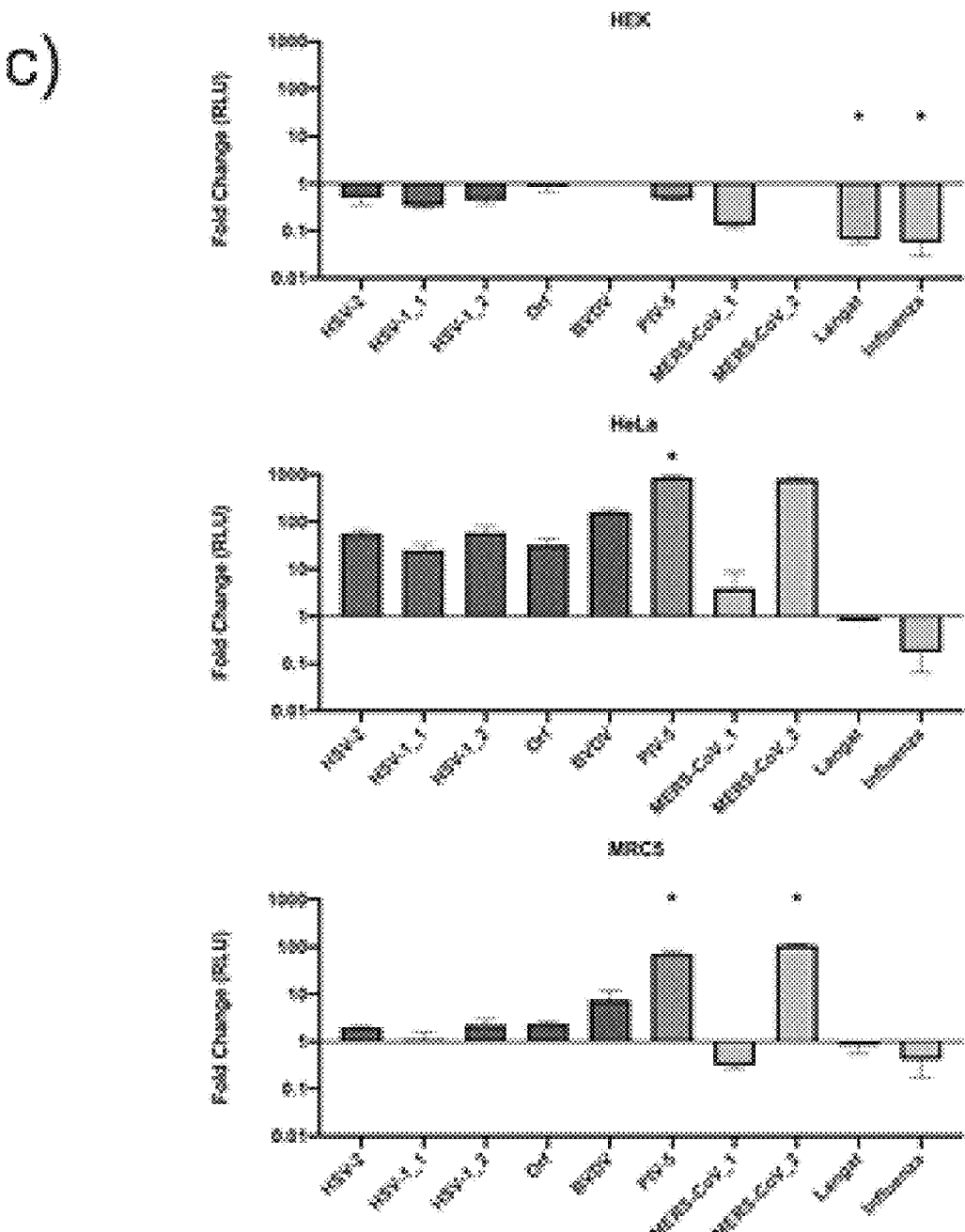

FIG. 9 shows schematic drawings of constructs of the invention, and in vitro protein expression from wild-type and IIP VEEV replicons. a) Schematic of wild-type and cis-encoding IIP VEEV replicons. b) Schematic of innate sensing of self-amplifying RNA. c) In vitro transfection of firefly luciferase saRNA in HEK 293T.17, HeLa and MRC5 cells measured as relative light units (RLU). Bars represent mean fold change±standard deviation normalized to wild type VEEV control, for n=3.

Figure 10:
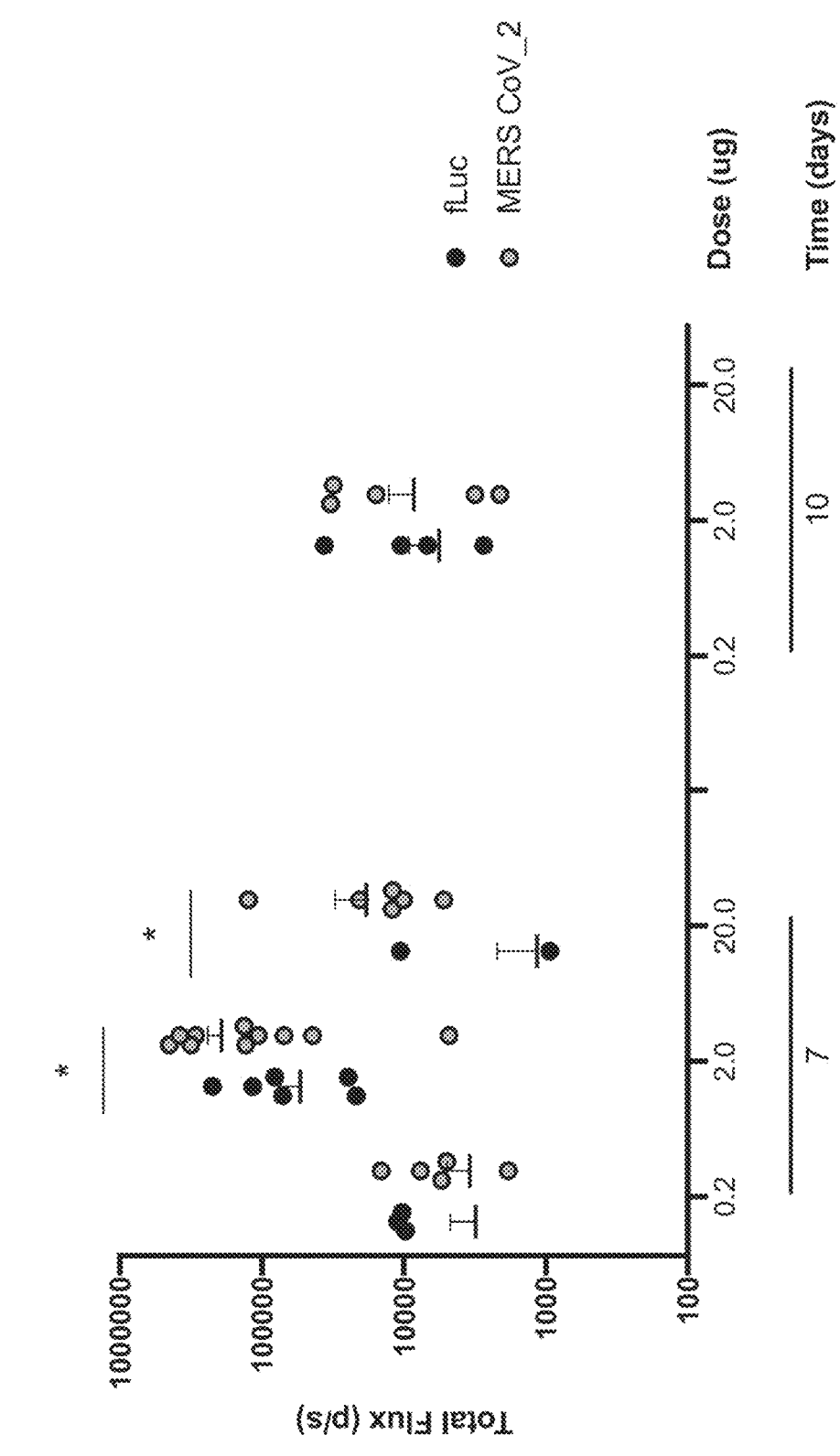

FIG. 10 shows dose titration of WT and MERS CoV-2 replicon in C57BL6/J mice. Protein expression was quantified at days 7 and 10 after intramuscular injection of either 0.2, 2 or 20 μg of RNA. Each dot represents a single mouse and the bar represents the mean±SEM with n=10. * indicates significance of $p<0.05$ as evaluated using a Kruskal-Wallis test with multiple comparisons.

Figure 11:
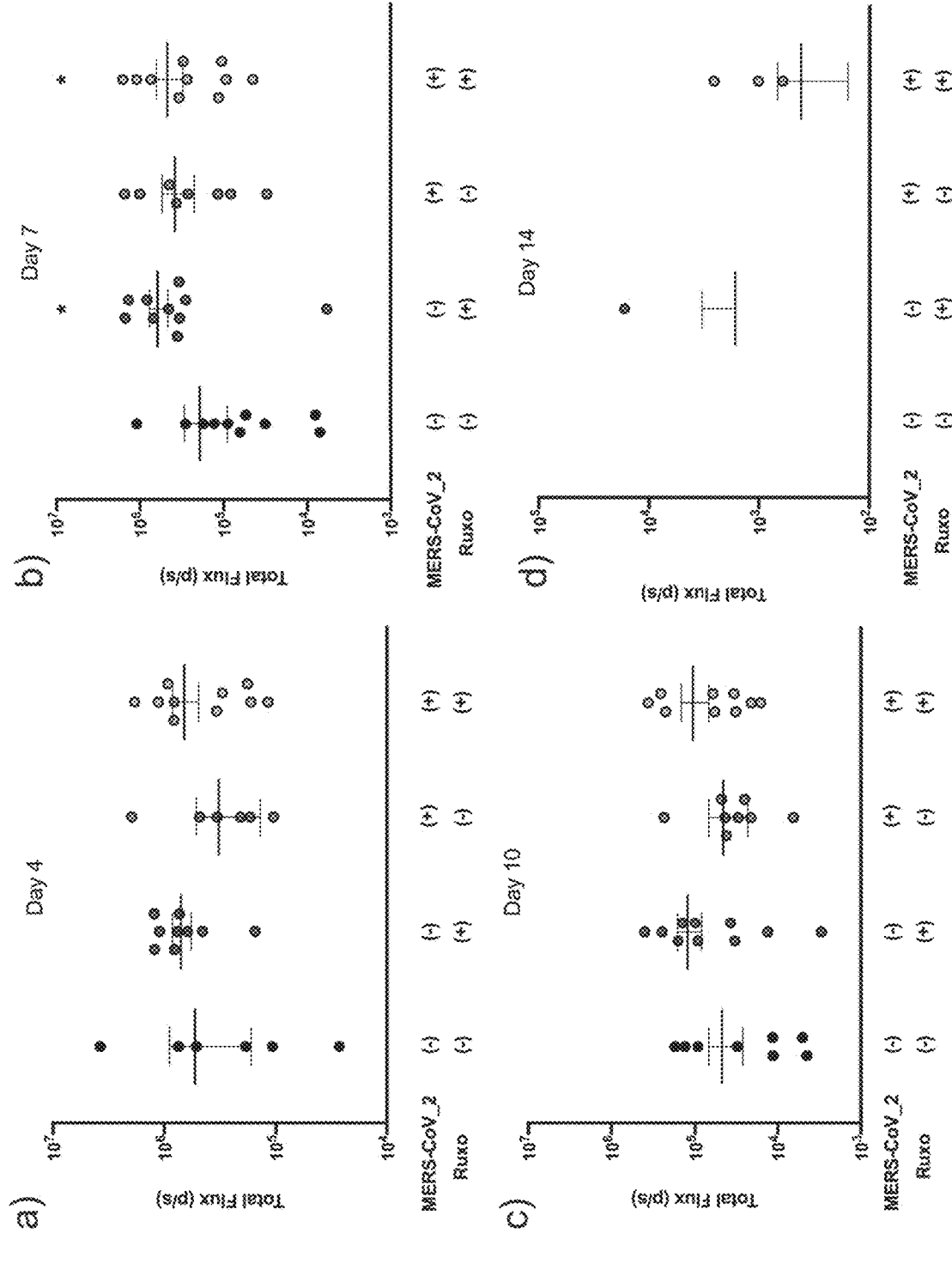

FIG. 11 shows co-formulation of WT and MERS CoV_2 replicons with JAK inhibitor ruxolitinib in C57BL6/J mice. Protein expression was quantified at days 4, 7, 10 and 14 (a, b, c, and d, respectively) after intramuscular injection of either 5 μg of RNA with 100 ug of ruxolitinib. Each dot represents a single mouse leg and the bar represents the mean f SEM with n=10.

Figure 12:
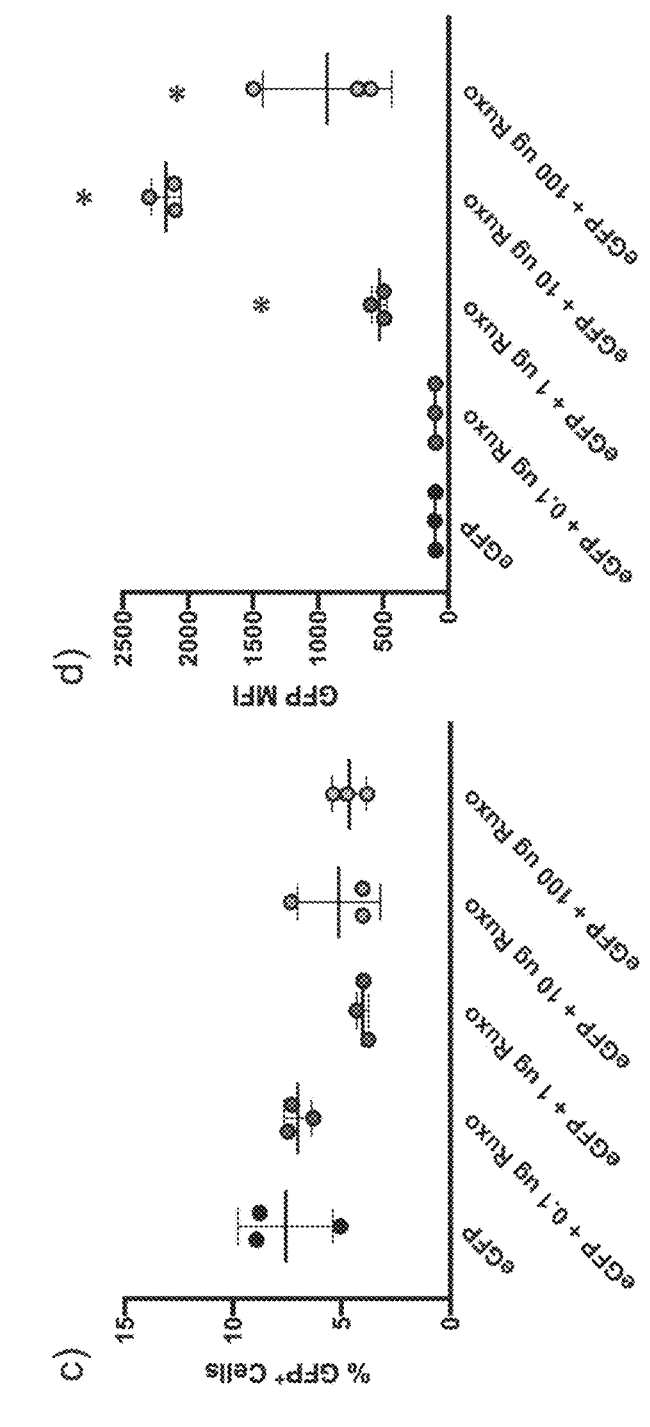

FIG. 12 shows protein expression of eGFP±MERS CoV_2 RNA (which corresponds to MERS-CoV ORF4a) (0.2, 2 or 20 μg) (a,b) or ±ruxolitinib (0.1, 1, 10 or 100 μg) (c,d) in human skin explants. Number of eGFP expression cells (% GFP+ cells) (a,c) and total protein expression per cell (GFP median fluorescent intensity (MFI)) (b,d) were quantified 72 h after injection. Each dot represents mean f SEM with n=3. * indicates significance of $p<0.05$ as evaluated using a Kruskal-Wallis test with multiple comparisons.

Figure 13:
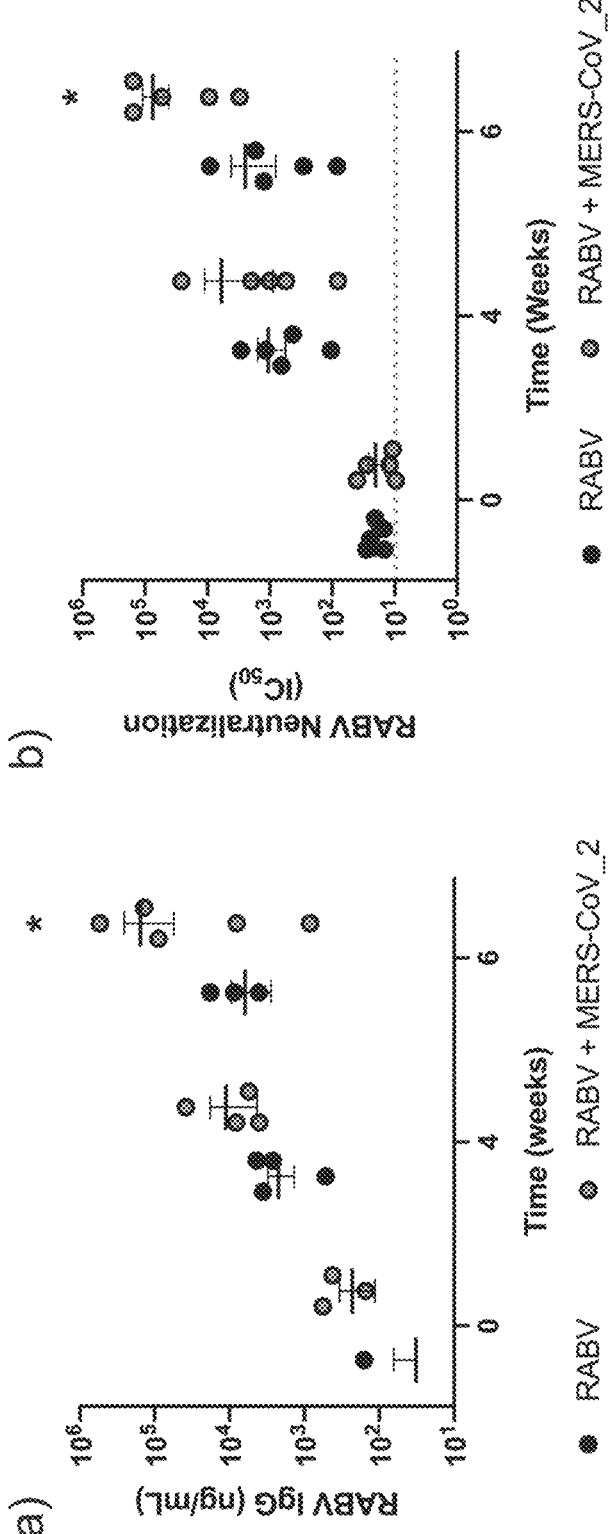

FIG. 13 shows immunogenicity of RABV MERS-CoV_2 (which corresponds to MERS-CoV ORF4a) in rabbits. a) RABV antigen-specific IgG antibody titers following intramuscular immunization with prime and boost of 20 μg at 0 and 4 weeks, with n=5. b) Neutralization IC50 against pseudotyped RABV virus with n=5, grey dotted line represents the limit of detection. * indicates significance of $p<0.05$ as evaluated using a Kruskal-Wallis test with multiple comparisons.

Figure 14:
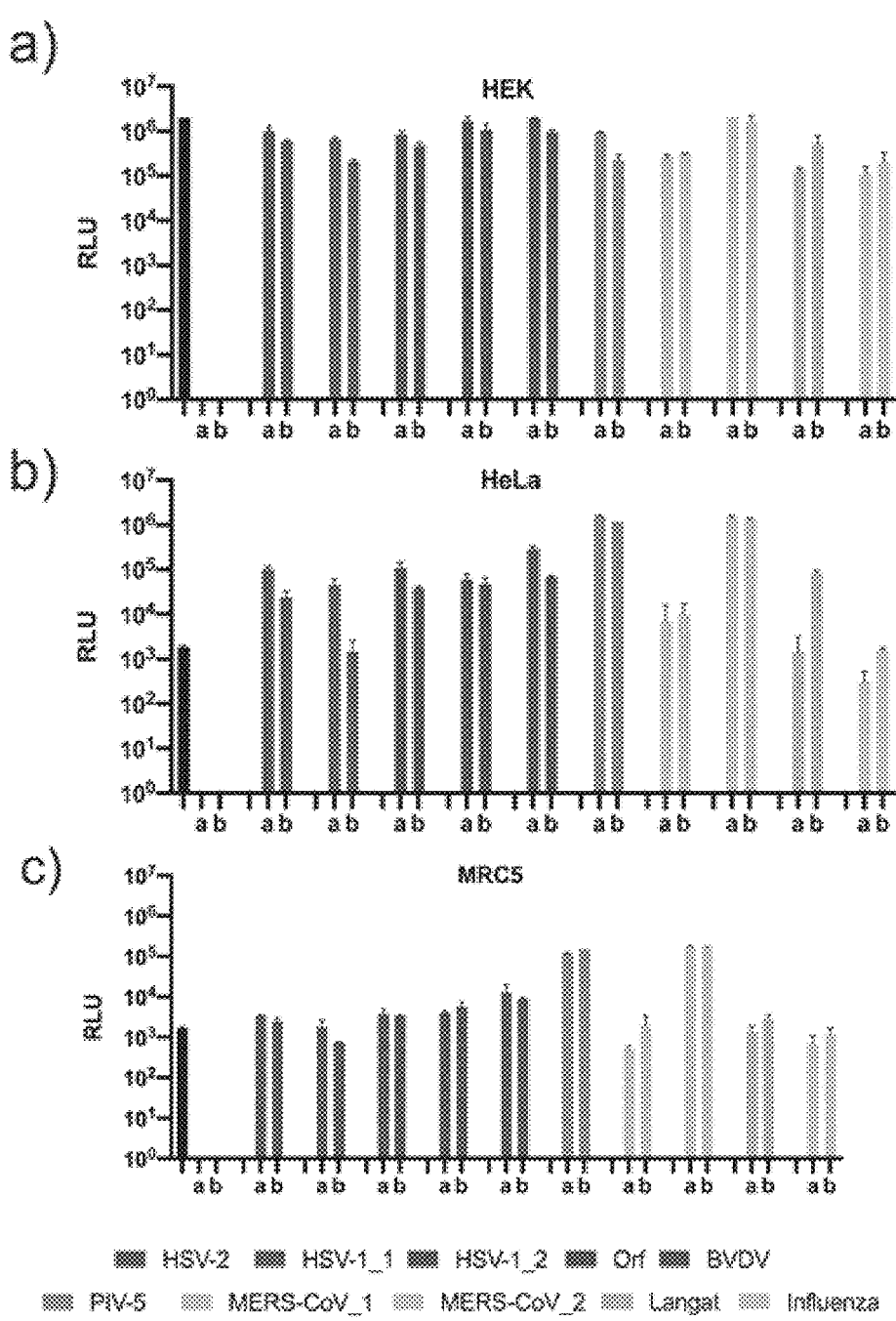

FIG. 14 shows in vitro transfection of firefly luciferase saRNA in HEK 293T.17, HeLa and MRC5 cells measured as relative light units (RLU). Bars represent mean f standard deviation control, for n=3. 'a' and 'b' indicate two separately prepared batches of RNA.

Figure 15:
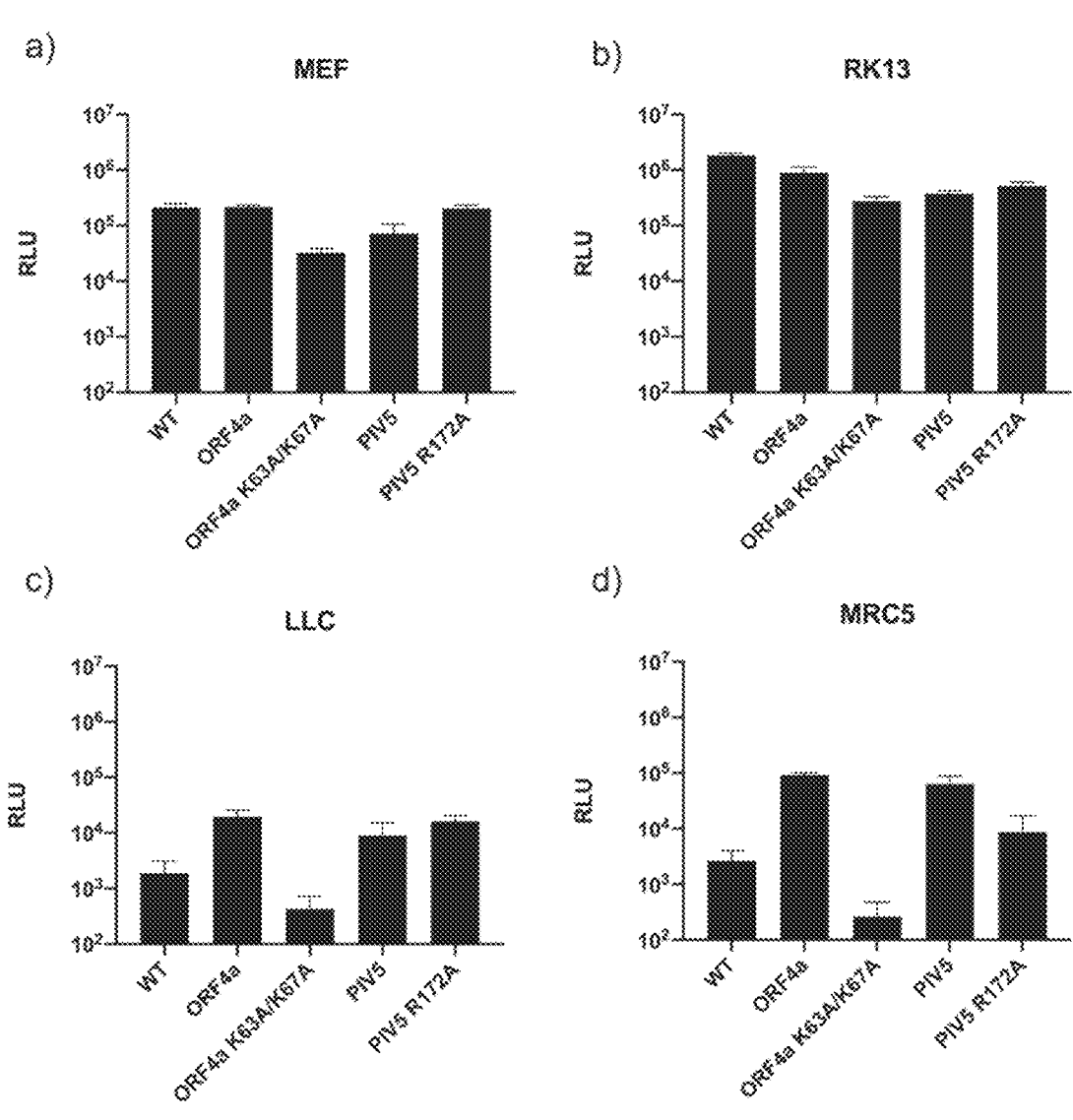

FIG. 15 shows in vitro transfections of WT fLuc, MERS-CoV_2 ORF4a and PIV-5 RNA in a) mouse (MEF), b) rabbit (RK13), c) nonhuman primate (LLC) and d) human (MRC5) cells measured as relative light units (RLU). Bars represent mean f standard deviation control, for n=3.

Figure 16:
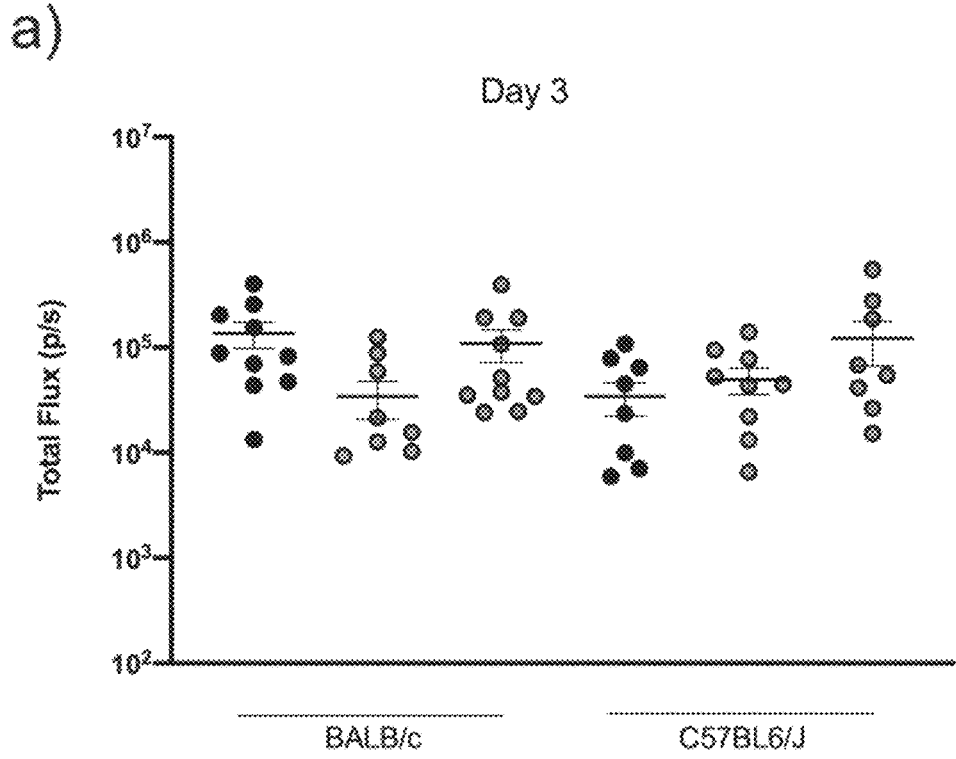
Figure 16:
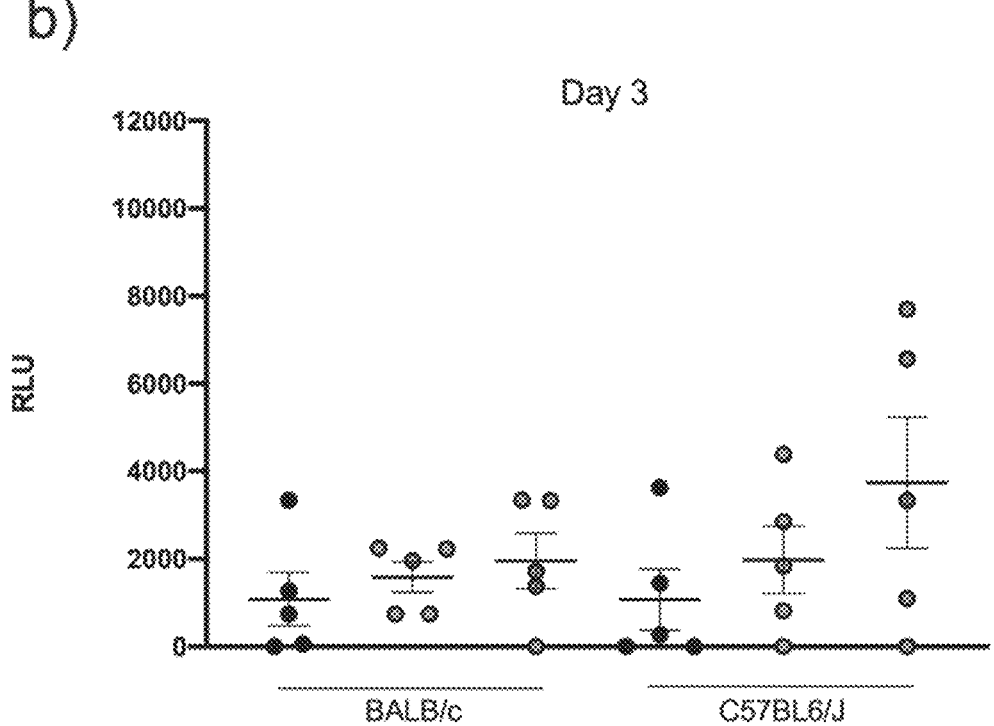
Figure 16:
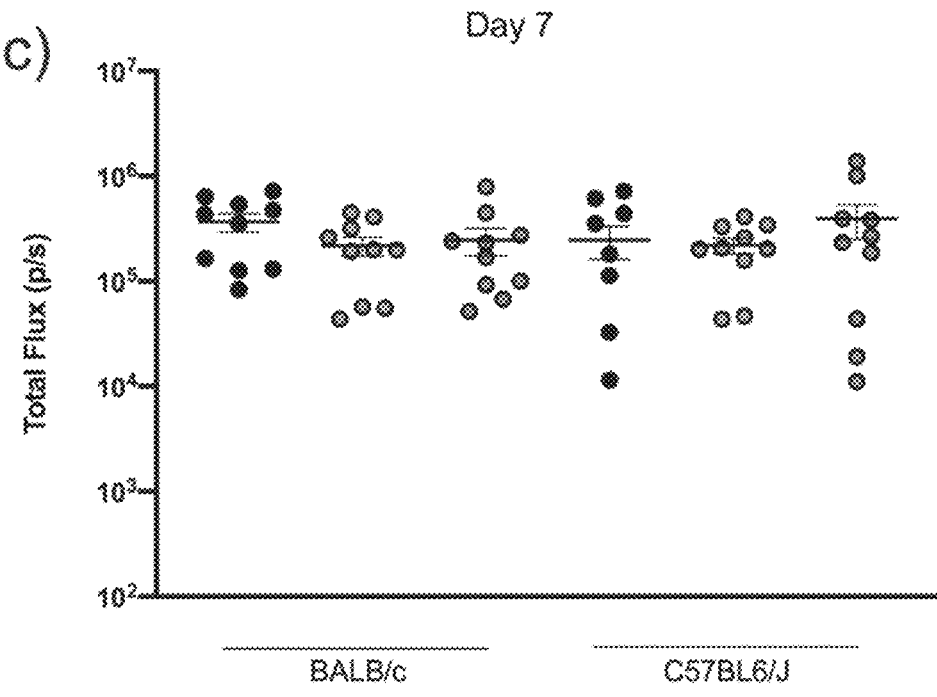
Figure 16:
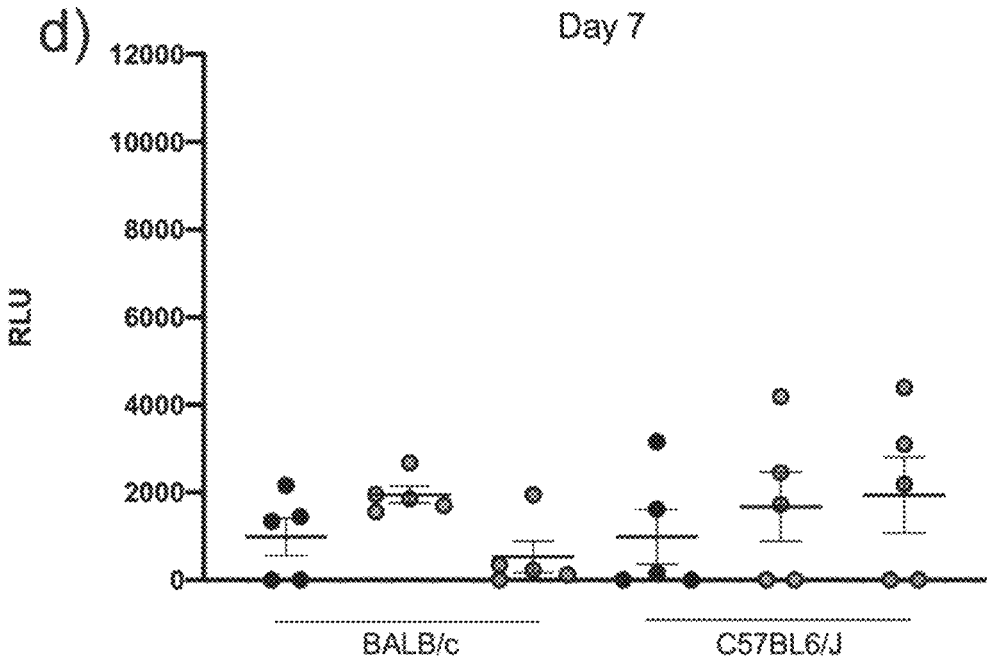
Figure 16:
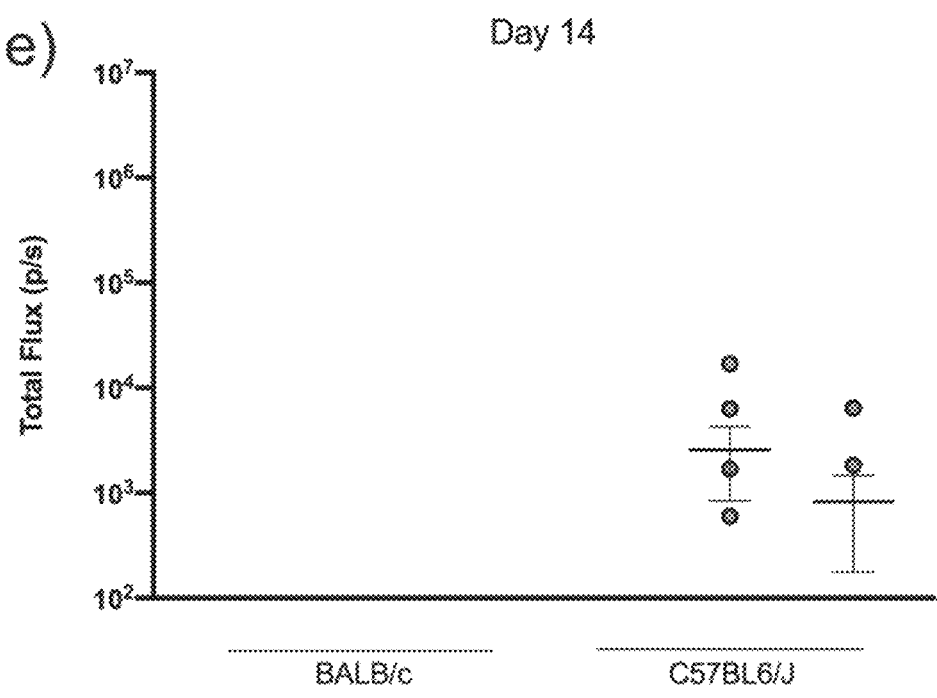
Figure 16:
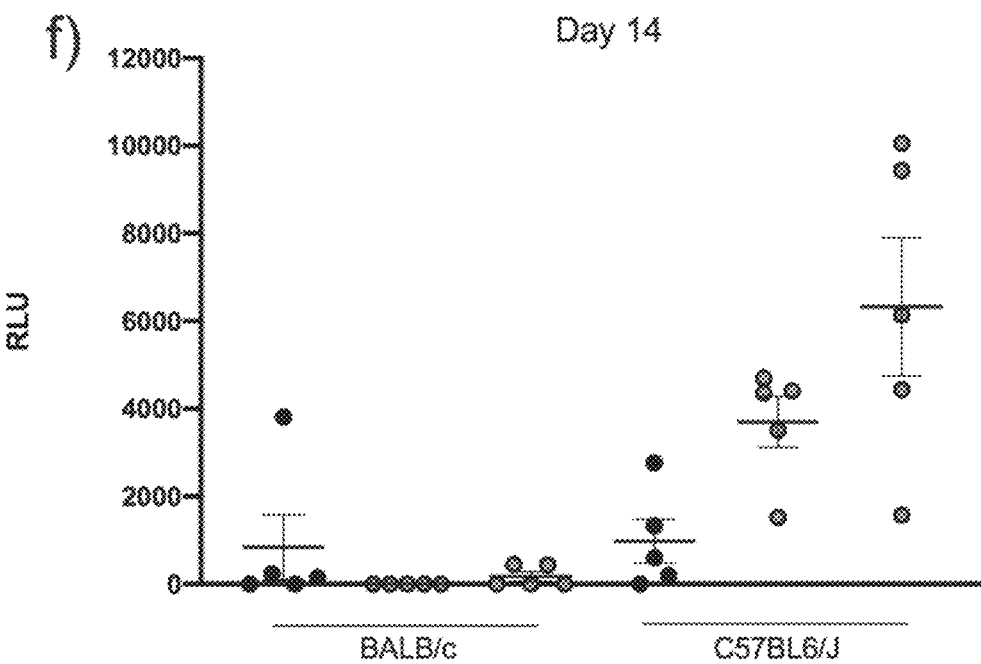

FIG. 16 shows in vivo luciferase expression of intracellular (firefly luciferase) and secreted (gaussia luciferase) proteins in BALB/c and C57BL6/J mice. Protein expression was quantified at day 3 (a,b) 7 (c,d) and 14 (e,f) either in the muscle (a,c,e) using an In Vivo Imaging System (IVIS) or in the serum (b,d,f). Each dot represents a single mouse and the bar represents the mean±SEM with n=10 for fLuc and n=5 for gLuc.

Figure 17:
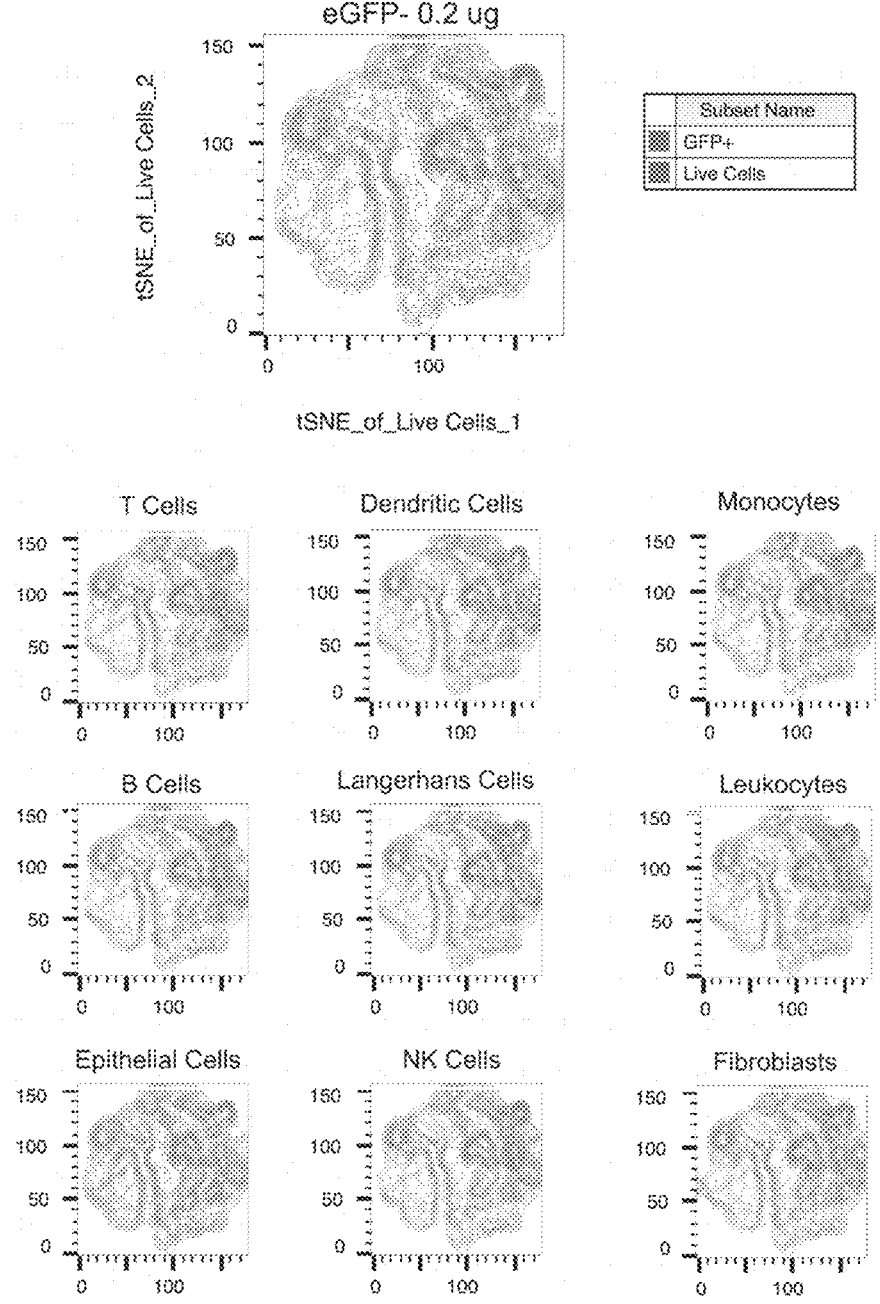

FIG. 17 shows t-Distributed Stochastic Neighbor Embedding (tSNE) plots of unsupervised cluster of live cells (grey), overlaid with gating for eGFP+ cells (green), separated by phenotype (blue), for human skin explants treated with 0.2 μg of eGFP RNA.

Figure 18:
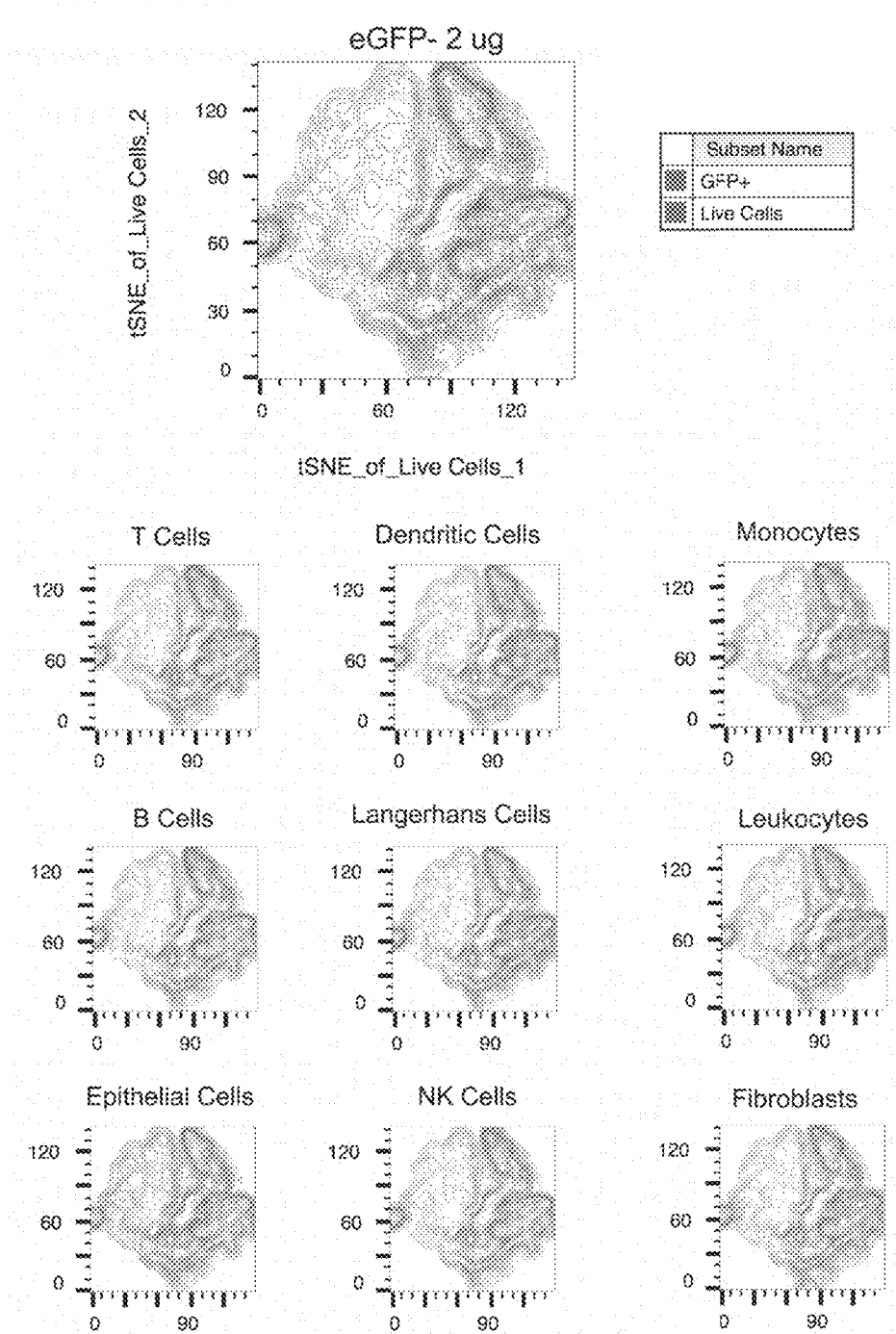

FIG. 18 shows t-Distributed Stochastic Neighbor Embedding (tSNE) plots of unsupervised cluster of live cells (grey), overlaid with gating for eGFP+ cells (green), separated by phenotype (blue), for human skin explants treated with 2 μg of eGFP RNA.

Figure 19:
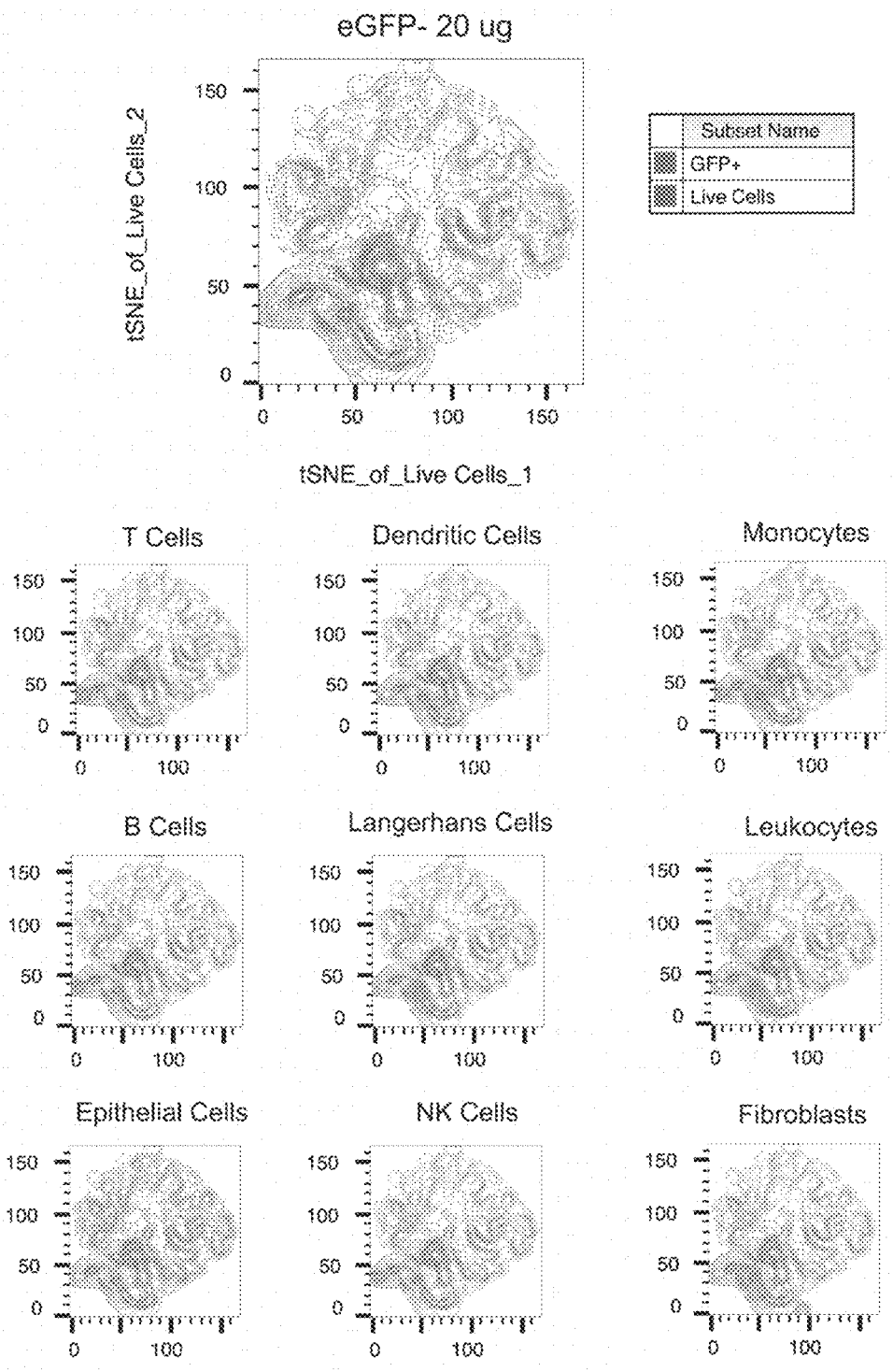

FIG. 19 shows t-Distributed Stochastic Neighbor Embedding (tSNE) plots of unsupervised cluster of live cells (grey), overlaid with gating for eGFP+ cells (green), separated by phenotype (blue), for human skin explants treated with 20 μg of eGFP RNA.

Figure 20:
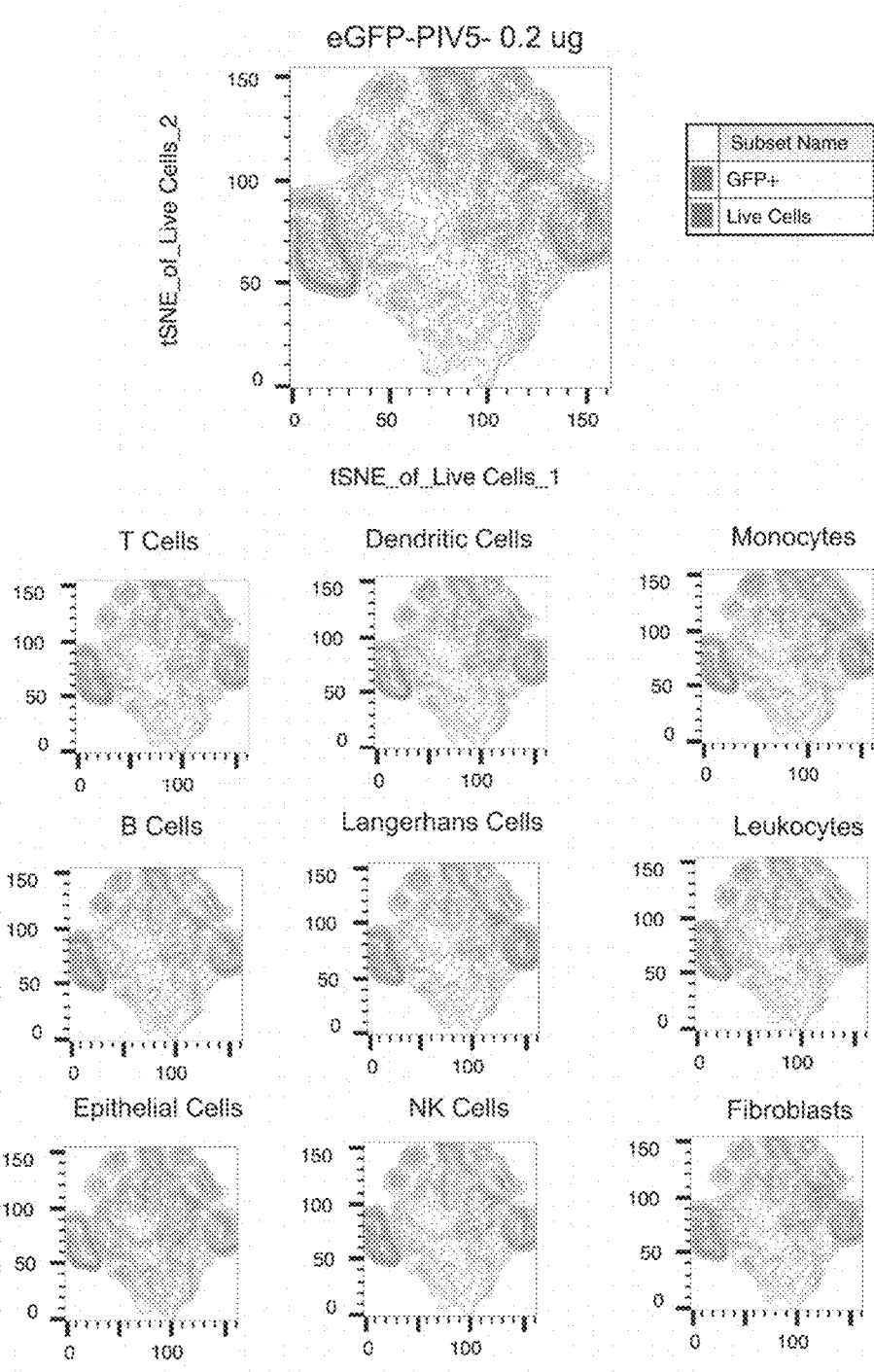

FIG. 20 shows t-Distributed Stochastic Neighbor Embedding (tSNE) plots of unsupervised cluster of live cells (grey), overlaid with gating for eGFP+ cells (green), separated by phenotype (blue), for human skin explants treated with 0.2 μg of eGFP-PIV-5 RNA.

Figure 21:
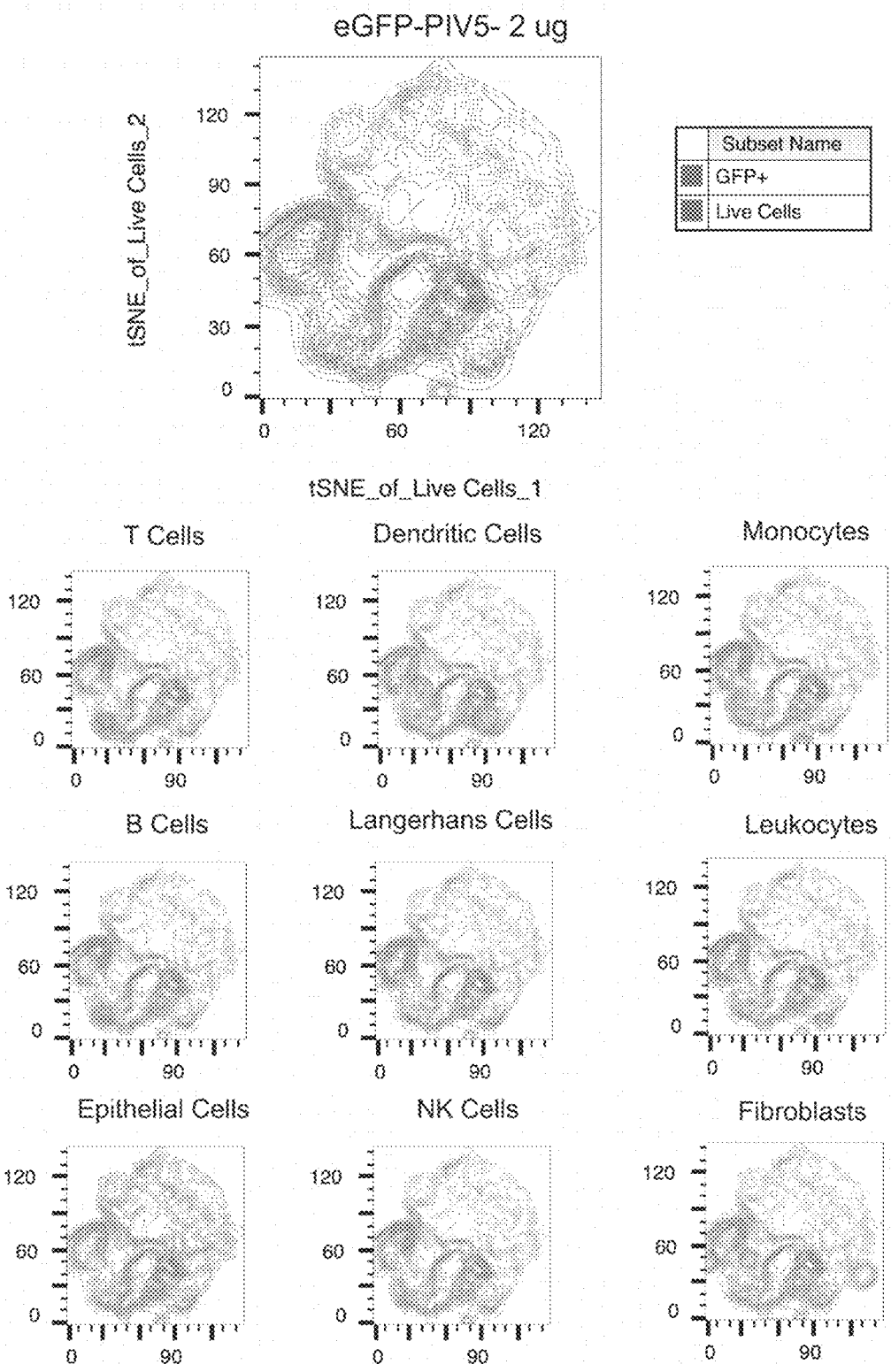

FIG. 21 shows t-Distributed Stochastic Neighbor Embedding (tSNE) plots of unsupervised cluster of live cells (grey), overlaid with gating for eGFP+ cells (green), separated by phenotype (blue), for human skin explants treated with 2 μg of eGFP-PIV-5 RNA.

Figure 22:
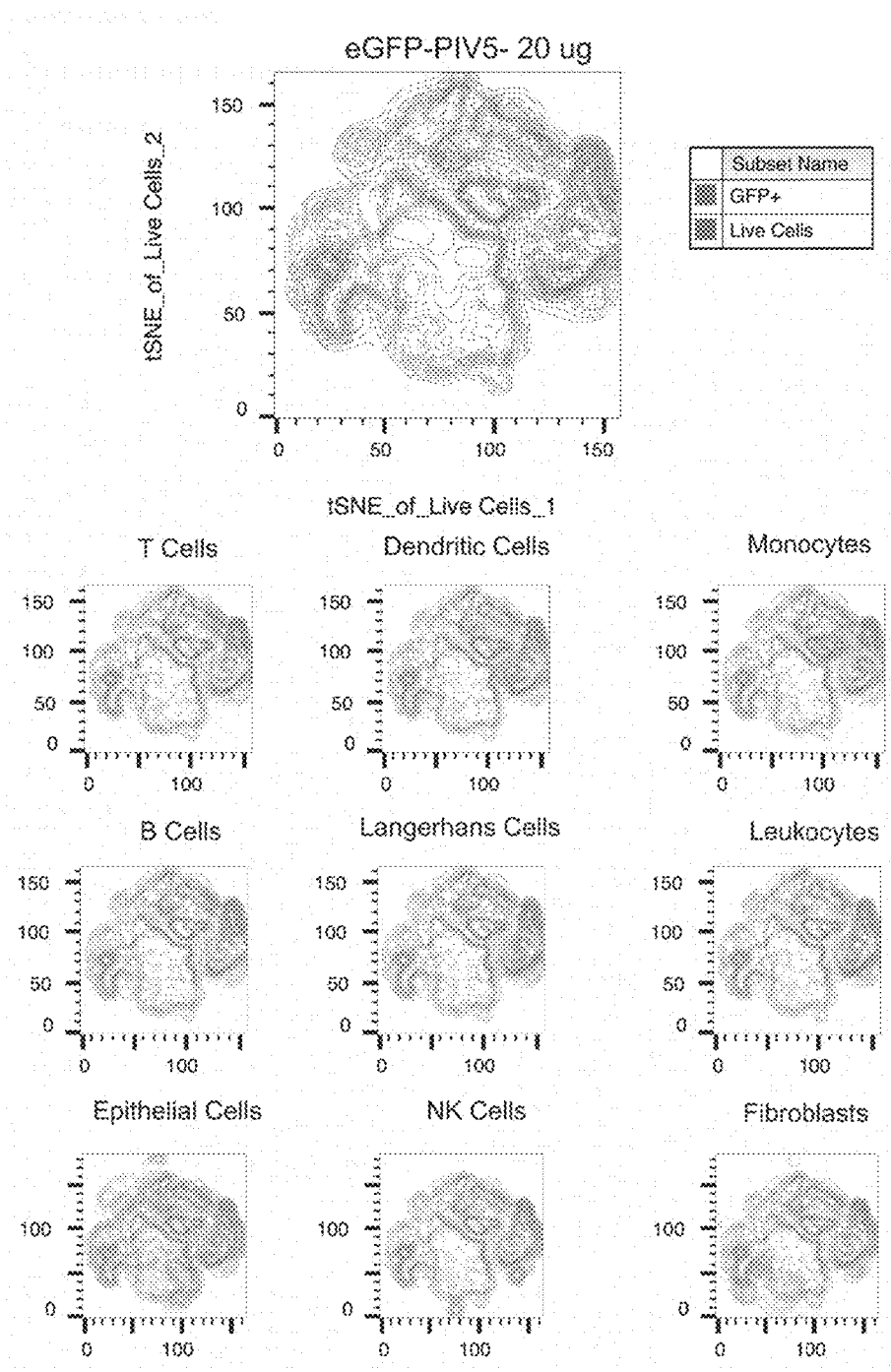

FIG. 22 shows t-Distributed Stochastic Neighbor Embedding (tSNE) plots of unsupervised cluster of live cells (grey), overlaid with gating for eGFP+ cells (green), separated by phenotype (blue), for human skin explants treated with 20 μg of eGFP-PIV-5 RNA.

Figure 23:
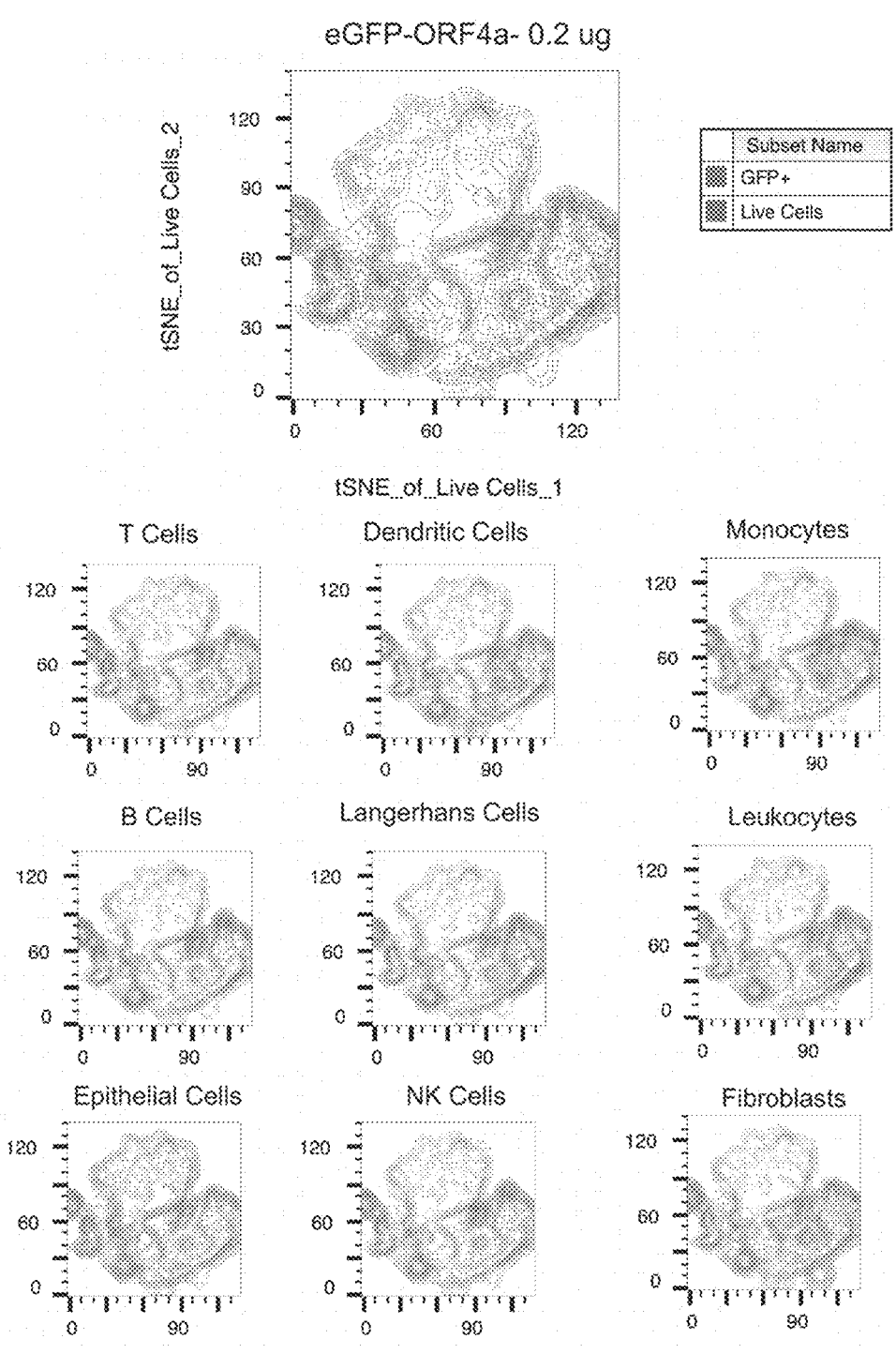

FIG. 23 shows t-Distributed Stochastic Neighbor Embedding (tSNE) plots of unsupervised cluster of live cells (grey), overlaid with gating for eGFP+ cells (green), separated by phenotype (blue), for human skin explants treated with 0.2 μg of eGFP-MERS-CoV_2 RNA (which corresponds to MERS-CoV ORF4a).

Figure 24:
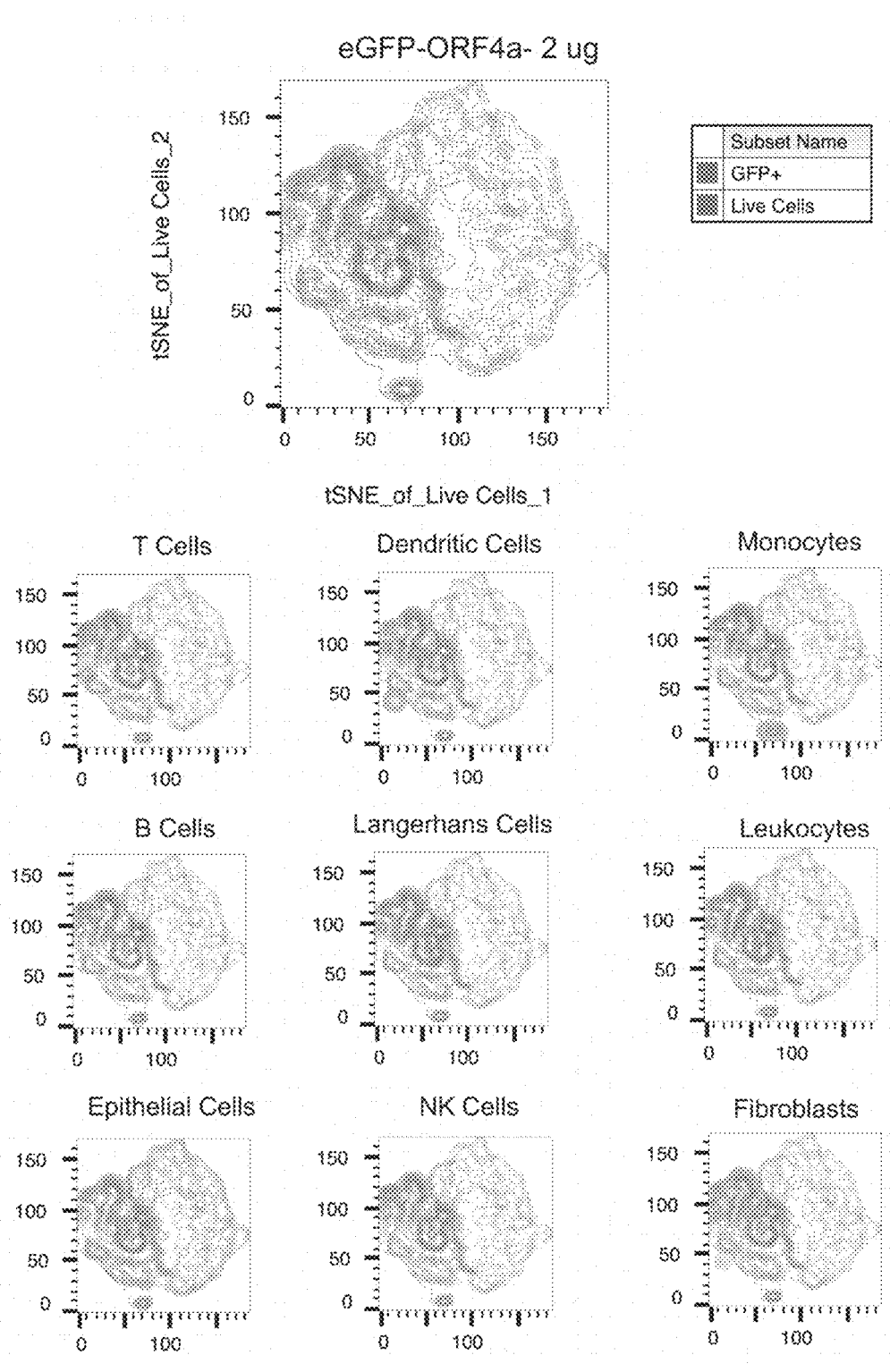

FIG. 24 shows t-Distributed Stochastic Neighbor Embedding (tSNE) plots of unsupervised cluster of live cells (grey), overlaid with gating for eGFP+ cells (green), separated by phenotype (blue), for human skin explants treated with 2 μg of eGFP-MERS-CoV_2 RNA.

Figure 25:
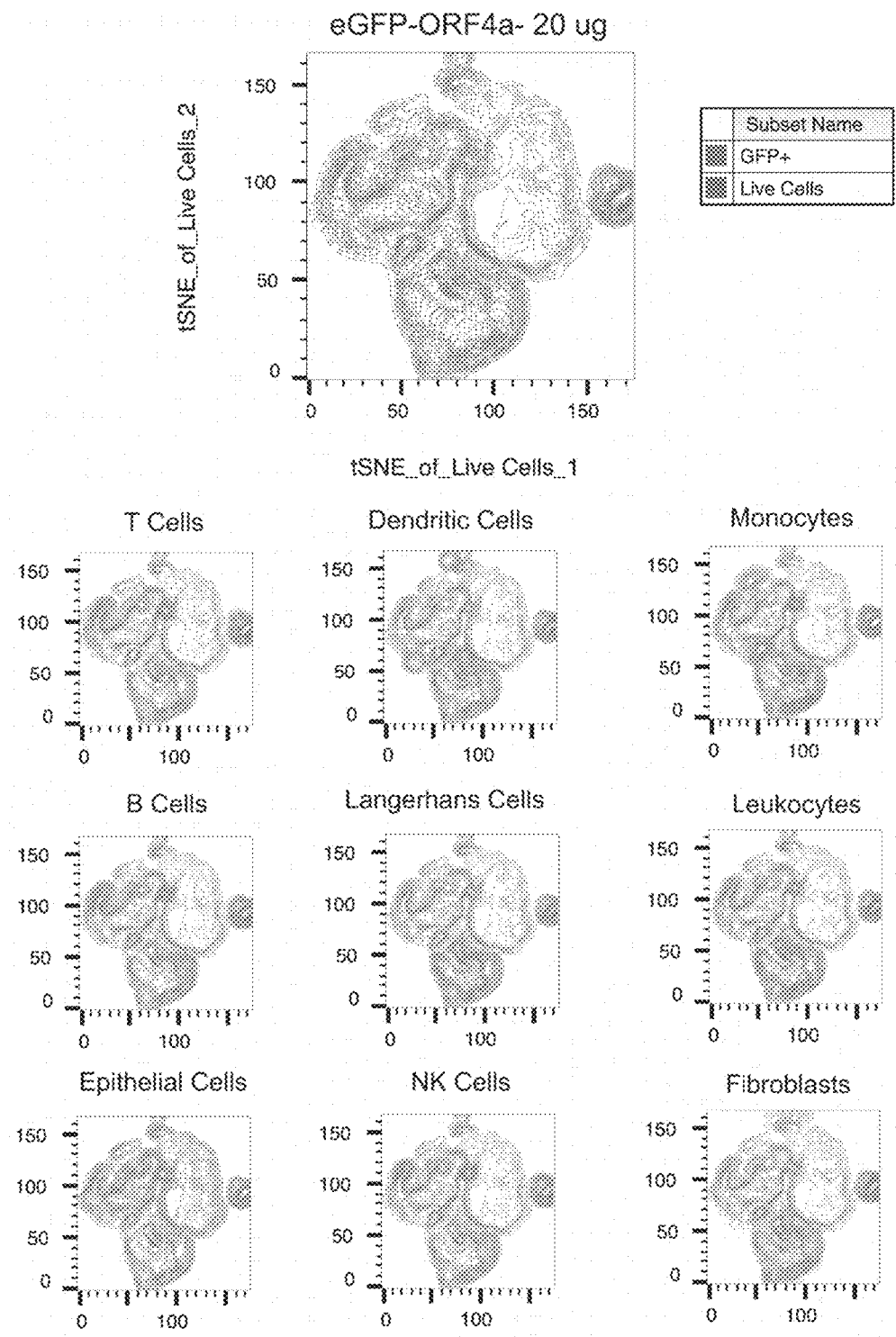

FIG. 25 shows t-Distributed Stochastic Neighbor Embedding (tSNE) plots of unsupervised cluster of live cells (grey), overlaid with gating for eGFP+ cells (green), separated by phenotype (blue), for human skin explants treated with 20 μg of eGFP-MERS-CoV_2 RNA (which corresponds to MERS-CoV ORF4a).

Figure 26:
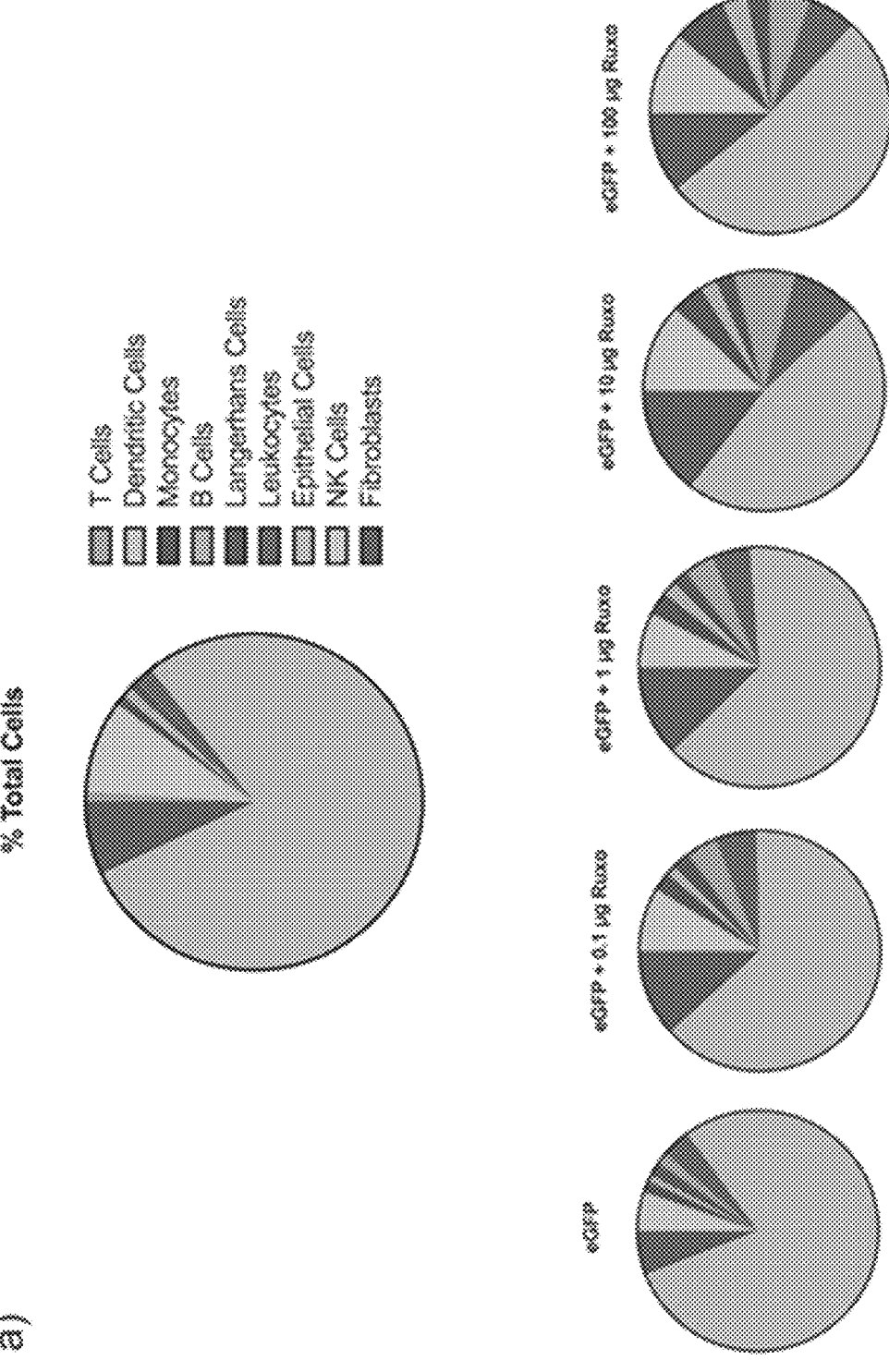
Figure 26:
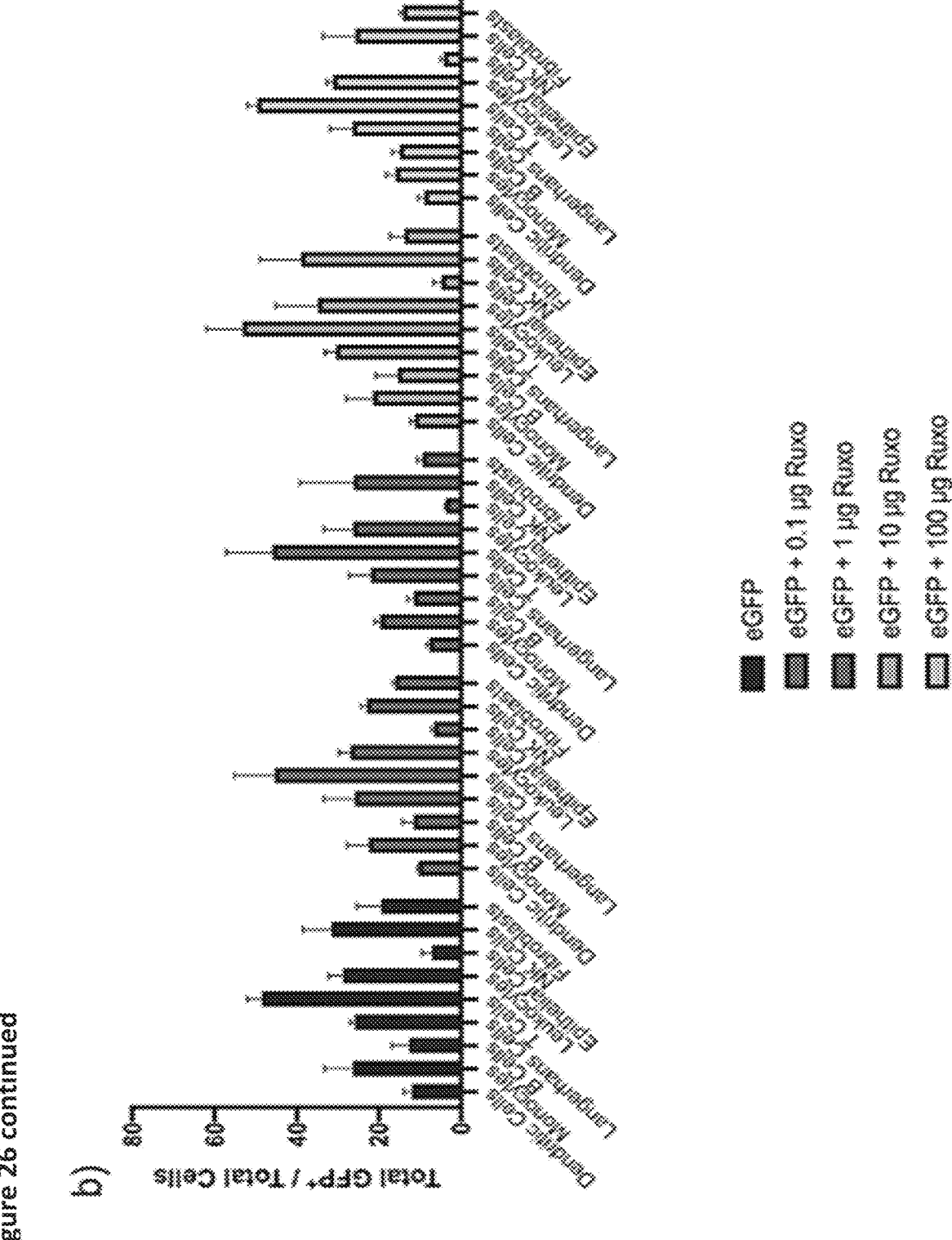

FIG. 26 shows phenotypic identity of cells present in human skin explants and GFP+ cells after intradermal (ID) injection of eGFP±ruxo formulations as determined by flow cytometry. a) Identity of cells in the population of total cells extracted from human skin explants and GFP-expressing skin cells from explants treated with 2 μg of eGFP-encoding saRNA±0.1, 1, 10 or 100 μg of ruxo with n=3. b) Percentage of cells of each phenotype expressiong GFP. Cells identified using the following antibodies: epithelial cells (CD45−), fibroblasts (CD90+), NK cells (CD56+), leukocytes (CD45+), Langerhans cells (CD1a+), monocytes (CD14+), dendritic cells (CD11c+), T cells (CD3+), and B cells (CD19+).

Figure 27:
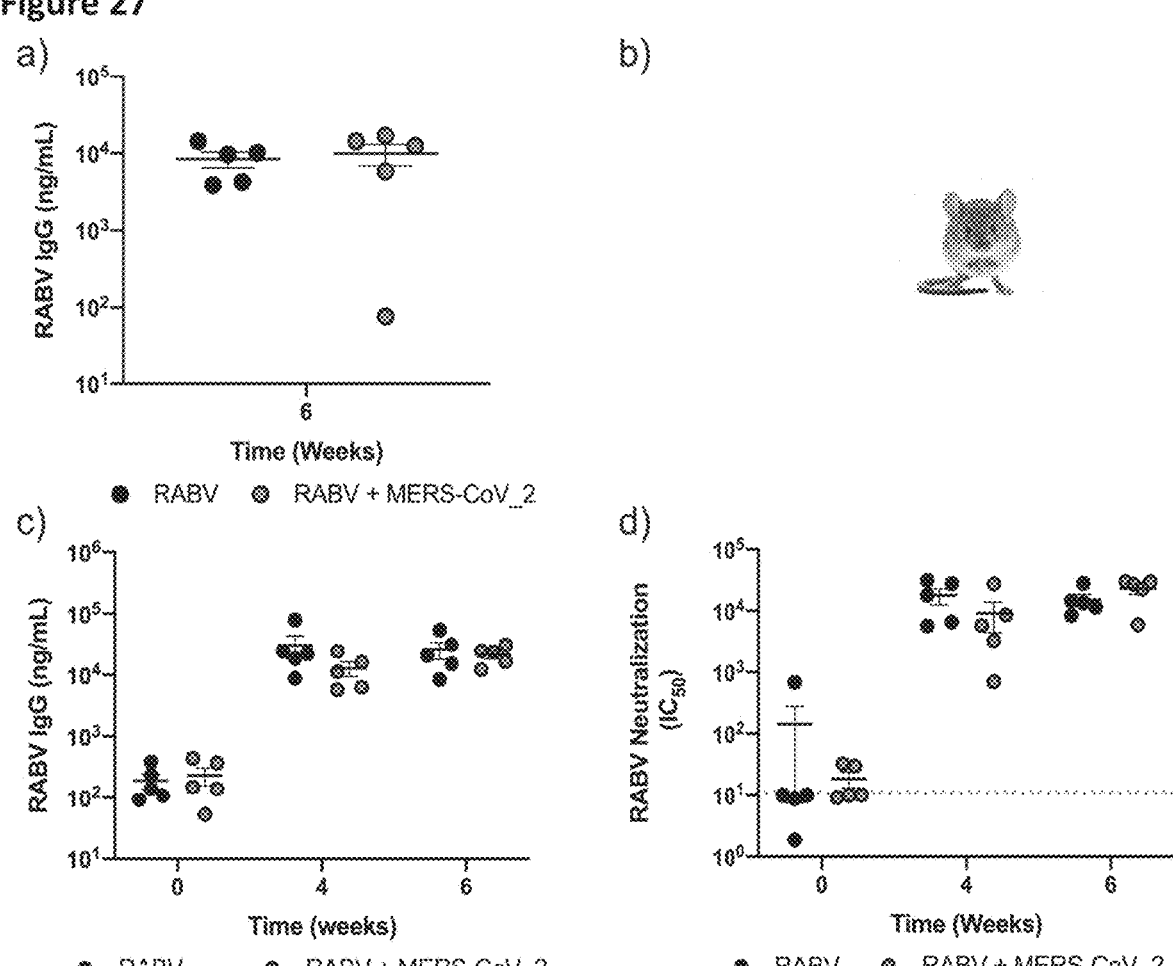

FIG. 27 shows immunogenicity of RABV±MERS-CoV_2 (which corresponds to MERS-CoV ORF4a) in mice and rats. a) RABV antigen-specific IgG antibody titers following intramuscular immunization of mice with prime and boost of 1 μg at 0 and 4 weeks, with n=5. b) Neutralization $IC_{50}$ of mice against pseudotyped RABV virus with n=5, grey dotted line represents the limit of detection. a) RABV antigen-specific IgG antibody titers following intramuscular immunization of rats with prime and boost of 20

μg at 0 and 4 weeks, with n=5. b) Neutralization $IC_{50}$ of rats against pseudotyped RABV virus with n=5, grey dotted line represents the limit of detection.

Figure 28:
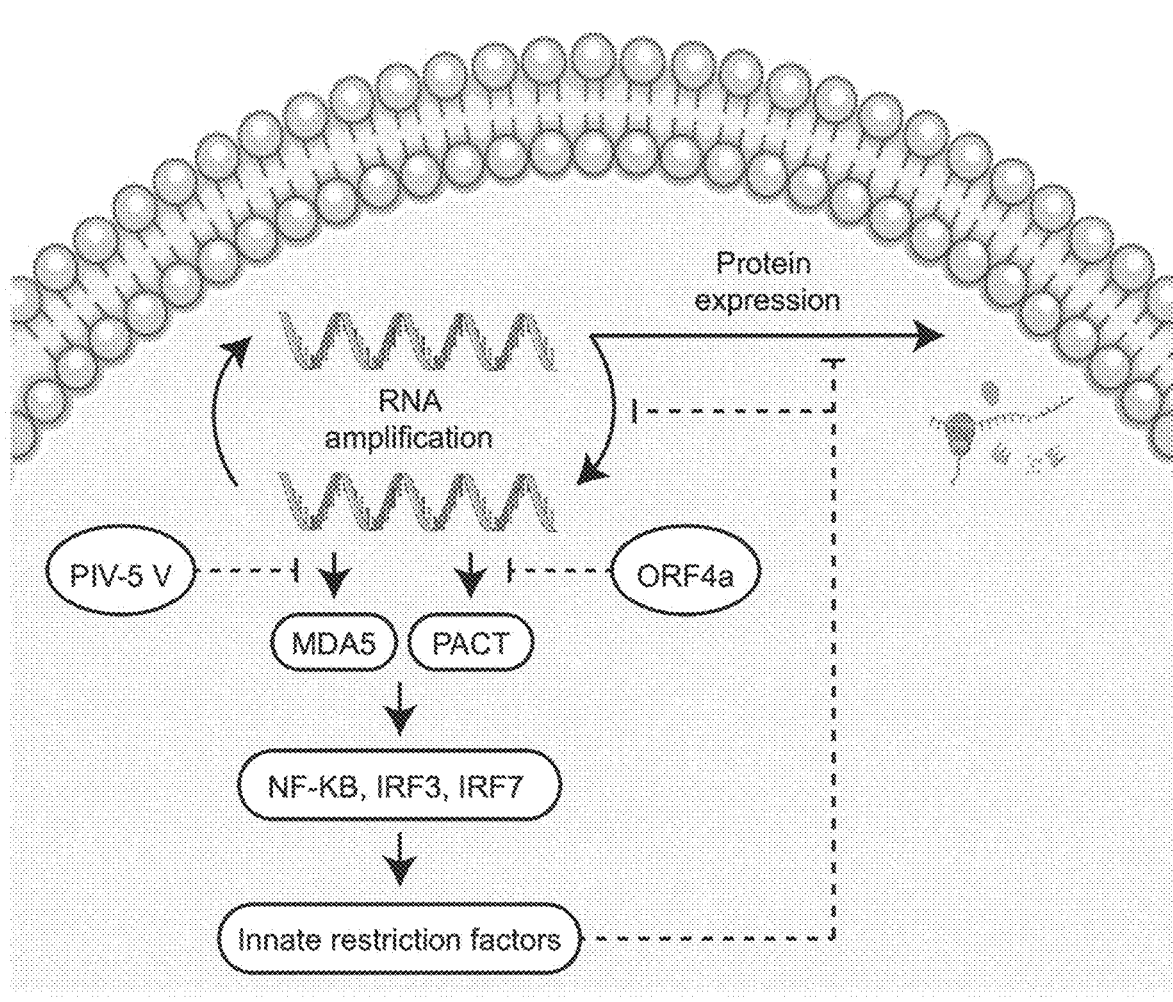

FIG. 28 show a schematic drawing of proposed mechanism of PIV-5 V and MERS-CoV ORF4a on saRNA sensing.

Figure 29:
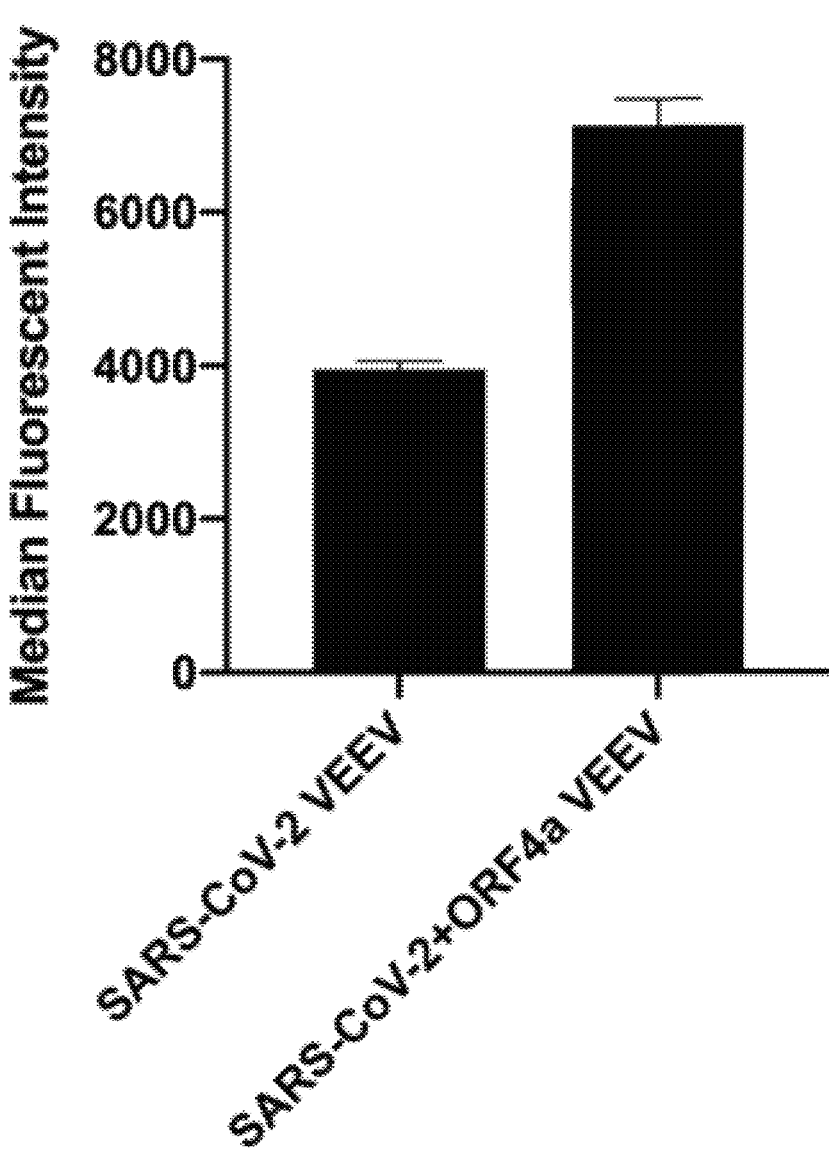

FIG. 29 shows Median Fluorescent Intensity (MFI) data showing the increased expression of SARS-CoV-2 glycoprotein from an saRNA according to one embodiment of the invention in Hela cells when co-expressed with the innate inhibitor protein, MERS-ORF4a, when compared to an saRNA encoding an SARS-CoV-2 glycoprotein only (i.e. no IIP).

EXAMPLES

The inventors hypothesized that cis-encoding proteins from viruses that are known to inhibit the innate recognition of saRNA would dampen the innate sensing and enhance both the protein expression and immunogenicity of saRNA vaccines. Thus, the inventors designed and tested a range of RNA replicons containing innate inhibiting proteins (IIPs) and a gene of interest, and then characterized whether these replicons enhance both intracellular and secreted protein expression (encoded by the gene of interest).

Materials and Methods

Cloning of Innate Inhibitory Proteins (IIP) Replicons

Self-amplifying RNA encoding firefly luciferase, Gaussia luciferase, enhanced green fluorescent protein (eGFP), rabies glycoprotein (RABV) and the replicase derived from the Venezuelan equine encephalitis were cloned into a plasmid vector, as previously described (53). The library of interferon inhibiting proteins was cloned into these vector backbones as part of the gene of interest (fLuc, GLuc, eGFP or RABV) with a T2A cleavage site (GenBank accession #AAC97195.1). The interferon inhibiting proteins can be found with the following GenBank accession numbers: HSV-2 Us1 (Z86099.2), HSV-1 Us1 (AW069381.1), HSV-1 Us11 (YP_009137147.1), OV20.0L (AF053969.1), BVDV Npro (AIE38066.1), PIV-5 V (YP_138513.1), MERS-CoV M (AHC74104.1), MERS-CoV ORF4a (AHC74090.1), Langat virus NS5 (AF253420) and influenza virus NS1 (DQ508893.1). For studies in mice, the PIV-5 V protein with an N100D mutation was used (45).

In Vitro Transcription of saRNA

Self-amplifying RNA was produced using in vitro transcription. Plasmid DNA (pDNA) was transformed into *Escherichia coli* (*E. coli*) (New England BioLabs, UK) and cultured in 100 mL of Luria Broth (LB) with 100 g/mL of carbenicillin (Sigma Aldrich, UK). The pDNA was subsequently isolated using a Plasmid Plus MaxiPrep kit (QIAGEN, UK) and the final concentration of pDNA was measured on a NanoDrop One (ThermoFisher, UK). pDNA was linearized using MluI for 3 h at 37° C. RNA for in vitro transfections was prepared using 1 μg of linearized pDNA template in a mMachine™ T7 Transcription (Invitrogen, UK) and purified using a MEGAclear™ Transcription Clean-Up Kit (Invitrogen, UK) using the manufacturer's protocol. RNA for ex vivo and in vivo experiments was prepared as previously described (2). Uncapped RNA transcripts were produced using 1 μg of linearized pDNA template using a MEGAScript™ T7 Transcription reaction (Invitrogen, UK) for 2 h at 37° C. using the manufacturer's protocol. Transcripts were then purified by overnight LiCl precipitation at −20° C., centrifuged at 14,000 RPM for 20 min at 4° C. to pellet the RNA, rinsed once with 70% EtOH, centrifuged again at 14,000 RPM for 5 min at 4° C. and resuspended in UltraPure $H_2O$ (Ambion, UK). Purified transcripts were capped using the ScriptCap™ Cap 1 Capping System kit (CellScript, WI, USA) for 2 h at 37° C. using the manufacturer's protocol. Capped transcripts were then purified a final time with LiCl precipitation as described above, resuspended in RNA storage buffer (10 mM HEPES, 0.1 mM EDTA and 100 mg/mL trehalose) and stored at −80° C. until further use saRNA Formulation fLuc, gLuc and eGFP saRNA for protein expression experiments was complexed with 100 kDa pABOL using the titration method as previously described (2). RABV saRNA for in vivo immunogenicity experiments was complexed with 8 kDa pABOL. Briefly, RNA and pABOL were diluted in HEPES buffer (20 mM HEPES, 5 wt. % glucose in $H_2O$, pH 7.4) and combined on a NanoAssemblr benchtop formulation unit (Precision Nanosystems, Inc., Vancouver, Canada) at a volume ratio of 4:1 (RNA to polymer) with at flow rate of 10 mL/min. The final ratio of polymer to saRNA was 45:1 (w/w). Polyplexes were prepared fresh and used within 1 h of preparation. For co-formulations, ruxolitinib (ruxo, Selleck Chemicals, UK) was added directly to the polyplexes at the indicated doses.

In Vitro Transfections

Transfections were performed in HEK293T.17 cells (ATCC, USA), HeL cells (ATCC, USA), MRC5 cells (ATCC, USA), mouse embryonic fibroblasts (MEF) cells (SigmaAldrich, UK), RK13 rabbit kidney cells (Public Health England, UK) and LLC-MK2 rhesus macaque kidney cells (ATCC, USA). Cells were cultured in complete Dulbecco's Modified Eagle's Medium (cDMEM) (Gibco, Thermo Fisher, UK) containing 10% (v/v) fetal bovine serum (FBS), 5 mg/mL L-glutamine and 5 mg/mL penicillin/streptomycin (ThermoFisher, UK) (HEK, HeLa, MEF cells), complete Modified Eagle's Medium (cMEM) with 10% (v/v) fetal bovine serum (FBS), 5 mg/mL L-glutamine and 5 mg/mL penicillin/streptomycin (ThermoFisher, UK) (MRC5, RK13 cells) or complete Medium 199 (cM199, SigmaAldrich, UK) with 1% horse serum (Gibco, ThermoFisher, UK) (LLC cells). Cells were plated at a density of 50,000 cells per well in a clear 96-well plate 24 h prior to transfection. Culture medium was then completely removed and replaced with 50 μL of pre-warmed transfection medium (DMEM+5 mg/mL L-glutamine, MEM+5 mg/mL L-glutamine or M199). Then 100 μL of the polyplex solution (containing 100 ng of saRNA) was added to each well and allowed to incubate for 4 h. Transfection medium was then completely removed and replaced with cDMEM, cMEM or cM199. After 24 h, 50 μL of medium was removed from each well and 50 μL of ONE-Glo D-luciferin substrate (Promega, UK) was added and mixed well by pipetting. The total volume from each well was then transferred to a white 96-well plate (Costar) for analysis and quantified on a FLUOstar OMEGA plate reader (BMG LABTECH, UK). Background fluorescence from the control wells was subtracted from each well.

In Vivo Luciferase Expression in Mice

All animals were handled in accordance with the UK Home Office Animals Scientific Procedures Act 1986 and with a local ethics board and UK government approved project license (P63FE629C) and personal license (IC37CBB8F). Food and water were supplied ad libitum. Female BABL/c mice (Charles River, UK) or C57BL/6 mice (Charles River, UK), aged 6-8 weeks, were housed in groups (n=5 per cage) and housed in a fully acclimatized room.

Mice were injected intramuscularly (IM) with either 5 μg of fLuc saRNA in both hind legs or 5 μg of GLuc in one hind leg, complexed with pABOL in a total volume of 50 μL. After 3, 4, 7, 10 or 14 days the mice were imaged for fLuc as previously described (54, 55) or blood was collected for GLuc analysis using a Gaussia Luciferase Glow Assay kit (Pierce, Thermo Scientific, UK) according to the manufacturer's protocol. The protein expression in the sera was quantified on a FLUOstar OMEGA plate reader (BMG LABTECH, UK). Background fluorescence from the control wells was subtracted from each well. For fLuc analysis, the mice were injected intraperitoneally (IP) with 150 μL of XenoLight RediJect D-luciferin substrate (PerkinElmer, UK) and allowed to rest for 10 min. Mice were then anesthetized using isoflurane and imaged on an In Vivo Imaging System (IVIS) FX Pro (Kodak Co., Rochester, NY, USA) equipped with Molecular Imaging software version 5.0 (Carestream Health, USA) for 2 min. Signal from each injection site was quantified using Molecular Imagine software and expressed as total flux (p/s).

In Vivo gLuciferase Expression in Mice

Female BALB/c mice or C57BL/6 mice (Charles River, UK) 6-8 weeks of age were placed into groups (n=5) and housed in a fully acclimatized room. Mice were injected intramuscularly (IM) in one hind leg with 5 μg of gLuc in a total volume of 50 μL. After 3, 7 and 14 days the mice were bled via the tail vein. The blood was allowed to clot and centrifuged for 5 min at 10,000 RPM and the sera removed. The serum from all timepoints was then assayed on a single 96-well white plate (Costar) using the Pierce™ Gaussia Luciferase Glow Assay Kit using 20 μL of sera and 100 uL of Working Solution prepared according to the manufacturer's protocol. The luminesce was analysed a FLUOstar Omega plate reader (BMG LABTECH, UK) and background from naïve animals was subtracted from each sample.

Vaccination of Mice, Rats and Rabbits.

BALB/c mice, Sprague Dawley rats and New Zealand white rabbits were immunized with 1 μg (mice) or 20 μg (rats, rabbits) of RABV-encoding saRNA formulated with pABOL in a total volume of 50 μL (mice) or 100 μL (rats, rabbits) IM in one hind leg. A boost injection was given 4 weeks after the initial prime. Blood was collected after 0, 4 and 6 weeks from study onset and centrifuged at 10,000 RPM for 5 min. Sera was then decanted and stored at −80° C. until further analysis.

RABV-Specific ELISAs.

A semiquantitative immunoglobulin ELISA protocol was performed as previously described (56). Briefly, 0.5 μg/mL of RABV-coated ELISA plates were blocked with 1% (w/v) bovine serum albumin (BSA) and 0.05% (v/v) Tween-20 in PBS. After washing, diluted serum samples were added to the plates, incubated for 2 h. The plates were then washed and a 1:4000 dilution of anti-mouse IgG-HRP (Southern Biotech, UK) was added for the mouse ELISAs, a 1:4000 dilution of goat anti-rat IgG-HRP (Southern Biotech, UK) was added for the rat ELISAs, and a 1:10000 dilution of mouse anti-rabbit IgG-HRP (Sigma, UK) was added for the rabbit ELISAs. Mouse standards were prepared by coating ELISA plate wells with anti-mouse Kappa (1:1,000) and Lambda (1:1,000) light chains (Serotec, UK), blocking with 1% (w/v) BSA/0.05% (v/v) Tween-20 in PBS, washing, and adding purified IgG (Southern Biotech, UK) starting at 1000 ng/mL and titrating down with a 5-fold dilution series. Rat standards were prepared by coating ELISA plate wells with purified rat IgG (R & D Systems, UK) starting at 1000 ng/mL and titrating down with a 5-fold dilution series.

Rabbit standards were prepared by coating ELISA plate wells with a 1:1250 anti-rabbit IgG Fe (Milipore), blocking with 1% (w/v) BSA/0.05% (v/v) Tween-20 in PBS, washing, and adding purified rabbit IgG (AbD Serotech, UK) starting at 1000 ng/mL and titrating down with a 5-fold dilution series. Samples and standard were developed using 3,3',5, 5'-tetramethylbenzidine (TMB). The reaction was stopped after 5 min with stop solution (Insight Biotechnologies, UK). Absorbance was read on a spectrophotometer (VersaMax, Molecular Devices, UK) with SoftMax Pro GxP v5 software.

RABV Microneutralization Assay.

Pseudotyped rabies microneutralization was performed on week 0, 4 and 6 samples. BHK-21 cells were seeded at 10,000 cells/well in cDMEM in a 96-well plate. Sera was heat-inactivated at 56° C. and then diluted in a 1:5 serial dilution in cDMEM. Samples were then diluted with an equal volume of pseudo-virus at a concentration of 100 $TCID_{50}$ in 50 μL, incubated for 1 h at 37° C. and then added to BHK-21 cells and cultured for 48 h at 37° C. Cells were then lysed and luciferase activity was quantified using a Bright-Glo luciferase assay (Promega, UK). The total volume from each well was then transferred to a white 96-well plate (Costar) for analysis and quantified on a FLUOstar OMEGA plate reader (BMG LABTECH, UK) and the $IC_{50}$ was calculated for each sample.

Human Skin Explant Culture and Injection.

For ex vivo studies, surgically resected specimens of human skin tissues were collected at Charing Cross Hospital, Imperial NHS Trust, London, UK. All tissues were collected after receiving signed informed consent from patients undergoing elective abdominoplasty or mastectomy surgeries, under protocols approved by the Local Research Ethics Committee (MED_RS_11_014) at Imperial College London. Skin tissue was refrigerated until use and was excised into 1 cm$^2$ section and cultured in 12-well plates with 2 mL of cDMEM at 37° C. with 5% $CO_2$. Explants were injected intradermally (ID) using a Micro-Fine Demi 0.3 mL syringe (Becton Dickinson, UK) with a dose of 2 μg of saRNA in a total volume of 50 μL. Media was replaced daily for the duration of culture.

Flow Cytometry

After 72 h from the time of injection, skin explants were trimmed to remove the subcutaneous fat layer, and the epidermal and dermal layers were minced well with scissors and incubated in 2 mL DMEM supplemented with 1 mg/mL collagenase P (Sigma Aldrich, UK) and 5 mg/mL dispase II (Sigma Aldrich, UK) for 4 h at 37° C. on a rotational shaker. Digests were then filtered through a 70 μm cell strainer and centrifuged at 1,750 RPM for 5 min. Cells were then resuspended in 100 μL of FACS buffer (PBS+2.5% FBS) and stained with fixable aqua live/dead cell stain (ThermoFisher, UK) diluted 1:400 in FACS buffer for 20 min on ice. Samples were then washed with 1 mL of FACS buffer, centrifuged at 1,750 RPM for 5 min and stained with a mixture of the following antibodies: CD3-V450 (BioLegend, UK), CD14-Qdot605 (BioLegend, UK), CD19-BV650 (BioLegend, UK), CD56-BV711 (BioLegend, UK), CD1a-PerCP-eFluor710 (BioLegend, UK), CD11c-PE (BioLegend, UK), CD90-PE-Cy7 (BioLegend, UK) and CD45-AF700 (BioLegend, UK). Samples were them washed with 1 mL of FACS buffer, centrifuged at 1,750 RPM for 5 min, resuspended in 250 μL of PBS, and then fixed with 250 μL of 3% paraformaldehyde for a final concentration of 1.5% paraformaldehyde, and refrigerated until flow cytometry analysis. Samples were analyzed on a LSRFortessa (BD Biosciences, UK) flow cytometer with FACSDiva software (BD Biosciences, UK) with 100,000 acquired cell events. Gating strategy was performed as previously described (58) and phenotypic identity of GFP+ cells was quantified using FlowJo version 10 (FlowJo LLC, Oregon, USA). t-Distributed Stochastic Neighbor Embedding (tSNE) analysis of unsupervised clusters of live cells was performed in FlowJo using 1000 iterations, a perplexity of 30, a learning rate of 15196, the Exact (vantage point tree) KNN algorithm and the Barnes-Hut gradient algorithm.

SARS-CoV-2 Glycoprotein In Vitro Work

The inventors used a plasmid vector to synthesize a self-amplifying RNA (saRNA) replicon, based on the Trinidad donkey Venezuelan equine encephalitis virus strain (VEEV) alphavirus genome. The viral structural proteins driven from the sub-genomic promoter were replaced by the surface 'spike' glycoprotein of the novel severe acute respiratory syndrome coronavirus 2 (SARS-CoV-2): GenBank accession number: QHD43416.1. We synthesized oligonucleotide fragments encoding the SARS-CoV-2 gene using oligonucleotide strings (GeneArt, Germany) and assembled these into the plasmid vector with the Gibson assembly method (NEB Ltd, UK). In a further modification of the SARS-CoV-2 replicon vector an oligonucleotide string was synthesised (GeneArt, Germany) encoding the MERS-CoV ORF4a (AHC74090.1), and inserted 3' to the SARS-CoV-2 coding region connected using a variant of the furin/T2A sequence (SEQ ID No: 26) in a continuous open reading frame, generating a new SARS-CoV-2 ORF4a vector. Cells were transfected separately with both the SARS-CoV-2 and the SARS-CoV-2 ORF4a saRNA and then stained with a polyclonal antibody to examine expression. Briefly, twenty-four hours post transfection, cells were harvested and resuspended in 1 mL of FACS buffer (PBS+2.5% FBS) at a concentration of $1 \times 10^7$ cells/mL. One hundred microliters of the resuspended cells were added to a FACS tube and stained with 50 µL of Live/Dead Fixable Aqua Dead Cell Stain (Thermo Fisher Scientific, UK) at a 1:400 dilution on ice for 20 min. Cells were then washed with 2.5 mL of FACS buffer and centrifuged at 1750 RPM for 7 min. After centrifugation, cells were stained with 2.5 µg of a SARS-CoV spike protein polyclonal antibody (PA1-41165, Thermo Fisher Scientific, UK) for 30 min on ice before washing with 2.5 mL of FACS buffer and centrifuging at 1750 RPM for 7 min. Cells were then stained with 0.4 µg of FITC goat anti-rabbit IgG (BD Pharmigen, UK) for 30 min on ice. After incubation, cells were washed with 2.5 mL of FACS buffer, centrifuged at 1750 RPM for 7 min and resuspended with 250 µL of PBS. Cells were fixed with 250 µL of 3% paraformaldehyde for a final concentration of 1.5%. Samples were analyzed on a LSRForterssa (BD Biosciences, UK) with FACSDiva software (BD Biosciences, UK). Data were analyzed using FlowJo Version 10 (FlowJo LLC, USA) and the Median Flourescence Intensity (MFI) of the positive population of cells was measured, with the negative/positive cut-off being set on cells that were gated as live and single and that were mock transfected using the same methodology as above but without the SARS-CoV-2 or SARS-CoV-2 ORF4a replicon saRNA.

Statistical Analysis.

Graphs and statistics were prepared in GraphPad Prism, version 8. Statistical differences were analyzed using either a two-way ANOVA or a Kruskal-Wallis test adjusted for multiple comparisons, with $p<0.05$ used to indicate significance.

Results and Discussion

RNA replicons have been postulated to be potential tools for the delivery and expression of genes of interest for vaccines and therapeutics. However, double stranded RNA (dsRNA) is detected intracellularly by innate sensing mechanisms that trigger signalling cascade that inhibits protein translation. As a consequence, expression of genes of interest encoded in the replicon is significantly impaired and thus the therapeutic potential of RNA replicons is limited.

The inventors set out to overcome this problem by developing RNA replicons that encode innate inhibiting proteins to abate the innate recognition of saRNA. The only previously published approach to abating the interferon response with saRNA used interferon inhibiting proteins from the vaccinia virus, E3, K3 and B18. However, in this study the interferon inhibiting proteins were delivered and formulated as separate mRNA molecules that were combined with the saRNA. This requires the manufacture of both saRNA and mRNA and necessitates the use of 3-6 times as much vaccinia mRNA as replicon RNA to ensure co-delivery into the same cells and provide any observable enhancement in protein expression. Furthermore, the kinetics of expression differ for mRNA and saRNA such that any beneficial effects of the IIPs expressed from mRNA would be of short duration in comparison the accompanying replicon.

In view of the current difficulties of using saRNAs in therapy, the inventors have designed a novel saRNA that would limit the immune response to them more effectively than prior art methods, increasing their utility in vaccination and therapeutics.

Use of PIV-5 and ORF4a as Novel IIPs

Figure 1:
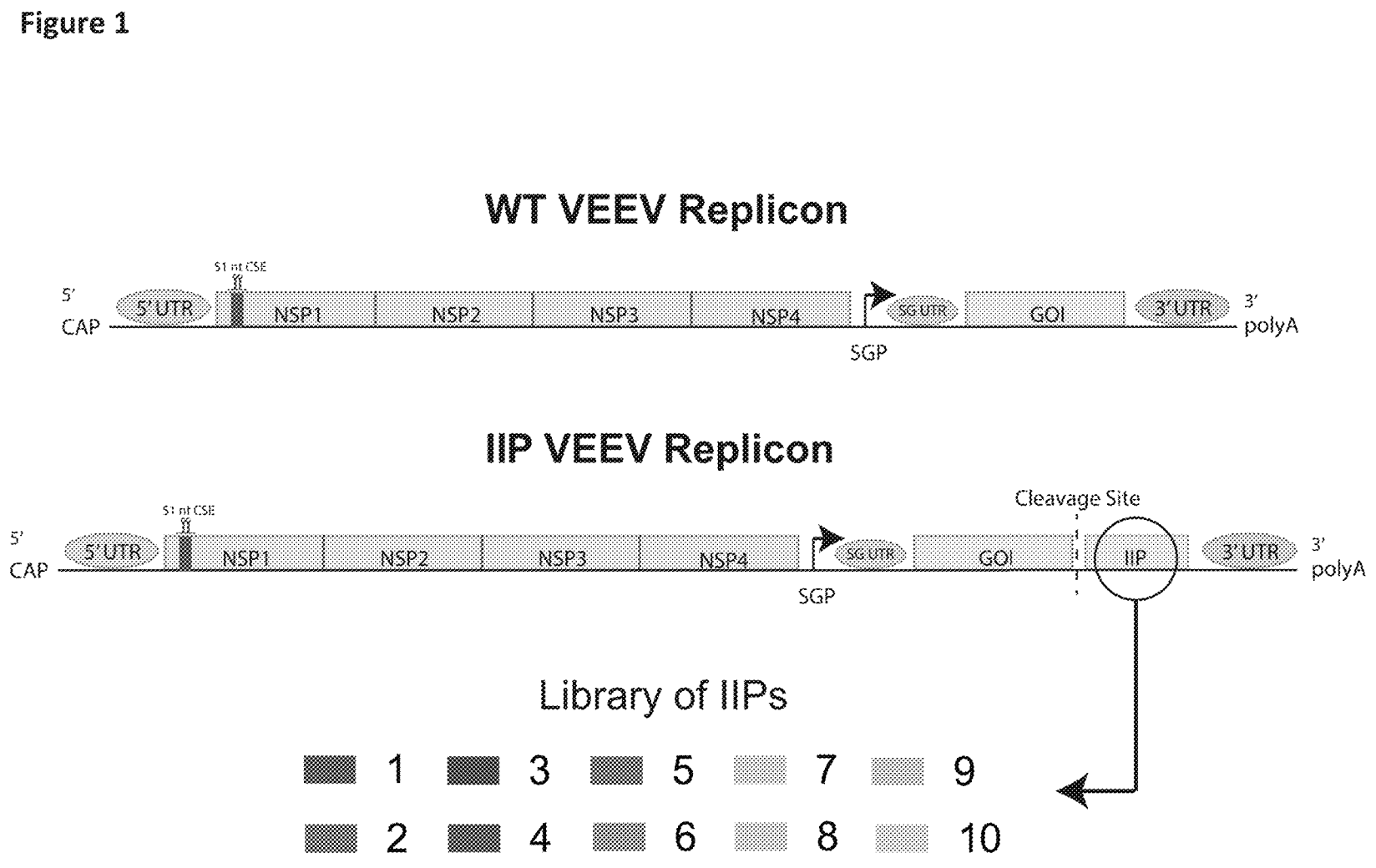

PIV-5 and ORF4a are known to block MDA-5, a cytoplasmic RNA helicase that signals through an adaptor molecule called MAVs that results in the induction of interferon regulatory factor 3 and 7 (IRF3 and IRF7), which respectively leads to the production of restriction factors that decrease the translation of the introduced synthetic saRNA (FIG. 1). These two IIPs were identified in an initial in vitro screen of 10 IIPs from a range of different viruses.

1. HSV-2 Us1—inhibits IFN-β production by suppressing association of IRF-3 with IFN-β promoter [1]
2. HSV-1 Us1 (modulatory factor from HSV-1)
3. HSV-1 Us11—prevent RIG-I signalling [2,3]
4. OV20.0L—binds to dsRNA and inhibits both PKR & PACT, blocking RIG-I signalling [4,5]
5. BVDV Npro: blocks and IRF3 phosphorylation and S100A9 signalling [6, 7]
6. PIV5 V: blocks MDA-5 and IRF3 by binding to MDA-5 [8,9]
7. MERS-CoV M: interacts with TRAF3 and disrupt TRAF3-TBK1 association leading to reduced IRF3 activation [10-12]
8. MERS-CoV ORF4a: binds to dsRNA (has a preference for long RNA), suppresses PACT triggering of MDA5 and RIG-I, PKR and stress response [13,14].
9. Langat virus NS5: down regulates IFNA1R, impairs JAK-STAT signalling [15-16]
10. Influenza NS1: binds to dsRNA, blocks RIG-I signalling [17]

Figure 2:
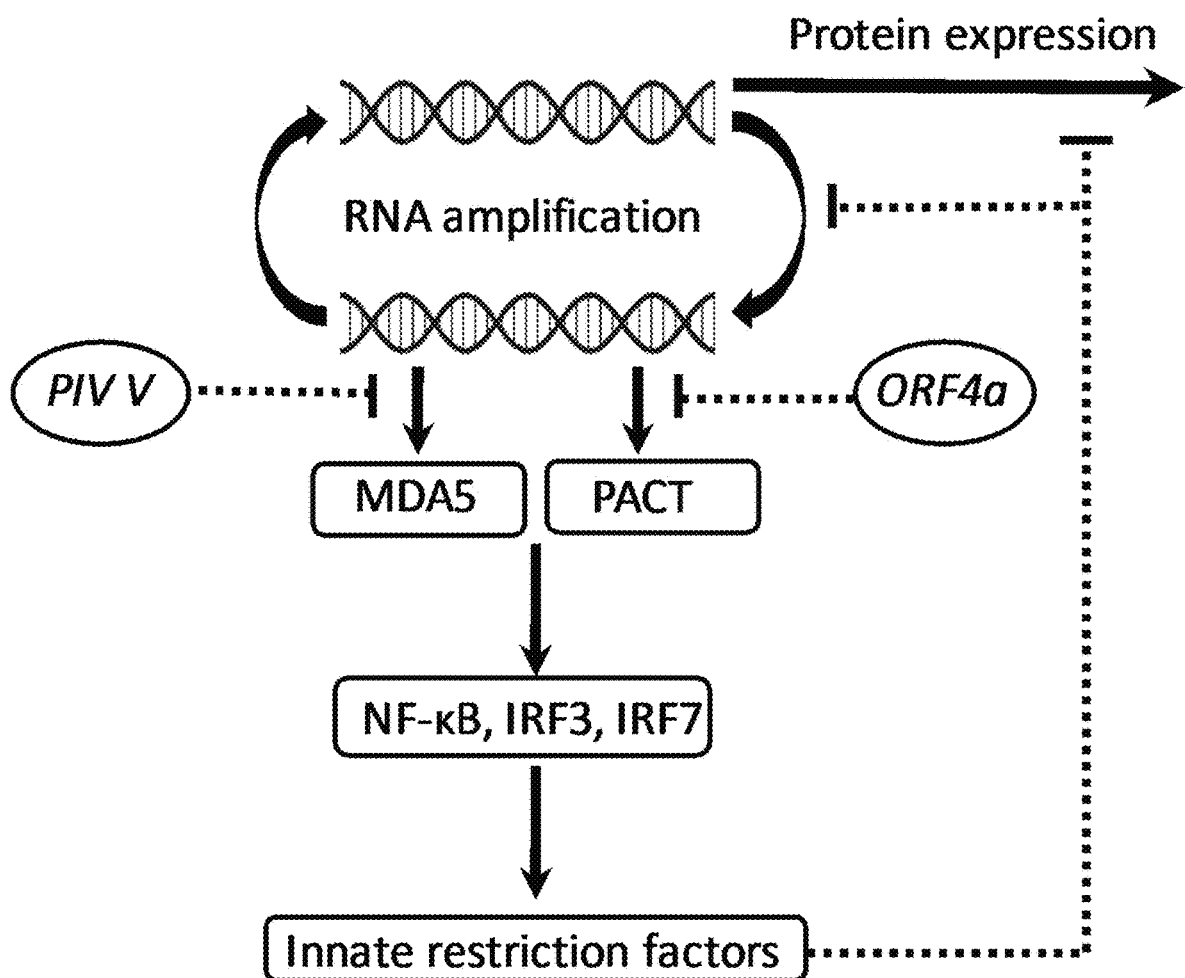
Figure 3A:
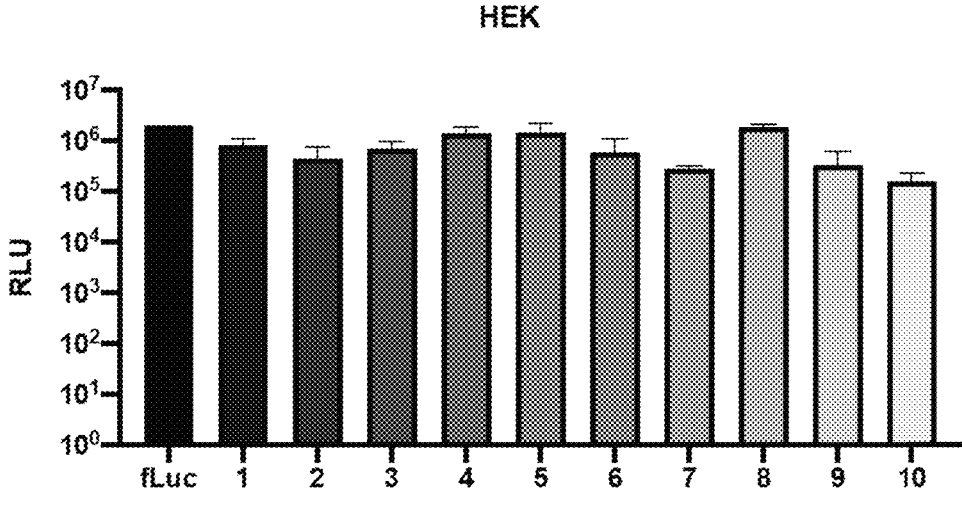
Figure 3A:
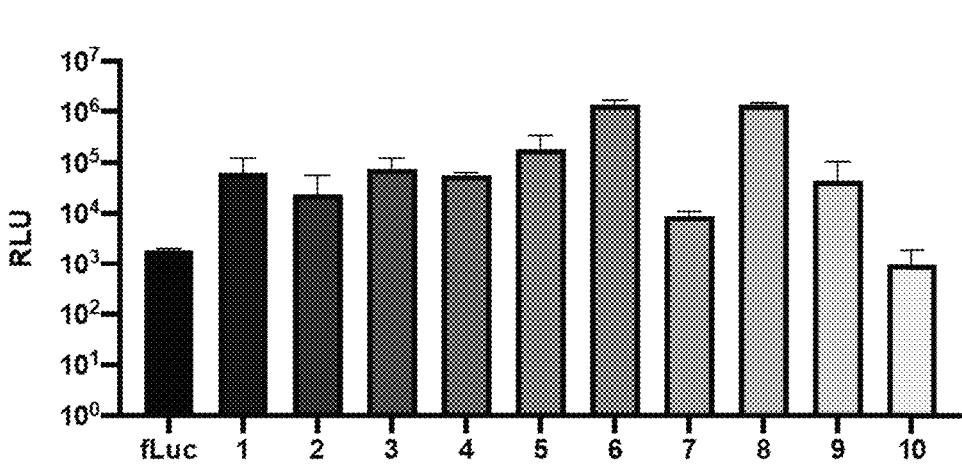
Figure 3A:
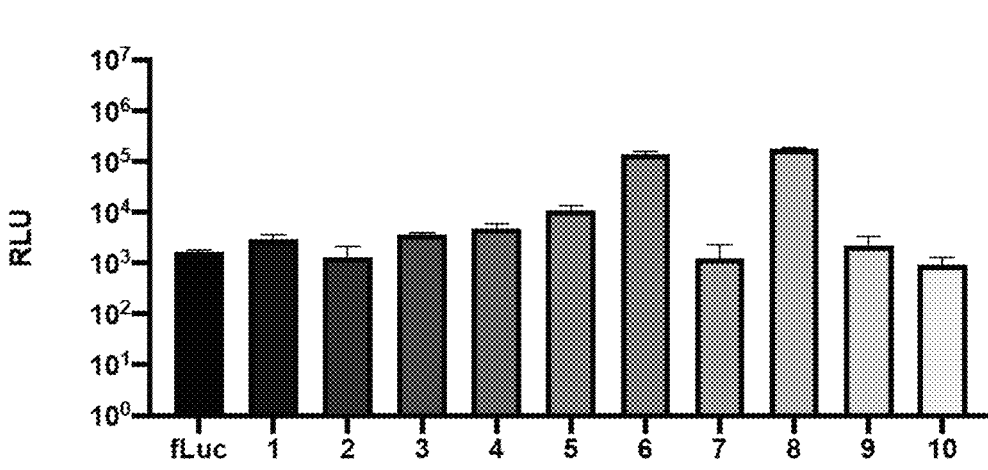
Figure 3B:
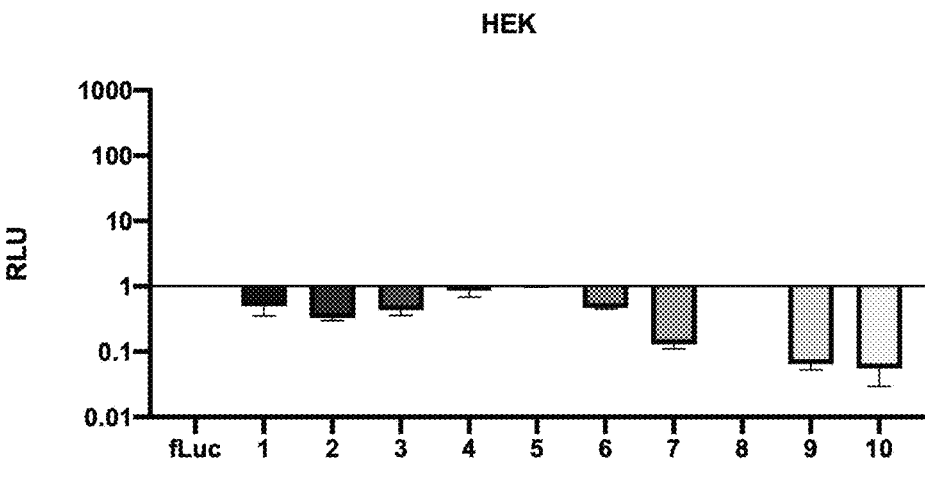
Figure 3B:
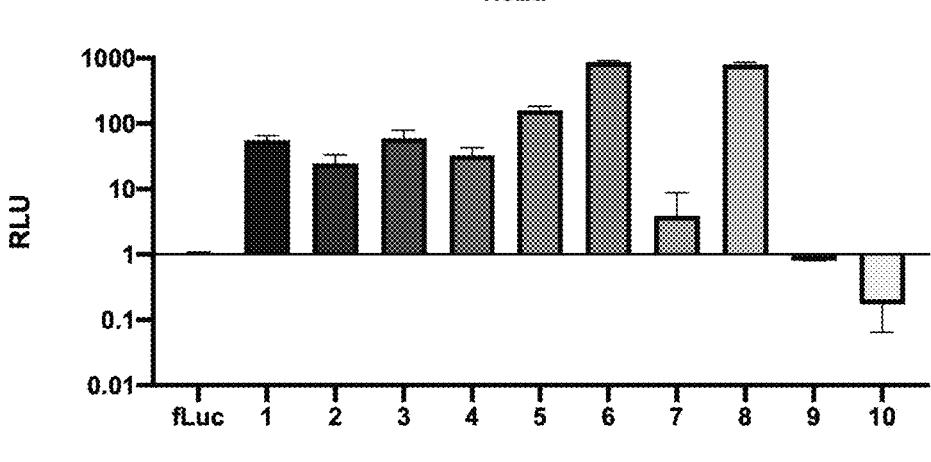
Figure 3B:
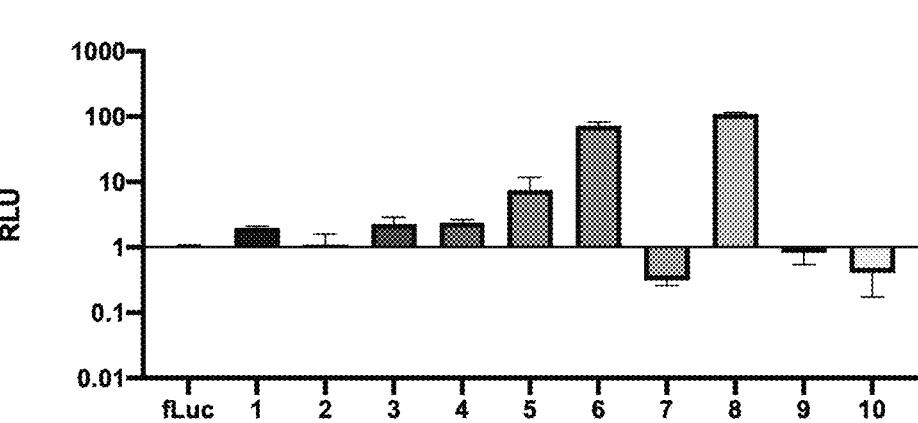
Figure 4:
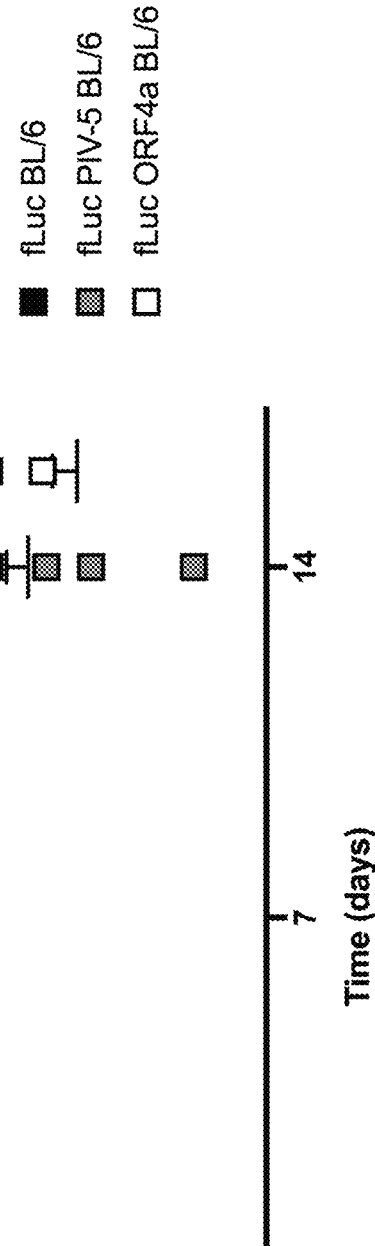
FIG. 4 shows screening of IIP-encoding replicons (#6 and #8) in BALB/c and BL/6 mice, using firefly luciferase as a reporter protein. BL/6 mice are known to express more IFN than BALB/c, and thus the IIPs enabled higher luciferase expression at 3 days, and longer expression, lasting >14 days.

These IIPs were incorporated within the inventor's standard VEEV saRNA replicon (FIG. 1) together with fLuciferase as the GOI and used as a marker of expression. The constructs were assessed in three human cell lines: HEK293T cells that have impaired innate sensing pathways, HeLa cells and primary MRC5 embryonic epithelial cells (FIGS. 3a and b). All of the IIP candidate saRNA replicated similarly to wild type saRNA in HEK293T cells in the absence of innate recognition. A range of IIPs (with the exception of MERS-CoV M and Influenza NS1) were able to enhance expression in HeLa cells, however the most pronounced enhancement (3 logs) was seen for PIV-V and ORF4a. Most importantly assessment in primary MRC5 cells indicated that only PIV-V and ORF4a were able to enhance luciferase expression by 2 logs. These data suggest that PIV-V and ORF4a are unique in their ability to enhance expression of the GOI in primary human cells. The identification of PIV-5 and ORF4a for inclusion in the RNA vector is based on these experimental data and their activity was not predictable given other IIPs evaluated were thought to work through similar mechanisms. To further support their use in gene delivery the inventors have conducted in vivo experiments in mice. Here the inventors have utilised Black 6 (BL6) mice, known to have a more robust innate sensing mechanism and downstream interferon response than BalBc mice, therefore comparison in the two models is instructive. The inventors assessed the relative expression of WT, PIV-5 and ORF4a replicons in BL/6 mice, using firefly luciferase (fLuc) as a reporter protein (FIG. 4).

Figure 5:
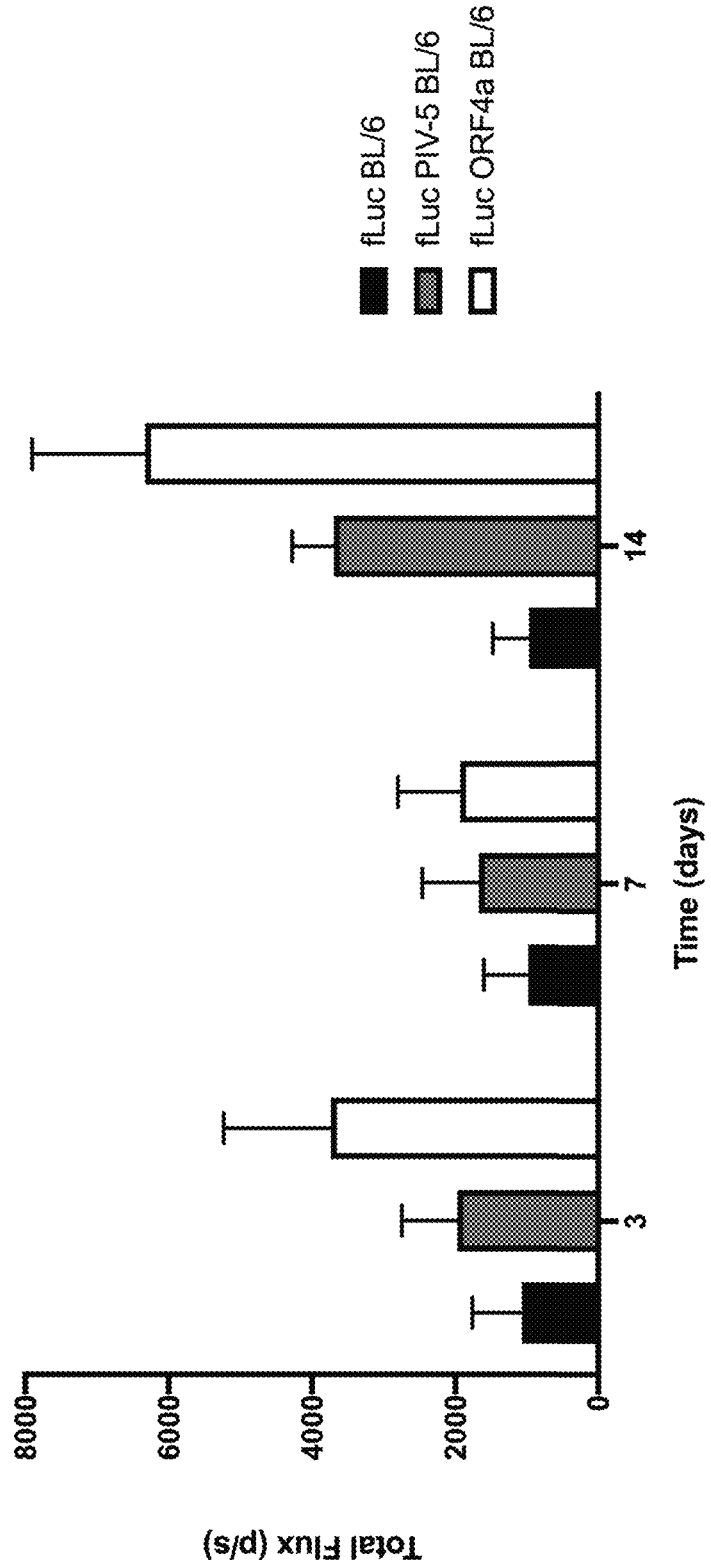
FIG. 5 shows screening of IIP-encoding replicons (#6 and #8) in BALB/c and BL/6 mice, using gaussia luciferase as a reporter protein. BL/6 mice are known to express more IFN than BALB/c, and thus the IIPs enabled longer expression of a soluble reporter protein, lasting >14 days.
Figure 6:
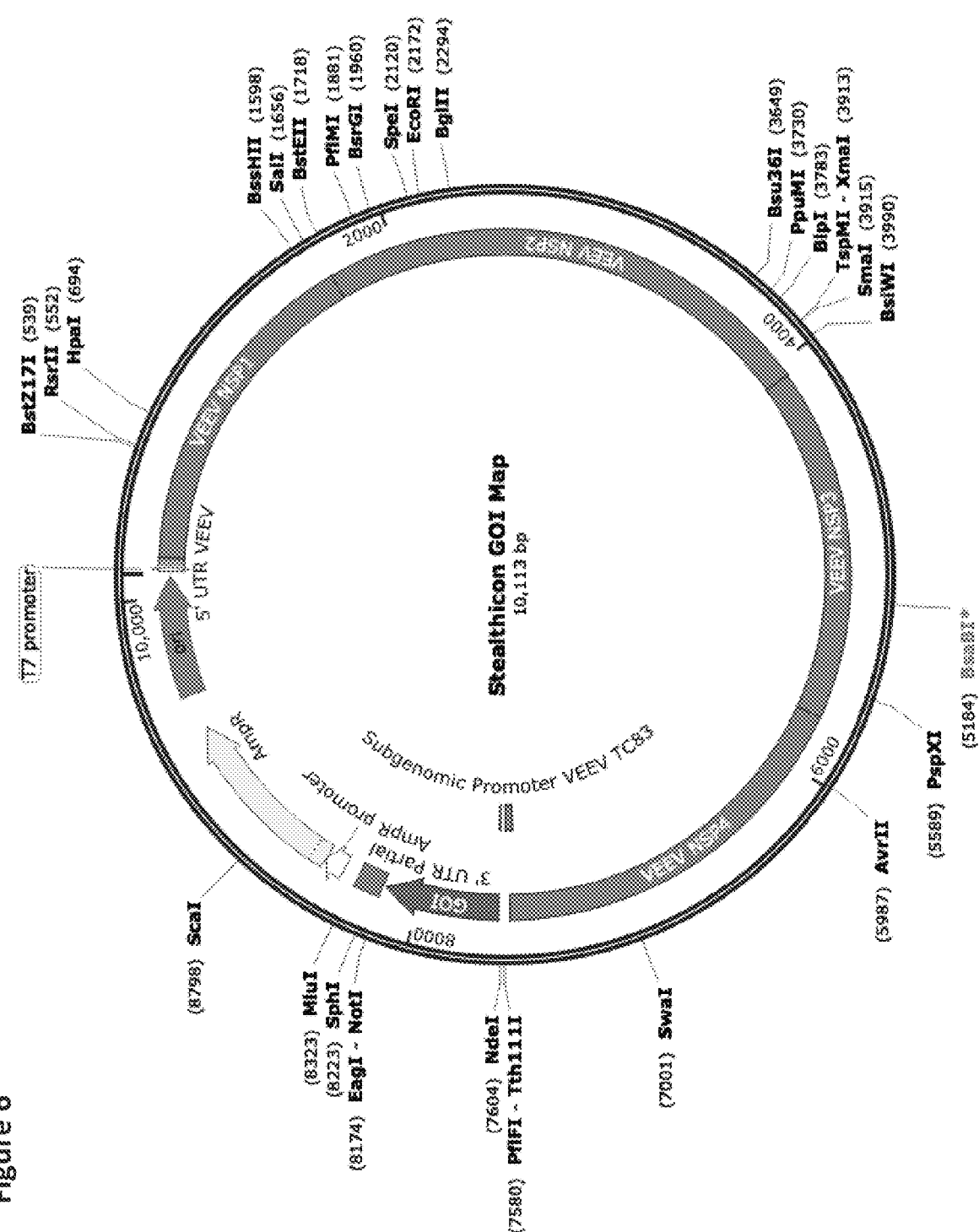
FIG. 6 shows the construct map of one embodiment of an expression vector encoding the RNA construct comprising an GOI.
Figure 7:
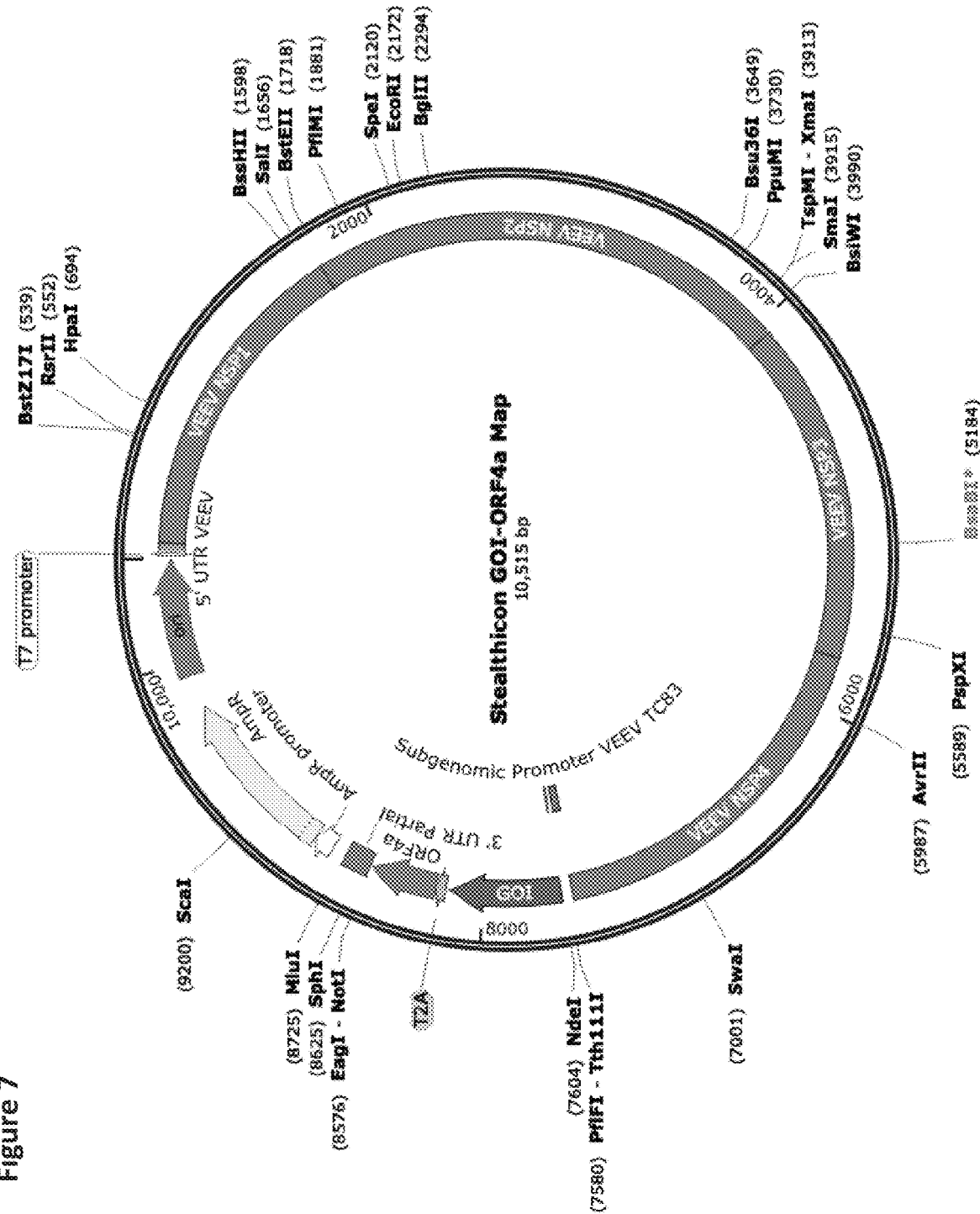
Figure 8:
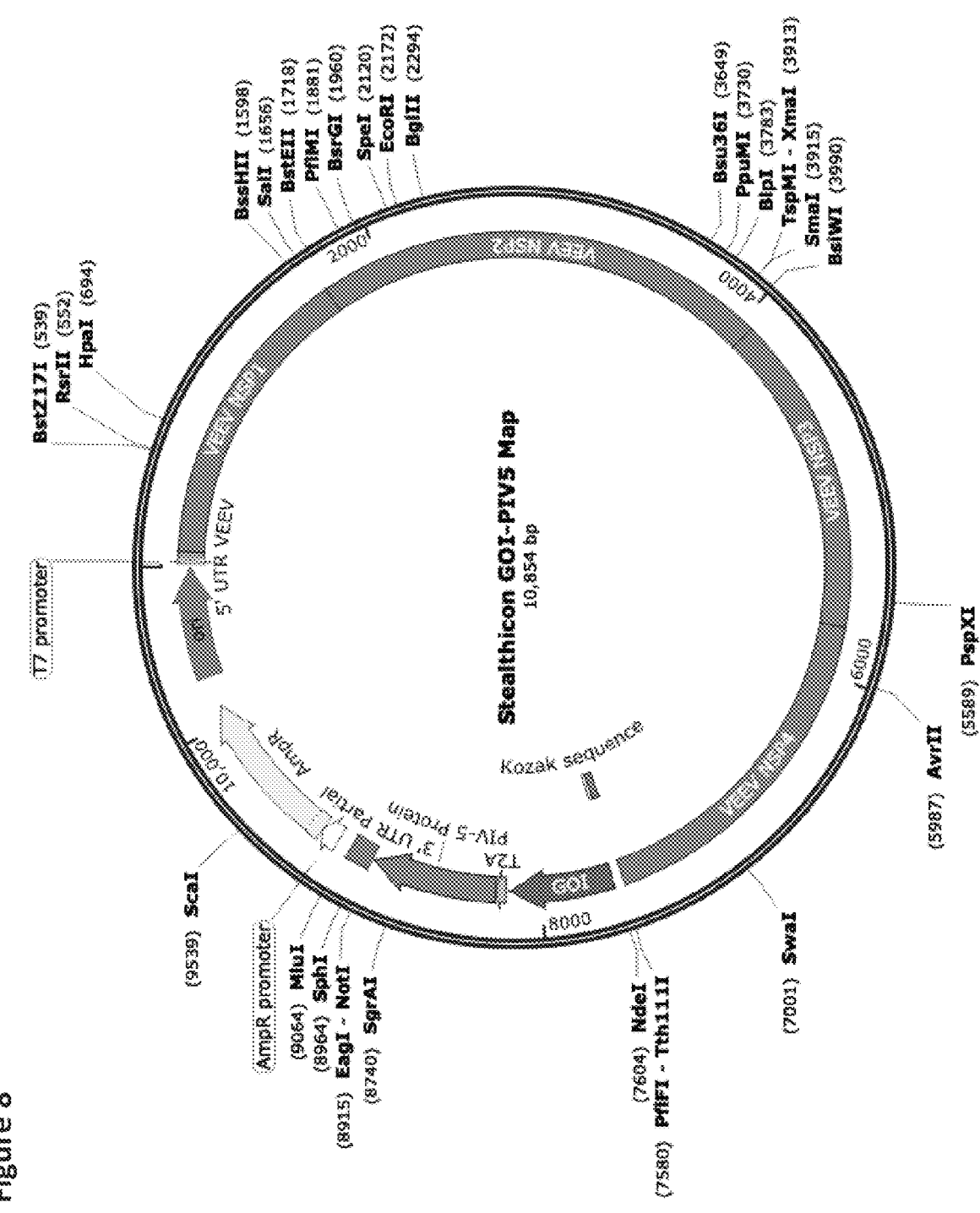
FIG. 8 shows the construct map of one embodiment of an expression vector encoding the RNA construct comprising GOI-PIV5.

As fLuc is expressed intracellularly, expression of this gene of interest is visualised as based on luciferase expression following intraperitoneally (IP) injection with the substrate D-Luciferin and is expressed as total flux (p/s) (see methods). These in vivo experiments demonstrate that PIV5 and ORF4a increased the duration of luciferase expression in BL/6 cells out to 14 days, while the WT construct was negative by this time point. In further studies, the inventors assessed the impact of these two RNA replicon constructs on the expression of gLuciferase (FIG. 5) of gLuc (as the GOI). GLuc is secreted as a soluble protein and its activity is measure in blood (see methods). These in vivo experiments demonstrate that PIV5 and ORF4a increased the duration of luciferase expression in BL/6 cells out to 14 days. Expression of gLuc as significantly higher for both PIV5 and ORF4a RNA replicons at day 14 (p=0.0244 and 0.00422, respectively). Calculation of "area under the curve" over 14 days indicated the following values he AUCs are as follows: fLuc BALBc=1950; PIV5 BALBc=2742; ORF4a BALBc=1596; fLuc BL6=2012; PIV5 BL6=4513; ORF4a BL6=6972 (total flux (p/s)). While these in vivo experiments are supportive, it is important to note that there are significant differences between humans and mice with respect to the specificity of innate restriction factors and interferon stimulated genes (of which there are >100, thus it is highly likely that these data may underestimate the likely impact in humans based on the in vitro observation see with human cell lines.

Interferon Inhibiting Proteins Enhance Protein Expression of saRNA In Vitro.

The inventors sought to determine whether the library of interferon inhibiting proteins enhanced firefly luciferase (fLuc) protein expression in vitro. They prepared a library of saRNA VEEV replicons with an IIP separated from the fLuc with a T2A cleavage site (FIG. 9a), with a variety of cytoplasmic interferon targets (Table 1), including IRF-3, MDA5, RIG-I, and JAK/STAT (FIG. 9b).

TABLE 1

Interferon inhibiting VEEV replicons and associated IFN targets.

| Construct | Pathway Target |
|---|---|
| HSV-2 Us1 | Inhibits IFN-B production by suppressing association of IRF-3 with IFN-B promoter. |
| HSV-1 Us1 | Control. |
| HSV-1 Us11 | Binds to PACT and blocks MDA5 and RIG-I signalling. |

TABLE 1-continued

Interferon inhibiting VEEV replicons and associated IFN targets.

| Construct | Pathway Target |
|---|---|
| OrfOV20.0L | Binds to dsRNA and inhibits both PKR and PACT, blocking RIG-I signalling. |
| BVDV Npro | Blocks IRF3 phosphorylation. |
| PIV-5 V | Blocks MDA-5 and IRF3 by binding to MDA-5. |
| MERS-CoV M | Interacts with TRAF3 and disrupts TRAF3-TBK1 association leading to reduced IRF3 activation. |
| MERS-CoV ORF4a | Binds to dsRNA with a preference for long RNA and suppressed PACT triggering of MDA5 and RIG-I. |
| Langat NS5 | Down regulates IFNA1R and impairs JAK/STAT signalling. |
| Influenza NS1 | Binds to dsRNA and blocks RIG-I signalling. |

The inventors then transfected the saRNA into HEK293T.17, HeLa and MRC5 cells using pABOL (FIG. 9c, Supplementary FIG. 1), a polymeric delivery system that has previously been characterized to yield relatively high protein expression but is relatively immune silent due to its bioreducible nature (2). The inventors chose these three cell lines for their variation in completeness of the IFN pathway; HEK293T.17 cells do not have a complete pathway as they lack endogenous RIG-I and MDA5 expression (37) and thus should be less sensitive to proteins affecting this pathway, whereas HeLa and MRC5 are more discriminatory (38, 39). The inventors observed that none of the IIP replicons enhanced protein expression in HEK293T.17 cells (FIG. 1c), but interestingly both the Langat and Influenza IIPs significantly decreased protein expression by 0.06-fold, with p=0.0097 and 0.0061, respectively. In HeLa cells, many of the IIPs enhanced protein expression; HSV-2, HSV-11_, HSV-1_2, Orf and BVDV ranged from 20-150-fold increase in fLuc expression. However, the PIV-5 V and MERS-CoV ORF4a proteins enhanced protein expression the most, with 796- and 893-fold, respectively, although only the PIV-5 group was statistically significant (p=0.0272) while the ORF4a group was not (p=0.0689). In MRC5 cells the inventors similarly observed the greatest enhancement from the PIV-5 V and MERS-CoV ORF4a proteins, with 72- and 10-fold greater fLuc expression with p=0.0485 and 0.025, respectively. There was good agreement between expression levels from two separately made batches of RNA (FIG. 14) in all cell types and for each construct.

The inventors further investigated how two mutations to the PIV-5 V and MERS-CoV ORF4a protein affected protein expression in mouse (MEF), rabbit (RK13), nonhuman primate (LLC) and human cells (MRC5) (FIG. 15a-d). The R172A mutation in PIV-5 V abrogates ability to block MDA5 but not STAT (40), and the K63A/K67A mutations in MERS-CoV ORF4a block binding to dsRNA (41). The inventors observed that the PIV-5 V and MERS-CoV ORF4a proteins did not enhance protein expression in MEF or RK13 cells. The MERS-CoV ORF4a protein did enhance protein expression in LLC and MRC5 cells (FIG. 15 c,d), and the K63A/K67A mutation greatly decreased the protein expression. The PIV-5 V protein enhanced protein expression in MRC5 cells but not LLC cells, and the R172A mutation decreased protein expression in MRC5 cells. Overall these data indicate that the PIV-5 V and MERS-CoV ORF4a proteins enhanced protein expression in interferon-competent human cells, and mutating the proteins with the K63A/K67A and R172A substitutions muted saRNA expression.

MERS-CoV ORF4a Protein Partially Abates Increasing Dose Nonlinearity In Vivo.

Given the enhancement of in vitro protein expression from the PIV-5 V and MERS-CoV ORF4a proteins, the inventors then sought to determine whether these constructs could enhance protein expression in vivo and abate the nonlinearity of increasing the dose of saRNA. The inventors tested saRNA encoding both firefly luciferase, an intracellular protein, and Gaussia luciferase, a secreted protein in vivo (Table 2).

TABLE 2

| Area under the curve (AUC) of total luciferase expression in BALB/c and C57BL6/J over the course of 14 days, with n = 5. | | | | | |
|---|---|---|---|---|---|
| | BALB/c | | | C57BL/6 | | |
| | WT | +PIV-5 | +MERS-CoV_2 | WT | +PIV-5 | +MERS-COV_2 |
| fLuc | 434210 ± 173923 | 235231 ± 103702 | 301294 ± 170309 | 263783 ± 191231 | 246182 ± 87859 | 453411 ± 331433 |
| gLuc | 1950 ± 1270 | 2742 ± 493 | 1596 ± 915 | 2012 ± 1373 | 4513 ± 1651 | 6972 ± 2789 |

The inventors chose to test these constructs in both BALB/c and C57BL/6 mice due to differences in the interferon generating capacities: BALB/c are poor producers of IFN whereas C57BL/6 mice have been previously found to be the high producers of IFN-$\alpha$/p and IFN-$\gamma$ (42), similar to the disparity of HEK293T.17 and HeLa/MRC5 cells in vitro. Inventors observed that incorporating the PIV-5 V and MERS-CoV ORF4a proteins did not enhance protein expression of either fLuc or GLuc in BALB/c mice (Table 2, FIG. 16). The inventors observed slight enhancement of total area under the curve (AUC) protein expression of fLuc in C57BL/6 mice with the MERS-CoV ORF4a protein, and GLuc with both the PIV-5 V and MERS-CoV ORF4a proteins, although the differences were not statistically significant.

The inventors have previously observed that increasing the dose of saRNA eventually results a lower level of protein expression, and thus sought to characterize whether the MERS-CoV ORF4a protein could abate the nonlinear dose dependency of saRNA in vivo. The inventors tested doses of 0.2, 2 and 20 $\mu$g of the wild-type fLuc and the fLuc+MERS-CoV ORF4a replicon and quantified protein expression at days 7 and 10 after intramuscular (IM) injection (FIG. 10). The inventors observed that both constructs had similar protein expression (~5000 p/s) at a dose of 0.2 $\mu$g after 7 days, and protein expression increased for both (to ~50,000 p/s for the WT and ~200,000 p/s for the MERS-CoV ORF4a construct), when the dose was increased to 2 $\mu$g, although the incorporation of MERS-CoV ORF4a protein enhanced protein expression 4-fold, with p=0.0029. Interestingly, both constructs exhibited lower protein expression at a dose of g after 7 days, although the WT was 18-fold lower than the MERS-CoV construct, with p<0.0001. After 10 days the protein expression levels had equalized for the 2 $\mu$g dose, with no expression observed in the 0.2 and 20 $\mu$g doses. Without wishing to be bound to any particular theory, these data indicate that the MERS-CoV ORF4a protein enables partial rescue of the nonlinear dose dependence of saRNA in vivo.

Ruxolitinib Enhances Protein Expression of saRNA In Vivo.

Given the role of the JAK/STAT pathway in the downstream interferon response, the inventors then sought to characterize how combining saRNA, the MERS-CoV ORF4a interferon inhibiting protein and ruxolitinib, a potent, selective inhibitor of JAK1 and JAK2 protein kinases (36), affects protein expression in vivo (FIG. 3). They injected mice IM with 5 $\mu$g of saRNA encoding fLuc f MERS-CoV ORF4a with or without co-formulation with 100 $\mu$g of ruxolitinib and quantified protein expression 4, 7, 10 and 14 days after injection. After 4 days (FIG. 11a), both of the formulations containing ruxolitinib had slightly higher protein expression (~$10^6$ p/s) compared to the WT or MERS-CoV ORF4a constructs (~$5 \times 10^5$ p/s), although it was not statistically significant. However, after 7 days both of the formulations containing ruxolitinib had higher protein expression compared to the saRNA-only parallel groups, with p=0.0347 and 0.0447, respectively. By day 10 these groups were still slightly elevated, but the difference was no longer statistically significant. After 14 days there was no protein expression observed in the saRNA groups without ruxolitinib, and only a few positive samples for the ruxolitinib groups. Without wishing to be bound to any particular theory, these data indicate that ruxolitinib enables a profound increase in saRNA protein expression but that there is no additive effect between the MERS-CoV ORF4a protein and ruxolitinib when combined.

PIV-5 V and MERS-CoV ORF4a Proteins Abate Increasing Dose Nonlinearity Ex Vivo in Human Skin Explants.

As the inventors observed that the IIPs exhibit differences in protein expression depending on the species of the cell type in vitro, they sought to test the saRNA IIP constructs in a more clinically relevant human skin explant model. The inventors characterized both the quantity (% of eGFP+ cells) and the quality of protein expression (median eGFP fluorescent intensity per cell) in resident human skin cells with incorporations of the PIV-5 V and MERS-CoV ORF4a proteins (referred to in the Figure as MERS-CoV_2), as well as co-formulation with ruxolitinib (FIG. 12). The inventors tested doses of 0.2, 2 and 20 $\mu$g of the eGFP saRNA with the PIV-5 V and MERS-CoV ORF4a proteins (FIG. 12a,b), and observed that increasing the dose of the WT construct from 0.2 to 2 $\mu$g resulted in an increase of the percentage of eGFP+ cells from 10% to 18%, but when the dose was increased to 20 $\mu$g the percentage of eGFP+ cells plummeted to ~5%. However, for the PIV-5 and MERS-CoV ORF4a constructs, there was a linear dose increase with increasing dose of saRNA. The 0.2 $\mu$g dose similarly resulted in ~12% of eGFP+ for both of these constructs, which further increased to 15% at 2 $\mu$g and 25% at 20 $\mu$g, at which point both the PIV-5 and MERS-CoV ORF4a constructs had a statistically significantly higher percentage of eGFP+ cells, with p<0.0001 for both. Interestingly, neither the dose nor incorporation of PIV-5 or MERS-CoV ORF4a proteins affected the eGFP MFI, which was ~350 for all samples (FIG. 12b).

The inventors further characterized which cells were expressing the saRNA using t-Distributed Stochastic Neighbour Embedding, a type of principle component analysis for flow cytometry data that allows for visualization by unsupervised clustering of cells with overlaid defined protein and phenotype gating (FIGS. 17-25) (43). The inventors observed that at the highest dose of saRNA (20 µg), the PIV-5 V and MERS-CoV ORF4a proteins enabled protein expression in the immune cells, including T cells, dendritic cells, monocytes, B cells, Langerhans cells, leukocytes and NK cells, as opposed to resident epithelial cells and fibroblasts.

Next the inventors tested how incorporating doses of ruxolinitib, ranging from 0-100 µg, affected saRNA expression in human skin resident cells. They observed that co-formulation of ruxolitinib with saRNA did not have any effect on the percentage of eGFP+ cells (FIG. 4c), although there was a slight trend that increasing the dose of ruxolitinib actually decreased the percentage of eGFP+ cells from ~8% to ~5%. However, the inventors did observe a profound effect on the per-cell quality of eGFP expression (FIG. 12d); increasing the dose of ruxolitinib increased the eGFP MFI from ~100 to ~2000 at a 10 µg dose of ruxolitinib, although the MFI decreased to ~1000 with a 100 µg dose of ruxolitinib. Similarly to the cells expressing the saRNA PIV-5 and MERS-CoV ORF4a proteins, they found that ruxolitinib enhanced protein expression in the immune cells, as opposed to epithelial cells and fibroblasts, and specifically increased uptake in T cells, Langerhans cells, leukocytes and NK cells (FIG. 26 a,b).

Taken together, and without wishing to be bound to any particular theory, these data show that the IIP replicons enhance expression in immune cells by increasing the percentage of cells expressing saRNA, while ruxolitinib enhances protein expression on a per cell basis.

MERS-CoV ORF4a Protein Enhances Immunogenicity of RABV Glycoprotein In Vivo in Rabbits Because protein expression of nucleic acid formulations is not always a direct predictor of immunogenicity (2), the inventors then sought to characterize the immunogenicity of a model protein acting as a therapeutic biomolecule, i.e. the rabies glycoprotein (RABV), represented by the GeneBank ID No: NP_056796.1, when combined with the MERS-CoV ORF4a protein (acting as the innate inhibitor protein or IIP) in an saRNA construct of the invention. The RABV protein was additionally used with an amino acid substitution, the F318V modification that prevents binding to the cellular p75NTR surface receptor. The inventors injected rabbits with a primary dose of 20 µg of saRNA and a boost after 4 weeks, and then sampled the RABV-specific IgG antibodies in their blood after 0, 4, and 6 weeks (FIG. 13a). The inventors observed that all the rabbits for both the wild type and MERS-CoV ORF4a constructs seroconverted after a single injection. The IgG titers for the MERS-CoV group was slightly higher (~$10^4$ ng/mL) compared to the wild type (~$5\times10^3$ ng/mL) after 4 weeks, but this was not statistically significant. However, after 6 weeks the antibody titers for animals in the MERS-CoV ORF4a group was significantly higher (~$10^5$ ng/mL) compared to the WT (~$10^4$ ng/mL), with p=0.0061. The RABV pseudotyped neutralization reflected the antibody trends (FIG. 13b). After 4 weeks the WT group had an average $IC_{50}$ of ~$10^3$ whereas the MERS-CoV group had an $IC_{50}$ of ~$10^4$. After 6 weeks the MERS- CoV group had a much higher $IC_{50}$ of ~$10^5$, whereas the WT group had stabilized at ~$10^3$. They also compared the immunogenicity of the WT RABV and RABV-MERS-CoV ORF4a saRNA in mice and rats (FIG. 27), but did not observe any differences between the antibody titers nor neutralization $IC_{50}$ in either of these species. Without wishing to be bound to any particular theory, these data indicate that the MERS-CoV ORF4a protein enhances the immunogenicity of the RABV glycoprotein encoded by saRNA in rabbits.

MERS-CoV ORF4a Protein Enhances Expression of SARS-CoV-2 Glycoprotein In Vitro

The inventors also characterized the immunogenicity of another model protein (i.e. therapeutic biomolecule), the SARS-CoV-2 glycoprotein represented by Genbank ID No: QHD43416.1, when combined with the MERS-CoV ORF4a protein (i.e. the innate inhibitor protein or IIP) in an saRNA construct of the invention.

Twenty-four hours after transfection into the HeLa cell line, the levels of surface expression were compared between SARS-CoV-2 (with no IIP) and SARS-CoV-2 combined with MERS-CoV ORF4a (IIP). Referring to FIG. 29, the median fluorescence intensity of the positive population of cells was measured, with the negative/positive cut-off being set on cells that were gated as live and single and that were mock transfected. Surprisingly, the MERS-CoV ORF4a protein almost doubled the per cell expression levels of the SARS-CoV-2 glycoprotein, when compared to an saRNA encoding an SARS-CoV-2 glycoprotein only (i.e. no IIP).

Discussion

The inventors screened a library of self-amplifying RNA with cis-encoded interferon inhibiting proteins for protein expression in vitro in mouse, rabbit, nonhuman primate and human cells, ex vivo in human skin explants and in vivo in mice, as well as immunogenicity in mice, rats and rabbits. The inventors observed that the PIV-5 V and MERS-CoV ORF4a proteins enhanced protein expression 100-500-fold in vitro in IFN-competent HeLa and MRC5 cells. They found that the MERS-CoV ORF4a protein partially abates dose nonlinearity in vivo, and that ruxolitinib, but not the IIPS, enhances protein expression of saRNA in vivo. Both the PIV-5 V and MERS-CoV ORF4a proteins were found to enhance the percentage of resident cells in human skin explants expressing saRNA and completely rescued dose nonlinearity of saRNA, while ruxolitinib increases the protein expression on a per cell basis. Finally, the inventors observed that the MERS-CoV ORF4a increased the RABV-specific IgG titer and neutralization $IC_{50}$ by ~10-fold in rabbits, but not mice or rats.

The protein designs, cells and mutations characterized in these experiments offer insights into the mechanism by which the PIV-5 V and MERS-CoV ORF4a proteins increase protein expression. The PIV-5 V protein blocks MDA-5 and IRF3 by binding to MDA-5 (26, 27), whereas the MERS-CoV ORF4a protein binds to dsRNA and suppresses PACT triggering of MDA-5 and RIG-I (29-31). After our in vitro screening, the inventors chose to move forward with the MERS-CoV ORF4a replicon as it was not feasible to screen all 10 candidates in vivo, and the PIV-5 V protein isn't conserved between species (e.g. the N100D mutation needed for adaption to mice (44)) whereas the ORF4a protein is more highly conserved between species (29-31). The inventors observed that the R172A mutation to the PIV-5 V protein, which abrogates the ability to block binding to MDA-5 but not STAT (45), slightly inhibits protein expression in MRC5 cells (FIG. 15d) thus indicating that binding to MDA5 is partially responsible for enhancing protein expression. Similarly the K63A/K67A mutations to MERS-CoV ORF4a protein limits the ability to bind dsRNA (46, 47), and was observed to reduce protein expression in both nonhuman primate and human cells (FIG. 15*c,d*). While a variety of the IIPs inhibit interferon by similar mechanisms to PIV-5 V and MERS-CoV ORF4a, the mechanism of action was not necessarily observed to be predictive of enhancing protein expression.

The inventors have previously observed that protein expression of saRNA formulations is not necessarily predictive of immunogenicity (2), and thus also characterized how the MERS-CoV ORF4a protein affected the immunogenicity of the rabies glycoprotein in mice, rats and rabbits. The inventors observed an increase in both the antibody titer and neutralization $IC_{50}$ with the saRNA encoding RABV and MERS-CoV ORF4a (FIG. 13*a,b*) in rabbits, but did not observe an increase in immunogenicity in mice or rats. While no preclinical animal model is perfectly predictive of human responses, rabbits are regarded as more immunologically similar to humans than mice or rats (48-50). Furthermore, the inventors did not observe any enhancement of protein expression by either the PIV-5 V or MERS-CoV ORF4a proteins in murine cells (FIG. 15*a*), and thus the lack of enhancement of immunogenicity is not unexpected. The inventors paired characterization in preclinical animal models with a human explant model, in which the cells are in a native tissue architecture and possess the inherent human IFN response. To their knowledge, the inventors are the first to observe that the IIPs enhance the percentage of cells expressing saRNA, whereas ruxolitinib enhanced the expression per cell. Given these promising results the inventors postulate that the MERS-CoV ORF4a protein may enhance immunogenicity of saRNA vaccines in humans, and may also be useful for saRNA application to protein replacement therapies (51, 52).

These experiments provide a proof-of-concept that IIPs can be directly encoded into saRNA vectors and effectively abate the nonlinear dose dependency and enhance immunogenicity. As indicated by the mechanistic studies, different aspects of the interferon pathway can be targeted and increase saRNA expression, thus motivating probing of combinations of IIPs and other IFN inhibitions strategies, such as ruxolitinib.

Statement of Financial Support

The project leaving to this application has received funding from European Union's Horizon 2020 research and innovation programme under the Marie Sklodowska-Curie grant agreement No. 794059.

REFERENCES

1. S. Perri et al., An alphavirus replicon particle chimera derived from venezuelan equine encephalitis and sindbis viruses is a potent gene-based vaccine delivery vector. *J Virol* 77, 10394-10403 (2003).
2. A. K. Blakney et al., Big is Beautiful: Enhanced saRNA Delivery and Immunogenicity by a Higher Molecular Weight, Bioreducible, Cationic Polymer. *ACS Nano* 10.1021/acsnano.0c00326 (2020).
3. L. A. Brito et al., A cationic nanoemulsion for the delivery of next-generation RNA vaccines. *Molecular therapy: the journal of the American Society of Gene Therapy* 22, 2118-2129 (2014).
4. A. K. Blakney, P. F. McKay, B. L Yus, Y. Aldon, R. J. Shattock, Inside out: optimization of lipid nanoparticle formulations for exterior complexation and in vivo delivery of saRNA. *Gene Therapy* 10.1038/s41434-019-0095-2 (2019).
5. A. J. Geall et al., Nonviral delivery of self-amplifying RNA vaccines. *Proceedings of the National Academy of Sciences of the United States of America* 109, 14604-14609 (2012).
6. J. S. Chahal et al., Dendrimer-RNA nanoparticles generate protective immunity against lethal Ebola, H1N1 influenza, and *Toxoplasma gondii* challenges with a single dose. *Proc Natl Acad Sci USA* 113, E4133-4142 (2016).
7. A. B. Vogel et al., Self-Amplifying RNA Vaccines Give Equivalent Protection against Influenza to mRNA Vaccines but at Much Lower Doses. *Mol. Ther.* 26, 446-455 (2018).
8. K. J. Kallen et al., A novel, disruptive vaccination technology: self-adjuvanted RNActive(®) vaccines. *Hum Vaccin Immunother* 9, 2263-2276 (2013).
9. N. Pardi, M. J. Hogan, F. W. Porter, D. Weissman, mRNA vaccines—a new era in vaccinology. *Nature Reviews Drug Discovery* 10.1038/nrd.2017.243 (2018).
10. C. de Haro, R. Méndez, J. Santoyo, The eLF-2alpha kinases and the control of protein synthesis. *Fasebj* 10, 1378-1387 (1996).
11. S. L. Liang, D. Quirk, A. Zhou, RNase L: its biological roles and regulation. *IUBMB Life* 58, 508-514 (2006).
12. M. Alberer et al., Safety and immunogenicity of a mRNA rabies vaccine in healthy adults: an open-label, non-randomised, prospective, first-in-human phase 1 clinical trial. *Lancet* 390, 1511-1520 (2017).
13. T. Hagai et al., Gene expression variability across cells and species shapes innate immunity. *Nature* 563, 197-202 (2018).
14. D. Y. Kim et al., Enhancement of protein expression by alphavirus replicons by designing self-replicating subgenomic RNAs. *Proceedings of the National Academy of Sciences* 111, 10708 (2014).
15. T. Pepini et al., Induction of an IFN-Mediated Antiviral Response by a Self-Amplifying RNA Vaccine: Implications for Vaccine Design. *J Immunol* 198, 4012-4024 (2017).
16. A. S. Devasthanam, Mechanisms underlying the inhibition of interferon signaling by viruses. *Virulence* 5, 270-277 (2014).
17. Y. Liu, J. M. Chin, E. L. Choo, K. K. L. Phua, Messenger RNA translation enhancement by immune evasion proteins: a comparative study between EKB (vaccinia virus) and NS1 (influenza A virus). *Scientific Reports* 9, 11972 (2019).
18. T. Beissert et al., Improvement of In Vivo Expression of Genes Delivered by Self-Amplifying RNA Using Vaccinia Virus Immune Evasion Proteins. *Human Gene Therapy* 28, 1138-1146 (2017).
19. M. Zhang et al., HSV-2 immediate-early protein US1 inhibits IFN-β production by suppressing association of IRF-3 with IFN-β promoter. *J Immunol* 194, 3102-3115 (2015).
20. C. Kew et al., Suppression of PACT-Induced Type I Interferon Production by Herpes Simplex Virus 1 Us11 Protein. *Journal of Virology* 87, 13141 (2013).
21. J. Xing, S. Wang, R. Lin, K. L. Mossman, C. Zheng, Herpes simplex virus 1 tegument protein US11 down-modulates the RLR signaling pathway via direct interaction with RIG-I and MDA-5. *J Virol* 86, 3528-3540 (2012).

22. Y. Y. Tseng, G. R. Liao, G. C. Sen, F. Y. Lin, W. L. Hsu, Regulation of PACT-Mediated Protein Kinase Activation by the OV20.0 Protein of Orf Virus. *J Virol* 89, 11619-11629 (2015).

23. D. M. Haig et al., The orf virus OV20.0L gene product is involved in interferon resistance and inhibits an interferon-inducible, double-stranded RNA-dependent kinase. *Immunology* 93, 335-340 (1998).

24. N. Horscroft et al., Establishment of a subgenomic replicon for bovine viral diarrhea virus in Huh-7 cells and modulation of interferon-regulated factor 3-mediated antiviral response. *J Virol* 79, 2788-2796 (2005).

25. M. F. Darweesh, M. K. S. Rajput, L. J. Braun, J. S. Rohila, C. C. L. Chase, BVDV Npro protein mediates the BVDV induced immunosuppression through interaction with cellular S100A9 protein. *Microb Pathog* 121, 341-349 (2018).

26. K. R. Rodriguez, C. M. Horvath, Paramyxovirus V protein interaction with the antiviral sensor LGP2 disrupts MDA5 signaling enhancement but is not relevant to LGP2-mediated RLR signaling inhibition. *J Virol* 88, 8180-8188 (2014).

27. R. Mandhana, L. K. Qian, C. M. Horvath, Constitutively Active MDA5 Proteins Are Inhibited by Paramyxovirus V Proteins. *J Interferon Cytokine Res* 38, 319-332 (2018).

28. P. Y. Lui et al., Middle East respiratory syndrome coronavirus M protein suppresses type I interferon expression through the inhibition of TE K1-dependent phosphorylation of IRF3. *Emerg Microbes Infect* 5, e39 (2016).

29. Y. Yang et al., The structural and accessory proteins M, ORF 4a, ORF 4b, and ORF 5 of Middle East respiratory syndrome coronavirus (MERS-CoV) are potent interferon antagonists. *Protein Cell* 4, 951-961 (2013).

30. S. Shokri, S. Mahmoudvand, R. Taherkhani, F. Farshadpour, Modulation of the immune response by Middle East respiratory syndrome coronavirus. *J Cell Physiol* 234, 2143-2151 (2019).

31. M. Batool, M. Shah, M. C. Patra, D. Yesudhas, S. Choi, Structural insights into the Middle East respiratory syndrome coronavirus 4a protein and its dsRNA binding mechanism. *Sci Rep* 7, 11362 (2017).

32. C. E. Comar et al., Antagonism of dsRNA-Induced Innate Immune Pathways by NS4a and NS4b Accessory Proteins during MERS Coronavirus Infection. *mBio* 10 (2019).

33. S. M. Best, The Many Faces of the Flavivirus NS5 Protein in Antagonism of Type I Interferon Signaling. *J Virol* 91 (2017).

34. K. Werme, M. Wigerius, M. Johansson, Tick-borne encephalitis virus NS5 associates with membrane protein scribble and impairs interferon-stimulated JAK-STAT signalling. *Cell Microbiol* 10, 696-712 (2008).

35. R. M. Krug, Functions of the influenza A virus NS1 protein in antiviral defense. *Curr Opin Virol* 12, 1-6 (2015).

36. E. M. Elli, C. Barate, F. Mendicino, F. Palandri, G. A. Palumbo, Mechanisms Underlying the Anti-inflammatory and Immunosuppressive Activity of Ruxolitinib. *Front Oncol* 9, 1186-1186 (2019).

37. M. E. Fitzgerald et al., Selective RNA targeting and regulated signaling by RIG-I is controlled by coordination of RNA and ATP binding. *Nucleic Acids Research* 45, 1442-1454 (2016).

38. K. Cantell, Production and action of interferon in HeLa cells. *Archiv für die gesamte Virusforschung* 10, 510-521 (1961).

39. E. Meurs, A. G. Hovanessian, L. Montagnier, Interferon-mediated Antiviral State in Human MRC5 Cells in the Absence of Detectable Levels of 2-5A Synthetase and Protein Kinase. *Journal of Interferon Research* 1, 219-234 (1981).

40. A. Ramachandran, C. M. Horvath, Dissociation of paramyxovirus interferon evasion activities: universal and virus-specific requirements for conserved V protein amino acids in MDA5 interference. *Journal of virology* 84, 11152-11163 (2010).

41. K.-L. Siu et al., Middle East Respiratory Syndrome Coronavirus 4a Protein Is a Double-Stranded RNA-Binding Protein That Suppresses PACT-Induced Activation of RIG-I and MDA5 in the Innate Antiviral Response. *Journal of Virology* 88, 4866 (2014).

42. T. Shirahata, A. Mori, H. Ishikawa, H. Goto, Strain Differences of Interferon-Generating Capacity and Resistance in *Toxoplasma*-Infected Mice. *Microbiology and Immunology* 30, 1307-1316 (1986).

43. L. Van Der Maaton, G. Hinton, Visualizing data using t-SNE. *J. Mach. Learn. Res.* 9, 2579-2625 (2008).

44. T. A. Kraus, L. Garza, C. M. Horvath, Enabled interferon signaling evasion in an immune-competent transgenic mouse model of parainfluenza virus 5 infection. *Virology* 371, 196-205 (2008).

45. A. Ramachandran, C. M. Horvath, Dissociation of Paramyxovirus Interferon Evasion Activities: Universal and Virus-Specific Requirements for Conserved V Protein Amino Acids in MDA5 Interference. *Journal of Virology* 84, 11152 (2010).

46. H. H. Rabouw et al., Middle East Respiratory Coronavirus Accessory Protein 4a Inhibits PKR-Mediated Antiviral Stress Responses. *PLoS pathogens* 12, e1005982-e1005982 (2016).

47. K.-L. Siu et al., Middle east respiratory syndrome coronavirus 4a protein is a double-stranded RNA-binding protein that suppresses PACT-induced activation of RIG-I and MDA5 in the innate antiviral response. *Journal of virology* 88, 4866-4876 (2014).

48. S. C. Jameson, D. Masopust, What Is the Predictive Value of Animal Models for Vaccine Efficacy in Humans? Reevaluating the Potential of Mouse Models for the Human Immune System. *Cold Spring Harbor perspectives in biology* 10, a029132 (2018).

49. V. Gerdts et al., Large animal models for vaccine development and testing. *Ilar j* 56, 53-62 (2015).

50. C. Vaure, Y. Liu, A comparative review of toll-like receptor 4 expression and functionality in different animal species. *Front Immunol* 5, 316 (2014).

51. A. Magadum, K. Kaur, L. Zangi, mRNA-Based Protein Replacement Therapy for the Heart. *Mol. Ther.* 27, 785-793 (2019).

52. P. S. Kowalski, A. Rudra, L. Miao, D. G. Anderson, Delivering the Messenger: Advances in Technologies for Therapeutic mRNA Delivery. *Molecular therapy: the journal of the American Society of Gene Therapy* 27, 710-728 (2019).

53. A. K. Blakney, P. F. McKay, R. J. Shattock, Structural Components for Amplification of Positive and Negative Strand VEEV Splitzicons. *Frontiers in Molecular Biosciences* 5, 71 (2018).

54. A. K. Blakney et al., Effects of cationic adjuvant formulation particle type, fluidity and immunomodulators on delivery and immunogenicity of saRNA. *Journal of Controlled Release* 304, 65-74 (2019).

55. A. K. Blakney, G. Yilmaz, P. F. McKay, C. R. Becer, R. J. Shattock, One Size Does Not Fit All: The Effect of Chain Length and Charge Density of Poly(ethylene imine) Based Copolymers on Delivery of pDNA, mRNA, and RepRNA Polyplexes. *Biomacromolecules* 19, 2870-2879 (2018).
56. A. Badamchi-Zadeh et al., Intramuscular Immunisation with Chlamydial Proteins Induces *Chlamydia trachomatis*

Specific Ocular Antibodies. *PLoS ONE* 10, e0141209 (2015).
57. A. K. Blakney et al., The Skin You Are In: Design-of-Experiments Optimization of Lipid Nanoparticle Self-Amplifying RNA Formulations in Human Skin Explants. *ACS Nano* 13, 5920-5930 (2019).

The invention claimed is:

1. An RNA construct encoding (i) at least one therapeutic biomolecule; and (ii) at least one innate inhibitor protein (IIP), wherein the RNA construct comprises or is derived from a virus selected from the group of species consisting of: Venezuelan Equine Encephalitis Virus (VEEV); enterovirus 71; Encephalomyocarditis virus; Kunjin virus; and Middle East respiratory syndrome virus.

2. The RNA construct according to claim 1, wherein the RNA construct comprises self-amplifying RNA (saRNA).

3. The RNA construct according to claim 1, wherein the construct is derived from VEEV.

4. The RNA construct according to claim 1, wherein the at least one therapeutic biomolecule:

(i) is an RNA molecule that is capable of regulating expression of endogenous host genes;

(ii) is derived from a bacterium, virus, fungus, protozoan or a parasite;

(iii) is selected from a group consisting of: an enzyme; an enzyme inhibitor; a hormone; an immune system protein; a receptor; a binding protein; a transcription or translation factor; tumour growth suppressing protein; a structural protein; and a blood protein;

(iv) is an antigen, optionally a tumour antigen.

5. The RNA construct according to claim 1, wherein the at least one therapeutic biomolecule encoded by the RNA molecule is a protein or peptide derived from a pathogen selected from a group consisting of: bacteria, viruses, fungi, protozoa; and parasites.

6. The RNA construct according to claim 5, wherein the protein or peptide is a viral antigen derived from a virus selected from the group consisting of: Orthomyxoviruses; Paramyxoviridae viruses; Metapneumovirus and Morbilliviruses; Pneumoviruses; Paramyxoviruses; Poxviridae; Metapneumoviruses; Morbilliviruses; Picornaviruses; Enteroviruseses; Bunyaviruses; Phlebovirus; Nairovirus; Heparnaviruses; Togaviruses; Alphavirus; Arterivirus, Flaviviruses; Pestiviruses; Hepadnaviruses; Rhabdoviruses; Caliciviridae; Coronaviruses; Retroviruses; Reoviruses; Parvoviruses; Delta hepatitis virus (HDV); Hepatitis E virus (HEV); Human Herpesviruses and Papovaviruses.

7. The RNA construct according to claim 6, wherein the Coronavirus is SARS COV-1, SARS-COV-2, MERS, Human respiratory coronavirus, Avian infectious bronchitis (IBV), Mouse hepatitis virus (MHV), or Porcine transmissible gastroenteritis virus (TGEV).

8. The RNA construct according to claim 1, wherein the at least one innate inhibitor protein is capable of either: (i) reducing or blocking the action of Melanoma Differentiation-Associated protein 5 (MDA5) and/or (ii) blocking or reducing the binding of PKR activating protein to RNA.

9. The RNA construct according to claim 1, wherein the at least one innate inhibitor protein is Middle East respiratory syndrome coronavirus MERS coronavirus (ORF4a).

10. The RNA construct according to claim 1, wherein the at least one innate inhibitor protein is Parainfluenza virus type 5 V protein (PIV5 V).

11. The RNA construct according to claim 1, wherein the at least one innate inhibitor protein is coronavirus ORF3b.

12. The RNA construct according to claim 1, wherein the RNA construct comprises an RNA nucleotide sequence which encodes SEQ ID No: 11, SEQ ID No: 15 and/or SEQ ID No: 20, or a variant or fragment thereof.

13. The RNA construct according to claim 1, wherein the RNA construct comprises an RNA nucleotide sequence as set out as SEQ ID No: 47, SEQ ID No: 48 and/or SEQ ID No: 56, or a variant or fragment thereof.

14. The RNA construct according to claim 1, wherein the at least one innate inhibitor protein is capable of inhibiting one or more pathway downstream of MDA5 activation, or blocking one or more pathways downstream of MDA/PACT recognition of dsRNA.

15. The RNA construct according to claim 14, wherein the at least one innate inhibitor protein is selected from a group consisting of: HSV-2 Us1; HSV-1 Us1; HSV-1 Us11; OV20.0L; BVDV Npro; Langat virus NS5; and Influenza NS1.

16. The RNA construct according to claim 1, wherein the RNA construct comprises a promoter or sub genomic promoter operably linked to the sequences encoding the at least one therapeutic biomolecule and the at least one innate inhibitor protein, such that it enables the transcription nucleotide sequence encoding the therapeutic biomolecule and the at least one innate inhibitor protein.

17. The RNA construct according to claim 16, wherein the promoter is 26S, optionally wherein the promoter comprises a nucleotide sequence as set out in SEQ ID No: 57, or a variant or fragment thereof.

18. The RNA construct according to claim 1, wherein the RNA construct comprises a linker sequence disposed between the sequence encoding the therapeutic biomolecule and the sequence encoding the at least one innate inhibitor protein, wherein the linker sequence encodes a peptide spacer that is configured to be digested to thereby separate the at least one therapeutic biomolecule and the at least one innate inhibitor protein.

19. The RNA construct according to claim 1, wherein the RNA construct comprises a nucleotide sequence as set out in SEQ ID No: 38 or 39, or a fragment or variant thereof.

20. A nucleic acid sequence encoding the RNA construct of claim 1.

21. A pharmaceutical composition comprising the RNA construct according to claim 1, or the nucleic acid sequence according to claim 20, and a pharmaceutically acceptable vehicle.

22. A vaccine comprising the RNA construct according to claim 1, or the nucleic acid according to claim 20, and optionally an adjuvant.

23. The RNA construct according to claim 11, wherein the at least one innate inhibitor protein is SARS-COV-2 ORF3b.

24. The RNA construct according to claim 18, wherein the peptide spacer is a 2A peptide or a furin/2A peptide.

* * * * *